(12) United States Patent
Tang et al.

(10) Patent No.: US 9,751,881 B2
(45) Date of Patent: Sep. 5, 2017

(54) INHIBITORS OF THE RENAL OUTER MEDULLARY POTASSIUM CHANNEL

(71) Applicant: Merck Sharp & Dohme Corp., Rahway, NJ (US)

(72) Inventors: Haifeng Tang, Metuchen, NJ (US); Barbara Pio, West Orange, NJ (US); Jinlong Jiang, Scotch Plains, NJ (US); Alexander Pasternak, Princeton, NJ (US); Shuzhi Dong, Plainsboro, NJ (US); Ronald Dale Ferguson, II, Scotch Plains, NJ (US); Zack Zhiqiang Guo, Morganville, NJ (US); Harry Chobanian, Aberdeen, NJ (US); Jessica Frie, Harleysville, PA (US); Yan Guo, Westfield, NJ (US); Zhicai Wu, Montvale, NJ (US); Yang Yu, Edison, NJ (US); Ming Wang, Belle Mead, NJ (US)

(73) Assignee: Merck Sharp & Dohme Corp., Rahway, NJ (US)

(*) Notice: Subject to any disclaimer, the term of this patent is extended or adjusted under 35 U.S.C. 154(b) by 18 days.

(21) Appl. No.: 14/908,222

(22) PCT Filed: Jul. 28, 2014

(86) PCT No.: PCT/US2014/048358
§ 371 (c)(1),
(2) Date: Jan. 28, 2016

(87) PCT Pub. No.: WO2015/017305
PCT Pub. Date: Feb. 5, 2015

(65) Prior Publication Data
US 2016/0207922 A1 Jul. 21, 2016

Related U.S. Application Data

(60) Provisional application No. 61/970,102, filed on Mar. 25, 2014, provisional application No. 61/860,270, filed on Jul. 31, 2013.

(51) Int. Cl.
| | |
|---|---|
| C07D 471/10 | (2006.01) |
| C07D 451/00 | (2006.01) |
| C07D 493/04 | (2006.01) |
| C07D 498/10 | (2006.01) |
| A61K 31/435 | (2006.01) |
| A61K 31/444 | (2006.01) |
| A61K 31/46 | (2006.01) |
| A61K 31/497 | (2006.01) |
| A61K 31/501 | (2006.01) |
| A61K 31/506 | (2006.01) |
| A61K 31/5386 | (2006.01) |
| A61K 45/06 | (2006.01) |

(52) U.S. Cl.
CPC ......... *C07D 471/10* (2013.01); *A61K 31/435* (2013.01); *A61K 31/444* (2013.01); *A61K 31/46* (2013.01); *A61K 31/497* (2013.01); *A61K 31/501* (2013.01); *A61K 31/506* (2013.01); *A61K 31/5386* (2013.01); *A61K 45/06* (2013.01); *C07D 451/00* (2013.01); *C07D 493/04* (2013.01); *C07D 498/10* (2013.01)

(58) Field of Classification Search
CPC .................................................. C07D 471/10
See application file for complete search history.

(56) References Cited

U.S. PATENT DOCUMENTS

| | | |
|---|---|---|
| 2,988,551 A | 6/1961 | Morren |
| 3,435,002 A | 3/1969 | Holub |

(Continued)

FOREIGN PATENT DOCUMENTS

| | | |
|---|---|---|
| EP | 0099148 B1 | 2/1988 |
| EP | 0175376 B1 | 4/1991 |

(Continued)

OTHER PUBLICATIONS

Han, H. "Targeted Prodrug Design to Optimize Drug Delivery." AAPS Pharmsci. (2000), vol. 2 (1) article 6, pp. 1-11.*

(Continued)

*Primary Examiner* — Noble Jarrell
*Assistant Examiner* — John S Kenyon
(74) *Attorney, Agent, or Firm* — Baerbel R. Brown; Catherine D. Fitch

(57) ABSTRACT

The present invention provides compounds of Formula I

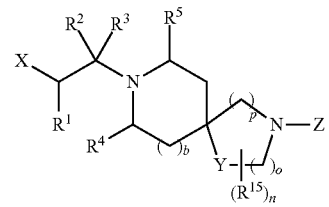

and the pharmaceutically acceptable salts thereof, which are inhibitors of the ROMK (Kir1.1) channel. The compounds may be used as diuretic and/or natriuretic agents and for the therapy and prophylaxis of medical conditions including cardiovascular diseases such as hypertension, heart failure and chronic kidney disease and conditions associated with excessive salt and water retention.

10 Claims, No Drawings

(56) References Cited

U.S. PATENT DOCUMENTS

| | | |
|---|---|---|
| 3,632,608 A | 1/1972 | Holub |
| 3,749,722 A | 7/1973 | Holub |
| 4,579,863 A | 4/1986 | Horwell et al. |
| 4,806,536 A | 2/1989 | Cross et al. |
| 4,992,547 A | 2/1991 | Berner et al. |
| 5,145,885 A | 9/1992 | Berner et al. |
| 5,215,989 A | 6/1993 | Baldwin et al. |
| 5,614,526 A | 3/1997 | Godel et al. |
| 5,736,546 A | 4/1998 | Kawashima et al. |
| 6,258,813 B1 | 7/2001 | Arlt et al. |
| 6,787,543 B2 | 9/2004 | Take et al. |
| 8,673,920 B2 | 3/2014 | Pasternak et al. |
| 8,952,166 B2 | 2/2015 | Ding et al. |
| 2002/0013325 A1 | 1/2002 | Fisher et al. |
| 2004/0110793 A1 | 6/2004 | Lloyd et al. |
| 2004/0204404 A1 | 10/2004 | Zelle et al. |
| 2005/0215526 A1 | 9/2005 | Hulme et al. |
| 2005/0267121 A1 | 12/2005 | Li et al. |
| 2006/0183739 A1 | 8/2006 | Tsaklakidis et al. |
| 2006/0183742 A1 | 8/2006 | Mederski et al. |
| 2006/0211692 A1 | 9/2006 | Mederski et al. |
| 2007/0004750 A1 | 1/2007 | Lorsbach et al. |
| 2007/0072865 A1 | 3/2007 | Fukatsu et al. |
| 2007/0093472 A1 | 4/2007 | Mederski et al. |
| 2007/0275990 A1 | 11/2007 | Ohmoto et al. |
| 2008/0003214 A1 | 1/2008 | Cezanne et al. |
| 2008/0090794 A1 | 4/2008 | Dinsmore et al. |
| 2013/0131042 A1 | 5/2013 | Duffy et al. |

FOREIGN PATENT DOCUMENTS

| | | |
|---|---|---|
| EP | 1094063 A1 | 4/2001 |
| EP | 1939175 A1 | 7/2009 |
| FR | 2673182 | 8/1992 |
| FR | 2673182 A1 | 8/1992 |
| GB | 949088 A | 2/1964 |
| GB | 1575310 A | 9/1980 |
| GB | 2116967 | 7/1986 |
| JP | 10203986 | 8/1998 |
| WO | 9744329 | 11/1997 |
| WO | 0051611 A1 | 9/2000 |
| WO | 0232874 | 4/2002 |
| WO | 0204314 A1 | 6/2002 |
| WO | 0250061 A1 | 6/2002 |
| WO | 2004020422 A1 | 3/2004 |
| WO | 2004037817 A1 | 5/2004 |
| WO | 2004046110 | 6/2004 |
| WO | 2005037843 | 4/2005 |
| WO | 2005044797 | 5/2005 |
| WO | 2006034341 A2 | 3/2006 |
| WO | 2006034769 A1 | 4/2006 |
| WO | 2006098342 A1 | 9/2006 |
| WO | 2006129199 A1 | 12/2006 |
| WO | 2007075629 A2 | 7/2007 |
| WO | 2008147864 | 12/2008 |
| WO | 2008147864 A2 | 12/2008 |
| WO | 2009149508 | 11/2009 |
| WO | 2010129379 A1 | 11/2010 |
| WO | 2012058116 A1 | 5/2012 |
| WO | 2012058134 A1 | 5/2012 |
| WO | 2013028474 A1 | 2/2013 |
| WO | 2013039802 A1 | 3/2013 |
| WO | 2013062892 A1 | 5/2013 |
| WO | 2013062900 A1 | 5/2013 |
| WO | 2013066714 A1 | 5/2013 |
| WO | 2013066717 A1 | 5/2013 |
| WO | 2013066718 A2 | 5/2013 |
| WO | 2013090271 A1 | 6/2013 |
| WO | 2014018764 A1 | 1/2014 |
| WO | 2014085210 A1 | 6/2014 |
| WO | 2014099633 A2 | 6/2014 |
| WO | 2014126944 A2 | 8/2014 |
| WO | WO2014150132 A1 | 9/2014 |
| WO | 2015065866 A1 | 5/2015 |
| WO | 2015095097 A2 | 6/2015 |
| WO | 2015100147 A1 | 7/2015 |
| WO | 2015105736 A1 | 7/2015 |

OTHER PUBLICATIONS

Ettmayer, P., et al. "Lessons Learned from Marketed and Investigational Prodrugs." J. Med. Chem. (2004) 47(10), pp. 2393-2404.*
Testa, B. "Prodrug research: futile or fertile?" Biochem. Pharm. (2004) 68, pp. 2097-2106.*
ACCF/AHA Practice Guideline, 2009 Focused update incorporated into the ACC/AHA 2005 guidelines . . . , Circulation, 2009, e391-e436, 119.
Baltzly, R., The preparation of N-mono-substituted and unsymmetrically disubstituted piperazines, J. Am. Chemoc., 1944, 263-266, 66.
Bhave, G., Small-molecule modulators of inward rectifier K+ channels: recent advances and future possibilities, Future Med Chem, 2010, 757-774, 2(5).
Bhave,G., Development of a selective small-molecule inhibitor Kir1.1, the renal outer medullary potassium channel, Mol. Pharmacol., 2011, 42-50, 79.
Brater et al., Diuretic Therapy, Drug Therapy, 1998, 387-395, 339.
Brewster et al., Antihypertensive 1,4-bis (2-indol-3-ylethyl)piperazines, Chimie Ther., 1973, 169-172 (English trans.), 2.
Cerkvenik-Flajs V, Determination of residues of azaperone in the kidneys by liquid chromatography with fluorescence, Anal. Chim. Acta., 2007, 374-382, 586.
Chemical Abstracts (2004), Abstract No. 697771-49-6, "1,3-Isobenzofurandione 5-[[4-[(5-chloro-2-methoxyphenyl) sulfonyl]-1- . . . "
Cheymol et al., Increase in the effects of epinephrine and acetylcholine . . . , Comptes Rendus des seances de la Societe de Biologie, 1951, 496-499 (English trans.), 145.
Dorwald, Side reactions in Organic Synthesis: A Guide to Successful Synthesis Design, 2005, Chapter 1.
Fallen, K., The Kir channel immunoglobuling domain is essential for Kir1.1 (ROMK) thermodynamic stability, trafficing and gating, Channels, 2009, 57-66, 3.
Felker et al, Diuretic strategies in patients with acute decompensated heart failure, New Eng. J. Med., 2011, 797-805, 364.
Frank, Managing hypertension using combination therapy, Am. Fam. Physician, 2008, 1279-1286, 77.
Fritch et al., Design, syntheses, and SAR of 2,8-diazaspiro[4.5]decanones at T-type calcium channel antagonists, Bioorganic & Medicinal Chemistry Letters, 2010, 6375-6378, 20.
International Search Report and Written Opinion for PCT/US2014/048358 mailed Jan. 2, 2015, 10 pages.
Kulkarni, YD, Possible antifertility agents, part III. Synthesis of 4-(substituted aminomethyl)-5,6,7-trimethoxy phthalid . . . (abstract)), Biol. Mem., 1987, 141-144, 13.
Lanyi et al., Piperazine-Derivatives II, Res. Lab. of Chinoin-Fabrik Chemisch-Pharma. Prod., 1968, 1431-1435 (English trans.), 18.
Lewis, L. M., High-throughput screening reveals a small-molecule inhibitor of the Renal Outer Medullary Potassium Channel and Kir7.1, Mol. Pharncol., 2009, 1094-1103, 76.
Lutz, R. E., Antimalarials. Some Piperazine Derivatives, J. Org. Chem., 1947, 771-775, 12, BO.
Miyake et al., Synthesis of 1-substituted isochroman . . . , Takeda Res. Lab., 1982, 24-40 (English trans.), 41.
Sica, D. A., Diuretic use in renal disease, Nature, 2012, 100-109, 8.
Zejc et al., Piperazine derivative of dimethylxanthines, Polish J. Pharmacol. & Pharm., 1975, 311-316 (English trans.), 27.

* cited by examiner

INHIBITORS OF THE RENAL OUTER MEDULLARY POTASSIUM CHANNEL

CROSS REFERENCE TO RELATED APPLICATIONS

This application is a U.S. National Phase application under 35 U.S.C. §371 of PCT Application No. PCT/US2014/048358 filed Jul. 28, 2014, which claims priority from U.S. Provisional Application Ser. No. 61/860,270, filed Jul. 31, 2013 and U.S. Provisional Application Ser. No. 61/970,102, filed Mar. 25, 2014.

RELATED APPLICATIONS

This application claims benefit of provisional application U.S. Ser. No. 61/860,270, filed Jul. 31, 2013, and provisional application U.S. Ser. No. 61/970,102, filed Mar. 25, 2014, both herein incorporated by reference.

BACKGROUND OF THE INVENTION

The Renal Outer Medullary Postassium (ROMK) channel Kir1.1) (see e.g., Ho, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the $Na^+/K^+/2Cl^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are expected to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Bartter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first publicly disclosed small molecule selective inhibitors of ROMK, including VU590, were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76(5): p. 1094-1103. The compound VU591 was later reported in Bhave, G. et al., *Development of a Selective Small-Molecule Inhibitor of Kir1.1, the Renal Outer Medullary Potassium Channel*, Mol Pharmacol, 2011, 79(1), p. 42-50, the text of which states that "ROMK (Kir1.1), is a putative drug target for a novel class of loop diuretics that would lower blood pressure without causing hypokalemia."

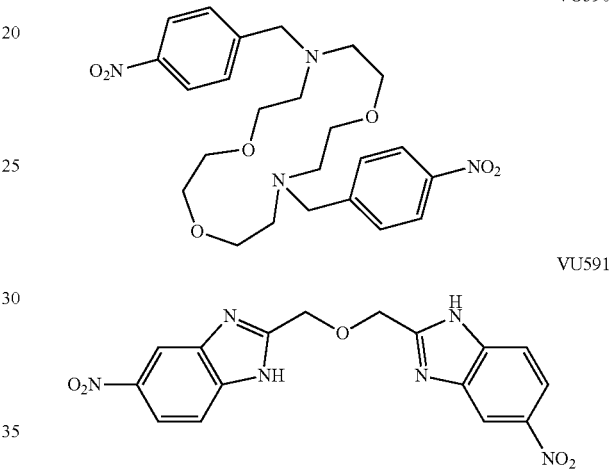

Patent application publication number WO2010/129379, published Nov. 11, 2010 having common representative Merck Sharp & Dohme Corp., (also published as US2010/0286123 on same date), describes ROMK inhibitors having the generic formula:

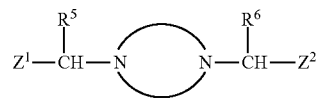

and, e.g., an embodiment

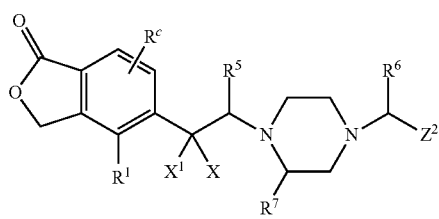

wherein $R^5$ and $R^6$ are independently —H, —$C_{1-6}$ alkyl, —$C_{3-6}$ cycloalkyl, —$CF_3$, —$CHF_2$, —$CH_2F$ or —$CH_2OH$; X is —H, —OH, —$OC_{1-3}$alkyl, —F, oxo, $NH_2$ or —$CH_3$; and $X^1$ is —H or —$CH_3$.

Patent application publication number WO2012/058134, published May 3, 2012, having common representative Merck Sharp & Dohme Corp., describes ROMK inhibitors having the generic formula:

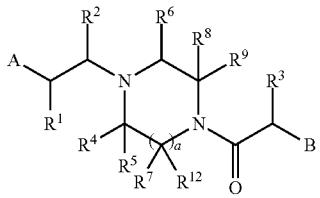

wherein A and B are mono and/or bicyclic aromatic groups; $R^2$ is —H, —$C_{1-6}$ alkyl, —$C_{3-6}$ cycloalkyl, $CF_3$, —$CH_2OH$, or —$CO_2R$, or $R^2$ can be joined to $R^1$ or $R^{10a}$ to form a ring; $R^3$ is —H, —$C_{1-6}$ alkyl, —$C_{3-6}$ cycloalkyl, —OH, —F, —$OC_{1-3}$ alkyl, or —$CH_2OH$, or $R^3$ can be joined to $R^{10a}$ to form a ring.

Patent application publication number WO2012/058116, published May 3, 2012, having common representative Merck Sharp & Dohme Corp., describes ROMK inhibitors having the generic formula:

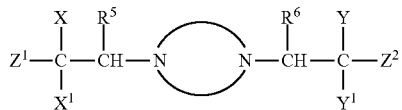

and, e.g., an embodiment

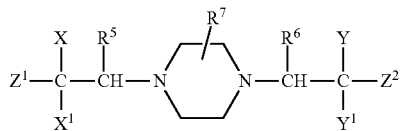

wherein $R^5$ and $R^6$ are independently —H, —$C_{1-6}$ alkyl or —C(O)O$C_{1-3}$alkyl; and X, $X^1$, Y and $Y^1$ are independently —H or —$C_{1-6}$alkyl; or $Y^1$ can be joined together with $Z^2$ to form a fused ring system. Additional published patent applications to Merck Sharp and Dohme, which describe ROMK inhibitors, include: WO2013/028474; WO2013/039802; WO2013/062892; WO2013/066714; WO2013/066717; WO2013/066718; and WO2013/090271.

However, continuing discovery of selective small molecule inhibitors of ROMK is still needed for the development of new treatments for hypertension, heart failure, edematous states and related disorders. The compounds of Formula I and salts thereof of this invention are selective inhibitors of the ROMK channel and could be used for the treatment of hypertension, heart failure and other conditions where treatment with a diuretic or natriuretic would be beneficial.

SUMMARY OF THE INVENTION

The present invention provides for compounds of the Formula

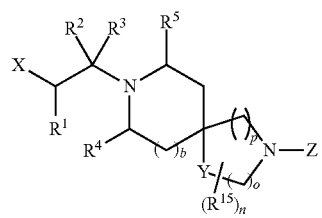

or a pharmaceutically acceptable salt thereof, wherein:
X is

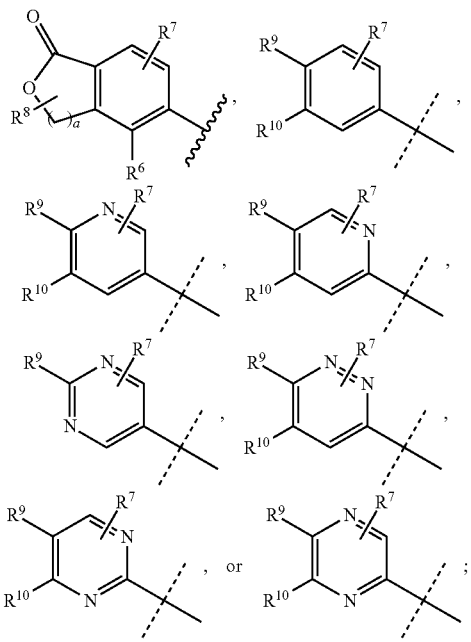

Y is —O— or a bond;
Z is

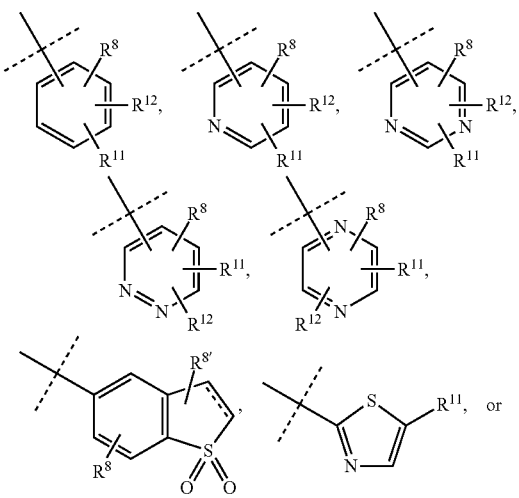

-continued

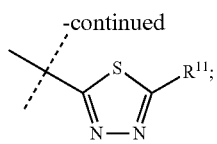

where Z ---- is a single or double bond;
R is independently H, alkyl or haloalkyl;
$R^1$ is H, alkyl, —F, —OR, or —N($R^{13}$)($R^{14}$);
$R^2$ is H or alkyl optionally substituted by 1-5 halogen atoms or —OR;
$R^3$ is H or alkyl;
$R^4$ is H or alkyl optionally substituted by 1-5 halogen atoms or —OR;
$R^5$ is H or alkyl optionally substituted by 1-5 halogen atoms or —OR;
   or $R^4$ and $R^5$ are joined together to represent —CH$_2$CH$_2$—, —CH$_2$NCH$_2$—, —CH$_2$N(CH$_3$)CH$_2$— or —CH$_2$OCH$_2$—;
$R^6$ is H, halo, alkyl optionally substituted by 1-5 halogen atoms or —OR, cycloalkyl or —OR;
   or $R^6$ and $R^1$ are joined together to represent —CH$_2$CH$_2$O—;
$R^7$ is H, halo, alkyl optionally substituted by 1-5 halogen atoms or —OR, cycloalkyl or —OR;
$R^8$ is independently H or alkyl;
$R^{8'}$ is H or alkyl;
$R^9$ is —CN, tetrazolyl, or —S(O)$_2R^{13}$;
$R^{10}$ is halo, —OR, alkyl optionally substituted by 1-5 halogen atoms or —OR, —S-alkyl, —N— alkyl or —O-cyclopropyl;
$R^{11}$ is —CN, —S(O)$_2R^{13}$, or optionally substituted heteroaryl (e.g., 1H-tetrazolyl, 2H-tetrazolyl, 1,2,4-oxadiazole, 4H-1,2,3-triazolyl or furanyl) wherein the optional substitutent is halogen or alkyl;
$R^{12}$ is H, halo, alkyl, cycloalkyl, or —OR;
$R^{13}$ is H, alkyl, allyl or cycloalkyl;
$R^{14}$ is H, alkyl or cycloalkyl;
$R^{15}$ independently oxo, —F, —CN, alkyl optionally substituted by 1-5 fluorine atoms or —OR, cycloalkyl, heteroaryl optionally substituted by halogen, —CN, alkyl or haloalkyl;
   a is 1 or 2;
   b is 0 or 1;
   n is 0, 1 or 2;
   o is 1, 2 or 3; and
   p is 1 or 2.

The compound of Formula I are inhibitors of the ROMK (Kir1.1) channel. As a result, the compounds of Formula I could be used in methods of treatment, inhibition or amelioration of one or more disease states that could benefit from inhibition of ROMK. The compounds of this invention could be used in methods of treatment which comprise administering a therapeutically or prophylactically effective amount of a compound of Formula I to a patient in need of a diuretic and/or natriuretic agent. Therefore, the compounds of Formula I could be valuable pharmaceutically active compounds for the therapy, prophylaxis or both of medical conditions, including, but not limited to, cardiovascular diseases such as hypertension and heart failure as well as chronic kidney disease, and conditions associated with excessive salt and water retention. The compounds of this invention could further be used in combination with other therapeutically effective agents, including but not limited to, other drugs which are useful for the treatment of hypertension, heart failure and conditions associated with excessive salt and water retention. The invention furthermore relates to processes for preparing compounds of Formula I, and pharmaceutical compositions which comprise compounds of Formula I. These and other aspects of the invention will be evident from the description contained herein.

DETAILED DESCRIPTION OF THE INVENTION

An embodiment of this invention is compounds of Formula I or pharmaceutically acceptable salts thereof.

Another embodiment of this invention is a compound of Formula I having the structural formula Formula

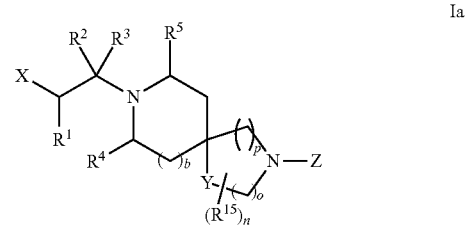

Ia or a pharmaceutically acceptable salt thereof, wherein:
X is

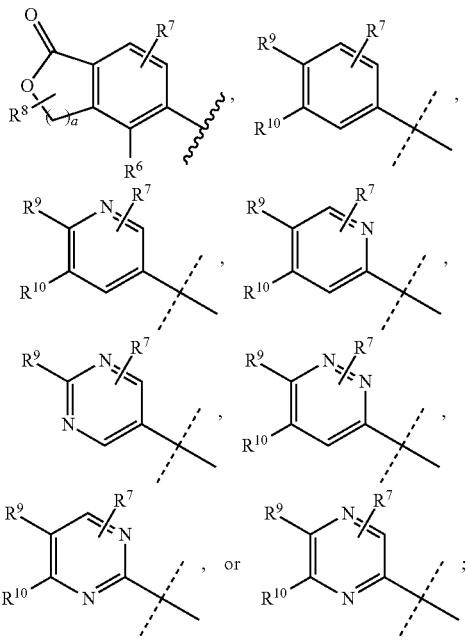

Y is —O— or a bond;
Z is

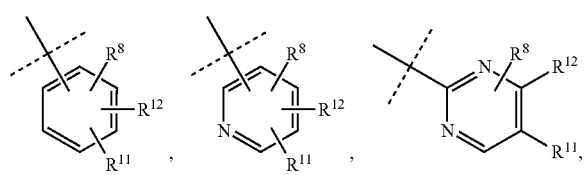

-continued

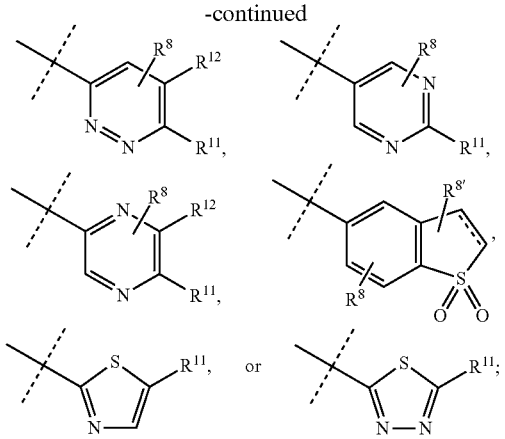

where ---- is a single or double bond;
R is independently H, alkyl or haloalkyl;
$R^1$ is H, alkyl, —F, —OR, or —N($R^{13}$)($R^{14}$);
$R^2$ is H or alkyl optionally substituted by 1-5 halogen atoms or —OR;
$R^3$ is H or alkyl;
$R^4$ is H or alkyl optionally substituted by 1-5 halogen atoms or —OR;
$R^5$ is H or alkyl optionally substituted by 1-5 halogen atoms or —OR;
  or $R^4$ and $R^5$ are joined together to represent —CH$_2$CH$_2$—, —CH$_2$NCH$_2$—, —CH$_2$N(CH$_3$)CH$_2$— or —CH$_2$OCH$_2$—;
$R^6$ is H, halo, alkyl optionally substituted by 1-5 halogen atoms or —OR, cycloalkyl or —OR;
  or $R^6$ and $R^1$ are joined together to represent —CH$_2$CH$_2$O—;
$R^7$ is H, halo, alkyl optionally substituted by 1-5 halogen atoms or —OR, cycloalkyl or —OR;
$R^8$ is independently H or alkyl;
$R^{8'}$ is H or alkyl;
$R^9$ is —CN, tetrazolyl, or —S(O)$_2R^{13}$;
$R^{10}$ is halo, —OR, alkyl optionally substituted by 1-5 halogen atoms or —OR, —S-alkyl, —N— alkyl or —O-cyclopropyl;
$R^{11}$ is —CN, —S(O)$_2R^{13}$, or optionally substituted heteroaryl (e.g., 1H-tetrazolyl, 2H-tetrazolyl, 1,2,4-oxadiazole or 4H-1,2,3-triazolyl) wherein the optional substituent is halogen or alkyl;
$R^{12}$ is H, halo, alkyl, cycloalkyl, or —OR;
$R^{13}$ is H, alkyl, allyl or cycloalkyl;
$R^{14}$ is H, alkyl or cycloalkyl;
$R^{15}$ independently oxo, —F, —CN, alkyl optionally substituted by 1-5 fluorine atoms or —OR, cycloalkyl, heteroaryl optionally substituted by halogen, —CN, alkyl or haloalkyl;
a is 1 or 2;
b is 0 or 1;
n is 0, 1 or 2;
o is 1, 2 or 3; and
p is 1 or 2.

Another embodiment of this invention is a compound of Formula I having the structural formula

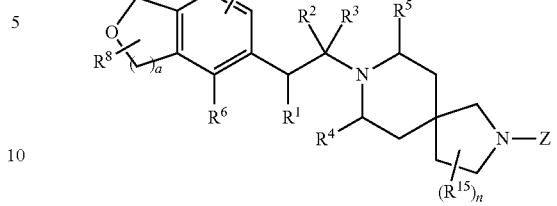

or a pharmaceutically acceptable salt thereof
wherein $R^1$, $R^2$, $R^3$, $R^4$, $R^5$, $R^6$, $R^7$, $R^8$, $R^{15}$, Z, a and n are as defined in Formula I.

Another embodiment of this invention is a compound of Formula II having the structural formula

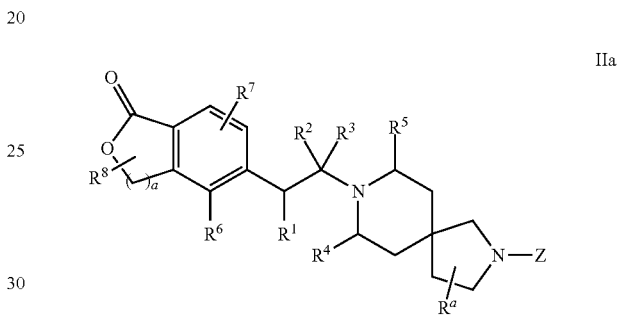

wherein:
$R^a$ is H, —F, —CN, alkyl optionally substituted by 1-5 fluorine atoms or —OR, or cycloalkyl; and
Z is

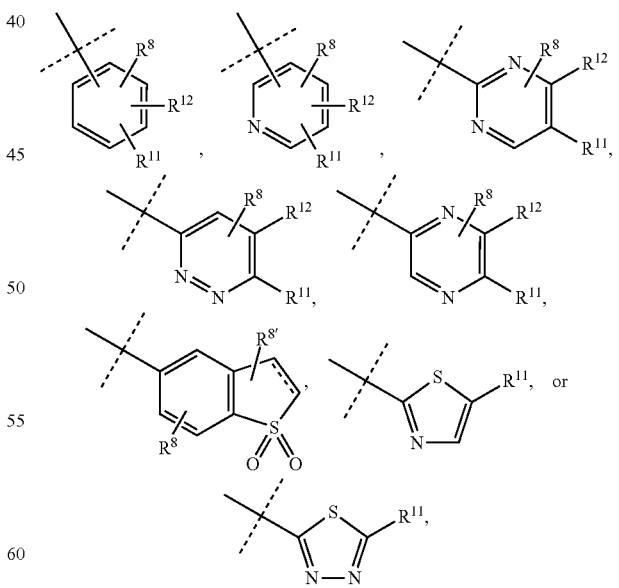

where ---- is a single or double bond, and the remaining variables are as defined in Formula I.

Another embodiment of this invention is a compound of Formula II having the structural formula

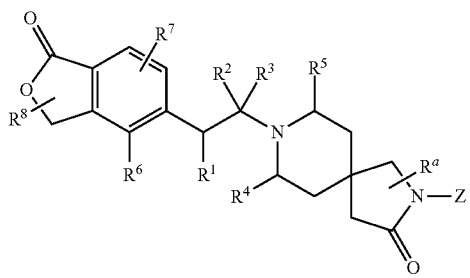

IIb wherein

R$^a$ is H, —F, —CN, alkyl optionally substituted by 1-5 fluorine atoms or —OR, or cycloalkyl; and Z is

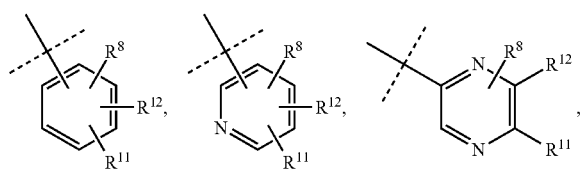

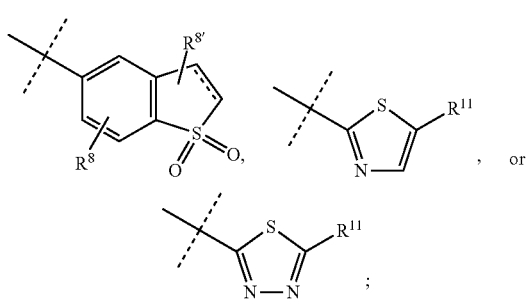

where ---- is a single or double bond, and the remaining variables are as defined in Formula I.

Another embodiment of this invention is compound of Formula II having the structural formula

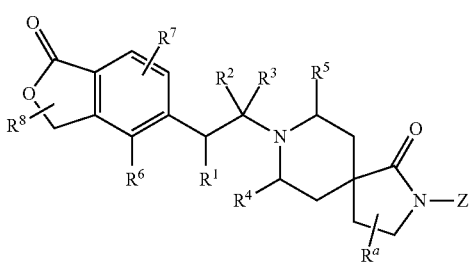

IIc wherein:

R$^a$ is H, —F, —CN, alkyl optionally substituted by 1-5 fluorine atoms or —OR, or cycloalkyl; and 1, Z is

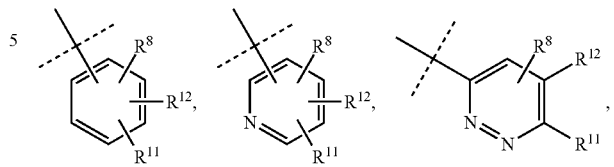

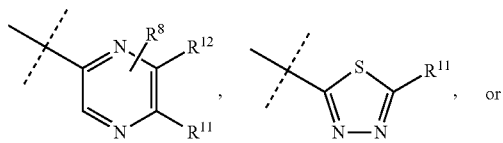

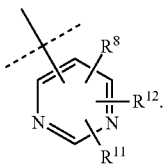

where ---- is a single or double bond, and the remaining variables are as defined in Formula I.

Another embodiment of this invention is a compound of Formula I having the structural formula

III or a pharmaceutically acceptable salt thereof, wherein:

Z is

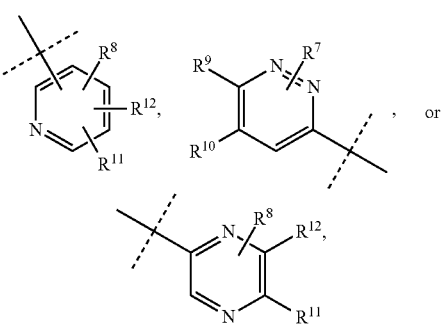

and the remaining variables are as defined in Formula I.

Another embodiment of this invention is a compound of Formula I having the structural formula

IV or a pharmaceutically acceptable salt thereof
wherein:
Z is and the remaining variables are as defined in Formula I.

Another embodiment of this invention is a compound of Formula I having the structural formula

V or a pharmaceutically acceptable salt thereof
wherein:
Z is and the remaining variables are as defined in Formula I.

Another embodiment of this invention is a compound of Formula I having the structural formula

VI or a pharmaceutically acceptable salt thereof
wherein:
Z is and the remaining variables are as defined in Formula I.

Another embodiment of this invention is a compound of Formula I having the structural formula

VII or a pharmaceutically acceptable salt thereof
wherein:
$R^a$ is H, alkyl optionally substituted by 1-5 fluorine atoms or —OR, or cycloalkyl; and
Z is and the remaining variables are as defined in Formula I Another embodiment of this invention is a compound of Formula I having the structural formula

VIII or a pharmaceutically acceptable salt thereof
wherein:
Z is and the remaining variables are as defined in Formula I.

Another embodiment is a compound of Formula I having the structural formula

IX or a pharmaceutically acceptable salt thereof,
wherein:
$R^a$ is H, —F, —CN, alkyl optionally substituted by 1-5 fluorine atoms or —OR, or cycloalkyl; and
Z is and the remaining variables are as defined in Formula I.

Another embodiment is a compound of Formula I having the structural formula

X or a pharmaceutically acceptable salt thereof,
wherein:
$R^a$ is H, halogen, —CN, alkyl optionally substituted by halogen or —OR, cycloalkyl; and
Z is and the remaining variables are as defined in Formula I.

Another embodiment is a compound of Formula I, which has the formula

XI or a pharmaceutically acceptable salt thereof
wherein
Z is and the remaining variables are as defined in Formula I.

Another embodiment of the invention is compounds of Formulae I, Ia, II, IIa, IIb, IIc, III, IV, V, VII, or VIII above where $R^1$ is —OH, —NH$_2$, or NH(C$_1$-C$_4$)alkyl; $R^2$ is H; $R^3$ is H; $R^4$ is H; $R^5$ is H or $R^4$ and $R^5$ join together to represent a —CH$_2$CH$_2$— group; $R^6$ is H, (C$_1$-C$_4$)alkyl (e.g., methyl or ethyl) or cyclopropyl; $R^7$ is H, $(C_1-C_4)$alkyl (e.g., methyl or ethyl) or cyclopropyl and $R^8$ is H or $(C_1-C_4)$alkyl (e.g., methyl or ethyl).

Another embodiment of the invention is compounds of Formulae VI, above where $R^2$ is H; $R^3$ is H; $R^4$ is H; $R^5$ is H or $R^4$ and $R^5$ join together to represent a —CH$_2$CH$_2$— group; $R^7$ is H, $(C_1-C_4)$alkyl (e.g., methyl or ethyl) or cyclopropyl and $R^8$ is H or $(C_1-C_4)$alkyl (e.g., methyl or ethyl).

Another embodiment of the invention is compounds of Formulae IX or X above where $R^1$ is —OH, —NH$_2$, or NH$(C_1-C_4)$alkyl; $R^2$ is H; $R^3$ is H; $R^4$ is H; $R^5$ is H or $R^4$ and $R^5$ join together to represent a —CH$_2$CH$_2$— group; $R^6$ is H, $(C_1-C_4)$alkyl (e.g., methyl or ethyl) or cyclopropyl; $R^7$ is H$(C_1-C_4)$alkyl (e.g., methyl or ethyl) or halo; $R^9$ is —CN or tetrazolyl; $R^{10}$ is a methoxy or ethoxy group.

Another embodiment of the invention is compounds of any of the embodiment above wherein $R^{11}$ is —CN, —S(O)$_2$$(C_1-C_4)$alkyl (e.g., —S(O)$_2$CH$_3$), 1H-tetrazolyl, 2H-tetrazolyl, 1,2,4-oxadiazole or 4H-1,2,3-triazolyl.

Another embodiment of the invention is a compound which is:

(R)-5-(1-Hydroxy-2-(2-(5-(methylsulfonyl)pyridin-2-yl)-2,8-diazaspiro[4.5]decan-8-yl)ethyl)-4-methylisobenzofuran-1(3H)-one;

(R)-5-(1-Hydroxy-2-(2-(5-(methylsulfonyl)pyrazin-2-yl)-2,8-diazaspiro[4.5]decan-8-yl)ethyl)-4-methylisobenzofuran-1(3H)-one;

(R)-8-(2-Hydroxy-2-(4-methyl-1-oxo-1,3-dihydroisobenzofuran-5-yl)ethyl)-2-(5-(methylsulfonyl)pyridin-2-yl)-2,8-diazaspiro[4.5]decan-3-one;

(R)-8-(2Hydroxy-2-(4-methyl-1-oxo-1,3-dihydroisobenzofuran-5-yl)ethyl)-2-(5-(methylsulfonyl)pyrazin-2-yl)-2,8-diazaspiro[4.5]decan-3-one;

(R)-6-(9-(2-Hydroxy-2-(4-methyl-1-oxo-1,3-dihydroisobenzofuran-5-yl)ethyl)-3-oxo-1-oxa-4,9-diazaspiro[5.5]undecan-4-yl)-4-methoxynicotinonitrile;

(R)-8-(2-Hydroxy-2-(4-methyl-1-oxo-1,3-dihydroisobenzofuran-5-yl)ethyl)-3-(5-(methylsulfonyl)pyrazin-2-yl)-1-oxa-3,8-diazaspiro[4.5]decan-2-one;

(R)-6-(8-(2-amino-2-(4-methyl-1-oxo-1,3-dihydroisobenzofuran-5-yl)ethyl)-2,8-diazaspiro[4.5]decan-2-yl)nicotinonitrile;

(R)-5-(8-(2-hydroxy-2-(4-methyl-1-oxo-1,3-dihydroisobenzofuran-5-yl)ethyl)-2,8-diazaspiro[4.5]decan-2-yl)pyrazine-2-carbonitrile;

(R)-6-(9-(2-hydroxy-2-(4-methyl-1-oxo-1,3-dihydroisobenzofuran-5-yl)ethyl)-3,9-diazaspiro[5.5]undecan-3-yl)pyrimidine-4-carbonitrile;

or a pharmaceutically acceptable salt thereof.

All structural Formulas, embodiments and classes thereof described herein include the pharmaceutically acceptable salts of the compounds defined therein.

As used herein except if noted otherwise, "alkyl" is intended to include both branched- and straight-chain saturated aliphatic hydrocarbon groups having, e.g., 1-12, 1-6 or 1-4 carbon atoms. Commonly used abbreviations for alkyl groups are used throughout the specification. For example the term "C$_{1-6}$ alkyl" (or "C$_1$-C$_6$ alkyl"), means linear or branched chain alkyl groups, including all isomers, having the specified number of carbon atoms and includes all of the hexyl and pentyl isomers as well as n-, iso-, sec- and tert-butyl (butyl, s-butyl, i-butyl, t-butyl; Bu=butyl), n- and i-propyl (Pr=propyl), ethyl (Et) and methyl (Me).

"Halogen" means a fluorine, chlorine, bromine or iodine atom. "Halo" means —F, —Cl, —Br, or —I. A non-limiting examples includes fluorine or fluoro.

"Haloalkyl" means a halo-alkyl group in which the halo and alkyl groups are as previously defined. The bond to the partent moiety is through the alkyl group. Non-limiting examples include —CH$_2$CF$_3$ and —CF$_3$.

"Cycloalkyl" is a cyclized alkyl ring having 3-12 or 3-6 carbon atoms. Examples of cycloalkyl include cyclopropyl, cyclobutyl, cyclopentyl and cyclohexyl.

"Oxo" is a "C=(O)" functional group, that is a carbonyl group.

"Heteroaryl" unless otherwise indicated, means a mono- or bicyclic aromatic ring or ring system having 5 to 10 atoms and containing at least one heteroatom selected from O, S and N. Examples include, but are not limited to, pyrrolyl, isoxazolyl, isothiazolyl, pyrazolyl, pyridyl, pyridinyl, oxazolyl, oxadiazolyl, thiadiazolyl, thiazolyl, imidazolyl, triazolyl, tetrazolyl, furanyl, triazinyl, thienyl, pyrimidyl, pyrimidinyl, pyridazinyl, pyrazinyl, and the like. Heteroaryl also includes aromatic heterocyclic groups fused to heterocycles that are non-aromatic or partially aromatic, and aromatic heterocyclic groups fused to cycloalkyl rings. Additional examples of heteroaryls include, but are not limited to, indazolyl, thienopyrazolyl, imidazopyridazinyl, pyrazolopyrazolyl, pyrazolopyridinyl, imidazopyridinyl and imidazothiazolyl. Heteroaryl also includes such groups in charged form, e.g., pyridinium. In an embodiment, heteroaryl is oxadiazolyl, pyrazolyl, oxazolyl, tetrazolyl, furanyl, pyridinyl and imidazolyl Unless expressly depicted or described otherwise, variables depicted in a structural formula with a "floating" bond, such as $R^{11}$ and $R^{12}$, are permitted on any available carbon atom in the ring to which the variable is attached.

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Where a substituent or variable has multiple definitions, it is understood that the substituent or variable is defined as being selected from the group consisting of the indicated definitions.

The compounds of Formula I may have one or more chiral (asymmetric) centers. The present invention encompasses all stereoisomeric forms of the compounds of Formula I. Centers of asymmetry that are present in the compounds of Formula I can all independently of one another have (R) or (S) configuration. When bonds to a chiral carbon are depicted as straight lines in the structural Formulas of the invention, or when a compound name is recited without an (R) or (S) chiral designation for a chiral carbon, it is understood that both the (R) and (S) configurations of each such chiral carbon, and hence each enantiomer or diastereomer and mixtures thereof, are embraced within the Formula or by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis.

Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Alternatively, absolute stereochemistry may be determined by Vibrational Circular Dichroism (VCD) spectroscopy analysis. Where compounds of this invention are capable of tautomerization, all individual tautomers as well as mixtures thereof are included in the scope of this invention. The present invention includes all such isomers, as well as salts, solvates (which includes hydrates) and solvated salts of such racemates, enantiomers, diastereomers and tautomers and mixtures thereof.

Reference to the compounds of Formula I herein encompasses the compounds of Formulae I-XI and all embodiments and classes thereof. Reference to the compounds of this invention as those of a specific formula or embodiment, e.g., Formulae I-XI or embodiments thereof, or any other generic structural formula or specific compound described or claimed herein, is intended to encompass the specific compound or compounds falling within the scope of the Formula or embodiment, including salts thereof, particularly pharmaceutically acceptable salts, solvates (including hydrates) of such compounds and solvated salt forms thereof, where such forms are possible, unless specified otherwise.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

When the compounds of Formula I contain one or more acidic or basic groups the invention also includes the corresponding pharmaceutically acceptable salts. Thus, the compounds of Formula I which contain acidic groups can be used according to the invention as, for example but not limited to, alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO⁻ depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention are inhibitors of ROMK, and therefore could be used as diuretic and/or natriuretic agents. ROMK inhibitors may be used to help to increase urination and increase urine volume and also to prevent or reduce reabsorption of sodium in the kidneys leading to increased excretion of sodium and water. Therefore, the compounds could be used for treatment or prophylaxis or both of disorders that benefit from increased excretion of water and sodium from the body. Accordingly, the compounds of this invention could be used in a method for inhibiting ROMK comprising administering a compound of Formula I in a ROMK-inhibitory effective amount to a patient in need thereof. This also encompasses the use of the compounds for inhibiting ROMK in a patient comprising administering a compound of claim 1 in a therapeutically effective amount to a patient in need of diuresis, natriuresis or both. The inhibition of ROMK by the compounds of Formula I can be examined, for example, in the Thallium Flux Assay described below. Moreover, this invention also relates to the use of the compounds of Formula I or salts thereof to validate in vitro assays, for example but not limited to the Thallium Flux Assay described herein.

The compounds of this invention could be used in a method for causing diuresis, natriuresis or both, comprising administering a compound of Formula I in a therapeutically effective amount to a patient in need thereof. Therefore, the compounds of Formula I of this invention could be used in methods for treatment of, prevention of or reduction of risk for developing medical conditions that benefit from increased excretion of water and sodium, such as but not limited to one or more of hypertension, such as essential hypertension (also known as primary or idiopathic hypertension) which is a form of hypertension for which no cause can be found, heart failure (which includes both acute heart failure and chronic heart failure, the latter also known as congestive heart failure) and/or other conditions associated with excessive salt and water retention. The compounds could also be used to treat hypertension which is associated with any of several primary diseases, such as renal, pulmonary, endocrine, and vascular diseases, including treatment of patients with medical conditions such as heart failure and/or chronic kidney disease. Furthermore, the compounds of Formula I could be used in methods for treatment of, prevention of or reduction of risk for developing one or more disorders such as pulmonary hypertension, particularly pulmonary arterial hypertension (PAH), cardiovascular disease, edematous states, diabetes mellitus, diabetes insipidus, post-operative volume overload, endothelial dysfunction, diastolic dysfunction, systolic dysfunction, stable and unstable angina pectoris, thromboses, restenosis, myocardial infarction, stroke, cardiac insufficiency, pulmonary hypertonia, atherosclerosis, hepatic cirrhosis, ascites, pre-eclampsia, cerebral edema, nephropathy, glomerulonephritis, nephrotic syndrome, acute kidney insufficiency, chronic kidney insufficiency (also referred to as chronic kidney disease, or more generally as renal impairment), acute tubular necrosis, hypercalcemia, idiopathic edema, Dent's disease, Meniere's disease, glaucoma, benign intracranial hypertension, and other conditions for which a diuretic or natriuretic or both would have therapeutic or prophylactic benefit. The compounds of the invention may be administered to a patient having, or at risk of having, one or more conditions for which a diuretic or natriuretic or both would have therapeutic or prophylactic benefit such as those described herein.

The compounds of Formula I may potentially have reduced liabilities (for example, hypo- or hyperkalemia, new onset of diabetes, dyslipidemia, etc.) over currently used clinical agents. Also the compounds may have reduced risk for diuretic tolerance, which can be a problem with long-term use of loop diuretics.

In general, compounds that are ROMK inhibitors can be identified as those compounds which, when tested, have an $IC_{50}$ of 5 µM or less, preferably 1 µM or less, and more preferably 0.25 µM or less, in the Thallium Flux Assay, described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, preferably 0.001 to 30 mg/kg, in particular 0.001 to 10 mg/kg (in each case mg per kg of bodyweight) is appropriate for administration to an adult weighing approximately 75 kg in order to obtain the desired results. The daily dose is preferably administered in a single dose or can be divided into several, for example two, three or four individual doses, and may be, for example but not limited to, 0.1 mg, 0.25 mg, 0.5 mg, 0.75 mg, 1 mg, 1.25 mg, 2 mg, 2.5 mg, 5 mg, 10 mg, 20 mg, 40 mg, 50 mg, 75 mg, 100 mg, 125 mg, 150 mg, 175 mg, 200 mg, etc., on a daily basis. In some cases, depending on the potency of the compound or the individual response, it may be necessary to deviate upwards or downwards from the given daily dose. Furthermore, the compound may be formulated for immediate or modified release such as extended or controlled release.

The term "patient" includes animals, preferably mammals and especially humans, who use the instant active agents for the prophylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The terms "preventing," "prevention," "prophylactic" and derivatives of these terms as used herein refer to administering a compound to a patient before the onset of clinical symptoms of a condition not yet present in the patient. It is understood that a specific daily dosage amount can simultaneously be both a therapeutically effective amount, e.g., for treatment of hypertension, and a prophylactically effective amount, e.g., for prevention or reduction of risk of myocardial infarction or prevention or reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous (IV), intramuscular, intrasternal injection or infusion techniques. Oral formulations are preferred for treatment of chronic indications such as hypertension or chronic heart failure, particularly solid oral dosage units such as pills, tablets or capsules, and more particularly tablets. IV dosing is preferred for acute treatment, for example for the treatment of acute heart failure.

This invention also provides pharmaceutical compositions comprised of a compound of Formula I and a pharmaceutically acceptable carrier which is comprised of one or more excipients or additives. An excipient or additive is an inert substance used to formulate the active drug ingredient. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Tablets contain the active ingredient in admixture with non-toxic pharmaceutically acceptable excipients which are suitable for the manufacture of tablets. The excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example but not limited to, wetting agents, stabilizers, emulsifiers, dispersants, preservatives, sweeteners, colorants, flavorings, aromatizers, thickeners, buffer substances, solvents, solubilizers, agents for achieving a depot effect, salts for altering the osmotic pressure, coating agents or antioxidants. Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example *arachis* oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I and/or its pharmaceutically acceptable salts in the pharmaceutical composition may be, for example but not limited to, from about 0.1 mg to 1 g, particularly 0.1 mg to about 200 mg, more particularly from about 0.1 mg to about 100 mg, and even more particularly from about 0.1 to about 50 mg, per dose on a free acid/free base weight basis, but depending on the type of the pharmaceutical composition, potency of the active ingredient and/or the medical condition being treated, it could also be lower or higher. Pharmaceutical compositions usually comprise about 0.5 to about 90 percent by weight of the active compound on a free acid/free base weight basis.

The compounds of Formula I inhibit ROMK. Due to this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. The additional active agent (or agents) is intended to mean a medicinal compound that is different from the compound of Formula I, and which is a pharmaceutically active agent (or agents) that is active in the body, including pro-drugs, for example esterified forms, that convert to pharmaceutically active form after administration, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of the one or more additional active agents which may be employed include but are not limited to thiazide-like diuretics, e.g., hydrochlorothiazide (HCTZ or HCT); angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; carbonic anhydrase inhibitors, such as acetazolamide; neutral endopeptidase inhibitors (e.g., thiorphan and phosphoramidon); aldosterone antagonists; aldosterone synthase inhibitors; renin inhibitors (e.g. enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine, bepridil, nisoldipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); nitrates or nitric oxide donating compounds, e.g. isosorbide mononitrate; lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium); and/or with an HMG-CoA reductase inhibitor; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; phosphodiesterase-5 (PDE5) inhibitors such as sildenafil (Revatio, Viagra), tadalafil (Cialis, Adcirca) vardenafil HCl (Levitra); or with other drugs beneficial for the prevention or the treatment of the above-mentioned diseases including but not limited to diazoxide; and including the free-acid, free-base, and pharmaceutically acceptable salt forms, pro-drug forms (including but not limited to esters), and salts of pro-drugs of the above medicinal agents where chemically possible. Trademark names of pharmaceutical drugs noted above are provided for exemplification of the marketed form of the active agent(s); such pharmaceutical drugs could be used in a separate dosage form for concurrent or sequential administration with a compound of Formula I, or the active agent(s) therein could be used in a fixed dose drug combination including a compound of Formula I.

Several methods for preparing the compounds of this invention are described in the following Schemes and Examples. Starting materials and intermediates are purchased, made from known procedures, or as otherwise illustrated. Some frequently applied routes to the compounds of Formula I are also described by the Schemes as follows. In some cases the order of carrying out the steps of reaction schemes may be varied to facilitate the reaction or to avoid unwanted reaction products. The "R" substituents in the Schemes correspond to the substituents defined in Formula I at the same positions on the structures.

Several methods for preparing the compounds of this invention are described in the examples. Starting materials and intermediates are purchased, made from known procedures, or as otherwise illustrated. Some frequently applied routes to the compounds of Formula I are also described by the Schemes as follows. In some cases the order of carrying out the steps of reaction schemes may be varied to facilitate the reaction or to avoid unwanted reaction products. The "R" substituents in the Schemes correspond to the substituent defined in Formula I at the same positions on the structures.

Compounds of Formula IA, which are substituted with an OH group, can be prepared following the sequence detailed in Scheme 1. Coupling of epoxide 1 to spirocyclic amines 2 at elevated temperatures leads to the formation of alcohols IA (Nomura, Y. et al. Chemical & Pharmaceutical Bulletin, 1995, 43(2), 241-6). The reaction can be carried out with conventional heating, or by heating using a microwave apparatus. A number of solvents can be used in this reaction, for example, ethanol, 2-propanol and toluene. Spirocyclic amines may be free bases, or they may be salts, in which case a base such as triethylamine or N,N-diisopropylethylamine may be added. Note that when enantiopure chiral epoxides are employed (such as (R)-1 in Scheme 1) epoxide opening occurs with retention of stereochemistry in the benzylic position and individual isomer (R)-IA may be obtained (and if the (S)-epoxide is employed the alcohol produced will have the opposite stereochemistry to that shown). Alternatively, chiral HPLC separation of enantiomers or diastereomers of IA may be performed to provide single enantiomers or diastereomers.

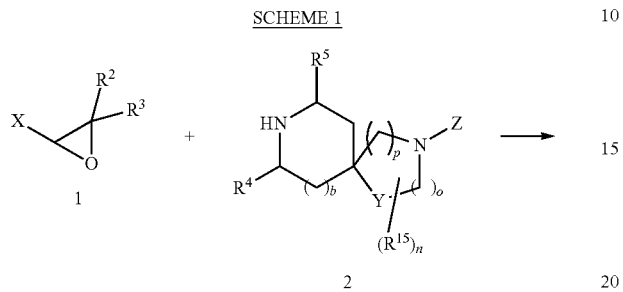

SCHEME 1

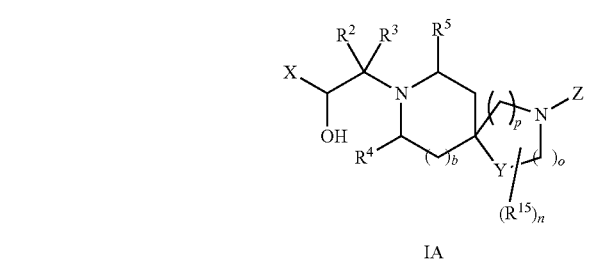

IA

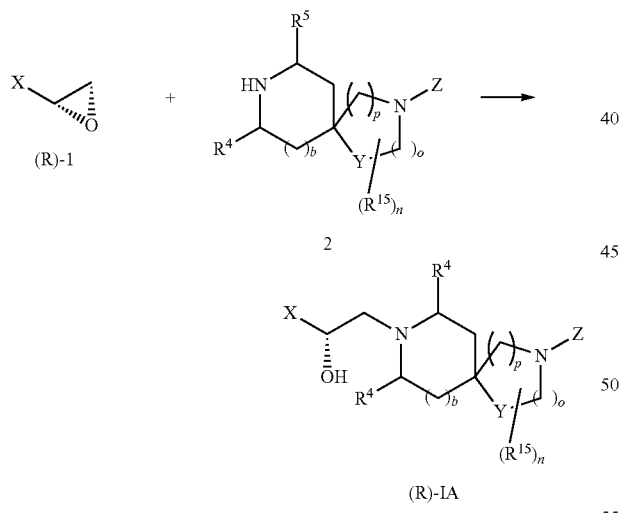

(R)-IA

Compounds of formula IB can be prepared by the sequence detailed in Scheme 2. Alhehydes or ketones 3 may be used in reductive alkylation reactions with spirocyclic amines 2 to afford ROMK inhibitors of the formula IB by using various reductive amination conditions (for example using sodium cyanoborohydride, sodium triacetoxy borohydride, or titanium tetra-isopropoxide, followed by sodium borohydride or sodium cyanoborohydride).

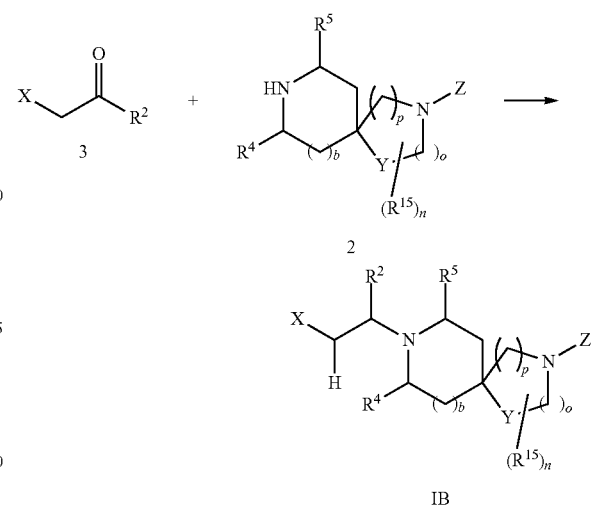

SCHEME 2

Alternatively, compounds of the Formula IC may be prepared by coupling of the NH in spirocycles 4 to an aromatic or heterocyclic halide (chloride, bromide, iodide, fluoride). This coupling reaction may be accomplished in a variety of ways, depending upon the nature of 4 and the halide (Z-halide). For example, in some cases, this coupling can be achieved by thermal or microwave heating in one of a variety of potential solvents, such as DMF or dioxane, in the presence or absence of a base such as triethylamine or potassium carbonate, or cesium carbonate. Alternatively, the coupling can be accomplished using a catalyst-ligand system, for example heating with Xantphos and $Pd_2(dba)_3$ in the presence of a base such as cesium carbonate in a solvent such as dioxane. Numerous other N—C coupling conditions, known from the literature, may be applied.

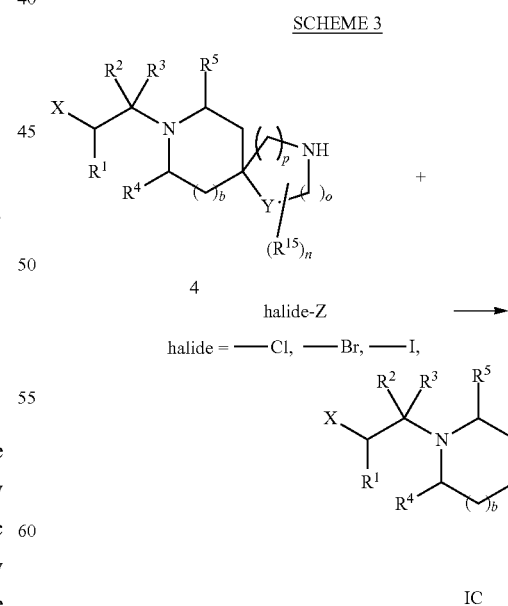

SCHEME 3

The epoxides 1 (and single enantiomers (R)-1 and (S)-1) can be prepared following the method detailed in Scheme 4. Treatment of 5 (where halide is chloride, bromide, iodide, and triflate represents trifluoromethane sulfonate) with commercially available potassium vinyl trifluoroborate (Molander, G.; Luciana, A. Journal of Organic Chemistry, 2005, 70(10), 3950-3956) under palladium catalyzed coupling conditions with an appropriate phosphine ligand gives rise to styrene 6 (Molander, G.; Brown, A. Journal of Organic Chemistry, 2006, 71(26), 9681-9686). Alternatively, other methods may be employed, for example, using vinylstannane reagents and palladium catalysis. The resulting styrenes 6 can be converted to the corresponding epoxides 1 (in this case 1A) under various epoxidation conditions, for example, with m-CPBA (Fringuelli, F. et al. Organic Preparations and Procedures International, 1989, 21(6), 757-761), or with N-bromosuccinimide and sodium hydroxide. The racemic epoxides 1A can be resolved under chiral HPLC chromatography conditions to afford the single enantiomers, which can be used in place of 1 according to Scheme 1.

SCHEME 4

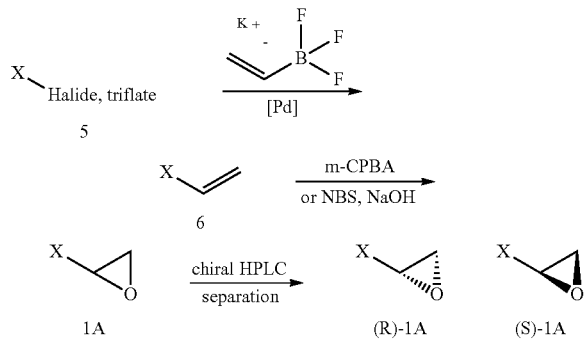

Alternatively, enantiopure epoxides (R)-1 or (S)-1 can be prepared as shown in Scheme 5. Treatment of 5 (where halide is chloride, bromide, iodide, and triflate represents trifluoromethane sulfonate) with commercial available vinyl butylether 7 under palladium catalyzed conditions with a suitable ligand (for example Pd(OAc)$_2$, DPPP) can provide the enol ethers 8. Enol ethers may be prepared using other methods known to the chemist. Treatment of the resulting enol ethers 8 with NBS or other similar reagents affords the corresponding bromomethyl ketones 9. These can be subjected to a variety of asymmetric ketone reduction conditions, for example with an enzyme that can affect such a transformation with high enantioselectivity. Subsequent treatment with a base such as triethylamine leads to cyclization, affording the enantioenriched epoxides (R)-1 or (S)-1 (depending upon the asymmetric reducing agent).

SCHEME 5

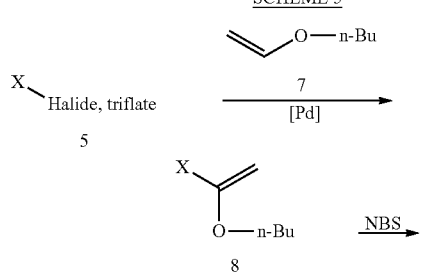

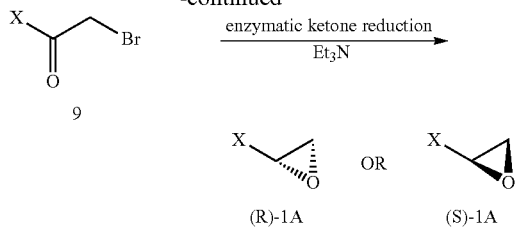

Aldehydes 3A may be prepared in numerous ways. For example, in Scheme 6 treatment of 5 (where halide is chloride, bromide, iodide, and triflate represents trifluoromethane sulfonate) with allyltributylstannane in the presence of palladium catalyst affords the allyl product 10. Oxidation, for example with ozone, followed by dimethyl sulfide, provides aldehydes 3A.

SCHEME 6

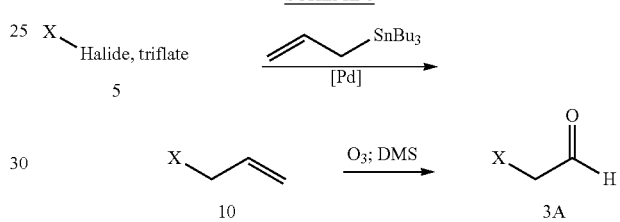

Spirocyclic intermediates 2 can be prepared as described in Scheme 7. Spirocyclic diamines or amino lactams, protected as appropriate (Greene, T.; Wuts, P. G. M. *protective Groups in Organic Synthesis*, John Wiley and Sons, Inc., New York, N.Y. 1991), for example with a tert-butoxycarbonyl group (11, commercially available, known from the literature or prepared as described herein), can be coupled to aryl or heterocyclic halides (chloride, bromide, iodide) to afford intermediates 12. This can be accomplished in a wide variety of ways as many methods for C—N coupling have been described in the literature and can be used to effect this transformation. For example this transformation can be accomplished by thermal heating in the presence or absence of a base. Alternatively, this transformation can be accomplished using a palladium catalyst and ligand, for example tris(dibenzylidineacetone)dipalladium (Pd$_2$(dba)$_3$) and 4,5-Bis(diphenylphosphino)-9,9-dimethylxanthene (Xantphos), in the presence of a base such as Cs$_2$CO$_3$ or K$_3$PO$_4$. In addition, this transformation can be accomplished using copper catalyzed conditions in the presence or absence of an amine ligand, for example with copper(I) iodide and N1,N2-dimethylcyclohexane-1,2-diamine. Intermediates 12 are converted to spirocyclic aminofuranones 2 by removal of the protective group, for example, tert-butoxycarbonyl can be removed with TFA or HCl.

SCHEME 7

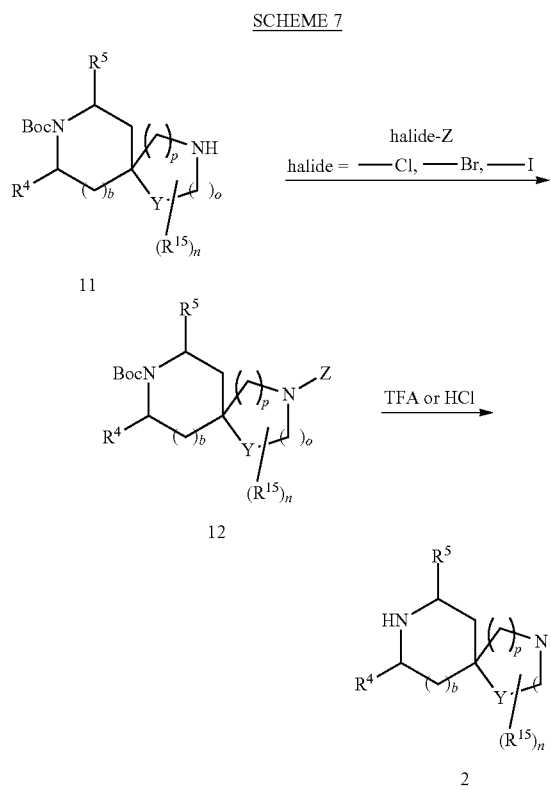

The independent synthesis of diastereomers and enantiomers or their chromatographic separations may be achieved as known in the art by appropriate modification of the methodology disclosed herein. Their absolute stereochemistry may be determined by x-ray crystallography of crystalline products or crystalline intermediates which are derivatized, if necessary, with a reagent containing an asymmetric center of known absolute stereochemistry, or by vibrational circular dichroism (VCD) spectroscopy.

The subject compounds may be prepared by modification of the procedures disclosed in the Examples as appropriate. Starting materials are commercially available or made by known procedures or as illustrated. The following examples are provided for the purpose of further illustration only and are not intended to be limitations on the disclosed invention.

Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60F-254, layer thickness 0.25 mm or liquid chromatography-mass spectrometry (LC-MS).

Typically the analytical LC-MS system used consisted of a Waters ZQ™ platform with electrospray ionization in positive ion detection mode with an Agilent 1100 series HPLC with autosampler. The column was usually a Water Xterra® MS C18, 3.0×50 mm, 5 μm. The flow rate was 1 mL/min, and the injection volume was 10 μL. UV detection was in the range 210-400 nm. The mobile phase consisted of solvent A (water plus 0.06% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using a mass spectrometry directed system. Usually they were performed on a Waters Chromatography Workstation configured with LC-MS System Consisting of: Waters ZQ™ single quad MS system with Electrospray Ionization, Waters 2525 Gradient Pump, Waters 2767 Injector/Collector, Waters 996 PDA Detector, the MS Conditions of: 150-750 amu, Positive Electrospray, Collection Triggered by MS, and a Waters Sunfire® C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 μL, and the UV detection range was 210-400 nm. Mobile phase gradients were optimized for the individual compounds.

Reactions performed using microwave irradiation were normally carried out using an Emrys Optimizer manufactured by Personal Chemistry, or an Initiator manufactured by Biotage®.

Concentration of solutions was carried out on a rotary evaporator under reduced pressure. Flash chromatography (FC) was usually performed using a Biotage® Flash Chromatography apparatus (Dyax Corp.) on silica gel (32-63 mM, 60 Å pore size) in pre-packed cartridges of the size noted. $^1$H NMR spectra were acquired at 500 MHz spectrometers in $CDCl_3$ solutions unless otherwise noted. Chemical shifts were reported in parts per million (ppm). Tetramethylsilane (TMS) was used as internal reference in $CD_3Cl$ solutions, and residual $CH_3OH$ peak or TMS was used as internal reference in $CD_3OD$ solutions. Coupling constants (J) were reported in hertz (Hz).

Generally, all chiral HPLC separations were done by SFC (supercritical fluid chromatography). Instruments: Berger analytical SFC; Berger MultiGram® II preparative SFC; Berger MultiGram® III preparative SFC. Chiral resolution columns: All analytical columns are 4.6×250 mm, 5 μm particle size; Prep-sep columns are 30×250 mm or 21×250 mm, 5 μm particle size. All columns are from Chiral Technologies Inc and they include: Chiralpak® AD; Chiralpak® IC; Chiralpak® AS; or Chiralcel® OD Solvents for SFC separation: Beside supercritical fluid $CO_2$, following solvents as modifier are used: methanol, isopropyl alcohol, and acetonitrile, 0.2% (v/v) of diethylamine is often added as modifier. General method for these separations: For analytical method: 10-70% modifier/90-30% $CO_2$, flow rate 2.1 ml/min; For preparative method: 10-70% modifier/90-30% $CO_2$, flow rate 50-70 ml/min.

Where retention times are provided in the Examples and Tables, they are not intended to be a definitive characteristic of a particular compound since, as known to those skilled in the art, retention times will vary and the timing and/or order of peak elution may change depending on the chromatographic conditions, such as the column used, the condition of the column, and the solvent system and instruments used.

Abbreviations and acronyms that may be used herein include: —C(O)CH$_3$ (Ac); —OC(O)CH$_3$ (OAc); acetic acid (AcOH; HOAc); 1-chloroethylchloroformate (ACE-Cl); 2,2'-bis(diphenylphosphino)-1,1'-binaphthyl (BINAP); benzyl (Bn); t-butyloxycarbonyl (Boc or BOC); di-t-butyl dicarbonate ((BOC)$_2$O, Boc$_2$O); benzyloxycarbonyl (Cbz); butyl (Bu); cyclopentyl methyl ether (CPME); carbonyldiimidazole (CDI); diethylaminosulfur trifluoride (DAST); dibenzylideneacetone (dba); 1,8-diazabicyclo[5.4.0]undec-7-ene (DBU); 1,2-dichloroethane (DCE); dichloromethane (DCM); diethyl amine (DEA); dimethoxyethane (DME); diisobutylaluminium hydride (DIBAL-H); N,N-diisopropylethylamine (DIEA, DIPEA, Hunig's base); dioxane is 1,4- dioxane; di-isopropylamine (DIPA); 1,1'-bis(diphenylphosphino)ferrocene (dppf, DPPF); Dess-Martin Periodinane (DMP; 1,1,1-Triacetoxy-1,1-dihydro-1,2-benziodoxol-3 (1H)-one); dimethylsulfide (DMS); dimethylsulfoxide (DMSO); N;N-dimethylformamide (DMF); 4-dimethylaminopyridine (DMAP); dimethylacetamide (DMA; DMAC); 1,3-bis(diphenylphosphino)propane (DPPP); (Oxydi-2,1-phenylene)bis(diphenylphosphine) (DPEPhos); ethyl acetate (EtOAc or EA); ethanol (EtOH); diethyl ether (ether or Et$_2$O); 1-ethyl-3-(3-dimethylaminopropyl)carbodiimide (EDC, EDAC or EDCI); 2-(7-Aza-1H-benzotriazole-1-yl)-1,1,3,3-tetramethyluronium hexafluorophosphate (HATU); hexane (Hex); hexamethylphosphoramide (HMPA); 1-hydroxybenzotriazole hydrate (HOBt); isopropanol (IPA); isopropyl acetate (IPAc); Potassium bis(trimethylsilyl)amide (KHMDS); lithium aluminum hydride (LAH); lithium diisopropylamide (LDA); 3-chloroperoxybenzoic acid (mCPBA); methanol (MeOH); CH$_3$SO$_2$— (mesyl or Ms); methane sulfonyl chloride or mesyl chloride (MsCl); methanesulfonic acid (MsOH); methyl tert-butyl ether (MTBE); nicotinamide adenine dinucleotide phosphate (NADP); N-bromo succinimide (NBS); N-chlorosuccinimide (NCS); N-iodosuccinimide (NIS); N-methylmorpholine N-oxide (NMO); N-methyl morpholine (NMP); sodium hexamethyldisilazide (NaHMDS); sodium triacetoxyborohydride (NaBH(OAc)$_3$); pyridinium chlorochromate (PCC); phenyl (Ph); petroleum ether (PE or petrol ether); tetrakis(triphenylphosphine)palladium (Pd(PPh$_3$)$_4$); tris(dibenzylidineacetone)dipalladium (Pd$_2$(dba)$_3$); Pd(dppf)Cl$_2$ or PdCl$_2$(dppf) is 1,1'-bis(diphenylphosphino)ferrocene]dichloropalladium (II) which may be complexed with CH$_2$Cl$_2$; tetra-n-butylammonium fluoride (TBAF); tert-butyldimethylsilyl chloride (TBS-Cl); triethylamine (TEA); trifluoroacetic acid (TFA); —SO$_2$CF$_3$ (Tf); trifluoromethanesulfonic acid (triflic acid, TfOH); trifluoromethanesulfonic anhydride (triflic anhydride, (Tf)$_2$O); 2-tetrahydrofuran (THF); N,N,N',N'-tetramethylethylenediamine (TMEDA); p-toluenesulfonic acid (TsOH or PTSA); Dicyclohexylphosphino-2',4',6'-triisopropylbiphenyl (X-Phos); diethylaminodifluorosulfinium tetrafluoroborate (XtalFluor-E®); 4,5-Bis(diphenylphosphino)-9,9-dimethylxanthene (Xantphos). Additional abbreviations and acronyms are: racemic or racemate (rac.); starting material (SM); round-bottom flask (RB or RBF); aqueous (aq); saturated aqueous (sat'd); saturated aqueous sodium chloride solution (brine); medium pressure liquid chromatography (MPLC); high pressure liquid chromatography (HPLC); preparative HPLC (prep-HPLC); flash chromatography (FC); liquid chromatography (LC); supercritical fluid chromatography (SFC); 2-Dicyclohexylphosphino-2',6'-dimethoxybiphenyl (SPhos); thin layer chromatography (TLC); preparative TLC (prep-TLC); mass spectrum (ms or MS); liquid chromatography-mass spectrometry (LC-MS, LCMS or LC/MS); column volume (CV); room temperature (rt, r.t. or RT); hour(s) (h or hr); minute(s) (min); retention time (R$_t$); gram(s) (g); milligram(s) (mg); milliliter(s) (mL); microliter(s) (μL); millimole (mmol); volume:volume (V/V). CELITE® is a trademark name for diatomaceous earth, and SOLKA FLOC® is a trademark name for powdered cellulose. X or x may be used to express the number of times an action was repeated (e.g., washed with 2×200 mL 1N HCl), or to convey a dimension (e.g., the dimension of a column is 30×250 mm).

It is understood that a chiral center in a compound may exist in the "S" or "R" stereo-configurations, or as a mixture of both. In many of the examples for intermediate compounds and final compounds, such compounds having a racemic chiral center were separated into individual stereoisomers, for example, referred to as isomer A (or enantiomer A or the like), which refers to the observed faster eluting isomer, and isomer B (or enantiomer B or the like), which refers to the observed slower eluting isomer, and each such isomer may be noted in the example as either the fast or slow eluting isomer. When a single "A" or "B" isomer intermediate is used to prepare a downstream compound, the downstream compound may take the "A" or "B" designation that corresponds to the previously used intermediate. Any Intermediates described below may be referred to herein by their number preceded by "I-." For illustration, in the example titled "Intermediate 2," the racemic parent title compound would be referred to as Intermediate 2 (or I-2), and the separated stereoisomers are noted as Intermediates 2A and 2B (or I-2A and I-2B). In some examples, compounds having a chiral center were derived synthetically from a single isomer intermediate; e.g., Example 2 was made using stereoisomer I-1B. Except for a defined chiral center in a parent isomer mixture, absolute stereochemistry (R or S) of each of the separated isomers was not determined, unless specifically described otherwise. An asterisk (*) may be used in a chemical structure drawing that indicates the location of a chiral center.

The following are representative procedures for the preparation of intermediates used to prepare the final products described in the Examples that follow thereafter. These examples are provided for the purpose of further illustration only and are not intended to be limitations on the disclosed invention.

Intermediate 1

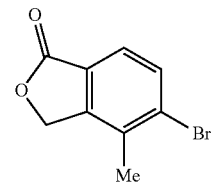 [SMILES: Cc1c(Br)ccc2c1COC2=O]

Step A: (3-bromo-2-methylphenyl)methanol: To a solution of 3-bromo-2-methyl benzoic acid (35 g, 163 mmol) in THF (200 mL) was added Borane THF Complex (1.0 M, 212 mL, 212 mmol). The mixture was allowed to stir for 24 h. TLC showed one single product spot. The reaction was quenched with water. The solvent THF was removed under reduced pressure. The resulting solid was dissolved in ethyl acetate (500 mL), washed with 1N HCl, sodium carbonate, and brine. The organic layer was dried over sodium sulfate and concentrated to afford (3-bromo-2-methylphenyl)methanol. $^1$H NMR (500 MHz, CDCl$_3$) δ 7.76 (d, J=8.0 Hz, 1H), 7.63 (d, J=8.0 Hz, 1H), 5.30 (s, 2H), 2.42 (s, 3H).

Step B: 5-bromo-4-methyl-2-benzofuran-1(3H)-one: To a flask charged with (3-bromo-2-methylphenyl)methanol (6.0 g, 30 mmol) was added a 1M TFA solution of thallium trifluoroacetate (16.2 g, 29.8 mmol). The mixture was stirred at RT overnight. Analysis by TLC showed no starting material remaining. The solvent was removed under vacuum, and the residue was pumped under high vacuum for 30 min to ensure complete removal of TFA. To the residue was then added palladium(II) chloride (529 mg, 2.98 mmol), lithium chloride (2.53 g, 59.7 mmol), magnesium oxide (2.41 g, 59.7 mmol), and MeOH (150 mL). The reaction was flushed with CO twice, and kept under CO at room temperature. Analysis by LC showed a big product spot within 2 hours. To this solution was added ethyl acetate to precipitate the salts. The black solution was filtered through a CELITE® pad, washed with EtOAc, adsorbed onto silica and purified by silica gel chromatography to afford 5-bromo-4-methyl-2-benzofuran-1(3H)-one. $^1$H-NMR (500 MHz, CDCl$_3$) δ ppm 7.71 (d, J=8.0 Hz, 1H), 7.58 (d, J=8.0 Hz, 1H), 5.25 (s, 2H), 2.37 (s, 3H).

Intermediate 2

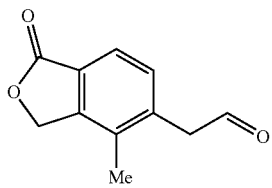 [SMILES: Cc1c(CC=O)ccc2c1COC2=O]

Step A: 4-methyl-5-prop-2-en-1-yl-2-benzofuran-1(3H)-one: To a flask charged with 5-bromo-4-methyl-2-benzofuran-1(3H)-one (320 mg, 1.409 mmol) and a stir bar was added allyl tri-n-butyltin (0.655 mL, 2.11 mmol), Pd(PPh$_3$)$_4$ (244 mg, 0.211 mmol), lithium chloride (179 mg, 4.23 mmol), and toluene (15 mL). The reaction was purged with nitrogen 2 times then was heated at reflux for 4 hours. The product was separated by silica gel chromatography to give 4-methyl-5-prop-2-en-1-yl-2-benzofuran-1(3H)-one.

Step B: (4-methyl-1-oxo-1,3-dihydro-2-benzofuran-5-yl) acetaldehyde: A solution of the above olefin (220 mg, 1.2 mmol) in MeOH (20 mL) was cooled to −78° C. To this solution was bubbled ozone until the reaction turned blue. Nitrogen was bubbled through the reaction to drive off excess ozone, followed by addition of DMS (0.870 mL, 11.7 mmol). The reaction was allowed to warm up to RT. The crude product was purified by flash chromatography to afford (4-Methyl-1-oxo-1,3-dihydro-2-benzofuran-5-yl)acetaldehyde. $^1$H-NMR (500 MHz, CDCl$_3$) δ ppm 9.78 (s, 1H), 7.75 (d, J=7.5 Hz, 1H), 7.34 (d, J=7.5 Hz, 1H), 5.27 (s, 2H), 3.90 (s, 2H), 2.23 (s, 3H).

Intermediate 3

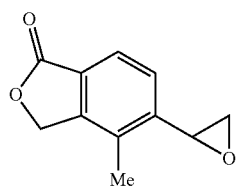 [SMILES: Cc1c(C2CO2)ccc2c1COC2=O]

Step A: 5-ethenyl-4-methyl-2-benzofuran-1(3H)-one: 5-Bromo-4-methyl-2-benzofuran-1(3H)-one (598 mg, 4.47 mmol), potassium vinyl trifluoroborate (507 mg, 2.23 mmmol), PdCl$_2$(dppf)-CH$_2$Cl$_2$Adduct (182 mg, 0.223 mmmol), and TEA (0.622 mL, 4.47 mmol) were added to 10 mL ethanol in a 20 mL microwave tube. The tube was sealed and degassed, then heated to 140° C. for 20 min. Analysis by LC-MS showed product peak. The reaction mixture was diluted with ethyl acetate, washed with brine twice, dried and evaporated to dryness. The crude product was purified by MPLC chromatography using a 120 g RediSep® column and 0-80% EtOAC/Hexane solvent system to yield 5-ethenyl-4-methyl-2-benzofuran-1(3H)-one. $^1$H-NMR (500 MHz, CDCl$_3$): δ ppm 7.76 (d, J=8 Hz, 1H), 7.03 (dd, J=11, 17 Hz, 1H), 5.84 (d, J=17 Hz, 1H), 5.55 (d, J=11 Hz, 1H), 5.29 (s, 2H), 2.34 (s, 3H); LC-MS: M+1=175;

Step B: 4-methyl-5-oxiran-2-yl-2-benzofuran-1(3H)-one: 5-ethenyl-4-methyl-2-benzofuran-1(3H)-one (1.46 g, 8.38 mmol) was added to DCM (25 mL) at 0° C. then mCPBA (2.89 g, 16.8 mmol) was added and the mixture was stirred at RT overnight. The reaction mixture was washed once each with saturated aqueous Na$_2$S$_2$O$_3$, NaHCO$_3$, and brine. The organic layer was dried over Na$_2$SO$_4$, filtered, and evaporated to dryness. The crude material was purified by MPLC chromatography through 120 g RediSep® column eluting with 0-80% EtOAc/hexane solvent system to yield target 4-methyl-5-oxiran-2-yl-2-benzofuran-1(3H)-one. $^1$H-NMR (500 MHz, CDCl$_3$): δ ppm 7.77 (d, J=8 Hz, 1H), 7.43 (d, J=8 Hz, 1H), 5.30 (s, 2 H), 4.12 (s, 1 H), 3.27 (t, J=4 Hz, 1 H), 2.735 (dd, J=2.2, 5.5 Hz, 1H), 2.43 (s, 3H). LC-MS: M+1=191.

Intermediates 3A and 3B (Method 1)

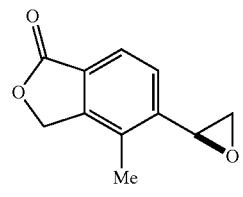

Slow eluting 3A

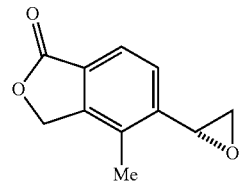

Fast eluting 3B

3A: 4-methyl-5-[(2S)-oxiran-2-yl]-2-benzofuran-1(3H)-one

3B: 4-methyl-5-[(2R)-oxiran-2-yl]-2-benzofuran-1(3H)-one

Racemic 4-methyl-5-oxiran-2-yl-2-benzofuran-1(3H)-one was resolved on a ChiralPak® AD-H column (5×25 cm) under supercritical fluid chromatography (SFC) conditions on a Berger MultiGram® III preparative SFC instrument. The racemate was diluted to 50 mg/mL in 1:1 DCM:MeOH. The separation was accomplished using 10% EtOH/CO$_2$, flow rate 200 mL/min, 100 bar, 25° C. 500 ul injections were spaced every 2.12 mins. The fast epoxide (4-methyl-5-[(2R)-oxiran-2-yl]-2-benzofuran-1(3H)-one, 4B) eluted first, and the slow epoxide (4-methyl-5-[(2S)-oxiran-2-yl]-2-benzofuran-1(3H)-one, 4A) eluted second.

Alternatively, the resolution could also be achieved using a mobile phase of 8% MeOH/98% CO$_2$ with a flow rate of 100 mL/min. In that case the sample was prepared by dissolving in methanol, 20 mg/mL, and using a 1 mL volume per injection. After separation, the fractions were dried off via rotary evaporator at bath temperature 40° C.

The absolute stereochemistry of each enantiomer was inferred based on the X-ray crystal structure determination of a final compound made with 3B and by Mosher ester and Trost ester HNMR analysis of esters made starting from 3B. Both epoxide isomers find utility in the present invention.

Intermediate 3B (Method 2)

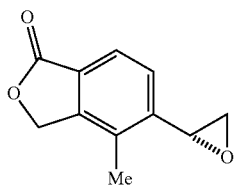 [SMILES: Cc1c([C@@H]2CO2)ccc2c1COC2=O]

Step A: 3-hydroxymethyl-2-methyl phenol: To a 5 L 3 neck RB equipped with overhead stirrer was charged NaBH$_4$ (87.0 g, 2.30 mol) and THF (3.0 L) and the resulting slurry was cooled to 10° C. To the slurry was then added 3-hydroxy-2-methyl benzoic acid (175 g, 1.15 mol) portionwise over 20 min (Tmax 17° C.). A stirrable slurry formed, and was aged for an additional 45 min at 10-15° C. after which BF$_3$—OEt$_2$ (321 mL, 2.53 mol) was added slowly over 1.5 hours. The slurry was aged at 10° C.-15° C. for 2 h then assayed for reaction completion (98.5% conversion). The slurry was cooled to <10° C. and quenched with 931 mL MeOH slowly over 1.5 h (gas evolution). The resulting slurry was aged overnight at RT. The batch was cooled to <10° C. then quenched with 1 N HCl (1.5 L) to get a homogeneous solution (pH solution~1), which was aged for 30 min and then the organic solvents were removed by rotary evaporation to approximately 1.8 L of total reaction volume (bath temperature was set to 50° C.; internal temp of concentrate after rotary evaporation was ~40° C.). The slurry was held at 45° C. for 30 min then cooled slowly to 15° C. The solids were filtered and washed with cold (15° C.) water (2×300 mL), providing 3-hydroxymethyl-2-methyl phenol. $^1$H-NMR (400 MHz, DMSO-d$_6$): δ 9.11 (s, 1H), 6.95 (t, J=7.8 Hz, 1H), 6.82 (d, J=7.4 Hz, 1H), 6.71 (d, J=7.8 Hz, 1H), 4.93 (t, J=5.5 Hz, 1H), 4.44 (d, J=5.5 Hz, 2H), 2.06 (s, 3H).

Step B: 4-bromo-3-hydroxymethyl-2-methyl phenol: 3-Hydroxymethyl-2-methyl phenol (113.9 g, 824.0 mmol) was dissolved in a mixture of acetonitrile (850 mL) and trifluoroacetic acid (750.0 mL, 9,735 mmol) in a 3-neck 5-L flask under nitrogen. The reaction mixture was cooled to −33° C. N-bromosuccinimide (141 g, 791 mmol) was added over 15 minutes, with the temperature during addition in the range of −35 to −33° C. The reaction mixture was allowed to stir for an additional 15 min during which time the temperature decreased to −40° C. The cooling bath was removed, and potassium carbonate (741.0 g, 5,358 mmol) diluted with water to a total of 1.0 L was added. Off-gassing was observed, and the temperature increased to 25° C. MTBE (1.5 L) was added, and the reaction mixture was transferred to a separatory funnel. The layers were separated. The aqueous layer was diluted with water (500 mL) and extracted with MTBE (1 L)+EtOAc (500 mL), and then MTBE (500 mL)+EtOAc (250 mL). The combined organic layers were washed with water (240 mL) and dried over sodium sulfate. The sodium sulfate was removed by filtration, washed with additional MTBE and concentrated under reduced pressure. MTBE (684 mL, 2 volumes) was added, and the suspension was heated to 40° C. to produce a homogeneous solution. The solution was allowed to cool to room temperature. Six volumes of heptane were added, and the suspension was stirred overnight. The suspension was filtered, and the crystals were washed with 4:1 heptane: MTBE (500 mL), followed by heptane (500 mL). The solid was dried under vacuum, providing 4-bromo-3-hydroxymethyl-2-methyl phenol. $^1$H NMR (400 MHz, DMSO-d$_6$): δ 9.52 (s, 1H), 7.21 (d, J=8.6 Hz, 1H), 6.71 (d, J=8.6 Hz, 1H), 4.88 (t, J=5.1 Hz, 1H), 4.59 (d, J=5.1 Hz, 2H), 2.23 (s, 3H)

Step C: 5-hydroxy-4-methyl-3H-isobenzofuran-1-one: To a 2 L 3 neck flask equipped with overhead stirrer, N$_2$ inlet, and condenser were charged 4-bromo-3-hydroxymethyl-2-methyl phenol (100 g, 461 mmol), CuCN (83.0 g, 921 mmol), and DMF (500 mL). The solution was sparged with N$_2$ for 15 min then heated to 145° C. to obtain a homogeneous solution. The solution was aged at 145° C. for 2 h, then the reaction mixture was cooled to 95° C. 41.5 mL water was added (sparged with N$_2$), and the reaction aged for 20 h. The reaction was cooled to RT then the solids filtered through Solka-Floc® and the cake washed with 50 mL DMF. To a 3 L flask containing 1 L EtOAc was added the DMF filtrate. A precipitate coating formed in bottom of flask. The DMF/EtOAc suspension was filtered through Solka-Floc® and the cake was washed with 250 mL EtOAc. The resulting filtrate was washed with 5% brine solution (3×500 mL). The aqueous layers were extracted with 500 mL EtOAc and the combined organics were dried over MgSO$_4$, filtered and evaporated. The solids were slurried in 250 mL MTBE at RT then filtered and washed with 100 mL MTBE. The solids were dried under vacuum at RT, providing 5-hydroxy-4-methyl-3H-isobenzofuran-1-one. $^1$H NMR (400 MHz, DMSO-d$_6$): δ 10.52 (s, 1H), 7.51 (d, J=8.3 Hz, 1H), 6.99 (d, J=8.3 Hz, 1H), 5.28 (s, 2H), 2.07 (s, 3H).

Step D: 4-methyl-1-oxo-1,3-dihydroisobenzofuran-5-yl trifluoromethanesulfonate: 5-Hydroxy-4-methyl-3H-isobenzofuran-1-one (46.8 g, 285 mmol) was suspended in dichloromethane (935 mL) in 2-L round bottom flask equipped with overhead stirrer under nitrogen. Triethylamine (59.5 mL, 427 mmol) was added, and the reaction mixture was cooled in an ice bath to 3.8° C. Trifluoromethanesulfonic anhydride (67.4 mL, 399 mmol) was added via addition funnel over 50 min, keeping the temperature <10° C. After stirring the reaction mixture for an additional 15 min, the reaction mixture was quenched with water (200 mL), then stirred with DARCO® KB (activated carbon, 25 g) for 15 min. The biphasic mixture was filtered over Solka-Floc®, washing with additional dichloromethane, and transferred to a separatory funnel, whereupon it was diluted with additional water (300 mL). The layers were separated, and the organic layer was washed with water (500 mL) and 10% brine (200 mL). The dichloromethane solution was dried over sodium sulfate, filtered and evaporated. The orange-red solid was adsorbed onto silica gel (27.5 g) and eluted through a pad of silica gel (271 g) with 25% ethyl acetate/hexanes. The resulting solution was concentrated under vacuum with the product crystallizing during concentration. The suspension was filtered, the solid washed with heptane and dried under vacuum and nitrogen, providing trifluoromethanesulfonic acid 4-methyl-1-oxo-1,3-dihydro-isobenzofuran-5-yl ester. $^1$H NMR (400 MHz, CDCl$_3$): δ 7.87 (d, J=8.4 Hz, 1H), 7.47 (d, J=8.4 Hz, 1H), 5.32 (s, 2H), 2.41 (s, 3H)

Step E: 5-(1-butoxy-vinyl)-4-methyl-3H-isobenzofuran-1-one: To a 1 L 3-neck was charged trifluoromethanesulfonic acid 4-methyl-1-oxo-1,3-dihydro-isobenzofuran-5-yl ester (63.0 g, 213 mmol), DMF (315 mL), butyl vinyl ether (138 mL, 1063 mmol) then Et₃N (35.6 mL, 255 mmol). The solution was sparged with N₂ for 20 min. To the solution was added Pd(OAc)₂ (1.19 g., 5.32 mmol) and DPPP (2.41 g., 5.85 mmol) and sparged for an additional 10 min then heated to 80° C. After a 1 hr age, the solution was cooled to <10° C. then quenched with 630 mL EtOAc and washed with 5% NH₄Cl (2×315 mL), 10% brine (2×315 mL), dried over MgSO₄, filtered, concentrated by rotary evaporation and flushed with EtOAc (3×100 mL) to remove excess butyl vinyl ether, providing crude 5-(1-butoxy-vinyl)-4-methyl-3H-isobenzofuran-1-one. ¹H NMR (400 MHz, DMSO-d₆): δ 7.67 (d, J=7.7 Hz, 1H), 7.48 (d, J=7.7 Hz, 1H), 5.42 (s, 2H), 4.54 (d, J=2.3 Hz, 1H), 4.27 (d, J=2.3 Hz, 1H), 3.85 (t, J=6.4 Hz, 2H), 2.27 (s, 3H), 1.71-1.64 (m, 2H), 1.46-1.37 (m, 2H), 0.92 (t, J=7.4 Hz, 3H)

Step F: 5-(2-bromo-acetyl)-4-methyl-3H-isobenzofuran-1-one: To a 1 L 3-neck flask equipped with overhead stirrer was added crude 5-(1-butoxy-vinyl)-4-methyl-3H-isobenzofuran-1-one (55.8 g) and THF (315 mL). The solution was cooled to <5° C. after which water (79 mL) was added and the solution was maintained at <5° C. NBS (41.6 g) was then added portion-wise while maintaining Tmax=19° C. The solution was then warmed to RT for 30 minutes. HBr (48%, 0.241 mL) was added and the reaction was aged at RT for approximately 1 h after which 236 mL water was then added to the batch. A water bath is used to maintain temp at 20° C. Another 315 mL of water was added (solvent composition 1:2 THF:water) and the slurry was cooled to 15° C. The resulting solids were filtered and washed with cold 1:2 THF:water (15° C.): 150 mL displacement wash followed by 100 mL slurry wash. The solids were dried under vacuum at RT to provide 5-(2-bromo-acetyl)-4-methyl-3H-isobenzofuran-1-one. ¹H NMR (400 MHz, DMSO-d₆): δ 7.99 (d, J=7.8 Hz, 1H), 7.82 (d, J=7.8 Hz, 1H), 5.49 (s, 2H), 4.92 (s, 2H), 2.33 (s, 3H)

Step G: 4-methyl-5-[(2R)-oxiran-2-yl]-2-benzofuran-1(3H)-one: 5-(2-Bromo-acetyl)-4-methyl-3H-isobenzofuran-1-one (48.8 g., 181 mmol) was charged to a 5 L 3 neck round bottom equipped with overhead stirrer, thermocouple, and heating mantle. 2-Propanol (1.22 L) was added, followed by 610 mL of pH 7 0.1M potassium phosphate buffer. Buffer solution (610 mL) was charged to a 1.0 L erlenmeyer, and 2.44 g of NADP was added to the erlenmeyer and swirled to dissolve. A reducing enzyme, KRED MIF-20 (2.44 g) (available from Codexis, Inc., 200 Penobscot Drive, Redwood City, Calif. 94063, www.codexis.com, tel. 1-650-421-8100) was added to the erlenmeyer flask and the mixture was swirled to dissolve the solids. The resulting solution was added to the 5 L round bottom, which was then heated to 28° C. and aged for 6 hours, at which point the reaction was cooled to RT and triethylamine (50.2 mL, 360 mmol) was added. The resulting solution was aged at 40° C. for 1 h. The light slurry solution was cooled to RT, after which 122 g NaCl was added. The solution was aged at RT then extracted with 1.22 L isopropyl acetate (IPAc). The aqueous layer was re-extracted with 400 mL IPAc and the combined organics were washed with 400 mL 20% brine solution, dried over MgSO₄, filtered and concentrated by rotary evaporation. The resulting solids were taken up in 100 mL IPAc (thick slurry). Hexanes were added (400 mL) and the suspension aged at RT then filtered and washed w/5:1 Hexanes:IPAc solution (150 mL). The crystalline solids were dried under vacuum at RT to provide 4-methyl-5-[(2R)-oxiran-2-yl]-2-benzofuran-1(3H)-one. ¹H NMR (400 MHz, CDCl₃): δ 7.75 (d, J=8.1 Hz, 1H), 7.42 (d, J=8.1 Hz, 1H), 5.28 (s, 2H), 4.10 (dd, J=4.0, 2.8, 1H), 3.26 (dd, J=5.6, 4.0, 1H), 2.72 (dd, J=5.6, 2.8, 1H), 2.42 (s, 3H).

Intermediate 4

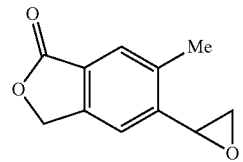 [SMILES: Cc1cc2c(cc1C1CO1)COC2=O]

Step A: 5-prop-2-en-1-yl-2-benzofuran-1(3H)-one: A mixture of 5-bromo-2-benzofuran-1(3H)-one (15.0 g, 70.4 mmol), allyl-tributyl-stannane (25.6 g, 77.5 mmol), LiCl (11.8 g, 282 mmol) and Pd(PPh₃)₄ (1.2 g, 1.0 mmol) in 100 mL toluene was heated under N₂ at 90~100° C. overnight. After cooling to r.t., the mixture was diluted with 250 mL EtOAc and filtered. The filtrate was washed with water and brine, dried over anhydrous Na₂SO₄ and concentrated to dryness. The residue was purified via column (DCM/PE=1: 5) to give title compound.

Step B: 5-(2-hydroxyethyl)-2-benzofuran-1(3H)-one: To a solution of 5-prop-2-en-1-yl-2-benzofuran-1(3H)-one (13.5 g, 45.2 mmol) in 200 mL DCM/MeOH (V/V=1:1) was bubbled O₃ at −78° C. for 30 min, and N₂ was bubbled for another 15 min at −78° C. Then 20 mL of Me₂S were added, and the mixture was stirred at r.t. overnight before concentrating to dryness. The residue was dissolved in MeOH (100 mL) and then cooled to 0° C. NaBH₄ (5.90 g, 155 mmol) was added in portions. The resulting mixture was stirred at 0° C. for 1 h, then quenched with citric acid (aq.) and extracted three times with EtOAc. The combined organic layers were washed with NaHCO₃ (aq.) and brine, dried over anhydrous Na₂SO₄ and concentrated to dryness. The residue was purified via column chromatography (EtOAc/Petrol Ether=1:5) to give title compound. ¹H-NMR (400 MHz, CDCl₃) δ ppm 7.86 (d, J=7.8 Hz, 1H), 7.41 (d, J=7.8 Hz, 1H), 7.38 (s, 1H), 5.29 (s, 2H), 3.92~3.98 (m, 2H), 3.01 (t, J=6.4 Hz, 2H).

Step C: 5-(2-hydroxyethyl)-6-iodo-2-benzofuran-1(3H)-one: To a cooled (0° C.) solution of 5-(2-hydroxyethyl)-2-benzofuran-1(3H)-one (9.00 g, 50.6 mmol) in 100 mL of TfOH was added NIS (12.5 g, 55.6 mmol), then the mixture was stirred at 0° C. for 2 hrs and then poured into ice-water (500 mL). The solution was extracted three times with 500 mL of EtOAc and the combined organic layers were washed with saturated NaHCO₃ and brine, dried over anhydrous sodium sulfate, filtered and concentrated. The residue was purified by column chromatography (EtOAc/Petrol Ether=1: 5) to give the desired 5-(2-hydroxyethyl)-6-iodo-2-benzofuran-1(3H)-one and isomeric by-product 5-(2-hydroxyethyl)-4-iodo-2-benzofuran-1(3H)-one. ¹H-NMR (400 MHz, CDCl₃) δ ppm 7.84 (d, J=7.8 Hz, 1H), 7.46 (d, J=7.8 Hz, 1H), 5.09 (s, 2H), 3.93 (q, J=6.3 Hz, 2H), 3.16 (t, J=6.3 Hz, 2H), 1.45 (t, J=5.5 Hz, 1H).

Step D: 5-(2-hydroxyethyl)-6-methyl-2-benzofuran-1(3H)-one: To a flask charged with 5-(2-hydroxyethyl)-6-iodo-2-benzofuran-1(3H)-one (6.00 g, 19.7 mmol) and a stir bar was added Pd₂(dba)₃ (452 mg, 0.493 mmol), PPh₃ (1 g, 4 mmol) and NMP (50 mL). The mixture was purged with N₂ and heated to 50° C. for 10 min, followed by addition of CuI (375 mg, 1.97 mmol). After the mixture was heated for another 10 min, Sn(CH₃)₄ (5.30 g, 29.6 mmol) was added into the reaction, and it was heated to 120° C. for 2 h. After cooled to room temperature, the mixture was diluted with saturated NH₄Cl (200 mL) and extracted with EtOAc (3 times 200 mL). The combined organic layers were washed with water and brine, dried over anhydrous sodium sulfate, filtered and concentrated. The residue was purified by prep-HPLC to give title compound. $^1$H-NMR (400 MHz, CDCl$_3$) δ ppm 7.72 (s, 1H), 7.33 (s, 1H), 5.27 (s, 2H), 3.93 (t, J=6.3 Hz, 2H), 3.01 (t, J=6.3 Hz, 2H), 2.44 (s, 3H).

Step E: 2-(6-methyl-1-oxo-1,3-dihydro-2-benzofuran-5-yl)ethyl methanesulfonate: To a solution of 5-(2-hydroxyethyl)-6-methyl-2-benzofuran-1(3H)-one (1.20 g, 6.25 mmol) and TEA (2.5 g, 25 mmol) in DCM (100 mL) was added MsCl (1.40 g, 12.5 mmol) at 0° C. The mixture was stirred at ambient temperature overnight, then was washed with water and brine. The organic layer was dried and concentrated to dryness. The collected title compound was used for the next step without any purification.

Step F: 5-ethenyl-6-methyl-2-benzofuran-1(3H)-one: To a mixture of 2-(6-methyl-1-oxo-1,3-dihydro-2-benzofuran-5-yl)ethyl methanesulfonate (2.00 g, 7.41 mmol) and TEA (5 mL) in DCM (50 mL) was added DBU (5 mL) slowly at 0° C. The mixture was stirred at r.t. overnight, and then was diluted with 50 mL of DCM, washed with 2 N HCl in three times and brine. The organic layer was dried and concentrated to dryness. The residue was purified by prep-TLC to give 5-ethenyl-6-methyl-2-benzofuran-1(3H)-one.

Step G: 6-methyl-5-oxiran-2-yl-2-benzofuran-1(3H)-one: To a solution of 5-ethenyl-6-methyl-2-benzofuran-1(3H)-one (1.00 g, 5.75 mmol) in 50 mL of DCM was slowly added mCPBA (3.50 g, 17.4 mmol) in 50 mL of DCM at 0° C. The mixture was warmed to room temperature, and stirred for 2 days. The mixture was washed with aqueous Na$_2$SO$_3$ until KI indicator paper did not change color. The organic layer was washed with brine and then concentrated. The residue was purified via silica column to give 6-methyl-5-oxiran-2-yl-2-benzofuran-1(3H)-one. LC-MS M+1 (calc. 191. found 191).

Intermediates 4A and 4B

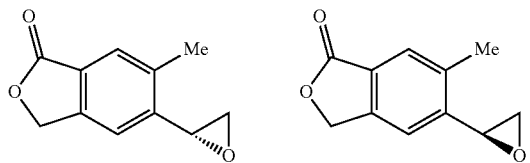 [SMILES: Cc1cc2c(cc1[C@@H]1CO1)COC2=O ; Cc1cc2c(cc1[C@H]1CO1)COC2=O]

(R)-6-methyl-5-(oxiran-2-yl)isobenzofuran-1(3H)-one and (S)-6-methyl-5-(oxiran-2-yl)isobenzofuran-1(3H)-one were obtained by chiral SFC separation of the racemic 6-methyl-5-oxiran-2-yl-2-benzofuran-1(3H)-one (INTERMEDIATE 7) using ChiralPak® AD column (250 mm×50 mm, 10 um); mobile phase: A: Supercritical CO$_2$, B: MeOH, A:B=85:15 at 250 ml/min. First peak to elute (4A): HNMR 400 MHz CDCl$_3$ δ 7.68 (s, 1H), 7.36 (s, 1H), 5.24 (d, J=3.6 Hz, 2H), 4.05 (dd, J=2.8 Hz, 3.6 Hz, 1H), 3.24 (dd, J=4.0 Hz, 6.4 Hz, 1H), 2.63 (dd, J=2.8 Hz, 6.4 Hz, 1H), 2.50 (s, 3H); second peak to elute (4B): 400 MHz CDCl3 δ 7.68 (s, 1H), 7.35 (s, 1H), 5.24 (d, J=3.6 Hz, 2H), 4.05 (dd, J=2.8 Hz, 3.6 Hz, 1H), 3.24 (dd, J=4.0 Hz, 6.4 Hz, 1H), 2.63 (dd, J=2.8 Hz, 6.4 Hz, 1H), 2.50 (s, 3H).

Intermediate 5

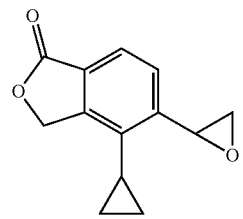 [SMILES: O=C1OCc2c1ccc(C1CO1)c2C1CC1]

Step A: 5-bromo-4-iodo-2-benzofuran-1(3H)-one: To a cooled (0° C.) solution of 5-bromo-2-benzofuran-1(3H)-one (50 g, 0.235 mol) in trifluoromethanesulfonic acid (400 mL) was added N-iodosuccinimide (55.5 g, 0.247 mol). The resulting mixture was stirred at room temperature overnight, then poured slowly into ice water (2 L), filtered and the filtrate extracted with EtOAc. The combined organic layers were washed with water and brine, dried and concentrated to give 5-bromo-4-iodo-2-benzofuran-1(3H)-one.

Step B: 5-bromo-4-vinyl-2-benzofuran-1(3H)-one: A mixture of 5-bromo-4-iodo-2-benzofuran-1(3H)-one (1 g, 2.95 mmol), potassium vinyltrifluoroborate (474 mg, 3.54 mmol) and Pd(dppf)Cl$_2$ (200 mg) in 20 mL of TEA and 20 mL of EtOH was heated to reflux under N$_2$ for 2 hours. TLC showed complete reaction. Most of the solvent was removed, and the residue was dissolved in EtOAc (100 mL). The solution was washed with 0.1 N HCl, sodium bicarbonate, and brine, dried over sodium sulfate, filtered and concentrated to provide 5-bromo-4-vinyl-2-benzofuran-1(3H)-one.

Step C: 5-bromo-4-cyclopropyl-2-benzofuran-1(3H)-one: To a cooled (0° C.) mixture of 5-bromo-4-vinyl-2-benzofuran-1(3H)-one (2.2 g, 9.21 mol) and Pd(OAc)$_2$ (100 mg) in EtOAc (50 mL) was added a solution of CH$_2$N$_2$ in ether (100 mL) slowly. The resulting mixture was stirred at room temperature overnight, then quenched with acetic acid, filtered and the filtrate washed with water and brine, dried and concentrated to provide 5-bromo-4-cyclopropyl-2-benzofuran-1(3H)-one.

Step D: 4-cyclopropyl-5-vinyl-2-benzofuran-1(3H)-one: A mixture of 5-bromo-4-cyclopropyl-2-benzofuran-1(3H)-one (760 mg, 3.004 mmol), potassium vinyltrifluoroborate (805 mg, 6.008 mmol) and Pd(dppf)Cl$_2$ (100 mg) in 20 mL of TEA and 20 mL of EtOH was heated to reflux under N$_2$ for 8 hours. When TLC showed complete reaction most of the solvent was removed, and the residue was dissolved in EtOAc (100 mL). The solution was washed with 0.1 N HCl, sodium bicarbonate, and brine, dried over sodium sulfate, filtered and concentrated. The resulting oil was purified by column chromatography to give 4-cyclopropyl-5-vinyl-2-benzofuran-1(3H)-one.

Step E: 4-cyclopropyl-5-oxiran-2-yl-2-benzofuran-1(3H)-one: To a solution of 4-cyclopropyl-5-vinyl-2-benzofuran-1(3H)-one (440 mg, 2.2 mmol) in 50 mL of DCM was slowly added mCPBA (1.14 g, 6.6 mmol) in 50 mL of DCM at 0° C. After warming to room temperature, the mixture was stirred for 12 hours. The mixture was washed with aqueous Na$_2$SO$_3$ until KI paper did not change color. The organic layers were combined, washed with brine and then concentrated. The residue was purified via preparative TLC to give 4-cyclopropyl-5-oxiran-2-yl-2-benzofuran-1(3H)-one.
$^1$H-NMR (400 MHz, CDCl$_3$) δ ppm 7.77 (d, J=8.6 Hz, 1H), 7.39 (d, J=7.8 Hz, 1H), 5.39 (s, 2H), 4.43-4.45 (m, 1H), 3.26-3.28 (m, 1H), 2.68-2.70 (m, 1H), 1.94-2.01 (m, 1H), 1.08-1.12 (m, 2H), 0.65-0.75 (m, 2H).

Intermediate 6

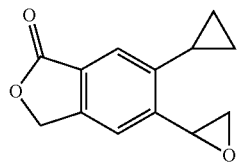 [SMILES: O=C1OCc2cc(C3CO3)c(C3CC3)cc21]

Step A: 5-(2-hydroxyethyl)-6-vinyl-2-benzofuran-1(3H)-one: To a 500 ml flask containing a stir bar was added 5-(2-hydroxyethyl)-6-iodo-2-benzofuran-1(3H)-one (5 g, 16.4 mmol), Potassium vinyltrifluoroborate (3.3 g, 24.7 mmol), Pd(dppf)Cl$_2$ (0.6 g, 0.822 mmol) and TEA (2.3 mL). The mixture was then dissolved in EtOH (50 mL) and heated at 100° C. in a silicon oil bath for 2 h; TLC showed complete reaction. The flask was cooled to room temperature, treated with EtOAc (150 mL) and poured into a separatory funnel and washed with brine (2×100 mL). The organic layer was then separated, dried (Na$_2$SO$_4$), filtered and concentrated to dryness. The resulting organic residue was dissolved in DCM and absorbed into silica gel and purified by MPLC (hexanes/EtOAc; 1/1 eluent) to provide title compound.

Step B: 6-cyclopropyl-5-(2-hydroxyethyl)-2-benzofuran-1(3H)-one: To a 100 mL flask containing a stir bar was added 5-(2-hydroxyethyl)-6-vinyl-2-benzofuran-1(3H)-one (0.9 g, 4.41 mmol), and palladium diacetate (0.049 g, 0.220 mmol), followed by addition of a freshly prepared diazomethane (3.7 g, 88 mmol) in diethyl ether (10 mL) over a course of 20 minutes. The resulting mixture was then stirred at room temperature in a shielded environment for 1 h. When the reaction was complete, the solvent was concentrated to dryness, dissolved in EtOAc, and washed with brine, dried (Na$_2$SO$_4$), filtered and concentrated to dryness. The resulting residue was used directly for the next step.

Step C: 6-cyclopropyl-5-vinyl-2-benzofuran-1(3H)-one: To a 100 mL flask containing a stir bar was added compound 6-cyclopropyl-5-(2-hydroxyethyl)-2-benzofuran-1(3H)-one, (0.5 g, 2.29 mmol), TEA (20 mL) followed by addition of dichloromethane (25 mL). The flask was placed in a cool bath of ° C., and slowly treated with methanesulfonyl chloride (6.5 mL, 83 mmol). The resulting mixture was then stirred for 20 min. The mixture was poured into saturated ammonium chloride and extracted with DCM. The combined organics were washed with 1 N HCl, saturated sodium bicarbonate solution, and brine, then dried (Na$_2$SO$_4$) and concentrated in vacuo. The residue (LC/MS: [(M+1)]$^+$=297) was dissolved in dichloromethane (25 mL) and treated with DBU (0.7 mL, 4.72 mmol) and stirred for 2 h. TLC monitoring showed conversion to the olefin. The reaction mixture was diluted with water and extracted with dichloromethane. The combined organics were washed with 1N HCl, saturated sodium bicarbonate solution, and brine, then dried (Na$_2$SO$_4$) and concentrated in vacuo.

Step D: 6-cyclopropyl-5-oxiran-2-yl-2-benzofuran-1(3H)-one: 6-Cyclopropyl-5-vinyl-2-benzofuran-1(3H)-one (0.45 g, 2.25 mmol) was dissolved in dichloromethane (10 mL) and treated with meta-chloro perbenzoic acid (1 g, 6.3 mmol) at 0° C. and stirred for 12 h. TLC indicated completion of the reaction; the mixture was diluted with saturated sodium bicarbonate solution and extracted with dichloromethane (2×). The combined organic extracts were washed with brine, dried (Na$_2$SO$_4$), filtered and concentrated in vacuo. The epoxide was purified by silica gel column chromatography (hexanes/EtOAc=1/1) to give 6-cyclopropyl-5-oxiran-2-yl-2-benzofuran-1(3H)-one. The oxirane was further resolved over a chiral column giving two isomers: Faster eluting—$^1$H NMR (500 MHz, CD$_3$Cl) δ 7.63 (s, 1H), 7.41 (s, 1H), 5.29-5.33 (m, 2H), 4.21-4.42 (m, 1H), 3.16-3.34 (m, 1H), 2.71-2.72 (m, 1H) 2.09-2.11 (m, 1H), 1.07-1.14 (m, 2H), 0.76-0.88 (m, 2H). Slower eluting—$^1$H NMR (500 MHz, CD$_3$Cl) δ 7.63 (s, 1H), 7.41 (s, 1H), 5.29-5.30 (m, 2H), 4.412-4.42 (m, 1H), 3.31-3.33 (m, 1H), 2.71-2.72 (m, 1H), 2.09-2.12 (m, 1H), 1.07-1.60 (m, 2H), 0.76-0.87 (m, 2H).

Intermediate 7 and Isomers (R)-7 and (S)-7

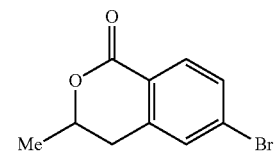

7

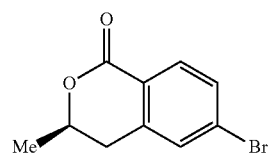

(R)-7

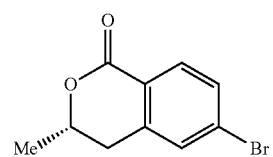

(S)-7

6-bromo-3-methyl-3,4-dihydro-1H-isochromen-1-one and individual isomers (3R)-6-bromo-3-methyl-3,4-dihydro-1H-isochromen-1-one and (3S)-6-bromo-3-methyl-3,4-dihydro-1H-isochromen-1-one: A −78° C. solution of diisopropylamine (13.3 mL, 93.0 mmol) in THF (155 mL) was treated with n-BuLi (1.6 M in hexanes; 58 mL, 93 mmol) over a period of 15 minutes using a syringe pump. In a separate flask, a solution of 2-methyl-4-bromo benzoic acid (10.0 g, 46.5 mmol) and HMPA (8.33 mL, 46.5 mmol) in THF (155 mL) was cooled to −78° C. Methyl lithium (29.1 mL, 46.5 mmol) was added slowly via syringe to the cooled solution. The resulting solution was stirred for 10 minutes and then transferred via cannula to the LDA solution at −78° C. The resulting solution was stirred at −78° C. for an additional 1 h before being quenched with anhydrous acetaldehyde (7.88 mL, 140 mmol) and the reaction was then taken out of the dry ice acetone bath and allowed to stir for an additional 1 h. The flask containing the reaction mixture was then resubmerged in the dry ice acetone bath before it was quenched with 4M HCl in dioxane (50 mL) followed by 25 mL of MeOH. The reaction was stirred at room temp for an additional 1 h. The crude reaction mixture was partitioned between 200 mL ethyl acetate and 200 mL water. The organic layer was washed with water, brine, dried with magnesium sulfate, filtered and concentrated. Purification via MPLC (30-70% DCM/hexanes) afforded 7 as a racemic mixture which was separable by chiral SFC HPLC using, for example, a Chiralpak® AS column to obtain (R)-7 and (S)-7. $^1$H NMR (500 MHz; CDCl$_3$): δ 7.98 (d, J=8.2 Hz, 1H), 7.56 (dd, J=1.5, 8.2 Hz, 1H), 7.45 (s, 1H), 4.71 (m, 1H), 2.94 (m, 2H), 1.55 (d, J=6.3 Hz, 3H); LC-MS (IE, m/z): 241 [M+1]$^+$. INTERMEDIATE (R)-7 (Method 2)

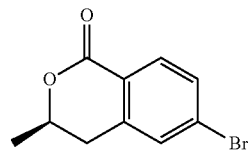

Step A: 4-bromo-N,N-diethyl-2-methylbenzamide: A solution of 4-bromo-2-methylbenzoic acid (25.0 g, 116 mmol) in DCM (400 mL) was treated with oxalyl chloride (11.7 mL, 134 mmol) and a catalytic amount of dry DMF (0.1 mL). The reaction was allowed to stir under nitrogen for 2 hours at room temperature. Removal of excess solvent gave crude acid chloride which was redissolved in DCM (400 mL). The mixture was then cooled to 0° C. and triethyl amine (40.5 mL, 291 mmol) was added followed by the slow addition of diethyl amine (24.3 mL, 233 mmol). The reaction was then allowed to warm to room temperature overnight. The crude mixture was then diluted with 400 mL of water and extracted with DCM (3×500 mL). The combined organic layers were then washed with brine (200 mL), dried over magnesium sulfate, filtered and then concentrated. The crude material was purified via MPLC (10% EtOAc/Hex) to afford 4-bromo-N,N-diethyl-2-methylbenzamide.

Step B: 4-bromo-N,N-diethyl-2-(2-oxopropyl)benzamide: A 2M solution of LDA (35.2 ml, 70.3 mmol) in THF (176 ml) cooled to −78° C. was treated with slow addition of 4-bromo-N,N-diethyl-2-methylbenzamide (19.0 g, 70.3 mmol) in dry THF (176 ml). The reaction was allowed to stir at −78° C. for 1 hour before it was quenched with N-methoxy-N-methylacetamide (22.43 ml, 211 mmol) and allowed to slowly warm to room temp. The reaction was stirred overnight and then partitioned between 1N HCl (200 mL) and EtOAc (400 mL). The aqueous layer was further extracted with EtOAc (2×150 mL). The combined organic layers were washed with brine (150 mL), dried over magnesium sulfate, filtered and concentrated. The crude material was an orange/brown oil out of which the product crystallizes. The oil was decanted off and the solid was washed with hexanes and dried using a Buchner funnel to afford title compound.

Step C: 4-bromo-N,N-diethyl-2-[(2R)-2-hydroxypropyl]benzamide: A flask equipped with an overhead stirrer was charge with pH=8 phosphate buffer (156 ml, 31.2 mmol) followed by D-glucose (1.298 g, 7.21 mmol) and then warmed to 30° C. Next, 135 mg glucose dehydrogenase and 270 mg NADP+ disodium was added to the glucose/buffer solution at once, a homogeneous solution was obtained after 1 min agitating. Next, 577 mg of keto-reductase enzyme KRED P1B2 (available from Codexis, Inc., 200 Penobscot Drive, Redwood City, Calif. 94063, www.codexis.com, tel 1-650-421-8100) was added to the reaction vessel and stirred at 500 rpm at 300° C. until enzyme is wetted (about 40 min). Lastly, a solution of 4-bromo-N,N-diethyl-2-(2-oxopropyl)benzamide (1.5 g, 4.80 mmol) dissolved in DMSO (14.56 ml) (pre-warmed on stir plate to 30° C.) was added to the reaction over ~3 min and agitate at 30° C. (400 rpm) overnight. After 48 hours the reaction was cooled to room temperature and then 75 g of potassium carbonate was added to the reaction in portions and stirred for 15 minutes until enzyme clumps together when stirring is stopped. Next, acetonitrile (50 mL) was poured into the reaction flask and the layers were thoroughly mixed. Stirring was stopped after 15-20 minutes, the layers allowed to separate and the upper layer decanted off. This was repeated two more times with additional 50 mL of acetonitrile. The combined organic layers were then filtered through a medium porosity funnel, concentrated and then 50 ml MTBE was added to the concentrate and stirred for 5 min and then transferred to a separatory funnel and the layers separated. The aqueous layer was extracted further another 50 ml MTBE. The combined organic extracts were dried over magnesium sulfate, filtered and concentrated. Purification via MPLC (30-70% EtOAc/Hex) afforded 4-bromo-N,N-diethyl-2-[(2R)-2-hydroxypropyl]benzamide.

Step D: (3R)-6-bromo-3-methyl-3,4-dihydro-1H-isochromen-1-one: A solution of 4-bromo-N,N-diethyl-2-[(2R)-2-hydroxypropyl]benzamide (12.2 g, 38.8 mmol) dissolved in 4N HCl in Dioxane (200 mL) was stirred at room temperature and monitored by tlc. After 3 days the reaction was partitioned between EtOAc (300 mL) and water (300 mL). The aqueous phase was further extracted with EtOAc (2×250 mL). The combined organic layers were then washed with water (200 mL), brine (200 mL), dried over magnesium sulfate, filtered and concentrated. The crude material was then purified via MPLC (15-30% EtOAc/Hexane) to afford (3R)-6-bromo-3-methyl-3,4-dihydro-1H-isochromen-1-one. $^1$H NMR (500 MHz; CDCl$_3$): 7.98 (d, J=8.2 Hz, 1H), 7.56 (dd, J=1.5, 8.2 Hz, 1H), 7.45 (s, 1H), 4.71 (m, 1H), 2.94 (m, 2H), 1.55 (d, J=6.3 Hz, 3H). (M+1)$^+$ 241.

Intermediate (S)-7 (Method 2)

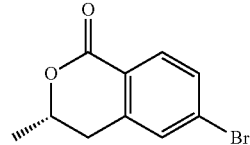

(3 S)-6-Bromo-3-methyl-3,4-dihydro-1H-isochromen-1-one was prepared in a similar manner as (3R)-6-bromo-3-methyl-3,4-dihydro-1H-isochromen-1-one except using keto-reductase enzyme KRED P1H9 (available from Codexis, Inc., 200 Penobscot Drive, Redwood City, Calif. 94063, www.codexis.com, tel. 1-650-421-8100) in Step C. $^1$H NMR (500 MHz; CDCl$_3$): 8.07 (d, J=8.1 Hz, 1H), 7.35 (d, J=8.0 Hz, 1H), 7.28 (s, 1H), 4.72 (dd, J=1.8, 10.5 Hz, 1H), 4.68 (m, 1H), 4.1-3.8 (bs, 2H), 3.96 (dd, J=3.0, 11.3 Hz, 2H), 3.48 (t, J=10.7 Hz, 1H), 2.95 (m, 4H), 2.74 (d, J=10.5 Hz, 1H), 2.2 (m, 3H), 1.54 (d, J=6.2 Hz, 3H), 1.49 (s, 9H). (M+1)$^+$ 403.

Intermediate (3R)-8

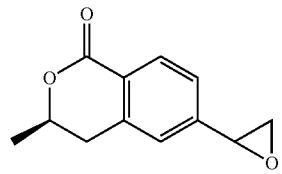

Step A: (3R)-6-ethenyl-3-methyl-3,4-dihydro-1H-isochromen-1-one: A solution of (3R)-6-bromo-3-methyl-3,4-dihydro-1H-isochromen-1-one (2.4 g, 9.96 mmol) and triethylamine (2.78 ml, 19.91 mmol) in EtOH (39.8 ml) was added to a microwave vial containing Cl₂Pd(dppf)₂-DCM (0.406 g, 0.498 mmol) and potassium vinyltrifluoroborate (2.000 g, 14.93 mmol). The contents of the vial were heated to 100° C. for 1 hour after which the mixture was cooled, diluted with chloroform (50 mL) and washed with aqueous ammonium chloride (25 mL). The organic layer was then dried over magnesium sulfate, filtered and the solvent was evaporated under reduced pressure. MPLC purification (15-60% EtOAc/Hex) gave title compound.

Step B: (3R)-3-methyl-6-(oxiran-2-yl)-3,4-dihydro-1H-isochromen-1-one: A solution of 6-ethenyl-3-methyl-3,4-dihydro-1H-isochromen-1-one (1.69 g, 8.98 mmol) in DCM (60 mL) was treated with m-CPBA (3.10 g, 17.96 mmol) overnight at room temperature. The reaction was then diluted with water (50 mL) and DCM (50 mL). The organic layer was further washed successively with saturated aqueous sodium bicarbonate (30 mL), water (30 mL), and brine (30 mL). The organic layer was then dried over magnesium sulfate, filtered and concentrated. The residue was purified via MPLC (15-40% EtOAc/Hex) to give 3-methyl-6-(oxiran-2-yl)-3,4-dihydro-1H-isochromen-1-one. $^1$H NMR (500 MHz; CDCl₃): 8.10 (d, J=8.0 Hz, 1H), 7.33 (m, 1H), 7.16 (d, J=4.4 Hz, 1H), 4.71 (m, 1H), 3.92 (dt, J=1.6, 2.5 Hz, 1H), 3.22 (dt, J=1.4, 4.1 Hz, 1H), 2.96 (m, 2H), 2.80 (dd, J=2.3, 3.5 Hz, 1H), 1.55 (d, J=7.6 Hz, 3H); LC/MS (M+H)⁺ 205.

Intermediate (3S)-8

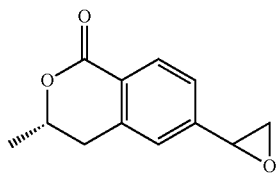

(3S)-3-Methyl-6-(oxiran-2-yl)-3,4-dihydro-1H-isochromen-1-one was prepared in an analogous fashion to that described for the synthesis of (3R)-3-methyl-6-(oxiran-2-yl)-3,4-dihydro-1H-isochromen-1-one except starting from (3S)-6-bromo-3-methyl-3,4-dihydro-1H-isochromen-1-one.

Intermediate 9

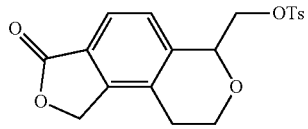

Step A: 5-bromo-4-iodo-2-benzofuran-1(3H]-one: To a solution of 5-bromo-2-benzofuran-1(3H)-one (5.00 g, 23.5 mmol) at 0° C. in TfOH (100 mL) was added NIS (5.55 g, 24.6 mmol). The mixture was stirred at room temperature over night; LC analysis of the reaction mixture indicated completion of the reaction. The reaction mixture was then poured slowly into ice-water (1 L) with stirring. To the solution was then added EtOAc (500 mL) and subsequently stirred for 10 min. The mixture was filtered and the organic layer separated. The aqueous layer was extracted with EtOAc (2×200 mL). The combined organic layers were washed with water (500 mL), brine (500 mL), dried over Na₂SO₄, filtered, concentrated to dryness; it was absorbed into silica gel and separated with the solvent systems of (hexanes/EtOAc=1/1) to yield title compound.

Step B: 5-bromo-4-prop-2-en-1-yl-2-benzofuran-1(3H)-one: A mixture of 5-bromo-4-iodo-2-benzofuran-1(3H]-one (2.42 g, 7.13 mmol), allyltributyltin (2.36 g, 7.13 mmol), LiCl (1.50 g, 35.7 mmol) and Pd(PPh₃)₄ (200 g, 0.173 mmol) in toluene (50 mL) was heated at 90-100° C. under N₂ overnight; LC indicated that reaction had gone to completion, to the solution was poured EtOAc (100 mL) and washed with brine. The organic layer was dried over Na₂SO₄, filtered and concentrated to dryness, absorbed into silica gel and was then separated over silica gel column to give title compound.

Step C: 5-bromo-4-(2-hydroxyethyl)-2-benzofuran-1(3H)-one: To a solution of 5-bromo-4-prop-2-en-1-yl-2-benzofuran-1(3H)-one (1.27 g, 5.02 mmol) in MeOH (50 mL) and DCM (50 mL) was bubbled O₃ at −78° C. until the solution turned blue; excess ozone was removed on high vacuum. After the solution's color changed into colorless, NaBH₄ (0.8 g, 20 mmol) was added to the reaction mixture and subsequently stirred at room temperature for 30 min; LC and TLC indicated that reaction had gone to completion; solvent was removed on high vacuum, the residue was then re-dissolved in EtOAc and washed with water, dried over Na₂SO₄, filtered and concentrated to dryness. The organic residue was absorbed into silica gel and was separated on silica gel column to give title compound.

Step D: 5-ethenyl-4-(2-hydroxyethyl)-2-benzofuran-1(3H)-one: A mixture of 5-bromo-4-(2-hydroxyethyl)-2-benzofuran-1(3H)-one (0.460 g, 1.78 mmol), tributyl(vinyl)tin (0.676 g, 2.13 mmol), LiCl (0.224 g, 5.33 mmol) and Pd(PPh₃)₄ (0.10 g, 0.087 mmol) in toluene (50 mL) was heated at 100-110° C. under N₂ overnight; TLC indicated that reaction had gone to completion and to the solution was poured EtOAc (100 mL) and washed with brine, water, dried over Na₂SO₄, filtered and concentrated to dryness. The residue was then absorbed into silica gel and separated over silica column to give title compound.

Step E: 4-(2-hydroxyethyl)-5-oxiran-2-yl-2-benzofuran-1(3H)-one: 5-Ethenyl-4-(2-hydroxyethyl)-2-benzofuran-1(3H)-one (1.2 g, 5.9 mmol) was added to a flask containing a stir bar. To the flask was then added dichloromethane (20 mL). The flask was placed in a cool bath of 0° C.; to the flask was poured m-CPBA (1.5 g, 8.8 mmol) and the resulting mixture was stirred at room temperature for overnight; LC as well as TLC (hexanes/EtOAc=1/1) indicated that reaction had gone to completion. The solution was treated with dichloromethane and washed with NaHCO₃, Na₂S₂O₃, and water, the organic layer was then dried over Na₂SO₄, filtered and concentrated to dryness, it was then treated with AcOH (20 mL) and stirred overnight; LC indicated formation of cyclized product. The solvent was removed and the resulting residue was absorbed into silica gel and the title compound was isolated with the solvent systems of hexane/EtOAc (1/1).

Step F: (3-oxo-3,6,8,9-tetrahydro-1H-furo[3,4-f]isochromen-6-yl)methyl-4-methylbenzenesulfonate: 6-(Hydroxymethyl)-8,9-dihydro-1H-furo[3,4-f]isochromen-3(6H)-one, in DCM (10 mL) was treated with p-Toluenesulfonyl chloride (0.40 g, 2.3 mmol); to the mixture was added pyridine (2 mL) and the resulting mixture stirred at room temperature for 12 h. TLC (hexanes/EtOAc=1/0.5) and LC indicated the consumption of starting material and formation of the desired product. Reaction mixture was treated with dichloromethane and washed with NaCl, water and dried over Na$_2$SO$_4$, filtered and concentrated to dryness, absorbed into silica gel and was then subjected for purification over silica gel; the title compound was isolated with the solvent system of hexane/EtOAc (1/0.5). $^1$H-NMR (400 MHz, CDCl$_3$) δ ppm 7.781 (d, J=8 Hz, 1H), 7.727 (d, J=8 Hz, 1H), 7.367 (d, J=8 Hz, 1H), 7.257 (d, J=8.5 Hz, 1H), 7.206 (d, J=8 Hz, 1H), 5.253 (s, 2H), 5.110 (s, 1H), 4.481-4.452 (m, 2H), 4.419-4.385 (m, 2H), 4.196-4.153 (m, 2H), 2.495 (s, 3H).

Intermediate 10

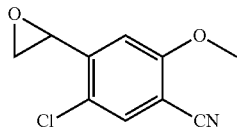

Step A: Di-t-Butyl 2-(2-chloro-4-cyano-5-fluorophenyl)malonate: To sodium hydride (60% in mineral oil, 3.75 g, 94 mmol) under nitrogen was added dry DMF (150 mL) and the suspension was cooled in an ice bath. Di-t-butyl malonate (8.1 g, 37.5 mmol) was added dropwise over 15 minutes via syringe with hydrogen evolution. The suspension was stirred for 30 minutes after which time 5-chloro-2,4-difluorobenzonitrile (5.0 g, 28.8 mmol) in DMF (10 mL) was added dropwise over 15 minutes and the reaction was heated to 80° C. for 12 hours when TLC (15% ethyl acetate/hexanes) indicated mostly product. The reaction was diluted with ether and quenched into water containing aq. ammonium chloride. The mixture was extracted twice with ethyl acetate and the organic layers were washed with brine, dried over sodium sulfate and concentrated in vacuo. The residue was purified on silica gel (2-10% ethyl acetate/hexanes) to give the title product. NMR indicated about a 6:1 mixture of product and the isomeric di-t-butyl, 2-(4-chloro-2-cyano-5-fluorophenyl)malonate.

Step B: methyl (2-chloro-4-cyano-5-fluorophenyl)acetate: A solution of di-tert-butyl 2-(2-chloro-4-cyano-5-fluorophenyl)malonate (9.10 g, 24.6 mmol) in 1:2 TFA:dichloromethane (25:50 mL) was stirred at RT for 3 hours and then concentrated in vacuo to give a solid (5.05 g) after twice evaporating toluene. An aliquot of 4 g of solid was taken up in 1:1 methanol:dichloromethane (50 mL) and 2M trimethylsilyldiazomethane in ether was added until the yellow color persisted. Excess diazomethane was quenched with acetic acid and the mixture was concentrated. The residue was purified by flash chromatography (5-15% ethyl acetate/hexane containing 5% DCM for solubility) to give separation from the higher R$_f$ 4-chloro-2-cyano-5-fluorophenyl isomer and still impure title product isomer. Flash chromatography was repeated (50-100% DCM/hexane) to afford clean title product.

Step C: methyl (2-chloro-4-cyano-5-methoxyphenyl)acetate: A solution of methyl (2-chloro-4-cyano-5-fluorophenyl)acetate (1.40 g, 6.15 mmol) in methanol (30 mL) was divided into two 20 mL microwave vials. Potassium carbonate (2×850 mg) was added to each vial. Each was heated in a microwave at 130° C. for 60 minutes at which time HPLC/MS indicated no starting material was left and the product was all hydrolyzed to the acid. Most of the methanol was removed in vacuo and the residue was diluted with water, acidified with 2M HCl and the mixture was extracted twice with ethyl acetate. The organic layers were washed with brine, dried over sodium sulfate and concentrated in vacuo. The crude product was taken up in 1:1 methanol:dichloromethane (50 mL) and 2M trimethylsilyldiazomethane in ether was added until the yellow color persisted to re-esterify the acid. The excess diazomethane was quenched with acetic acid and the mixture was concentrated. Flash chromatography (40% DCM/hexanes to 100% DCM) gave the methyl (2-chloro-4-cyano-5-methoxyphenyl)acetate.

Step D: 2-(2-chloro-4-cyano-5-methoxyphenyl)ethanol: To a solution of methyl (2-chloro-4-cyano-5-methoxyphenyl)acetate (200 mg, 0.835 mmol) in THF (5 mL) was added 2M lithium borohydride (0.835 mL, 1.67 mmol) and the reaction was stirred at RT for 16 hours. The reaction was diluted with ether and quenched into water containing 2N HCl. The mixture was extracted twice with ethyl acetate and the organic layers were washed with brine, dried over sodium sulfate and concentrated in vacuo. The product mixture was separated by MPLC (40+S; 20-60% ethyl acetate/hexane) to afford the title product.

Step E: 2-(2-chloro-4-cyano-5-methoxyphenyl)ethyl methanesulfonate: A solution of 2-(2-chloro-4-cyano-5-methoxyphenyl)ethanol (205 mg, 0.969 mmol) DIPEA (0.846 mL, 4.84 mmol) and pyridine (0.0780 mL, 0.969 mmol) in DCM (3 mL) was treated dropwise with mesyl chloride (0.110 mL, 1.42 mmol). The reaction was stirred for 2 hours and was then diluted with DCM and washed twice with aq. citric acid, then washed with brine, and dried over sodium sulfate. Purification of the residue by flash chromatography (20-50% ethyl acetate/hexane) afforded the title intermediate.

Step F: (2-chloro-4-cyano-5-methoxyphenyl)ethylene: A solution of 2-(2-chloro-4-cyano-5-methoxyphenyl)ethyl methanesulfonate (274 mg, 0.945 mmol) in DCM (4 mL) was treated with DBU (0.712 mL, 4.73 mmol) and stirred for 3 hours at 50° C., then at RT for 12 hours. TLC (50% ethyl acetate/hexane) showed complete conversion to a faster intense UV band for the product. The reaction was then diluted with DCM and aq. citric acid and the mixture was extracted twice with DCM. The organic layers were washed with brine, dried over sodium sulfate and concentrated in vacuo. Purification of the residue by flash chromatography (10-20% ethyl acetate/hexanes) afforded the title intermediate.

Step G: (2-chloro-4-cyano-5-methoxyphenyl)ethylene oxide: A solution of (2-chloro-4-cyano-5-methoxyphenyl)ethylene (130 mg, 0.671 mmol) in DCM (6 mL) was treated with 85% m-CPBA (226 mg, 1.10 mmol) and stirred for 5 hours at RT when another portion of m-CPBA (115 mg) was added. The reaction stirred at room temperature for another 16 hours and was then diluted with DCM and stirred with saturated sodium bicarbonate containing some sodium bisulfite. The mixture was then extracted twice with DCM and the organic layers were washed with another portion of sodium bicarbonate and brine, dried over sodium sulfate and concentrated in vacuo to afford the crude title epoxide. $^1$H-NMR (500 MHz, CDCl$_3$) δ ppm 2.67 (dd, J=2.6, 5.8 Hz, 1H), 3.28 (dd, J=4.1, 5.5 Hz, 1H), 3.95 (s, 3H), 4.22 (dd, J=2.5, 3.9 Hz, 1H), 6.91 (s, 1H), 7.564 (s, 1H).

Intermediate 11

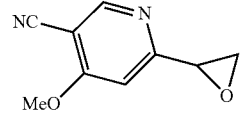 [SMILES: COc1cc(C2CO2)ncc1C#N]

Step A: 5-bromo-2-chloro-4-methoxypyridine: To a solution of 2-chloro-4-methoxypyridine (10.0 g, 69.7 mmol) in 50 mL of sulfuric acid at 0° C. was added NBS. The reaction mixture was allowed to stir and warm up to room temperature for 2 hour and then heated at 60° C. for 5 h. Then it was cooled to room temperature and neutralized with 1 N NaOH (pH~7), diluted with water (50 mL) and the aqueous layer was extracted with ethyl acetate (2×100 mL). The organic layers were washed with water (2×50 mL), sat. NaHCO$_3$, brine, dried over Mg$_2$SO$_4$ and concentrated to provide an oil, which was chromatographed. On elution with 0-25% EtOAc/hexanes, the final product was obtained.

Step B: 6-chloro-4-methoxypyridine-3-carbonitrile: A solution of 5-bromo-2-chloro-4-methoxypyridine (5.0 g, 22.48 mmol) in DMF (80 mL) was purged with nitrogen for 15 min. At this point, Zn(CN)$_2$ (3.96 g, 33.7 mmol) and Pd(Ph$_3$P)$_4$ (2.60 g, 2.25 mmol) were added, successively. The resulting suspension was stirred at 95° C. for 12 h under nitrogen atm. The reaction mixture was cooled to ambient temperature, filtered to remove inorganic solid. The solvent (DMF) was evaporated to provide the crude residue as an oil, which was purified on silica gel and eluted with 0-30% ethyl acetate/hexane to afford the product.

Step C: 6-ethenyl-4-methoxypyridine-3-carbonitrile: A 20 mL microwave tube was charged with 6-chloro-4-methoxypyridine-3-carbonitrile (200.0 mg, 1.2 mmol), bis(diphenylphosphino)ferrocene]dichloropalladium(II), complex with dichloromethane (97.0 mg, 0.12 mmol), potassium vinyl trifluoroborate (318.0 mg, 2.37 mmol), and triethylamine (0.33 mL, 2.37 mmol), and EtOH (6 mL). The microwave tube was evacuated and filled with nitrogen (two times) and heated to 140° C. After 1 h, the reaction mixture was diluted with water and extracted with EtOAc. The combined organic layers were washed with brine and dried over Na$_2$SO$_4$. The extracts were concentrated and chromatographed over a column of SiO$_2$ (0-30% EtOAc/hexane as eluent). Evaporation of the solvent yielded the title compound.

Step D: 6-(2-bromo-1-hydroxyethyl)-4-methoxypyridine-3-carbonitrile: A solution of 6-ethenyl-4-methoxypyridine-3-carbonitrile (80.0 mg, 0.499 mmol) in 1, 4-dioxane (8 mL) and H$_2$O (4 mL) was treated with N-bromosuccinimide (89.0 mg, 0.499 mmol, 1.0 equiv). The reaction mixture was allowed to stir at room temperature overnight. The reaction mixture was poured into H$_2$O (8 mL) and extracted with EtOAc (3×30 mL). The combined organic layers were washed with saturated aqueous NaCl (1×30 mL), dried over Na$_2$SO$_4$. Evaporation of the solvent gave an oil that was purified over SiO$_2$ (0-30% EtOAc/hexane as eluent) the title compound.

Step E: 4-methoxy-6-(oxiran-2-yl)pyridine-3-carbonitrile: A solution of 6-(2-bromo-1-hydroxyethyl)-4-methoxypyridine-3-carbonitrile (74.0 mg, 0.288 mmol) in anhydrous methanol (7 mL) was treated with sodium carbonate (61.0 mg, 0.576 mmol, 2.0 equiv), and allowed to stir at room temperature overnight. The solvent was evaporated. The residue was taken up in EtOAc (30 mL) and washed with water and brine. After drying over Na$_2$SO$_4$, the organic layer was removed and the residue was purified over SiO$_2$ (10-45% EtOAc/hexane) to yield title compound. $^1$H NMR (500 MHz, DMSO-d$_6$), δ 8.64 (s, 1H), 6.87 (s, 1H), 4.08 (dd, J=2.6 Hz, J=2.3 Hz, 1H), 4.03 (s, 3H), 3.26 (dd, J=4.6 Hz, J=5.4 Hz, 1H), 2.87 (dd, J=2.2 Hz, J=2.4 Hz, 1H); LC/MS (M+1)$^+$=177.

Intermediate 12

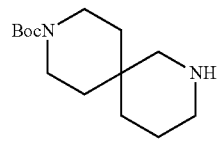

Step A: tert-butyl 4-(hydroxymethyl)piperdinecarboxylate: The mixture of 70 g of LiAlH$_4$ in 1500 mL of THF was cooled to 0° C., then 180 g of 1-tert-butyl 4-methyl piperidine-1,4-dicarboxylate in THF was added dropwise. When the reaction was finished, 200 mL of ethyl acetate and solid anhydrous Na$_2$SO$_4$ were added. Water was added until solution became clear. The mixture was filtered and the filtrate was evaporated to afford title compound.

Step B: tert-butyl 4-formypiperidinecarboxylate: The solution of 200 mL of DMSO in CH$_2$Cl$_2$ cooled to −78° C., 118 mL of (COCl)$_2$ was added drop-wise. Then 255 g of tert-butyl 4-(hydroxymethyl)piperdinecarboxylate was also added drop-wise. The mixture was stirred for 4 h. After the reaction was finished, 638 mL of Et$_3$N was added at −78° C. The organic layer was washed by brine, dried and purified by column chromatography to afford title compound.

Step C: tert-butyl 4-formyl-4-propylpiperidinecarboxylate: tert-Butyl 4-formypiperidinecarboxylat was dissolved in 66 mL of acrylonitrile, and 5 g of 50% aq. sodium hydroxide solution was added. Heated to 50° C., the reaction was finished (TLC). The mixture was then poured into 700 mL of ether. Washed with brine and purified with column chromatography to afford tert-butyl 4-formyl-4-propylpiperidinecarboxylate.

Step D: tert-butyl 3,8-diazaspiro[5,5]undecane-3-carboxylate: The 30 g of tert-butyl 4-formyl-4-propylpiperidinecarboxylate was dissolved in methanol of saturated ammonia, and 15 g of Raney Ni was added. The reaction mixture was heated to 110° C. and allowed to 80 atmospheres in 2 L of high-pressure autoclave. The mixture was filtered to remove the catalyst and the filtrate was concentrated to give residue which was purified by column chromatography to afford tert-butyl 3,8-diazaspiro[5,5]undecane-3-carboxylate.

Intermediate 13

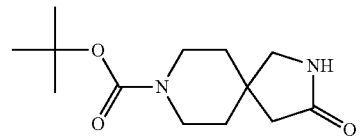 [SMILES: CC(C)(C)OC(=O)N1CCC2(CC1)CNC(=O)C2]

Step A: tert-butyl 4-(2-ethoxy-2-oxoethylidene)piperidine-1-carboxylate: Into a 10-L 4-necked round-bottom flask purged and maintained with an inert atmosphere of nitrogen was placed a suspension of NaH (74.0 g, 2.16 mol 1.05 equiv, 70%) in tetrahydrofuran (2000 mL) at 0° C., then added dropwise ethyl 2-(diethoxyphosphoryl)acetate (514 g, 2.06 mol, 1.05 equiv, 98%) with stirring at 0° C. This was followed by the addition of a solution of tert-butyl 4-oxopiperidine-1-carboxylate (400 g, 1.97 mol, 1.00 equiv, 98%) in tetrahydrofuran (1200 mL) dropwise with stirring at 0° C. The resulting solution was stirred for 60 min at room temperature, then quenched by the addition of 2000 mL of water. The resulting solution was extracted with 2×1000 mL of ethyl acetate. The organic layers were combined, dried over anhydrous magnesium sulfate and concentrated under vacuum. The residue was washed with 1×1000 mL of hexane and dried. This resulted in tert-butyl 4-(2-ethoxy-2-oxoethylidene)piperidine-1-carboxylate.

Step B: tert-butyl 4-(2-ethoxy-2-oxoethyl)-4-(nitromethyl)piperidine-1-carboxylate: Into a 3000-mL 4-necked round-bottom flask were potassium carbonate (93.2 g, 662 mmol, 0.50 equiv) and DMSO (2000 mL). The resulting solution was heated to 80° C. This was followed by the addition of tert-butyl 4-(2-ethoxy-2-oxoethylidene)piperidine-1-carboxylate (368 g, 1.30 mol, 1.00 equiv, 95%) and $CH_3NO_2$ (417 g, 6.70 mol, 5.00 equiv, 98%) slowly. The resulting solution was stirred for 120 min at 90° C. After cooled to room temperature, the reaction mixture was adjusted to Ph 5 with HCl (0.5 mol/L) and diluted with 2000 mL of water. The resulting solution was extracted with 3×1500 mL of ether. The organic layers were combined, washed with 1×2000 mL of water and 1×2000 mL of saturated brine, dried and concentrated under vacuum. The residue was applied onto a silica gel column and eluted with ethyl acetate/petroleum ether (1:20~1:15~1:10) to afford the title compound.

Step C: tert-butyl 3-oxo-2,8-diazaspiro[4.5]decane-8-carboxylate: A mixture of tert-butyl 4-(2-ethoxy-2-oxoethyl)-4-(nitromethyl)piperidine-1-carboxylate (330 g, 990 mmol, 1.00 equiv, 99%) and Ni (40 g, 0.15 equiv) in ethanol (1200 mL) was stirred for 24 h under a hydrogen atmosphere at room temperature. The solid was filtered out. The filtrate was concentrated under vacuum. The crude product was purified by re-crystallization from ether to afford the title compound. LC-MS (ES, m/z): 199 [M+H]+; H-NMR (400 MHz, CDCl3, ppm): 1.447-1.476 (9H, s), 1.597-1.673 (4H, m, J=30.4 Hz), 2.235 (2H, s), 3.226 (2H, s), 3.284-3.348 (2H, m, J=25.6 Hz), 3.507-3.567 (2H, m, J=24 Hz), 6.048 (1H, s).

Intermediate 14

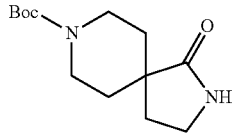 [SMILES: CC(C)(C)OC(=O)N1CCC2(CCNC2=O)CC1]

tert-Butyl 3,8-diazaspiro[5.5]undecane-3-carboxylate compound is commercially available from a number of vendors, for example, Shanghai AQ BioPharma Co., Ltd, catalog #ABP 1882. Alternatively, it may be prepared in various ways, including the procedure described below.

Step A: 1-tert-butyl 4-methyl 4-(cyanomethyl)piperidine-1,4-dicarboxylate: To a solution of commercially available 1-tert-butyl 4-methyl piperidine-1,4-dicarboxylate (200 g, 0.82 mol) in anhydrous THF (2 L) was added LDA (2M in THF, 575 mL, 1.15 mol) drop-wise at −65° C. under $N_2$. The mixture was stirred at −65° C. for 1.5 h. To the mixture was added bromoacetonitrile (148 g, 1.23 mol) in anhydrous THF (500 mL) at −65° C. The mixture was stirred at −65° C. for 1 h, then warmed up to room temperature and stirred overnight. The reaction was quenched with water (800 mL) at 0° C. and the combined reaction mixture was concentrated in vacuum to give a crude product, which was extracted with ethyl acetate (1 L three times). The combined organic phases were washed with brine (1 L) and dried over $Na_2SO_4$. The organic layer was filtered and the filtrate was concentrated under vacuum to give a crude product, which was purified by column chromatography on silica gel eluting with petroleum ether/ethyl acetate (from petroleum ether to 2/1) to give the title compound. $^1$H-NMR (400 MHz, CDCl$_3$) δ 3.900-3.750 (m, 5H), 3.120-3.000 (m, 2H), 2.612-2.562 (m, 2H), 2.190-2.111 (m, 2H), 1.590-1.502 (m, 2H), 1.402 (s, 9H).

Step B: tert-butyl 1-oxo-2,8-diazaspiro[4.5]decane-8-carboxylate: A suspension of 1-tert-butyl 4-methyl 4-(cyanomethyl)piperidine-1,4-dicarboxylate (70.0 g, 247.9 mmol) and Raney Ni (60 g) in MeOH (1500 mL) and $NH_3 \cdot H_2O$ (80 mL) was stirred at 2 MPa of hydrogen pressure at 50° C. for 18 h. The reaction mixture was filtered through a pad of CELITE® and the filtrate was concentrated under vacuum to give a crude product, which was washed with ethyl acetate (200 mL) to give the title compound. $^1$H-NMR (400 MHz, CDCl$_3$) δ 6.05 (s, 1H), 4.0 (s, 2H), 3.37-3.34 (m, 2H), 3.02-2.96 (m, 2H), 2.08-2.05 (m, 2H), 1.88-1.87 (m, 2H), 1.51-1.41 (m, 11H).

Intermediate 15

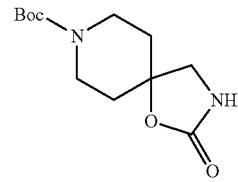 [SMILES: CC(C)(C)OC(=O)N1CCC2(CC1)CNC(=O)O2]

Step A: tert-butyl 4-(2-ethoxy-2-oxoethyl)-4-hydroxypiperidine-1-carboxylate: To a solution of lithium bis(trimethylsilyl)amide (120 mL, 1.0 M solution in THF, 0.12 mol) in THF (120 mL) at −78° C. was added ethyl acetate (13 mL); then, a solution of tert-butyl 4-oxopiperidine-1-carboxylate (20 g, 0.1 mol) in THF (80 mL) was added at −78° C. After the addition, the mixture was warmed up to 0° C. and stirred for another 2 h. The aqueous layer was extracted with ethyl acetate; the organic phase was washed with brine, dried over $Na_2SO_4$ and concentrated to afford the crude title compound.

Step B: 2-(1-(tert-butoxycarbonyl)-4-hydroxypiperidin-4-yl)acetic acid: A solution of tert-butyl 4-(2-ethoxy-2-oxoethyl)-4-hydroxypiperidine-1-carboxylate (30.0 g, 0.105 mol) in methanol (130 mL) and 2N NaOH solution (100 mL, 0.2 mol) was stirred at 25° C. for 1.5 h, then the mixture was evaporated and the aqueous layer was extracted with ethyl acetate. The water phase was adjusted to pH 6 with 2N HCl, the aqueous layer was extracted with ethyl acetate, then the organic phase was washed with brine, dried over $Na_2SO_4$ and concentrated to afford the crude title compound.

Step C: tert-butyl 2-oxo-1-oxa-3,8-diazaspiro[4.5]decane-8-carboxylate: A mixture of 2-(1-(tert-butoxycarbonyl)-4-hydroxypiperidin-4-yl)acetic acid (22 g, 0.085 mol), DPPA (30 g, 0.11 mol), Et$_3$N (150 mL) in Toluene (400 mL) was stirred at 105° C. under nitrogen for 12 h. The reaction mixture was quenched by the addition of the saturated aqueous NaHCO$_3$, the organic phase was washed with brine, dried over Na$_2$SO$_4$, the mixture was concentrated to remove most of toluene, then ether was added and filtered. The filter cake was washed with ether, the solid was dried under vacuum to afford the pure title compound. $^1$H NMR (300

MHz, CDCl₃) δ: 5.35 (brs, 1H), 3.83-3.85 (m, 2H), 3.26-3.35 (m, 4H), 1.93-1.97 (m, 2H), 1.68-1.75 (m, 2H), 1.46 (s, 9H).

Intermediate 16

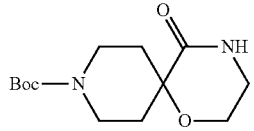 [SMILES: CC(C)(C)OC(=O)N1CCC2(CC1)OCCNC2=O]

Step A: 1-tert-butyl 4-methyl 4-(allyloxy)piperidine-1,4-dicarboxylate: NaH (0.92 g, 15.4 mol, 60% dispersion in mineral oil) was added the five portions to a stirred solution of compound 1-tert-butyl 4-methyl 4-hydroxypiperidine-1,4-dicarboxylate (2 g, 7.7 mmol) being cooled to 0° C. in DMF (20 mL). After the mixture was stirred at 0° C., the 3-allyl bromide (1.2 g, 10 mmol) was added, dropwise. The mixture was stirred at rt for 16 h. The reaction mixture was quenched by the addition of the saturated aqueous NH₄Cl and evaporated to afford the crude product. The crude product was purified by column chromatography on silica gel eluted with (PE/EA 50:1→30:1→15:1) to give the title compound.

Step B: 1-tert-butyl 4-methyl 4-(2-oxoethoxy)piperidine-1,4-dicarboxylate: To a solution of 1-tert-butyl 4-methyl 4-(allyloxy)piperidine-1,4-dicarboxylate (1.2 g, 4 mmol) in MeOH (30 mL) was added osmium tetroxide (30 uL, 0.006 mmol, 0.81 g/mL H₂O) and sodium periodate (16 ml, 16 mmol, 1M). The mixture was allowed to stir at rt for 16 hours. The mixture was quenched with Na₂S₂O₃ (50 mg), extracted with ethyl acetate (20 mL×3), dried over Na₂SO₄ and concentrated to afford the crude product, which was further purified by column chromatography on silica gel eluted with (PE/EA 20:1→10:1→5:1→1:1) to give the title compound.

Step C: 1-tert-butyl 4-methyl 4-(2-(dibenzylamino) ethoxy)piperidine-1, 4-dicarboxylate: To a stirred solution of 1-tert-butyl 4-methyl 4-(2-oxoethoxy)piperidine-1,4-dicarboxylate (0.3 g, 1 mmol) in DCE (5 mL) was added dibenzyl amine (0.3 g, 1.5 mmol), the resulted mixture was stirred at room temperature for 1 h. Then sodium triacetoxyborohydride (0.42 g, 2 mmol) was added to the reaction mixture, the reaction mixture was stirred for further 4 h at room temperature. The mixture was quenched with water (5 mL), extracted with DCM (5 mL×3), the combined organic portions were concentrated and purified by column chromatography gel eluted with (PE/EA 5:1→2:1→1:1) to give the title compound.

Step D: tert-butyl 5-oxo-1-oxa-4,9-diazaspiro[5.5]undecane-9-carboxylate: A mixture of 1-tert-butyl 4-methyl 4-(2-(dibenzylamino)ethoxy)piperidine-1,4-dicarboxylate (290 mg, 0.6 mmol) and 10% palladium hydroxide on carbon (20%, w/w, 30 mg) in MeOH (10 mL) was hydrogenated under 40 psi of hydrogen at 30° C. overnight. Then the mixture was cooled to room temperature and the catalyst was filtered off. The filtrate was concentrated in vacuo to give title compound.

Intermediate 17

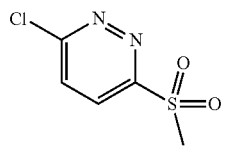

Step A: 3-chloro-6-(methyl sulfanyl)pyridazine: A stirred solution of 3,6-dichloropyridazine (7.4 g, 50 mmol) in DMF (15 mL) was treated with sodium thiomethoxide (3.5 g, 50 mmol). After 2 h, the solution was diluted with brine and extracted with EtOAc. The organic layer was removed, dried over MgSO₄, filtered and concentrated giving rise to an oil. The oil was used crude in next step.

Step B: 3-chloro-6-(methylsulfonyl)pyridazine: A solution of 3-chloro-6-(methylsulfanyl)pyridazine (530 mg, 3.3 mmol) was dissolved in MeOH (15 mL) and treated with a solution of oxone (6.1 g, 9.9 mmol) in H₂O (15 mL). Upon completion of the reaction, the solution was filtered to remove solid and the aqueous filtrate was extracted with 3:1 CHCl₃:IPA. The desired sulfone was isolated as a solid with no further purification required. LCMS: m/z 193.08 (M+H)⁺.

Intermediate 18

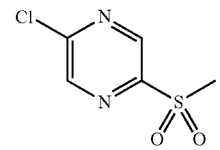

Step A: 2-chloro-5-(methylsulfanyl)pyrazine: A stirred solution of 2,5-dichloropyrazine (1.6 g, 11 mmol) in DMF (15 mL) was treated with sodium thiomethoxide (0.8 g, 12 mmol). After 2 h, the solution was diluted with brine and extracted with EtOAc. The organic layer was removed, dried over MgSO₄, filtered and concentrated giving rise to an oil. The oil was used crude in next step.

Step B: 2-chloro-5-(methylsulfonyl)pyrazine: A solution of 2-chloro-5-(methylsulfanyl)pyrazine (2.2 g, 14 mmol) was dissolved in MeOH (15 mL) and treated with a solution of oxone (17 g, 28 mmol) in H₂O (50 mL). Upon completion of the reaction, the solution was filtered to remove solid and the aqueous filtrate was extracted with 3:1 CHCl₃:IPA. The desired sulfone was isolated as a solid with no further purification required. ¹H NMR (500 MHz, (CD₃)₂CO) δ 3.30 (s, 3H) 8.94 (s, 1H), 9.04 (s, 1H).

Intermediate 19

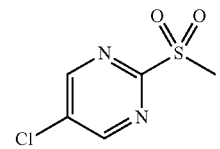

Step A: 5-chloro-2-(methylsulfanyl)pyrimidine: A stirred solution of 2,5-dichloropyrimidine (2.0 g, 13 mmol) in DMF (10 mL) was treated with sodium thiomethoxide (1.0 g, 15 mmol). After 2 h, the solution was diluted with brine and extracted with EtOAc. The organic layer was removed, dried over MgSO$_4$, filtered and concentrated giving rise to an oil. The oil was used crude in next step.

Step B: 5-chloro-2-(methylsulfonyl)pyrimidine: A solution of 5-chloro-2-(methylsulfanyl)pyrimidine (0.6 g, 3.9 mmol) was dissolved in MeOH (15 mL) and treated with a solution of oxone (7.2 g, 12 mmol) in H$_2$O (50 mL). Upon completion of the reaction, the solution was filtered to remove solid and the aqueous filtrate was extracted with 3:1 CHCl$_3$:IPA. The desired sulfone was isolated as a solid with no further purification required. LCMS: m/z 193.02 (M+H)$^+$.

Intermediate 20

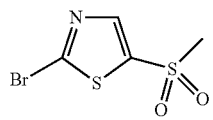

Step A: 5-(methylsulfanyl)-1,3-thiazol-2-amine: A solution of 5-bromo-1,3-thiazol-2-amine (5 g, 28 mmol) and sodium thiomethoxide (2.3 g, 34 mmol) in DMF (25 mL) was heated to 50° C. After 24 h, LC/MS indicated mostly complete conversion. The solution was diluted with brine and extracted with EtOAc. The EtOAc layer was removed, dried over MgSO$_4$, filtered and concentrated giving rise to an oil. The oil was purified using a 100 g Biotage® SNAP cartridge (0-80% EtOAc:hexanes) to yield 5-(methylsulfanyl)-1,3-thiazol-2-amine. LCMS: m/z 146.90 (M+H)$^+$.

Step B: 2-bromo-5-(methylsulfanyl)-1,3-thiazole: A stirred solution of 5-(methylsulfanyl)-1,3-thiazol-2-amine (1.1 g, 7.9 mmol) dissolved in acetonitrile (100 mL) was treated with tert-butyl nitrite (1.9 mL, 15 mmol) followed by CuBr$_2$ (3.5 g, 15 mmol). A dark colored solution ensued which was stirred at 0° C. After 2 h, TLC and LC/MS analysis indicated complete conversion. The solution was diluted with brine and extracted with EtOAc. The organic layer was removed, dried over MgSO$_4$, filtered and concentrated giving rise to an oil. The oil was purified using a 100 g Biotage® SNAP cartridge (0-100% EtOAc). LCMS: m/z 209.95 (M+H)$^+$.

Step C: 2-bromo-5-(methylsulfonyl)-1,3-thiazole: 2-Bromo-5-(methylsulfanyl)-1,3-thiazole (0.6 g, 3.0 mmol) was dissolved in dichloromethane (15 mL) and treated with MCPBA (1.5 g, 9.0 mmol) at rt. After 20 mins, TLC and LC/MS analysis indicated complete conversion. The solution was diluted with 2N sodium carbonate solution and stirred vigorously. The organic layer was removed, dried over MgSO$_4$, filtered and concentrated giving rise to an oil. The oil was purified using a 50 g Biotage® SNAP cartridge (0-60% EtOAc). $^1$H-NMR (500 MHz, ((CD$_3$)$_2$CO) δ ppm 3.40 (s, 3H), 8.20 (s, 1H). LCMS: m/z 243.84 (M+H)$^+$.

Intermediate 21

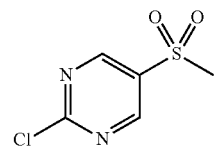

To a solution of 2-chloro-5-(methylthio)pyrimidine (120 mg, 0.75 mmol) in DCM was added m-CPBA (320 mg, 1.9 mmol). The mixture was allowed to stir vigorously at RT for 2 hours. LC showed formation of the desired product. To the reaction was added saturated NaHCO$_3$, and the aqueous phase was extracted twice with DCM. The extractions were combined and concentrated, and the residue was purified by MPLC to furnish 2-chloro-5-(methylsulfonyl)pyrimidine as a white solid. LCMS: m/z 193 (M+H)$^+$.

Intermediate 22

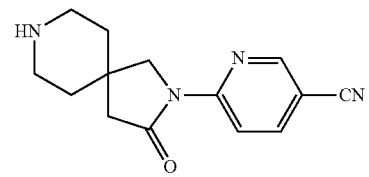 [SMILES: N#Cc1ccc(N2CC3(CCNCC3)CC2=O)nc1]

Step A: tert-butyl 2-(5-cyanopyridin-2-yl)-3-oxo-2,8-diazaspiro[4.5]decane-8-carboxylate: To a 5 mL microwave tube was added copper(I) iodide (67 mg, 0.35 mmol), N1,N2-dimethylcyclohexane-1,2-diamine (101 mg, 0.71 mmol), tert-butyl 3-oxo-2,8-diazaspiro[4.5]decane-8-carboxylate (450 mg, 1.8 mmol), 6-bromonicotinonitrile (486 mg, 2.6 mmol), and K$_3$PO$_4$ (751 mg, 3.54 mmol). The tube was sealed, and dioxane (2 mL) was added via a syringe. The reaction was purged three times with nitrogen before it was heated to 125° C. for 30 minutes in a microwave reactor. The reaction was diluted with EtOAc, washed with brine, concentrated and purified by MPLC to afford the title compound. LCMS: m/z 257 (M−Boc+H)$^+$.

Step B: 6-(3-oxo-2,8-diazaspiro[4.5]decan-2-yl)nicotinonitrile: The above material was further treated with TFA (5 mL) at RT for 30 minutes. The volatiles were removed under reduced pressure. The residue was dissolved in saturated NaHCO$_3$ (20 mL), extracted with chloroform-IPA (3:1) twice. The extracts were combined, dried over sodium sulfate, filtered and concentrated. The resulting solid was used without further purification.

Intermediate 23

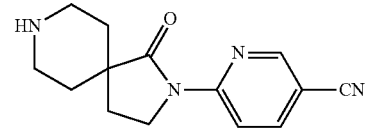 [SMILES: N#Cc1ccc(N2CCC3(CCNCC3)C2=O)nc1]

6-(1-oxo-2,8-diazaspiro[4.5]decan-2-yl)nicotinonitrile was made in an analogous fashion to that described for the synthesis of INTERMEDIATE 22 (6-(3-oxo-2,8-diazaspiro[4.5]decan-2-yl)nicotinonitrile) from tert-butyl 1-oxo-2,8-diazaspiro[4.5]decane-8-carboxylate and 6-bromonicotinonitrile. LCMS: m/z 257 (M+H)⁺.

Intermediate 24

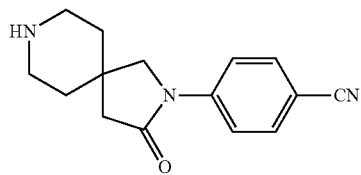 [SMILES: N#Cc1ccc(N2CC3(CCNCC3)CC2=O)cc1]

4-(3-oxo-2,8-diazaspiro[4.5]decan-2-yl)benzonitrile was made in an analogous fashion to that described for the synthesis of INTERMEDIATE 22 (6-(3-oxo-2,8-diazaspiro[4.5]decan-2-yl)nicotinonitrile) from tert-butyl 1-oxo-2,8-diazaspiro[4.5]decane-8-carboxylate and 4-bromobenzonitrile. LCMS: m/z 256 (M+H)⁺.

Intermediate 25

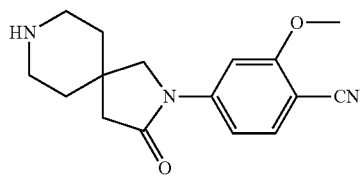 [SMILES: COc1cc(N2CC3(CCNCC3)CC2=O)ccc1C#N]

2-methoxy-4-(3-oxo-2,8-diazaspiro[4.5]decan-2-yl)benzonitrile was made in an analogous fashion to that described for the synthesis of INTERMEDIATE 22 (6-(3-oxo-2,8-diazaspiro[4.5]decan-2-yl)nicotinonitrile) from tert-butyl 1-oxo-2,8-diazaspiro[4.5]decane-8-carboxylate and 4-bromo-2-methoxybenzonitrile. LCMS: m/z 286 (M+H)⁺.

Intermediate 26

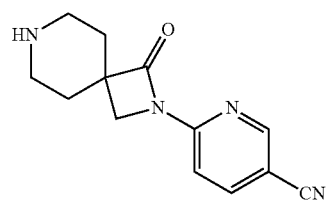 [SMILES: N#Cc1ccc(N2CC3(CCNCC3)C2=O)nc1]

Step A: tert-butyl 2-(5-cyanopyridin-2-yl)-1-oxo-2,7-diazaspiro[3.5]nonane-7-carboxylate: To a 5 mL microwave tube charged with tert-butyl 1-oxo-2,7-diazaspiro[3.5]nonane-7-carboxylate (commercially available from several vendors, for example WuXi AppTec Co., Ltd, catalog #WX100003, 350 mg, 1.5 mmol) and a stir bar was added 6-chloronicotinonitrile (400 mg, 2.9 mmol), K₂CO₃ (300 mg, 2.2 mmol), and DMF (2 mL). The tube was sealed and heated to 150° C. for 15 min. The crude reaction was diluted with EtOAc, washed with water and brine. The organic phase was collected, dried over Na2SO4, filtered and concentrated. The resulting oil was purified by MPLC with hexane and EtOAc. LCMS: m/z 243 (M−Boc+H)⁺.

Step B: 6-(1-oxo-2,7-diazaspiro[3.5]nonan-2-yl)nicotinonitrile: The material from Step A was treated with TFA (5 mL) at RT for 30 minutes. The volatiles were removed under reduced pressure. The residue was dissolved in saturated NaHCO₃ (20 mL), extracted with chloroform-IPA (3:1) twice. The extracted were combined, dried over sodium sulfate, filtered and concentrated. The resulting solid was used directly.

Intermediate 27

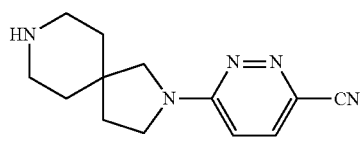 [SMILES: N#Cc1ccc(N2CCC3(CCNCC3)C2)nn1]

6-(2,8-diazaspiro[4.5]decan-2-yl)pyridazine-3-carbonitrile was prepared using an analogous procedure to that used for the preparation of INTERMEDIATE 26 (6-(1-Oxo-2,7-diazaspiro[3.5]nonan-2-yl)nicotinonitrile) starting from tert-butyl 2,8-diazaspiro[4.5]decane-8-carboxylate (commercially available from many vendors, for example AstaTech, Inc. catalog #11097) and 6-chloropyridazine-3-carbonitrile and using DIEA as the base (3 equivalents). LCMS: m/z 244 (M+H)⁺.

Intermediate 28

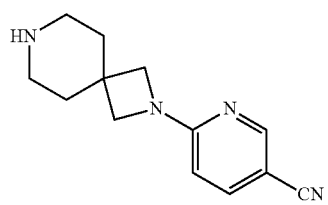 [SMILES: N#Cc1ccc(N2CC3(CCNCC3)C2)nc1]

Step A: tert-butyl2-(5-cyanopyridin-2-yl)-2,7-diazaspiro[3.5]nonane-7-carboxylate: tert-Butyl 2,7-diazaspiro[3.5]nonane-7-carboxylate (commercially available from numerous vendors, for example, AstaTech, Inc., catalog #52326; 100 mg, 0.442 mmol) and 6-bromopyridine-3-carbonitrile (81 mg, 0.44 mmol) were combined with K₃PO₄ (188 mg, 0.884 mmol), Pd₂(dba)₃ (20.2 mg, 0.022 mmol), and X-phos (31.6 mg, 0.066 mmol) in dioxane (2.2 mL) and heated under an atmosphere of nitrogen at 120° C. using a microwave apparatus for 12 minutes. The crude product was isolated by an aqueous workup and was purified by MPLC (10-50% gradient of EtOAc/Hex).

Step B: 6-(2,7-diazaspiro[3.5]non-2-yl)pyridine-3-carbonitrile: The tert-butyl 2,7-diazaspiro[3.5]nonane-7-carboxylate was stirred in 5:1 DCM:4N HCl/dioxane for 30 minutes. The excess solvent was removed and the residue was suspended in chloroform/1N NaOH and stirred for an additional 20 minutes. The layers were separated and the aqueous phase was further extracted with chloroform. The combined extracts were dried over magnesium sulfate, filtered and concentrated to afford the title compound.

Intermediate 29

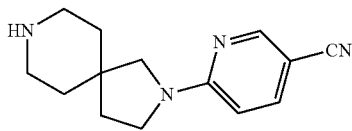 [SMILES: N#Cc1ccc(N2CCC3(CCNCC3)C2)nc1]

Step A: tert-Butyl 2-(5-cyanopyridin-2-yl)-2,8-diazaspiro[4.5]decane-8-carboxylate: To a solution of tert-butyl 2,8-diazaspiro[4.5]decane-8-carboxylate (commercially available from multiple vendors, for example AstaTech, Inc. catalog #11097; 0.15 g, 0.6 mmol) in DMF (10 mL) was added 6-chloropyridine-3-carbonitrile (0.9 g, 0.6 mmol) followed by Hunig's base (0.2 mL, 1.2 mmol). The resulting solution was heated in a microwave reactor to 130° C. for 45 min. Upon completion of the reaction as judged by TLC and LC/MS analysis, the solution was diluted with $H_2O$, extracted with EtOAc, washed with brine (3×), dried over $MgSO_4$, filtered, concentrated to afford the title compound.

Step B: 6-(2,8-diazaspiro[4.5]dec-2-yl)pyridine-3-carbonitrile: The tert-butyl-9-(5-cyanopyridin-2-yl)-3,9-diazaspiro[5.5]undecane-3-carboxylate was treated with 5 mL of 4N HCl at room temp for 1 h giving rise to 6-(2,8-diazaspiro[4.5]dec-2-yl)pyridine-3-carbonitrile. The resulting HCl salt was dissolved in aqueous $NaHCO_3$, extracted with IPA-Chloform (3:1), dried over sodium sulfate, and concentrated to the title compound. LCMS: m/z 243.28 $(M+H)^+$.

Intermediate 30

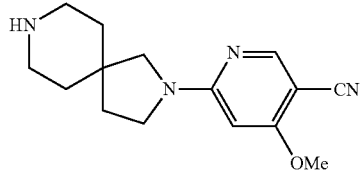 [SMILES: COc1cc(N2CCC3(CCNCC3)C2)ncc1C#N]

4-methoxy-6-(2,8-diazaspiro[4.5]decan-2-yl)nicotinonitrile was made following the same procedure of INTERMEDIATE 29 (6-(2,8-diazaspiro[4.5]decan-2-yl)nicotinonitrile) from tert-butyl 2,8-diazaspiro[4.5]decane-8-carboxylate (commercially available from multiple vendors, for example AstaTech, Inc. catalog #11097) and 6-chloro-4-methoxynicotinonitrile. LCMS: m/z 273 $(M+H)^+$.

Intermediate 31

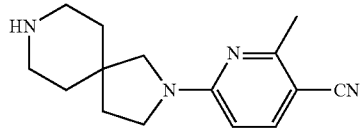 [SMILES: Cc1nc(N2CCC3(CCNCC3)C2)ccc1C#N]

2-methyl-6-(2,8-diazaspiro[4.5]decan-2-yl)nicotinonitrile was made following the same procedure of INTERMEDIATE 29 (6-(2,8-diazaspiro[4.5]decan-2-yl)nicotinonitrile) from tert-butyl 2,8-diazaspiro[4.5]decane-8-carboxylate (commercially available from multiple vendors, for example AstaTech, Inc. catalog #11097) and 6-bromo-2-methylnicotinonitrile. LCMS: m/z 257 $(M+H)^+$.

Intermediate 32

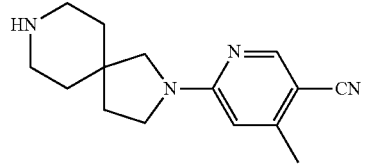 [SMILES: Cc1cc(N2CCC3(CCNCC3)C2)ncc1C#N]

4-methyl-6-(2,8-diazaspiro[4.5]decan-2-yl)nicotinonitrile was made following the same procedure of INTERMEDIATE 29 (6-(2,8-diazaspiro[4.5]decan-2-yl)nicotinonitrile) from tert-butyl 2,8-diazaspiro[4.5]decane-8-carboxylate (commercially available from multiple vendors, for example AstaTech, Inc. catalog #11097) and 6-bromo-4-methylnicotinonitrile. LCMS: m/z 257 $(M+H)^+$ Intermediate 33

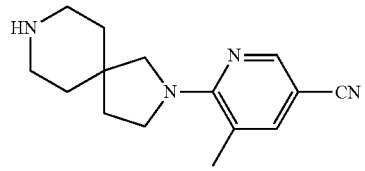 [SMILES: Cc1cc(C#N)cnc1N1CCC2(CCNCC2)C1]

5-methyl-6-(2,8-diazaspiro[4.5]decan-2-yl)nicotinonitrile was made following the same procedure of INTERMEDIATE 29 (6-(2,8-diazaspiro[4.5]decan-2-yl)nicotinonitrile) from tert-butyl 2,8-diazaspiro[4.5]decane-8-carboxylate (commercially available from multiple vendors, for example AstaTech, Inc. catalog #11097) and 6-bromo-5-methylnicotinonitrile. LCMS: m/z 257 $(M+H)^+$.

Intermediate 34

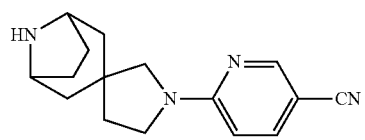 [SMILES: N#Cc1ccc(N2CCC3(CC4CCC(C3)N4)C2)nc1]

Step A: tert-butyl 1'-(5-cyanopyridin-2-yl)-8-azaspiro[bicyclo[3.2.1]octane-3,3'-pyrrolidine]-8-carboxylate: To a microwave tube was added tert-butyl 8-azaspiro[bicyclo[3.2.1]octane-3,3'-pyrrolidine]-8-carboxylate (PCT Int. Appl. (2011), WO 2011034741 A1 20110324; 150 mg, 0.56 mmol), 6-bromonicotinonitrile (103 mg, 0.56 mmol), $Pd_2(dba)_3$ (26 mg, 0.028 mmol), X-Phos (40 mg, 0.084 mmol), $K_3PO_4$ (240 mg, 1.1 mmol), and dioxane (2.8 mL). The tube was purged with nitrogen before it was heated to 120° C. for 12 minutes in a microwave reactor. The reaction was diluted with EtOAc, washed with water, and separated. The organic layer was dried over Na2SO4, concentrated, and purified by silica gel chromatography. LCMS: m/z 369 $(M+H)^+$.

Step B: 6-(8-azaspiro[bicyclo[3.2.1]octane-3,3'-pyrrolidin]-1'-yl)nicotinonitrile: The product from Step A was treated with TFA (2 mL) at RT for 30 minutes. The volatiles were removed under reduced pressure. The residue was dissolved in saturated NaHCO₃ (10 mL), extracted with chloroform-IPA (3:1) twice. The extracts were combined, dried over sodium sulfate, filtered and concentrated. The resulting title compound was used without further purification.

Intermediate 35

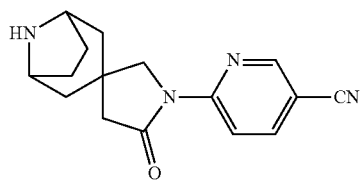 [SMILES: N#Cc1ccc(N2CC3(CC2=O)CC2CCC(C3)N2)nc1]

6-(5'-Oxo-8-azaspiro[bicyclo[3.2.1]octane-3,3'-pyrrolidin]-1'-yl)nicotinonitrile was made following an analogous procedure to that for INTERMEDIATE 34 (6-(8-azaspiro[bicyclo[3.2.1]octane-3,3'-pyrrolidin]-1'-yl)nicotinonitrile) from tert-Butyl 5'-oxo-8-azaspiro[bicyclo[3.2.1]octane-3,3'-pyrrolidine]-8-carboxylate (commercially available from, for example, D-L Chiral Chemicals, LLC, catalog #CP11484) and 6-bromonicotinonitrile, except using Xantphos as the ligand and Cs₂CO₃ as the base. LCMS: m/z 283 (M+H)⁺

Intermediate 36

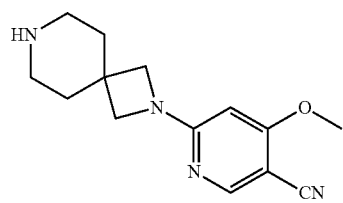 [SMILES: COc1cc(N2CC3(CCNCC3)C2)ncc1C#N]

Step A: tert-Butyl 2-(5-cyano-4-methoxypyridin-2-yl)-2,7-diazaspiro[3.5]nonane-7-carboxylate: To a flask charged with tert-butyl 2,7-diazaspiro[3.5]nonane-7-carboxylate (commercially available from numerous vendors, for example, AstaTech, Inc., catalog #52326; 130 mg, 0.59 mmol) and a stir bar was added 6-chloro-4-methoxynicotinonitrile (100 mg, 0.59 mmol), Pd₂(dba)₃ (27 mg, 0.030 mmol), S-Phos (49 mg, 0.12 mmol), Cs₂CO₃ (580 mg, 1.8 mmol), and THF (10 mL). The mixture was heated at reflux for 16 h. The reaction was diluted with water, and extracted with EtOAc. The extracts were combined, washed with brine, dried over MgSO₄, filtered and concentrated. The crude product was purified by silica gel chromatography. LCMS: m/z 359 (M+H)⁺.

Step B: 4-Methoxy-6-(2,7-diazaspiro[3.5]nonan-2-yl)nicotinonitrile: The intermediate from Step A was treated with 4N HCl (2 mL) at RT for 2 hours. The volatiles were removed under reduced pressure. The residue was dissolved in saturated NaHCO₃ (10 mL), extracted with chloroform-IPA (3:1) twice. The extracted were combined, dried over sodium sulfate, filtered and concentrated. The resulting solid was used without further purification.

Intermediate 37

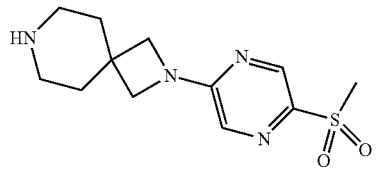 [SMILES: CS(=O)(=O)c1cnc(N2CC3(CCNCC3)C2)cn1]

Step A: tert-butyl 2-(5-(methylsulfonyl)pyrazin-2-yl)-2,7-diazaspiro[3.5]nonane-7-carboxylate: A mixture of tert-butyl 2,7-diazaspiro[3.5]nonane-7-carboxylate (commercially available from numerous vendors, for example, AstaTech, Inc., catalog #52326; 75 mg, 0.33 mmol), 2-Chloro-5-(methylsulfonyl)pyrazine (64 mg, 0.33 mmol), Pd₂(dba)₃ (15 mg, 0.017 mmol), X-Phos (24 mg, 0.050 mmol), K₃PO₄ (140 mg, 0.66 mmol), and dioxane (1.7 mL) in a microwave tube was heated to 120° C. under an atmosphere of nitrogen for 12 minutes. The reaction was diluted with EtOAc, washed with brine, dried over Na₂SO₄, and concentrated. The crude product was purified by silica gel chromatography to furnish the title compound. LCMS: m/z 383 (M+H)⁺

Step B: 2-(5-(Methylsulfonyl)pyrazin-2-yl)-2,7-diazaspiro[3.5]nonane: The intermediate from Step A was treated with 4N HCl (5 mL) in dioxane at RT for 30 minutes. The volatiles were removed under reduced pressure. The residue was dissolved in saturated NaHCO₃ (20 mL), extracted with chloroform-IPA (3:1) twice. The extracted were combined, dried over sodium sulfate, filtered and concentrated. The resulting solid was used without further purification.

Intermediate 38

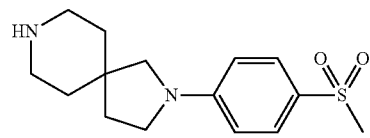 [SMILES: CS(=O)(=O)c1ccc(N2CCC3(CCNCC3)C2)cc1]

2-(4-(Methylsulfonyl)phenyl)-2,8-diazaspiro[4.5]decane was prepared in an analogous fashion as that described for INTERMEDIATE 37 (2-(5-(methylsulfonyl)pyrazin-2-yl)-2,7-diazaspiro[3.5]nonane) from tert-butyl 2,8-diazaspiro[4.5]decane-8-carboxylate (commercially available from multiple vendors, for example AstaTech, Inc. catalog #11097) and 1-bromo-4-(methylsulfonyl)benzene. LCMS: m/z 295 (M+H)⁺.

Intermediate 39

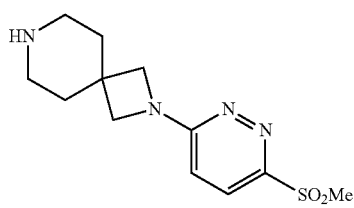 [SMILES: CS(=O)(=O)c1ccc(N2CC3(CCNCC3)C2)nn1]

Step A: tert-butyl-2-[6-(methylsulfonyl)pyridazin-3-yl]-2,7-diazaspiro[3.5]nonane-7-carboxylate: The title compound was prepared in an analogous fashion to that described for INTERMEDIATE 37 (2-(5-(Methylsulfonyl)pyrazin-2-yl)-2,7-diazaspiro[3.5]nonane) using tert-butyl 2,7-diazaspiro[3.5]nonane-7-carboxylate (commercially available from numerous vendors, for example, AstaTech, Inc., catalog #52326) and 3-chloro-6-(methylsulfonyl)pyridazine.

Step B: 2-[6-(methylsulfonyl)pyridazin-3-yl]-2,7-diazaspiro[3.5]nonane: The tert-butyl-2-[6-(methylsulfonyl)pyridazin-3-yl]-2,7-diazaspiro[3.5]nonane-7-carboxylate was treated with 5 mL of 4N HCl at room temp for 1 h giving rise to the title compound.

Intermediate 40

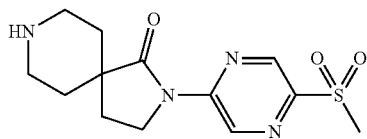 [SMILES: CS(=O)(=O)c1cnc(N2CCC3(CCNCC3)C2=O)cn1]

2-(5-(Methylsulfonyl)pyrazin-2-yl)-2,8-diazaspiro[4.5]decan-1-one was prepared in an analogous fashion to that described for INTERMEDIATE 37 (2-(5-(methylsulfonyl)pyrazin-2-yl)-2,7-diazaspiro[3.5]nonane) from tert-butyl 1-oxo-2,8-diazaspiro[4.5]decane-8-carboxylate and 2-chloro-5-(methylsulfonyl)pyrazine. LCMS: m/z 311 (M+H)$^+$.

Intermediate 41

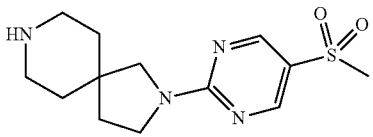 [SMILES: CS(=O)(=O)c1cnc(N2CCC3(CCNCC3)C2)nc1]

Step A: tert-butyl-2-(5-bromopyrimidin-2-yl)-2,8-diazaspiro[4.5]decane-8-carboxylate: A solution of tert-butyl 2,8-diazaspiro[4.5]decane-8-carboxylate (commercially available from multiple vendors, for example AstaTech, Inc. catalog #11097; 2 g, 8.0 mmol) and 5-bromo-2-chloropyrimidine (1.7 g, 9.2 mmol) in DMF (15 mL) were treated with Hunig's base (4.4 mL, 25 mmol). The resulting solution was heated to 150° C. for 10 min in a microwave reactor. The solution was diluted with brine and extracted with EtOAc. The EtOAc layer was removed, dried over MgSO$_4$, filtered, and concentrated. The crude product was purified using a 340 g Biotage® SNAP cartridge (0-100% EtOAc) to yield the title compound. LCMS: m/z 298.99 (M+H–BOC)$^+$.

Step B: tert-butyl-2-[5-(methylsulfanyl)pyrimidin-2-yl]-2,8-diazaspiro[4.5]decane-8-carboxylate: A stirred solution of tert-butyl-2-(5-bromopyrimidin-2-yl)-2,8-diazaspiro[4.5]decane-8-carboxylate (216 mg, 0.5 mmol) in THF (15 mL) was cooled to −78° C. At which point BuLi (0.3 mL, 0.7 mmol, 2.5 M in hexanes) was added giving rise to a yellow solution. The solution was stirred for 30 mins at −78° C. After 30 mins, the dimethyl disulfide (0.07 mL, 0.8 mmol) was added. The solution was warmed to 0° C. The solution was quenched with saturated aqueous NH$_4$Cl solution and allowed to warm to rt. The oil was purified using a 50 g Biotage® SNAP cartridge (0-100% EtOAc:hexanes) to yield the title compound. LCMS: m/z 265.06 (M+H–BOC)$^+$.

Step C: tert-butyl-2-[5-(methylsulfonyl)pyrimidin-2-yl]-2,8-diazaspiro[4.5]decane-8-carboxylate: tert-Butyl-2-[5-(methylsulfanyl)pyrimidin-2-yl]-2,8-diazaspiro[4.5]decane-8-carboxylate (0.02 g, 0.05 mmol) was dissolved in MeOH (15 mL) and treated with a solution of oxone (0.12 g, 0.2 mmol) in H$_2$O (10 mL). Upon completion of the reaction, the solution was filtered to remove solid and the aqueous filtrate was extracted with 3:1 CHCl$_3$:IPA. The desired sulfone was isolated. LCMS: m/z 397.15 (M+H)$^+$.

Step D: 2-(5-(methylsulfonyl)pyrimidin-2-yl)-2,8-diazaspiro[4.5]decane: The intermediate from Step C was treated with 5 mL of 4N HCl at room temp for 1 h giving rise to the title compound.

Intermediate 42

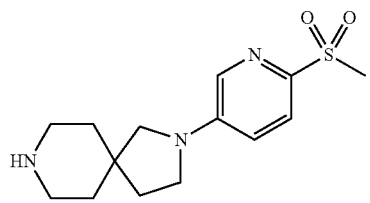 [SMILES: CS(=O)(=O)c1ccc(N2CCC3(CCNCC3)C2)cn1]

Step A: tert-butyl 2-[6-(Methylsulfonyl)pyridin-3-yl]-2,8-diazaspiro[4.5]decane-8-carboxylate:

A stirred solution of 5-bromo-2-(methylsulfonyl)pyridine (0.1 g, 0.5 mmol), tert-butyl 2,8-diazaspiro[4.5]decane-8-carboxylate (commercially available from multiple vendors, for example AstaTech, Inc. catalog #11097; 0.1 g, 0.4 mmol), Pd$_2$dba$_3$ (0.02 g, 0.02 mmol), S-Phos (0.03 g, 0.08 mmol), and Cs$_2$CO$_3$ (0.4 g, 1.2 mmol) in THF (20 mL) were heated to reflux for 12 h. The solution was diluted with H$_2$O and stirred vigorously. The organic layer was removed, dried over MgSO$_4$, filtered and concentrated giving rise to an oil. The oil was purified using a 25 g Biotage SNAP cartridge (7-60% EtOAc:hexanes) giving rise to title compound. LCMS: m/z 396.20 (M+H)$^+$.

Step B: 2-(6-(methylsulfonyl)pyridin-3-yl)-2,8-diazaspiro[4.5]decane: The tert-butyl 2-[6-(Methylsulfonyl) 77yridine-3-yl]-2,8-diazaspiro[4.5]decane-8-carboxylate (128 mg, 0.3 mmol) was treated with 5 Ml of 4N HCl at room temp for 1 h. Excess solvent was then removed on the rotovap and the crude material was then redissolved in 4:1 CHCl$_3$/IPA and treated with 3 mL of 1N NaOH for 5 minutes. The solution was then passed through a SPE column, washing with 4:1 CHCl$_3$/IPA. The eluant was then concentrated to give rise to 2-[6-(methylsulfonyl)77yridine-3-yl]-2,8-diazaspiro[4.5]decane.

Intermediate 43

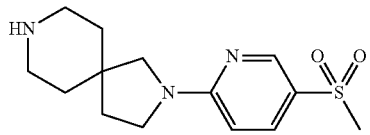 [SMILES: CS(=O)(=O)c1ccc(N2CCC3(CCNCC3)C2)nc1]

2-(5-(methylsulfonyl)pyridin-2-yl)-2,8-diazaspiro[4.5]decane was prepared following the same procedure as INTERMEDIATE 42 (2-[6-(methylsulfonyl)pyridin-3-yl]-2,8-diazaspiro[4.5]decane) from tert-butyl 2,8-diazaspiro[4.5]decane-8-carboxylate (commercially available from multiple vendors, for example AstaTech, Inc. catalog #11097) and 2-bromo-5-(methylsulfonyl)pyridine. LCMS: m/z 296 (M+H)+.

Intermediate 44

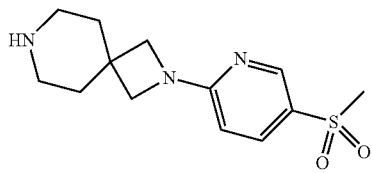 [SMILES: CS(=O)(=O)c1ccc(N2CC3(CCNCC3)C2)nc1]

2-(5-(methylsulfonyl)pyridin-2-yl)-2,7-diazaspiro[3.5]nonane was prepared following the same procedure as INTERMEDIATE 42 (2-[6-(methylsulfonyl)pyridin-3-yl]-2,8-diazaspiro[4.5]decane) from tert-butyl 2,7-diazaspiro[3.5]nonane-7-carboxylate (commercially available from numerous vendors, for example, AstaTech, Inc., catalog #52326) and 2-bromo-5-(methylsulfonyl)pyridine. LCMS: m/z 282 (M+H)+.

Intermediate 45

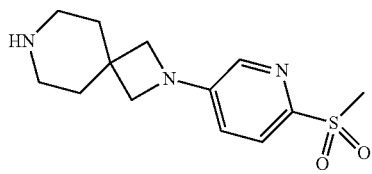 [SMILES: CS(=O)(=O)c1ccc(N2CC3(CCNCC3)C2)cn1]

2-(6-(Methylsulfonyl)78yridine-3-yl)-2,7-diazaspiro[3.5]nonane was prepared following the same procedure as INTERMEDIATE 42 (2-[6-(methylsulfonyl)pyridine-3-yl]-2,8-diazaspiro[4.5]decane) from tert-butyl 2,7-diazaspiro[3.5]nonane-7-carboxylate (commercially available from numerous vendors, for example, AstaTech, Inc., catalog #52326) and 5-bromo-2-(methylsulfonyl)pyridine. LCMS: m/z 282 (M+H)+.

Intermediate 46

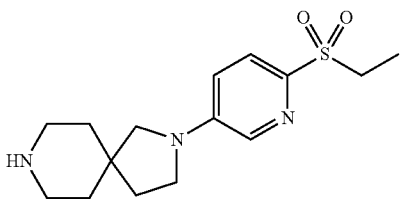 [SMILES: CCS(=O)(=O)c1ccc(N2CCC3(CCNCC3)C2)cn1]

2-[6-(Ethylsulfonyl)pyridin-3-yl]-2,8-diazaspiro[4.5]decane was prepared following the same procedure as INTERMEDIATE 42 (2-[6-(methylsulfonyl)pyridin-3-yl]-2,8-diazaspiro[4.5]decane) from tert-butyl 2,8-diazaspiro[4.5]decane-8-carboxylate (commercially available from multiple vendors, for example AstaTech, Inc. catalog #11097). LCMS: m/z 310 (M+H)+.

Intermediate 47

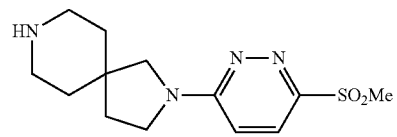 [SMILES: CS(=O)(=O)c1ccc(N2CCC3(CCNCC3)C2)nn1]

Step A: tert-butyl-2-[6-(methylsulfonyl)pyridazin-3-yl]-2,8-diazaspiro[4.5]decane-8-carboxylate:

A solution of tert-butyl 2,8-diazaspiro[4.5]decane-8-carboxylate (0.2 g, 0.8 mmol) and 3-chloro-6-(methylsulfonyl)pyridazine (0.2 g, 0.8 mmol) in DMF (15 mL) were treated with TEA (0.1 mL, 0.8 mmol). The resulting solution was heated to 150° C. for 10 min in a microwave reactor. The solution was diluted with brine and extracted with EtOAc. The EtOAc layer was removed dried over MgSO4, filtered and concentrated giving rise to an oil. The oil was purified on an MPLC (10-50% EtOAc:hexanes) to yield the title compound. LCMS: m/z 397.14 (M+H)+.

Step B: 2-(6-(methylsulfonyl)pyridazin-3-yl)-2,8-diazaspiro[4.5]decane: The intermediate from Step B was treated with 4N HCl at room temp giving rise to the title compound.

Intermediate 48

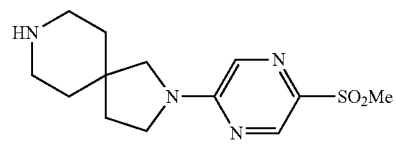 [SMILES: CS(=O)(=O)c1cnc(N2CCC3(CCNCC3)C2)cn1]

2-[5-(methylsulfonyl)pyrazin-2-yl]-2,8-diazaspiro[4.5]decane was prepared following the same procedure as INTERMEDIATE 42 (2-(6-(methylsulfonyl)pyridazin-3-yl)-2,8-diazaspiro[4.5]decane) from tert-butyl 2,8-diazaspiro[4.5]decane-8-carboxylate (commercially available from multiple vendors, for example AstaTech, Inc. catalog #11097) and 2-chloro-5-(methylsulfonyl)pyrazine.

Intermediate 49

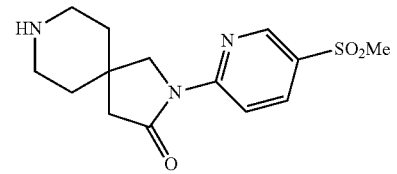 [SMILES: CS(=O)(=O)c1ccc(N2CC3(CCNCC3)CC2=O)nc1]

Step A: tert-butyl 2-[5-(methylsulfonyl)pyridin-2-yl]-3-oxo-2,8-diazaspiro[4.5]decane-8-carboxylate: A stirred solution of 2-bromo-5-(methylsulfonyl)pyridine (0.08 g, 0.3 mmol), tert-butyl-3-oxo-2,8-diazaspiro[4.5]decane-8-carboxylate (0.08 g, 0.3 mmol), Pd2dba3 (0.02 g, 0.02 mmol), Xanthphos (0.02 g, 0.03 mmol), and Cs₂CO₃ (0.2 g, 0.5 mmol) in dioxane (17 mL) were heated to 120° C. for 12 min. The solution was diluted with H₂O and stirred vigorously. The organic layer was removed, dried over MgSO₄, filtered and concentrated. The crude product was purified using a 25 g Biotage® SNAP cartridge (25-90% EtOAc:hexanes) giving rise to title compound. LCMS: m/z 411.17 (M+H)⁺.

Step B: 2-[6-(methylsulfonyl)pyridin-3-yl]-2,8-diazaspiro[4.5]decane: The tert-butyl 2-[5-(methylsulfonyl)pyridin-2-yl]-3-oxo-2,8-diazaspiro[4.5]decane-8-carboxylate was treated with 5 mL of 4N HCl at room temp for 1 h, then concentrated to provide the title compound.

Intermediate 50

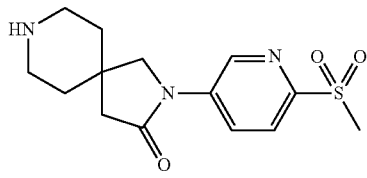 [SMILES: CS(=O)(=O)c1ccc(N2CC3(CCNCC3)CC2=O)cn1]

2-(6-(Methylsulfonyl)pyridin-3-yl)-2,8-diazaspiro[4.5]decan-3-one was prepared following the same procedure as INTERMEDIATE 49 (2-[5-(methylsulfonyl)pyridin-2-yl]-2,8-diazaspiro[4.5]decan-3-one) from tert-butyl-3-oxo-2,8-diazaspiro[4.5]decane-8-carboxylate and 5-bromo-2-(methylsulfonyl)pyridine. LCMS: m/z 310 (M+H)⁺.

Intermediate 51

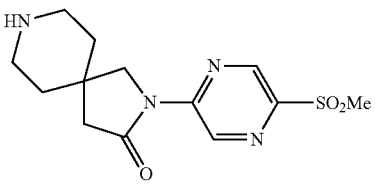 [SMILES: CS(=O)(=O)c1cnc(N2CC3(CCNCC3)CC2=O)cn1]

2-[5-(Methylsulfonyl)pyrazin-2-yl]-2,8-diazaspiro[4.5]decan-3-one was prepared following the same procedure as INTERMEDIATE 49 (2-[5-(methylsulfonyl)pyridin-2-yl]-2,8-diazaspiro[4.5]decan-3-one) from tert-butyl-3-oxo-2,8-diazaspiro[4.5]decane-8-carboxylate and 2-chloro-5-(methylsulfonyl)pyrazine. LCMS: m/z 311 (M+H)⁺.

Intermediate 52

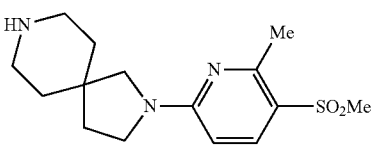 [SMILES: Cc1nc(N2CCC3(CCNCC3)C2)ccc1S(C)(=O)=O]

Step A: tert-butyl 2-[6-methyl-5-(methylsulfonyl)pyridin-2-yl]-2,8-diazaspiro[4.5]decane-8-carboxylate: A stirred solution of 6-fluoro-2-methyl-3-(methylsulfonyl)pyridine (0.3 g, 1.3 mmol), tert-butyl 2,8-diazaspiro[4.5]decane-8-carboxylate (0.3 g, 1.3 mmol), Pd₂dba₃ (0.06 g, 0.06 mmol), S-Phos (0.1 g, 0.25 mmol), and Cs₂CO₃ (1.2 g, 3.7 mmol) in THF (10 mL) were heated to reflux for 12 h. The solution was diluted with H₂O and stirred vigorously. The organic layer was removed, dried over MgSO₄, filtered and concentrated. The crude product was purified using a 50 g Biotage® SNAP cartridge (7-80% EtOAc:hexanes) to give the title compound. LCMS: m/z 410.18 (M+H)⁺.

Step B: 2-[6-methyl-5-(methylsulfonyl)pyridin-2-yl]-2,8-diazaspiro[4.5]decane: The tert-butyl 2-[6-methyl-5-(methylsulfonyl)pyridin-2-yl]-2,8-diazaspiro[4.5]decane-8-carboxylate was treated with 5 mL of 4N HCl at room temp for 1 h, then concentrated to afford title compound.

Intermediate 53

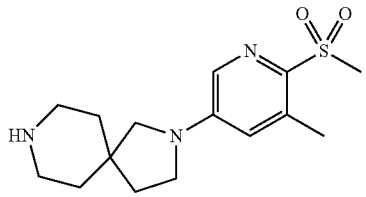 [SMILES: Cc1cc(N2CCC3(CCNCC3)C2)cnc1S(C)(=O)=O]

2-(5-Methyl-6-(methylsulfonyl)pyridin-3-yl)-2,8-diazaspiro[4.5]decane was prepared following the same procedure as INTERMEDIATE 52 (2-[6-methyl-5-(methylsulfonyl)pyridin-2-yl]-2,8-diazaspiro[4.5]decane) from tert-butyl 2,8-diazaspiro[4.5]decane-8-carboxylate (commercially available from multiple vendors, for example AstaTech, Inc. catalog #11097) and 5-bromo-3-methyl-2-(methylsulfonyl)pyridine. LCMS: m/z 310 (M+H)⁺.

Intermediate 54

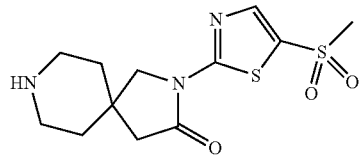 [SMILES: CS(=O)(=O)c1cnc(N2CC3(CCNCC3)CC2=O)s1]

Step A: tert-butyl 2-(5-(methylsulfonyl)thiazol-2-yl)-3-oxo-2,8-diazaspiro[4.5]decane-8-carboxylate: A stirred solution of 2-bromo-5-(methylsulfonyl)-1,3-thiazole (0.2 g, 0.8 mmol), tert-butyl-3-oxo-2,8-diazaspiro[4.5]decane-8-carboxylate (0.2 g, 0.8 mmol), Pd₂dba₃ (0.04 g, 0.04 mmol), Xanthphos (0.05 g, 0.08 mmol), and Cs₂CO₃ (0.4 g, 1.2 mmol) in THF (10 mL) were heated to reflux for 12 h. The solution was diluted with H₂O and stirred vigorously. The organic layer was removed, dried over MgSO₄, filtered and concentrated giving rise to an oil. The oil was purified using a 25 g Biotage® SNAP cartridge (7-60% EtOAc:hexanes) to give title compound. LCMS: m/z 416.02 (M+H)⁺.

Step B: 2-[5-(methylsulfonyl)-1,3-thiazol-2-yl]-2,8-diazaspiro[4.5]decan-3-one: The tert-butyl-2-[5-(methylsulfonyl)-1,3-thiazol-2-yl]-3-oxo-2,8-diazaspiro[4.5]decane-8-carboxylate was treated with 5 mL of 4N HCl at room temp for 1 hour. The volatiles were removed under vacuo, and the residue was redissolved in saturated NaHCO₃ (10 mL), extracted with chloroform-IPA (3:1) twice. The extractions Intermediate 55

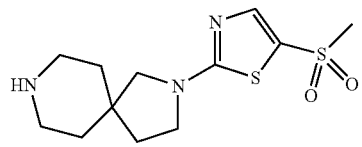 [SMILES: CS(=O)(=O)c1cnc(N2CCC3(CCNCC3)C2)s1]

Step A: tert-butyl 2-(5-(methylsulfonyl)thiazol-2-yl)-2,8-diazaspiro[4.5]decane-8-carboxylate: A stirred solution of 2-bromo-5-(methylsulfonyl)-1,3-thiazole (0.20 g, 0.83 mmol), tert-butyl 2,8-diazaspiro[4.5]decane-8-carboxylate (0.20 g, 0.83 mmol), $Pd_2dba_3$ (0.038 g, 0.042 mmol), S-Phos (0.068 g, 0.17 mmol), and $Cs_2CO_3$ (0.81 g, 2.5 mmol) in 1,4-Dioxane (5 mL) were heated to reflux for 12 hours. The solution was diluted with $H_2O$ and stirred vigorously. The organic layer was removed, dried over $MgSO_4$, filtered and concentrated giving rise to an oil. The oil was purified using a 25 g Biotage® SNAP cartridge (7-60% EtOAc:hexanes) to give title compound. LCMS: m/z 424 $(M+Na)^+$.

Step B: 5-(methylsulfonyl)-2-(2,8-diazaspiro[4.5]decan-2-yl)thiazole: The material obtained above was treated with 4N HCl in dioxane at RT for 30 minutes. The volatiles were removed under vacuo, and the residue was redissolved in saturated $NaHCO_3$ (10 mL), extracted with chloroform-IPA (3:1) twice. The extracts were combined, dried over sodium sulfate, filtered and concentrated to give the title compound.

Intermediate 56

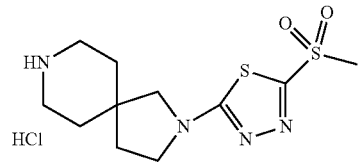 [SMILES: Cl ; CS(=O)(=O)c1nnc(N2CCC3(CCNCC3)C2)s1]

Step A: 2-bromo-5-(methylsulfonyl)-1,3,4-thiadiazole: To an ice cooled DCM solution (10 mL) of 2-bromo-5-(methylsulfanyl)-1,3,4-thiadiazole (250 mg, 1.2 mmol) was added mCPBA (660 mg, 3.0 mmol). The reaction was warmed to ambient temperature for one hour and then quenched by the addition of aqueous sodium bicarbonate. The aqueous layer was extracted with DCM (3×25 mL). The combined organic layers were then dried over sodium sulfate, filtered and concentrated in vacuo. The crude residue was purified via MPLC (0-100% EtOAc/Hex gradient) to afford title compound.

Step B: tert-butyl 2-[5-(methylsulfonyl)-1,3,4-thiadiazol-2-yl]-2,8-diazaspiro[4.5]decane-8-carboxylate: To a microwave vial was added tert-butyl 2,8-diazaspiro[4.5]decane-8-carboxylate (59 mg, 0.25 mmol), 2-bromo-5-(methylsulfonyl)-1,3,4-thiadiazole (60 mg, 0.25 mmol), tris(dibenzylideneacetone)dipalladium(0) (11 mg, 0.012 mmol), 2-dicyclohexylphosphino-2',4',6'-triisopropylbiphenyl (18 mg, 0.037 mmol), and potassium phosphate tribasic (104 mg, 0.49 mmol). The vial was sealed and vacuum purged with nitrogen three times. Anhydrous dioxane (5 mL, 0.05M) was then added and degassed with nitrogen for 15 minutes. The reaction mixture was then heated to 100° C. for 15 hours, cooled, filtered over a CELITE® pad, and concentrated in vacuo. The crude residue was purified via MPLC (0-100% EtOAc/hexanes gradient) to afford title compound. LCMS: m/z 403 $(M+H)^+$.

Step C: 2-[5-(methylsulfonyl)-1,3,4-thiadiazol-2-yl]-2,8-diazaspiro[4.5]decane hydrochloride To a solution of tert-butyl 2-[5-(methylsulfonyl)-1,3,4-thiadiazol-2-yl]-2,8-diazaspiro[4.5]decane-8-carboxylate (65 mg, 0.16 mmol, 1 mL MeOH) was added an excess amount of a 4 N HCl in dioxane solution. After addition, the reaction was allowed to stir at ambient temperature for one hour and then concentrated in vacuo to afford title compound.

Intermediate 57

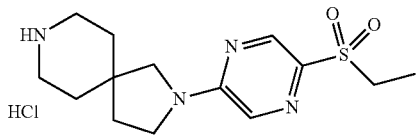 [SMILES: Cl ; CCS(=O)(=O)c1cnc(N2CCC3(CCNCC3)C2)cn1]

Step A: 2-bromo-5-(ethylsulfanyl)pyrazine: To a solution of 2,5-dibromopyrazine (5.0 g, 21.0 mmol) in DMF (10 mL) was added a suspension of sodium ethanethiolate (1.77 g, 21.0 mmol) in DMF (10 mL) dropwise. The reaction mixture was stirred at ambient temperature for 45 minutes, diluted with water and extracted with EtOAc. The combined organic layers were then dried over sodium sulfate, filtered and concentrated in vacuo. The crude residue was purified via MPLC (0-5% EtOAc/hexane gradient) to afford 4.36 g of a mixture of 2-bromo-5-(ethylsulfanyl)pyrazine and 2,5-bis(ethylsulfanyl)pyrazine. That mixture was separated via HPLC (50-100% $CH_3CN/H_2O$+v 0.1% TFA gradient), the desired fractions were combined and concentrated in vacuo in order to remove $CH_3CN$. The aqueous portions remaining were extracted with EtOAc, the combined organic layers were dried over sodium sulfate, filtered and concentrated in vacuo affording title compound [LCMS: m/z 219 (M+H)+];

Step B: 2-bromo-5-(ethylsulfonyl)pyrazine: A 600 mg mixture of 2-bromo-5-(ethylsulfanyl)pyrazine and 2,5-bis(ethylsulfanyl)pyrazine (side product from above) was dissolved in DCM (7 mL), cooled to 0° C. and treated with m-CPBA (960 mg, 4.3 mmol). The reaction mixture was gradually warmed to ambient temperature over 15 hours and quenched with aqueous sodium bicarbonate. The aqueous layer was extracted with EtOAc. The combined organic layers were dried over sodium sulfate, filtered and concentrated in vacuo. The crude residue was purified via MPLC (0-100% EtOAc/hexane gradient) to afford title compound. LCMS: m/z 251 $(M+H)^+$.

Step C: 2-[5-(ethylsulfonyl)pyrazin-2-yl]-2,8-diazaspiro[4.5]decane hydrochloride: The title compound was prepared in two steps via the same procedure as INTERMEDIATE 56 (2-(methylsulfonyl)-5-(2,8-diazaspiro[4.5]decan-2-yl)-1,3,4-thiadiazole hydrochloride, Steps B and C) from 2-bromo-5-(ethyl sulfonyl)pyrazine and tert-butyl 2,8-diazaspiro[4.5]decane-8-carboxylate. LCMS: m/z 311 $(M+H)^+$.

Intermediate 58

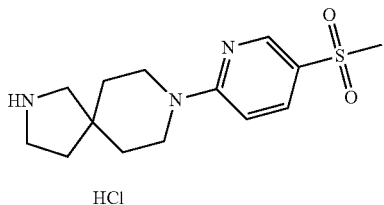 [SMILES: CS(=O)(=O)c1ccc(N2CCC3(CCNC3)CC2)nc1 ; Cl]

HCl 8-(5-(Methylsulfonyl)pyridin-2-yl)-2,8-diazaspiro[4.5]decane hydrochloride was prepared in two steps via the same procedure as INTERMEDIATE 56 (2-(methylsulfonyl)-5-(2,8-diazaspiro[4.5]decan-2-yl)-1,3,4-thiadiazole hydrochloride, Steps B and C) from 2-Bromo-5-(methylsulfonyl)pyridine and tert-butyl 2,8-diazaspiro[4.5]decane-2-carboxylate (commercially available from a number of vendors, for example, Matrix Scientific, catalog #042619). LCMS: m/z 296 (M+H)$^+$.

Intermediate 59

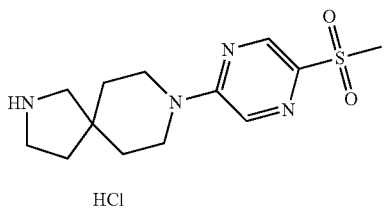 [SMILES: CS(=O)(=O)c1cnc(N2CCC3(CCNC3)CC2)cn1 ; Cl]

HCl

Step A: 2-bromo-5-(methylsulfanyl)pyrazine: A DMF solution (15 mL) of 2,5-dibromopyrazine (2.5 g, 10.5 mmol) and sodium thiomethoxide (740 mg, 10.5 mmol) was heated to 50° C. for 45 minutes and quenched by the addition of water. The aqueous layer was extracted with ethyl acetate (3×25 mL). The combined organic layers were then dried over sodium sulfate, filtered and concentrated in vacuo. The crude residue was purified via MPLC (0-100% EtOAc/hexane gradient) to afford title compound.

Step B: 2-bromo-5-(methylsulfonyl)pyrazine: An aqueous solution of Oxone® (4.0 g, 6.6 mmol, 3.13 mL) was added dropwise to a methanol solution of 2-bromo-5-(methylsulfanyl)pyrazine (450 mg, 2.2 mmol, 19 mL) at ambient temperature. The reaction mixture was stirred for 3 hours, filtered over a pad of CELITE® and then organic layer was concentrated in vacuo. The crude residue was purified via MPLC (0-100% EtOAc/hexane gradient) to afford title compound.

Step C: 8-[5-(methylsulfonyl)pyrazin-2-yl]-2,8-diazaspiro[4.5]decane hydrochloride: The title compound was prepared in two steps via the same procedure as INTERMEDIATE 56 (2-(methylsulfonyl)-5-(2,8-diazaspiro[4.5]decan-2-yl)-1,3,4-thiadiazole hydrochloride, Steps B and C) from 2-bromo-5-(methylsulfonyl)pyrazine and tert-butyl 2,8-diazaspiro[4.5]decane-2-carboxylate (commercially available from a number of vendors, for example, Matrix Scientific, catalog #042619). LCMS: m/z 297 (M+H)$^+$.

Intermediate 60

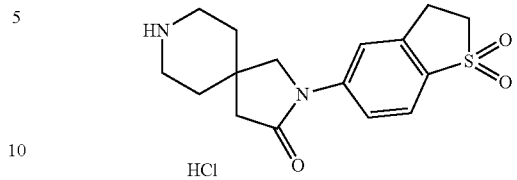

HCl

Step A: tert-butyl 2-(1-benzothiophen-5-yl)-3-oxo-2,8-diazaspiro[4.5]decane-8-carboxylate: To a microwave vial was added tert-butyl 3-oxo-2,8-diazaspiro[4.5]decane-8-carboxylate (250 mg, 0.98 mmol), 5-bromo-1-benzothiophene (210 mg, 0.98 mmol), tris(dibenzylideneacetone)dipalladium(0) (45 mg, 0.049 mmol), 9,9-dimethyl-4,5-bis(diphenylphosphino)xanthene (57 mg, 0.098 mmol), and cesium carbonate (480 mg, 1.5 mmol). The vial was sealed and vacuum purged with nitrogen three times. Anhydrous dioxane (5 mL, 0.2M) was then added and degassed with nitrogen for 15 minutes. The reaction mixture was then heated to 100° C. for 15 hours, cooled, filtered over a CELITE® pad, and concentrated in vacuo. The crude residue was purified via MPLC (0-100% EtOAc/hexane gradient) to afford the title compound.

Step B: tert-butyl 2-(1,1-dioxido-1-benzothiophen-5-yl)-3-oxo-2,8-diazaspiro[4.5]decane-8-carboxylate: To an ice cooled solution tert-butyl 2-(1-benzothiophen-5-yl)-3-oxo-2,8-diazaspiro[4.5]decane-8-carboxylate (330 mg, 0.85 mmol, 20 mL DCM was added m-CPBA (470 mg, 2.1 mmol) portion wise. The reaction was allowed to warm gradually to ambient temperature and stirred for 15 hours. The reaction was quenched by the addition of aqueous sodium bicarbonate and extracted three times with DCM (10 mL). The combined organic layers were then dried over sodium sulfate, filtered and concentrated in vacuo. The crude residue was purified via MPLC (0-100% EtOAc/hexane gradient) to afford the title compound. LCMS: m/z 404 (M+H-15)$^+$.

Step C: tert-butyl 2-(1,1-dioxido-2,3-dihydro-1-benzothiophen-5-yl)-3-oxo-2,8-diazaspiro[4.5]decane-8-carboxylate: A solution of tert-butyl 2-(1,1-dioxido-1-benzothiophen-5-yl)-3-oxo-2,8-diazaspiro[4.5]decane-8-carboxylate (320 mg, 0.76 mmol) in DCM (5 mL) was added to a slurry of 10% Pd/C (8.1 mg, 0.076 mmol) in DCM (5 mL). This solution was then subjected to hydrogenation conditions (1 atm at 23° C. for 15 hours) and then filtered over a pad of CELITE® and concentrated in vacuo to afford the title compound which was used without further purification. LCMS: m/z 406 (M+H-15)$^+$.

Step D: 2-(1,1-dioxido-2,3-dihydro-1-benzothiophen-5-yl)-2,8-diazaspiro[4.5]decan-3-one hydrochloride: The above material was treated with 4N HCl in dioxane. When LC indicated complete reaction, the solvents were removed under vacuum, and the residue was used without further purification. LCMS: m/z 321 (M+H)$^+$.

Intermediate 61

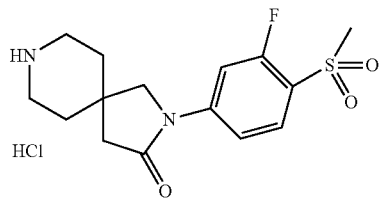 [SMILES: Cl ; CS(=O)(=O)c1ccc(N2CC3(CCNCC3)CC2=O)cc1F]

Step A: 4-chloro-2-fluoro-1-(methylsulfonyl)benzene: 4-Chloro-2-fluorobenzenesulfonyl chloride (500 mg, 2.2 mmol) was added to an aqueous (3.1 mL) solution containing sodium sulfite (380 mg, 3.1 mmol) and sodium bicarbonate (257 mg, 3.06 mmol), heated to 100° C. for one hour and then cooled to ambient temperature. Once at ambient temperature, tetrabutylammonium bromide (210 mg, 0.66 mmol) and iodomethane (0.85 μL, 1.92 g, 13.6 mmol) were added and the reaction mixture was heated to 70° C. for 15 hours. Once cooled, the aqueous layer was extracted with ethyl acetate (3×25 mL). The combined organic layers were then dried over sodium sulfate, filtered and concentrated in vacuo. The crude residue was purified via MPLC (0-100% EtOAc/hexane gradient) to afford title compound. LCMS: m/z 209 (M+H)$^+$.

Step B: 2-(3-fluoro-4-(methylsulfonyl)phenyl)-2,8-diazaspiro[4.5]decan-3-one hydrochloride:

The title compound was prepared in two steps via an analogous procedure as INTERMEDIATE 60 (2-(1,1-Dioxido-2,3-dihydrobenzo[b]thiophen-5-yl)-2,8-diazaspiro[4.5]decan-3-one hydrochloride, Steps A and D) from 4-chloro-2-fluoro-1-(methylsulfonyl)benzene and tert-butyl 3-oxo-2,8-diazaspiro[4.5]decane-8-carboxylate. LCMS: m/z 327 (M+H)$^+$.

Intermediate 62

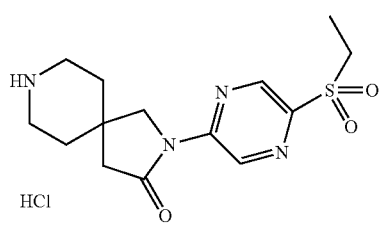 [SMILES: Cl ; CCS(=O)(=O)c1cnc(N2CC3(CCNCC3)CC2=O)cn1]

2-(5-(Ethylsulfonyl)pyrazin-2-yl)-2,8-diazaspiro[4.5]decan-3-one hydrochloride was prepared in two steps via an analogous procedure as INTERMEDIATE 60 (2-(1,1-Dioxido-2,3-dihydrobenzo[b]thiophen-5-yl)-2,8-diazaspiro[4.5]decan-3-one hydrochloride, Steps A and D) from 2-bromo-5-(ethylsulfonyl)pyrazine and tert-butyl 3-oxo-2,8-diazaspiro[4.5]decane-8-carboxylate. LCMS: m/z 325 (M+H)$^+$.

Intermediate 63

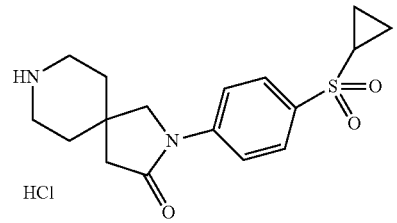 [SMILES: Cl ; O=C1CC2(CCNCC2)CN1c1ccc(S(=O)(=O)C2CC2)cc1]

Step A: 1-bromo-4-(cyclopropylsulfonyl)benzene: To an ice cooled DCM solution (10 mL) of 1-bromo-4-(cyclopropylsulfanyl)benzene (500 mg, 2.2 mmol) was added m-CPBA (1.22 g, 5.5 mmol). The reaction was warmed to ambient temperature for one hour and then quenched by the addition of aqueous sodium bicarbonate. The aqueous layer was extracted with DCM (3×25 mL). The combined organic layers were then dried over sodium sulfate, filtered and concentrated in vacuo. The crude residue was purified via MPLC (0-100% EtOAc/hexane gradient) to afford title compound. LCMS: m/z 262 (M+H)$^+$.

Step B: 2-(4-(cyclopropylsulfonyl)phenyl)-2,8-diazaspiro[4.5]decan-3-one hydrochloride: The title compound was prepared in two steps via an analogous procedure as INTERMEDIATE 60 (2-(1,1-dioxido-2,3-dihydrobenzo[b]thiophen-5-yl)-2,8-diazaspiro[4.5]decan-3-one hydrochloride, Steps A and D) from 1-bromo-4-(cyclopropylsulfonyl)benzene and tert-butyl 3-oxo-2,8-diazaspiro[4.5]decane-8-carboxylate. LCMS: m/z 335 (M+H)$^+$.

Intermediate 64

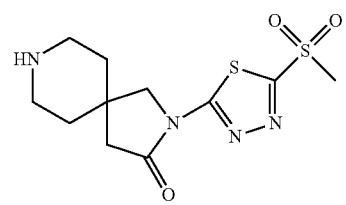

2-[5-(methylsulfonyl)-1,3,4-thiadiazol-2-yl]-2,8-diazaspiro[4.5]decan-3-one hydrochloride was prepared in two steps via an analogous procedure as INTERMEDIATE 60 (2-(1,1-dioxido-2,3-dihydrobenzo[b]thiophen-5-yl)-2,8-diazaspiro[4.5]decan-3-one hydrochloride, Steps A and D) from 2-bromo-5-(methylsulfonyl)-1,3,4-thiadiazole and tert-butyl 3-oxo-2,8-diazaspiro[4.5]decane-8-carboxylate. LCMS: m/z 317 (M+H)$^+$.

Intermediate 65

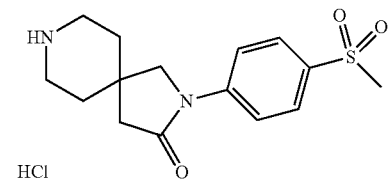 [SMILES: Cl ; CS(=O)(=O)c1ccc(N2CC3(CCNCC3)CC2=O)cc1]

2-[4-(Methylsulfonyl)phenyl]-2,8-diazaspiro[4.5]decan-3-one hydrochloride was prepared in two steps via an analogous procedure as INTERMEDIATE 60 (2-(1,1-dioxido-2,3-dihydrobenzo[b]thiophen-5-yl)-2,8-diazaspiro[4.5]decan-3-one hydrochloride, Steps A and D) from 1-bromo-4-(methylsulfonyl)benzene and tert-butyl 3-oxo-2,8-diazaspiro[4.5]decane-8-carboxylate. LCMS: m/z 309 (M+H)+.

Intermediate 66

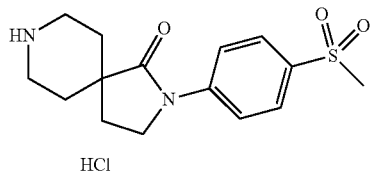

HCl

Step A: tert-butyl 2-[4-(methylsulfonyl)phenyl]-1-oxo-2,8-diazaspiro[4.5]decane-8-carboxylate:

To a microwave vial was added tert-butyl 1-oxo-2,8-diazaspiro[4.5]decane-8-carboxylate (100 mg, 0.39 mmol), 1-bromo-4-(methylsulfonyl)benzene (140 mg, 0.59 mmol), potassium phosphate tribasic (167 mg, 0.79 mmol), trans-N,N'-dimethylcyclohexane-1,2-diamine (2.5 μL, 0.02 mmol) and copper(I) iodide (15 mg, 0.08 mmol). Anhydrous dioxane (2 mL) was added, the vial was sealed and vacuum purged with nitrogen three times. The reaction mixture was then heated to 130° C. for 16 h, cooled, filtered over a pad of CELITE® and concentrated in vacuo. The crude residue was purified via MPLC (0-75% EtOAc/hexane gradient) to afford title compound. LCMS: m/z 409 (M+H)+.

Step B: 2-[4-(methylsulfonyl)phenyl]-2,8-diazaspiro[4.5]decan-1-one hydrochloride: To the material obtained above was added excess amount of 4N HCl in dioxane. The mixture was allowed to stir at RT for 1 hour, and then it was concentrated in vacuo to afford the title compound. LCMS: m/z 309 (M+H)+.

Intermediate 67

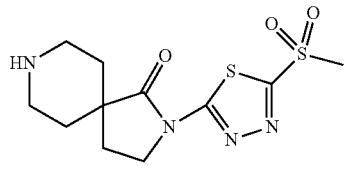

HCl

2-[5-(Methylsulfonyl)-1,3,4-thiadiazol-2-yl]-2,8-diazaspiro[4.5]decan-1-one hydrochloride was prepared in two steps via an analogous procedure as INTERMEDIATE 60 (2-(1,1-diioxido-2,3-dihydrobenzo[b]thiophen-5-yl)-2,8-diazaspiro[4.5]decan-3-one hydrochloride, Steps A and D) from 2-bromo-5-(methylsulfonyl)-1,3,4-thiadiazole and tert-butyl 1-oxo-2,8-diazaspiro[4.5]decane-8-carboxylate. LCMS: m/z 317 (M+H)+.

Intermediate 68

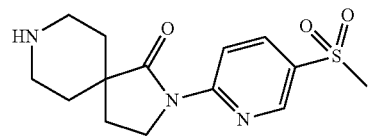 [SMILES: CS(=O)(=O)c1ccc(N2CCC3(CCNCC3)C2=O)nc1]

Step A: tert-butyl 2-(5-(methylsulfonyl)pyridin-2-yl)-1-oxo-2,8-diazaspiro[4.5]decane-8-carboxylate: To a microwave vial was charged with tert-butyl 1-oxo-2,8-diazaspiro[4.5]decane-8-carboxylate (200 mg, 0.78 mmol), 2-bromo-5-(methylsulfonyl)pyridine (204 mg, 0.86 mmol), Pd2(dba)3 (36 mg, 0.039 mmol), Xantphos (46 mg, 0.079 mmol), and Cs2CO3 (380 mg, 1.2 mmol). The vial was sealed, degassed, and filled with THF (3.9 mL). The reaction mixture was refluxed overnight, and was diluted with water, extracted with EtOAc, washed with brined, dried, evaporated to give the crude product, which was purified by column chromatography (0-100% EtOAc/hex) to give the title compound. LCMS: m/z 410 (M+H)+.

Step B: 2-(5-(methylsulfonyl)pyridin-2-yl)-2,8-diazaspiro[4.5]decan-1-one: tert-Butyl 2-(5-(methylsulfonyl)pyridin-2-yl)-1-oxo-2,8-diazaspiro[4.5]decane-8-carboxylate (40 mg, 0.098 mmol) in DCM (0.5 mL) was treated with TFA (0.5 mL) to free Boc protection and give TFA salt, which was evaporated, and treated with 1N NaOH and IPA/CHCl3 (1/3) to give the free base title compound. LCMS: m/z 310 (M+H)+.

Intermediate 69

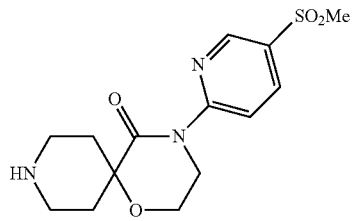 [SMILES: CS(=O)(=O)c1ccc(N2CCOC3(CCNCC3)C2=O)nc1]

4-(5-(Methyl sulfonyl)pyridin-2-yl)-1-oxa-4,9-diazaspiro[5.5]undecan-5-one was prepared in two steps via an analogous procedure as INTERMEDIATE 68 (2-(5-(methylsulfonyl)pyridin-2-yl)-2,8-diazaspiro[4.5]decan-1-one) from 2-bromo-5-(methylsulfonyl)pyridine and tert-butyl 1-oxo-2,8-diazaspiro[4.5]decane-8-carboxylate. LCMS: m/z 326 (M+H)+.

Intermediate 70

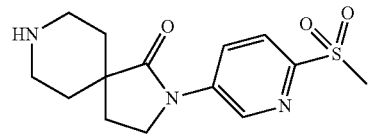 [SMILES: CS(=O)(=O)c1ccc(N2CCC3(CCNCC3)C2=O)cn1]

2-(6-(Methylsulfonyl)pyridin-3-yl)-2,8-diazaspiro[4.5]decan-1-one was prepared in two steps via an analogous procedure as INTERMEDIATE 68 (2-(5-(methylsulfonyl)pyridin-2-yl)-2,8-diazaspiro[4.5]decan-1-one) from 5-bromo-2-(methylsulfonyl)pyridine and tert-butyl 1-oxo-2,8-diazaspiro[4.5]decane-8-carboxylate. LCMS: m/z 310 (M+H)+.

Intermediate 71

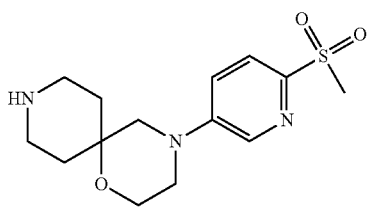 [SMILES: CS(=O)(=O)c1ccc(N2CCOC3(CCNCC3)C2)cn1]

4-(6-(Methylsulfonyl)pyridin-3-yl)-1-oxa-4,9-diazaspiro[5.5]undecane was prepared in two steps via an analogous procedure as INTERMEDIATE 68 (2-(5-(methylsulfonyl)pyridin-2-yl)-2,8-diazaspiro[4.5]decan-1-one) from 5-bromo-2-(methylsulfonyl)pyridine and tert-butyl 1-oxa-4,9-diazaspiro[5.5]undecane-9-carboxylate (commercially available from several vendors, for example AstaTech catalog #52432). LCMS: m/z 312 (M+H)+.

Intermediate 72

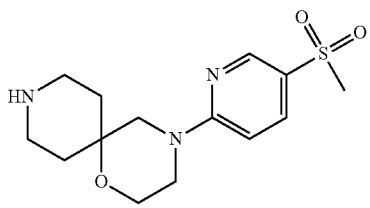 [SMILES: CS(=O)(=O)c1ccc(N2CCOC3(CCNCC3)C2)nc1]

4-(5-(methylsulfonyl)pyridin-2-yl)-1-oxa-4,9-diazaspiro[5.5]undecane was prepared in two steps via an analogous procedure as INTERMEDIATE 68 (2-(5-(methylsulfonyl)pyridin-2-yl)-2,8-diazaspiro[4.5]decan-1-one) from 2-bromo-5-(methylsulfonyl)pyridine and tert-butyl 1-oxa-4,9-diazaspiro[5.5]undecane-9-carboxylate (commercially available from several vendors, for example AstaTech catalog #52432). LCMS: m/z 312 (M+H)+.

Intermediate 73

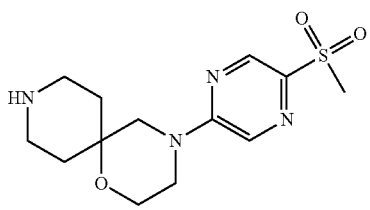 [SMILES: CS(=O)(=O)c1cnc(N2CCOC3(CCNCC3)C2)cn1]

4-(5-(methylsulfonyl)pyrazin-2-yl)-1-oxa-4,9-diazaspiro[5.5]undecane was prepared in two steps via an analogous procedure as INTERMEDIATE 68 (2-(5-(methylsulfonyl)pyridin-2-yl)-2,8-diazaspiro[4.5]decan-1-one) from 2-chloro-5-(methylsulfonyl)pyrazine and tert-butyl 1-oxa-4,9-diazaspiro[5.5]undecane-9-carboxylate (commercially available from several vendors, for example AstaTech catalog #52432). LCMS: m/z 312 (M+H)+.

Intermediate 74

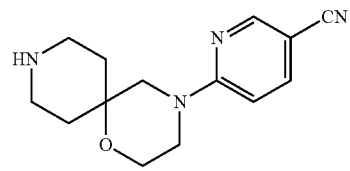 [SMILES: N#Cc1ccc(N2CCOC3(CCNCC3)C2)nc1]

6-(1-oxa-4,9-diazaspiro[5.5]undecan-4-yl)nicotinonitrile was prepared in two steps via an analogous procedure as INTERMEDIATE 68 (2-(5-(methylsulfonyl)pyridin-2-yl)-2,8-diazaspiro[4.5]decan-1-one) from 6-chloronicotinonitrile and tert-butyl 1-oxa-4,9-diazaspiro[5.5]undecane-9-carboxylate (commercially available from several vendors, for example AstaTech catalog #52432). LCMS: m/z 259 (M+H)+.

Intermediate 75

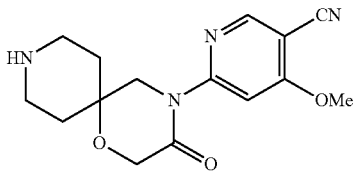 [SMILES: COc1cc(N2CC3(CCNCC3)OCC2=O)ncc1C#N]

4-Methoxy-6-(3-oxo-1-oxa-4,9-diazaspiro[5.5]undecan-4-yl)nicotinonitrile was prepared in two steps via an analogous procedure as INTERMEDIATE 68 (2-(5-(methylsulfonyl)pyridin-2-yl)-2,8-diazaspiro[4.5]decan-1-one) from 6-chloro-4-methoxynicotinonitrile and tert-butyl 3-oxo-1-oxa-4,9-diazaspiro[5.5]undecane-9-carboxylate (commercially available from several vendors, for example Accel Pharmtech catalog #SC1408). LCMS: m/z 303 (M+H)+.

Intermediate 76

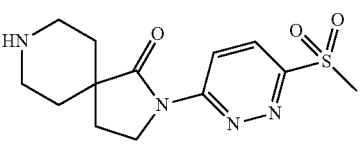 [SMILES: CS(=O)(=O)c1ccc(N2CCC3(CCNCC3)C2=O)nn1]

2-(6-(Methylsulfonyl)pyridazin-3-yl)-2,8-diazaspiro[4.5]decan-1-one was prepared in two steps via an analogous procedure as INTERMEDIATE 68 (2-(5-(methylsulfonyl)pyridin-2-yl)-2,8-diazaspiro[4.5]decan-1-one) from 3-bromo-6-(methylsulfonyl)pyridazine and tert-butyl 1-oxo-2,8-diazaspiro[4.5]decane-8-carboxylate. LCMS: m/z 311 (M+H)+.

Intermediate 77

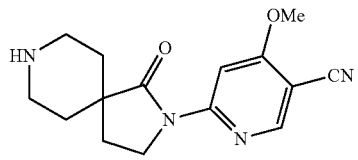 [SMILES: COc1cc(N2CCC3(CCNCC3)C2=O)ncc1C#N]

4-Methoxy-6-(1-oxo-2,8-diazaspiro[4.5]decan-2-yl)nicotinonitrile was prepared in two steps via an analogous procedure as INTERMEDIATE 68 (2-(5-(methylsulfonyl)pyridin-2-yl)-2,8-diazaspiro[4.5]decan-1-one) from 6-chloro-4-methoxynicotinonitrile and tert-butyl 1-oxo-2,8-diazaspiro[4.5]decane-8-carboxylate. LCMS: m/z 331 (M+H)$^+$.

Intermediate 78

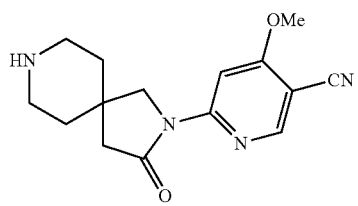 [SMILES: COc1cc(N2CC3(CCNCC3)CC2=O)ncc1C#N]

4-Methoxy-6-(3-oxo-2,8-diazaspiro[4.5]decan-2-yl)nicotinonitrile was prepared in two steps via an analogous procedure as INTERMEDIATE 68 (2-(5-(methylsulfonyl)pyridin-2-yl)-2,8-diazaspiro[4.5]decan-1-one) from 6-chloro-4-methoxynicotinonitrile and tert-butyl 3-oxo-2,8-diazaspiro[4.5]decane-8-carboxylate. LCMS: m/z 331 (M+H)$^+$.

Intermediate 79

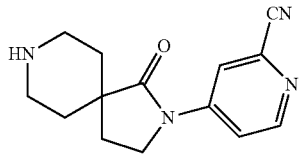 [SMILES: N#Cc1cc(N2CCC3(CCNCC3)C2=O)ccn1]

4-(1-Oxo-2,8-diazaspiro[4.5]decan-2-yl)picolinonitrile was prepared in two steps via an analogous procedure as INTERMEDIATE 68 (2-(5-(methylsulfonyl)pyridin-2-yl)-2,8-diazaspiro[4.5]decan-1-one) from 4-iodopicolinonitrile and tert-butyl 1-oxo-2,8-diazaspiro[4.5]decane-8-carboxylate. LCMS: m/z 257 (M+H)$^+$.

Intermediate 80

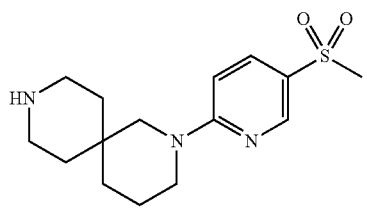 [SMILES: CS(=O)(=O)c1ccc(N2CCCC3(CCNCC3)C2)nc1]

Step A: tert-butyl 2-(5-(methylsulfonyl)pyridin-2-yl)-2,9-diazaspiro[5.5]undecane-9-carboxylate: To a microwave vial was charged with tert-butyl 2,9-diazaspiro[5.5]undecane-9-carboxylate (100 mg, 0.39 mmol), 2-bromo-5-(methylsulfonyl)pyridine (102 mg, 0.43 mmol), Pd$_2$(dba)$_3$ (18 mg, 0.020 mmol), S-Phos (32 mg, 0.079 mmol), and Cs$_2$CO$_3$ (380 mg, 1.2 mmol). The vial was sealed, degassed, and filled with THF (2000 μl). The reaction mixture was refluxed overnight, diluted with water, extracted with EtOAc, washed with brined, dried, evaporated to give the crude product, which was purified by column chromatography (0-100% EtOAc/hex) to give tert-butyl 2-(5-(methylsulfonyl)pyridin-2-yl)-2,9-diazaspiro[5.5]undecane-9-carboxylate as a white solid. LCMS: m/z 410 (M+H)$^+$.

Step B: 2-(5-(methylsulfonyl)pyridin-2-yl)-2,9-diazaspiro[5.5]undecane: The material above in 0.5 mL DCM was treated with TFA (0.5 mL) to free Boc protection and give TFA salt, which was evaporated, and treated with 1N NaOH and IPA/CHCl$_3$ (1/3) to give the free base product. LCMS: m/z 310 (M+H)$^+$.

Intermediate 81

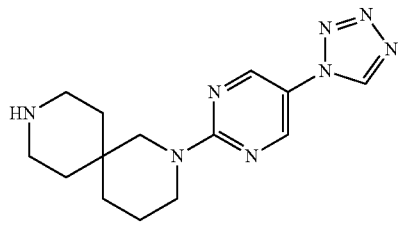 [SMILES: c1nc(N2CCCC3(CCNCC3)C2)ncc1-n1cnnn1]

Step A: tert-butyl-2-(5-nitropyrimidin-2-yl)-2,9-diazaspiro[5.5]undecane-9-carboxylate: A stirred solution of 2-chloro-5-nitropyrimidine (0.1 g, 0.6 mmol), tert-butyl 2,9-diazaspiro [5.5]undecane-9-carboxylate (0.1 g, 0.6 mmol), Pd$_2$dba$_3$ (0.02 g, 0.02 mmol), XPhos (0.04 g, 0.09 mmol), and K$_3$PO$_4$ (0.2 g, 1.1 mmol) in dioxane (17 mL) were heated to 85° C. for 12 h. The solution was diluted with H$_2$O and stirred vigorously. The organic layer was removed, dried over MgSO$_4$, filtered, concentrated and purified using a 50 g Biotage® SNAP cartridge (10-60% EtOAc:hexanes). LCMS: m/z 378.07 (M+H)$^+$.

Step B: tert-butyl 2-(5-aminopyrimidin-2-yl)-2,9-diazaspiro[5.5]undecane-9-carboxylate: tert-Butyl-2-(5-nitropyrimidin-2-yl)-2,9-diazaspiro[5.5]undecane-9-carboxylate (0.1 g, 0.3 mmol) was reduced using H$_2$ and 10% Pd/C in EtOAc on a Parr shaker at 40 psi for 4 h. After which point, the crude amine was filtered through a pad of CELITE®, and washed with EtOAc. The filtrate was concentrated to afford title compound.

Step C: tert-butyl 2-[5-(1H-tetrazol-1-yl)pyrimidin-2-yl]-2,9-diazaspiro[5.5]undecane-9-carboxylate: A flask containing tert-butyl 2-(5-aminopyrimidin-2-yl)-2,9-diazaspiro[5.5]undecane-9-carboxylate, NaN$_3$ (0.03 g, 0.4 mmol), triethyl orthoformate (0.1 mL, 0.946 mmol) and AcOH (15 mL) was heated to 80° C. for 2 h, cooled, and then partitioned between water and EtOAc. The organic layer was washed with water, dried over magnesium sulfate, filtered and concentrated to give a product which was purified via MPLC (10-55% EtOAc/hexane) to give title compound.

Step D: 2-[5-(1H-tetrazol-1-yl)pyrimidin-2-yl]-2,9-diazaspiro[5.5]undecane: The tert-butyl 2-[5-(1H-tetrazol-1-yl)pyrimidin-2-yl]-2,9-diazaspiro[5.5]undecane-9-carboxylate was treated with 5 mL of 4N HCl at room temp for 1 h. The volatiles were removed under vacuo, and the residue was dissolved in saturated NaHCO$_3$ (5 mL), extracted with chloroform-IPA (3:1) twice. The extracted were combined, dried over sodium sulfate, filtered and concentrated to afford the title compound.

Intermediate 82

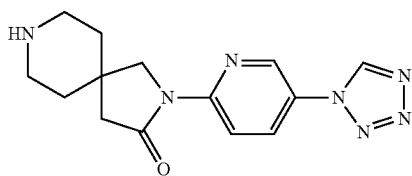 [SMILES: O=C1CC2(CCNCC2)CN1c1ccc(-n2cnnn2)cn1]

Step A: tert-butyl 2-(5-nitropyridin-2-yl)-3-oxo-2,8-diazaspiro[4.5]decane-8-carboxylate: To a microwave tube charged with tert-butyl 3-oxo-2,8-diazaspiro[4.5]decane-8-carboxylate (350 mg, 1.4 mmol) and 2-bromo-5-nitropyridine (420 mg, 2.1 mmol) was added copper iodide (52 mg, 0.28 mmol), rac-trans-N,N-dimethylcyclohexane-1,2-diamine (8 mg, 0.06 mmol), K$_2$CO$_3$ (580 mg, 2.8 mmol), and dioxane (2 mL). The mixture was purged with nitrogen and then heated to 125° C. in a microwave reactor for 16 hours. The reaction was diluted with EtOAc, washed with brine, dried over sodium sulfate, and concentrated. The residue was purified by silica gel chromatography.

Step B: tert-butyl 2-(5-(1H-tetrazol-1-yl)pyridin-2-yl)-3-oxo-2,8-diazaspiro[4.5]decane-8-carboxylate: The material (55 mg, 0.15 mmol) obtained above was treated with Palladium on carbon under an atmosphere of hydrogen in EtOAc. LC showed complete reaction after 16 hours. The reaction was filtered through a pad of CELITE® and concentrated to afford the title compound. LCMS: m/z 247 (M−Boc+H)$^+$. To the above residue was added sodium azide (11 mg, 0.18 mmol), triethyl orthoformate (49 μL, 0.29 mmol), and HOAc (0.5 mL). The mixture was heated to 80° C. for 2 hours. LC showed good reaction. The reaction was cooled, added water, and extracted with EtOAc. The organic layer was washed with water and brine, dried over MgSO$_4$, filtered and concentrated to give the crude product, which was purified by silica gel chromatography. LCMS: m/z 400 (M+H)$^+$.

Step C: 2-(5-(1H-tetrazol-1-yl)pyridin-2-yl)-2,8-diazaspiro[4.5]decan-3-one: The above material was further treated with TFA (1 mL) at RT for 30 minutes. The volatiles were removed under reduced pressure. The residue was dissolved in saturated NaHCO$_3$ (5 mL), extracted with chloroform-IPA (3:1) twice. The extracted were combined, dried over sodium sulfate, filtered and concentrated to afford the title compound.

Intermediate 83

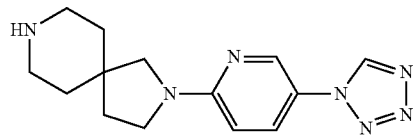 [SMILES: c1cc(N2CCC3(CCNCC3)C2)ncc1-n1cnnn1]

Step A: tert-butyl 2-(5-nitropyridin-2-yl)-2,8-diazaspiro[4.5]decane-8-carboxylate: A mixture of tert-butyl 2,8-diazaspiro[4.5]decane-8-carboxylate (commercially available from multiple vendors, for example AstaTech, Inc. catalog #11097; 150 mg, 0.62 mmol), 2-bromo-5-nitropyridine (86 mg, 0.62 mmol), and DIEA (0.22 mL, 1.2 mmol) in NMP (0.2 mL) was heated to 130° C. for 1.5 hours. The reaction was diluted with water, extracted with EtOAc. The organic layer was dried over sodium sulfate, and concentrated. The residue was purified by silica gel chromatography. LCMS: m/z 263 (M−Boc+H)$^+$.

Step B: tert-butyl 2-(5-(1H-tetrazol-1-yl)pyridin-2-yl)-2,8-diazaspiro[4.5]decane-8-carboxylate:

The product from Step A (200 mg, 0.55 mmol) was treated with Palladium on carbon under an atmosphere of hydrogen in EtOAc. LC showed complete reaction after 16 hours. The reaction was filtered through a pad of CELITE® and concentrated to afford the title compound. LCMS: m/z 333 (M+H)$^+$. To the above residue was added sodium azide (43 mg, 0.66 mmol), triethyl orthoformate (0.18 mL, 1.1 mmol), and HOAc (1.8 mL). The mixture was heated to 80° C. for 2 hours. The reaction was cooled, water was added, and the mixture was extracted with EtOAc. The organic layer was washed with water and brine, dried over MgSO$_4$, filtered and concentrated to give the crude product, which was purified by silica gel chromatography.

Step C: 2-(5-(1H-tetrazol-1-yl)pyridin-2-yl)-2,8-diazaspiro[4.5]decane: The product from Step B was treated with TFA (1 mL) at RT for 30 minutes. The volatiles were removed under reduced pressure. The residue was dissolved in saturated NaHCO$_3$ (5 mL), extracted with chloroform-IPA (3:1) twice. The extracted were combined, dried over sodium sulfate, filtered and concentrated to afford title compound.

Intermediate 84

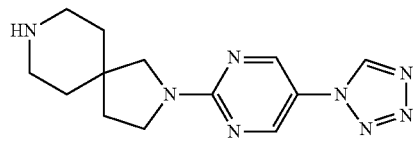 [SMILES: c1nc(N2CCC3(CCNCC3)C2)ncc1-n1cnnn1]

2-(5-(1H-tetrazol-1-yl)pyrimidin-2-yl)-2,8-diazaspiro[4.5]decane was prepared in an analogous fashion as INTERMEDIATE 83 (2-(5-(1H-tetrazol-1-yl)pyridin-2-yl)-2,8-diazaspiro[4.5]decane) from tert-butyl 2,8-diazaspiro[4.5]decane-8-carboxylate (commercially available from multiple vendors, for example AstaTech, Inc. catalog #11097) and 2-chloro-5-nitropyrimidine. LCMS: m/z 287 (M+H)⁺.

Intermediate 85

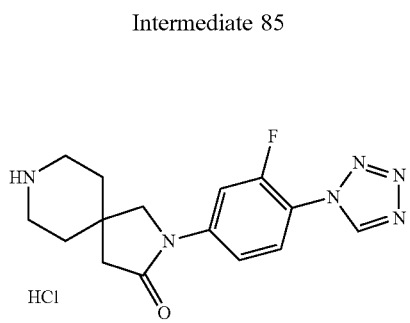

Step A: tert-butyl 2-(3-fluoro-4-nitrophenyl)-3-oxo-2,8-diazaspiro[4.5]decane-8-carboxylate: To a microwave vial was added tert-butyl 3-oxo-2,8-diazaspiro[4.5]decane-8-carboxylate (100 mg, 0.39 mmol), 4-bromo-2-fluoro-1-nitrobenzene (18 mg, 0.02 mmol), tris(dibenzylideneacetone)dipalladium(0) (45 mg, 0.049 mmol), 9,9-dimethyl-4,5-bis(diphenylphosphino)xanthene (22 mg, 0.040 mmol), and cesium carbonate (192 mg, 0.59 mmol). The vial was sealed and vacuum purged with nitrogen three times. Anhydrous dioxane (5 mL, 0.2M) was then added and degassed with nitrogen for 15 minutes. The reaction mixture was then heated to 100° C. for 15 hours, cooled, filtered over a pad CELITE®, and concentrated in vacuo. The crude residue was purified via MPLC (0-100% EtOAc/hexane gradient) to afford title compound. LCMS: m/z 294 (M+H−BOC)+.

Step B: tert-butyl 2-(4-amino-3-fluorophenyl)-3-oxo-2,8-diazaspiro[4.5]decane-8-carboxylate: A solution of tert-butyl 2-(3-fluoro-4-nitrophenyl)-3-oxo-2,8-diazaspiro[4.5]decane-8-carboxylate (115 mg, 0.29 mmol) in DCM (5 mL) was added to a slurry of 10% Pd/C (12.4 mg, 0.12 mmol) in DCM (5 mL). This solution was then subjected to hydrogenation conditions (1 atm at 23° C. for 15 hours) and then filtered over a pad of CELITE® and concentrated in vacuo to afford the title compound. LCMS: m/z 364 (M+H)⁺.

Step C: tert-butyl 2-[3-fluoro-4-(1H-tetrazol-1-yl)phenyl]-3-oxo-2,8-diazaspiro[4.5]decane-8-carboxylate: To a solution of tert-butyl 2-(4-amino-3-fluorophenyl)-3-oxo-2,8-diazaspiro[4.5]decane-8-carboxylate (110 mg, 0.30 mmol) in glacial acetic acid (5 mL) was added triethyl orthoformate (151 μL, 0.91 mmol) and sodium azide (59 mg, 0.91 mmol). The reaction mixture was heated at 80° C. for 3 hours in a sealed vial and then cooled to ambient temperature. Once cooled, water (5 mL) was added and the aqueous layer was extracted with ethyl acetate (3×20 mL). The combined organic layers were then dried over sodium sulfate, filtered and concentrated in vacuo. The crude residue was purified via MPLC (0-100% EtOAc/hexane gradient) to afford the title compound. LCMS: m/z 417 (M+H)⁺.

Step D: 2-[3-fluoro-4-(1H-tetrazol-1-yl)phenyl]-2,8-diazaspiro[4.5]decan-3-one hydrochloride:

To the material obtained above was added excess amount of 4N HCl in dioxane. The mixture was allowed to stir at RT for 1 hour, and then it was concentrated in vacuo. LCMS: m/z 289 (M+H-28)⁺.

Intermediate 86

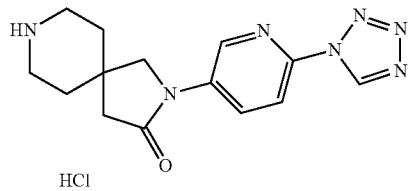 [SMILES: O=C1CC2(CCNCC2)CN1c1ccc(-n2cnnn2)nc1 ; Cl]

2-[6-(1H-tetrazol-1-yl)pyridin-3-yl]-2,8-diazaspiro[4.5]decan-3-one hydrochloride was prepared following the same procedures as INTERMEDIATE 85 (2-[3-fluoro-4-(1H-tetrazol-1-yl)phenyl]-2,8-diazaspiro[4.5]decan-3-one hydrochloride) from 5-bromo-2-nitropyridine and tert-butyl 3-oxo-2,8-diazaspiro[4.5]decane-8-carboxylate. LCMS: m/z 300 (M+H)⁺.

Intermediate 87

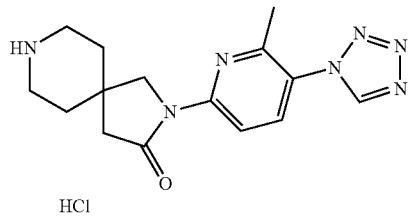 [SMILES: Cc1nc(N2CC3(CCNCC3)CC2=O)ccc1-n1cnnn1 ; Cl]

2-[6-Methyl-5-(1H-tetrazol-1-yl)pyridin-2-yl]-2,8-diazaspiro[4.5]decan-3-one hydrochloride was prepared following the same procedures as INTERMEDIATE 85 (2-[3-fluoro-4-(1H-tetrazol-1-yl)phenyl]-2,8-diazaspiro[4.5]decan-3-one hydrochloride) from 6-chloro-2-methyl-3-nitropyridine and tert-butyl 3-oxo-2,8-diazaspiro[4.5]decane-8-carboxylate. LCMS: m/z 286 (M+H−28)⁺.

Intermediate 88

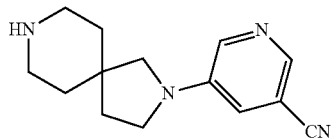 [SMILES: N#Cc1cncc(N2CCC3(CCNCC3)C2)c1]

5-(2,8-Diazaspiro[4.5]decan-2-yl)nicotinonitrile was prepared following the same procedure as INTERMEDIATE 28 (6-(2,7-Diazaspiro[3.5]non-2-yl)pyridine-3-carbonitrile) from tert-butyl 2,8-diazaspiro[4.5]decane-8-carboxylate and 5-bromonicotinonitrile. LCMS: m/z 243 (M+H)⁺.

Intermediate 89

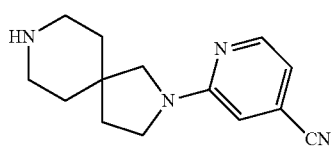 [SMILES: N#Cc1ccnc(N2CCC3(CCNCC3)C2)c1]

2-(2,8-Diazaspiro[4.5]decan-2-yl)isonicotinonitrile was prepared following the same procedure as INTERMEDIATE 28 (6-(2,7-diazaspiro[3.5]non-2-yl)pyridine-3-carbonitrile) from tert-butyl 2,8-diazaspiro[4.5]decane-8-carboxylate and 2-bromonicotinonitrile. LCMS: m/z 243 (M+H)+.

Intermediate 90

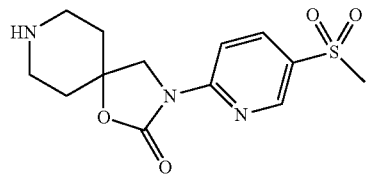

Step A: tert-butyl 3-(5-(methylsulfonyl)pyridin-2-yl)-2-oxo-1-oxa-3,8-diazaspiro[4.5]decane-8-carboxylate: To a microwave vial was charged tert-butyl 2-oxo-1-oxa-3,8-diazaspiro[4.5]decane-8-carboxylate (50 mg, 0.195 mmol), 2-bromo-5-(methylsulfonyl)pyridine (50.7 mg, 0.215 mmol), Pd$_2$(dba)$_3$ (8.93 mg, 9.75 μmol), Xantphos (11.29 mg, 0.020 mmol), and Cs$_2$CO$_3$ (95 mg, 0.293 mmol). The vial was sealed, degassed, and filled with THF (1.0 mL). The reaction mixture was refluxed overnight, and diluted with water, extracted with EtOAc, washed with brined, dried, evaporated to give the crude product, which was purified by column chromatography (0-100% EtOAc/hexane) to give the title compound. LC/MS: [(M+1)]+=412

Step B: 3-(5-(methylsulfonyl)pyridin-2-yl)-1-oxa-3,8-diazaspiro[4.5]decan-2-one: tert-butyl 3-(5-(methylsulfonyl)pyridin-2-yl)-2-oxo-1-oxa-3,8-diazaspiro[4.5]decane-8-carboxylate (76 mg, 0.185 mmol) in DCM (0.5 mL) was treated with TFA (0.5 mL) to free Boc protection and give TFA salt, which was evaporated, and treated with MP-carbonate (2.92 mmol/g: 0.6 g) in MeOH to give the free base product 3-(5-(methylsulfonyl)pyridin-2-yl)-1-oxa-3,8-diazaspiro[4.5]decan-2-one. LC/MS: [(M+1)]+=312.

Intermediate 91

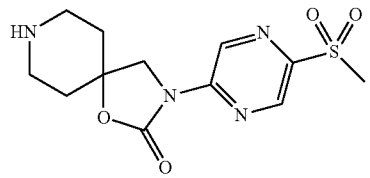 [SMILES: CS(=O)(=O)c1cnc(N2CC3(CCNCC3)OC2=O)cn1]

3-(5-(Methylsulfonyl)pyrazin-2-yl)-1-oxa-3,8-diazaspiro[4.5]decan-2-one was prepared in an analogous fashion to that described for 3-(5-(methylsulfonyl)pyridin-2-yl)-1-oxa-3,8-diazaspiro[4.5]decan-2-one from tert-butyl 2-oxo-1-oxa-3,8-diazaspiro[4.5]decane-8-carboxylate and 2-chloro-5-(methylsulfonyl)pyrazine LC/MS: [(M+1)]+=313.

Intermediate 92

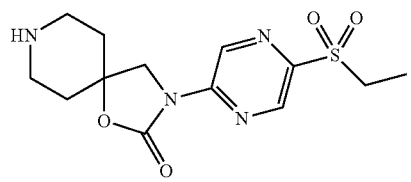 [SMILES: CCS(=O)(=O)c1cnc(N2CC3(CCNCC3)OC2=O)cn1]

3-(5-(Ethylsulfonyl)pyrazin-2-yl)-1-oxa-3,8-diazaspiro[4.5]decan-2-one was prepared in an analogous fashion to that described for 3-(5-(methylsulfonyl)pyridin-2-yl)-1-oxa-3,8-diazaspiro[4.5]decan-2-one from tert-butyl 2-oxo-1-oxa-3,8-diazaspiro[4.5]decane-8-carboxylate and 2-bromo-5-(ethylsulfonyl)pyrazine. LC/MS: [(M+1)]+=327.

Intermediate 93

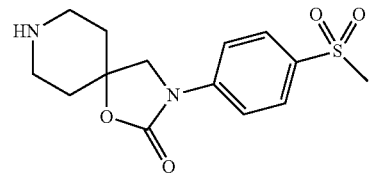 [SMILES: CS(=O)(=O)c1ccc(N2CC3(CCNCC3)OC2=O)cc1]

3-(4-(Methylsulfonyl)phenyl)-1-oxa-3,8-diazaspiro[4.5]decan-2-one was prepared in an analogous fashion to that described for 3-(5-(methylsulfonyl)pyridin-2-yl)-1-oxa-3,8-diazaspiro[4.5]decan-2-one from tert-butyl 2-oxo-1-oxa-3,8-diazaspiro[4.5]decane-8-carboxylate and 1-bromo-4-(methylsulfonyl)benzene. LC/MS: [(M+1)]+=311.

Intermediate 94

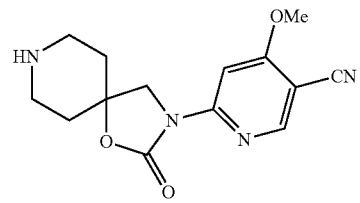 [SMILES: COc1cc(N2CC3(CCNCC3)OC2=O)ncc1C#N]

4-Methoxy-6-(2-oxo-1-oxa-3,8-diazaspiro[4.5]decan-3-yl)nicotinonitrile was prepared in an analogous fashion to that described for 3-(5-(methylsulfonyl)pyridin-2-yl)-1-oxa-3,8-diazaspiro[4.5]decan-2-one from tert-butyl 2-oxo-1-oxa-3,8-diazaspiro[4.5]decane-8-carboxylate and 6-chloro-4-methoxynicotinonitrile. LC/MS: [(M+1)]+=289.

Intermediate 95

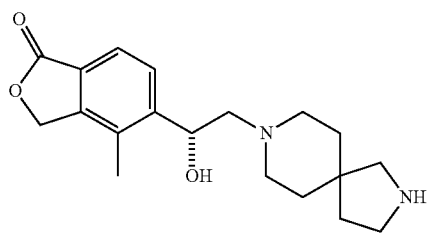 [SMILES: Cc1c([C@@H](O)CN2CCC3(CCNC3)CC2)ccc2c1COC2=O]

Step A: (R)-tert-butyl 8-(2-hydroxy-2-(4-methyl-1-oxo-1,3-dihydroisobenzofuran-5-yl)ethyl)-2,8-diazaspiro[4.5]decane-2-carboxylate: A solution of tert-butyl 2,8-diazaspiro[4.5]decane-2-carboxylate (commercially available from a number of vendors, for example, Matrix Scientific, catalog #042619; 2.5 g, 10.5 mmol) and (R)-4-methyl-5-(oxiran-2-yl)isobenzofuran-1(3H)-one (2.0 g, 10.5 mmol) in EtOH (15 mL) was heated to 150° C. for 70 min. The solvent was removed, and the crude product was purified by flash chromatography. LCMS: m/z 431 (M+H)+.

Step B: (R)-5-(1-hydroxy-2-(2,8-diazaspiro[4.5]decan-8-yl)ethyl)-4-methylisobenzofuran-1(3H)-one: The material obtained above was treated with 4N HCl at RT for 1 hour. When LC showed complete cleavage of the Boc group, the solvents were removed under reduced pressure. The residue was dissolved in saturated NaHCO₃ (5 mL), extracted with chloroform-IPA (3:1) twice. The extracted were combined, dried over sodium sulfate, filtered and concentrated to afford the title compound. LCMS: m/z 331 (M+H)+.

Intermediate 96

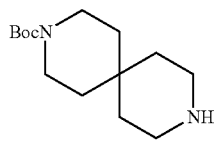

Step A: 9-benzyl-2,4-dioxo-3,9-diazaspiro[5.5]undecane-1,5-dicarbonitrile: A mixture of 1-benzylpiperidin-4-one (1 kg) and ethyl cyanoacetate (1.195 kg) in a saturated ethanolic ammonia solution (3 L) was stirred for 12 h at 0~2° C. After completed detected by TLC, the reaction mixture was filtered and the solid was dried in vacuo to afford the title compound which was used for next step directly without further purification.

Step B: diethyl 2,2'-(1-benzylpiperidine-4,4-diyl)diacetate: The crude 9-benzyl-2,4-dioxo-3,9-diazaspiro[5.5]undecane-1,5-dicarbonitrile in concentrated H₂SO₄ (1.2 L) and water (1 L) was refluxed for 3 days until the starting material was consumed. The reaction mixture was neutralized by sodium carbonate (1.9 kg) and extracted with ethyl acetate. The combined organic layer was washed with brine, dried and concentrated in vacuo to afford the title compound.

Step C: diethyl 2,2'-(1-(tert-butoxycarbonyl)piperidine-4,4-diyl)diacetate: A mixture of diethyl 2,2'-(1-benzylpiperidine-4,4-diyl)diacetate (500 g, 1.44 mol), Boc₂O (380 g) and Pd(OH)₂/C (50 g) in methanol (500 mL) under H₂ atmosphere (50 psi) was stirred for 24 hours at RT. The mixture was filtered and the filtrate was concentrated in vacuo to afford the title compound.

Step D: tert-butyl 4,4-bis(2-hydroxyethyl)piperidine-1-carboxylate: To a suspension of LiAlH₄ (81.9 g, 2.15 mol) in dry THF (6 L) at −40° C. was added a solution of diethyl 2,2'-(1-(tert-butoxycarbonyl)piperidine-4,4-diyl)diacetate (478 g, 1.34 mol) in dry THF (2 L) for 2 hours, the reaction mixture was stirred for 0.5 h at this same temperature and warmed to RT slowly. Then the mixture was cooled to 0° C., water (85.8 mL), 1N sodium hydroxide solution (171.6 mL) and water (195 ml) was added slowly, the mixture was stirred for 0.5 h and filtered, washed with THF (150 mL×3). The filtrate was concentrated in vacuo to afford the title compound.

Step E: tert-butyl 4,4-bis(2-((methylsulfonyl)oxy)ethyl)piperidine-1-carboxylate: To a solution of tert-butyl 4,4-bis(2-hydroxyethyl)piperidine-1-carboxylate (329 g, 1.21 mol) in dry DCM (3.5 L) at −25° C. was added TEA (505 mL, 3.62 mol) followed by addition of DMAP (32.9 g, 0.27 mol) and MsCl (310 g). The reaction mixture was stirred for 0.5 h at the same temperature. Then a solution of 10% citric acid was added, the organic layer was separated and the aqueous layer was extracted with ethyl acetate. The combined organic layer was washed with brine, dried and concentrated in vacuo to afford the title compound.

Step F: tert-butyl 9-benzyl-3,9-diazaspiro[5.5]undecane-3-carboxylate: A mixture of tert-butyl 4,4-bis(2-((methylsulfonyl)oxy)ethyl)piperidine-1-carboxylate (500 g, 1.17 mol) and BnNH₂ (508 g, 4.75 mol) in ethanol (5 L) was refluxed for 20 h. The solvent was removed in vacuo, the residue was diluted with ethyl acetate and filtered to remove the salt. The filtrate was concentrated in vacuo and purified by column chromatography on silica gel (PE/EA=10/1) to afford the title compound.

Step G: tert-butyl 3,9-diazaspiro[5.5]undecane-3-carboxylate: A mixture of tert-butyl 9-benzyl-3,9-diazaspiro[5.5]undecane-3-carboxylate (240 g, 0.7 mol) and Pd(OH)₂/C (24 g) in methanol (1.5 L) under hydrogen atmosphere (60 psi) at 40° C. for 24 h. The mixture was filtered and the filtrate was concentrated in vacuo. The residue was treated with 1N HCl/methanol and filtered to afford compound the title compound as the HCl salt. ¹H NMR (400 MHz, DMSO-d6) δ 8.91 (br s, 1H), 3.28 (t, J=4.8 Hz, 4H), 2.99 (t, J=5.6 Hz, 4H), 1.62 (t, J=6 Hz, 4H), 1.42-1.33 (m, 4H), 1.38 (s, 9H).

Intermediate 97

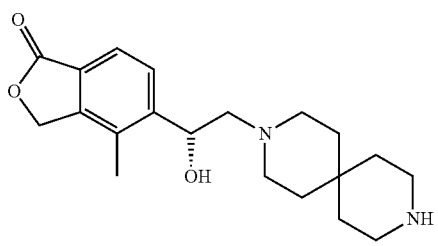

Step A: (R)-tert-butyl 9-(2-hydroxy-2-(4-methyl-1-oxo-1,3-dihydroisobenzofuran-5-yl)ethyl)-3,9-diazaspiro[5.5]undecane-3-carboxylate: To a solution of tert-butyl 3,9-diazaspiro[5.5]undecane-3-carboxylate hydrochloride (114 g, 0.39 mol) (INTERMEDIATE 96) in ethanol (1 L) was added Et₃N (60 mL). The mixture was stirred for 2 hours. Then (R)-4-methyl-5-(oxiran-2-yl)isobenzofuran-1(3H)-one (75 g, 0.39 mol) was added. The mixture was heated to reflux for 24 h. The mixture was concentrated, washed with brine, dried over Na$_2$SO$_4$ and concentrated to provide the crude product. The crude product was purified by SFC separation to provide the title compound. $^1$H NMR (400 MHz, CDCl$_3$) δ 7.80-7.75 (m, 2H), 5.23 (s, 2H), 5.14-5.11 (m, 1H), 3.39-3.36 (m, 5H), 3.18-3.10 (m, 1H), 3.05-2.99 (m, 1H), 2.82-2.72 (m, 2H), 2.60-2.35 (m, 4H), 2.25 (s, 3H), 1.83-1.80 (m, 1H), 1.65-1.55 (m, 3H), 1.50-1.35 (m, 18H).

Step B: (R)-5-(1-hydroxy-2-(3,9-diazaspiro[5.5]undecan-3-yl)ethyl)-4-methylisobenzofuran-1(3H)-one: To a solution of (R)-tert-butyl 9-(2-hydroxy-2-(4-methyl-1-oxo-1,3-dihydroisobenzofuran-5-yl)ethyl)-3,9-diazaspiro[5.5]undecane-3-carboxylate (83 g, 0.19 mol) in CH$_2$Cl$_2$ (1 L) was slowly added a 4 M HCl solution (300 mL). The mixture was stirred for 8 h, then filtered. The solid was washed with CH$_2$Cl$_2$, dried to give product as HCl salt. NMR showed DEA remained. The product was dissolved in methanol, NaHCO$_3$ was added. The mixture was stirred for 3 h. After filtration, the filtrate was concentrated, washed with ethyl acetate. The residue was concentrated in vacuo to give the title compound. $^1$H NMR (400 MHz, CDCl$_3$) δ 7.79 (m, 2H), 5.30 (s, 1H), 5.25 (s, 2H), 5.07 (m, 1H), 4.03 (s, 1H), 3.14 (m, 4H), 2.76 (m, 2H), 2.55 (m, 1H), 2.41 (m, 3H), 2.26 (s, 3H), 1.80 (m, 4H), 1.65 (m, 4H).

Intermediate 98

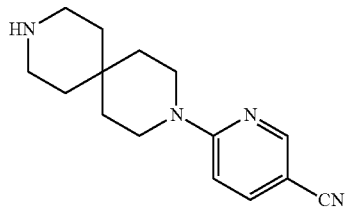 [SMILES: N#Cc1ccc(N2CCC3(CCNCC3)CC2)nc1]

Step A: tert-butyl 9-(5-cyanopyridin-2-yl)-3,9-diazaspiro[5.5]undecane-3-carboxylate: A mixture of tert-butyl 3,9-diazaspiro[5.5]undecane-3-carboxylate (50 mg, 0.197 mmol), 6-chloronicotinonitrile (27 mg, 0.197 mmol), and Hunig's base (69 mL, 0.393 mmol) in DMF (0.6 mL) was microwaved at 130° C. for 45 min. The reaction mixture was purified by column chromatography (0-100% EtOAc/hexanes) to give the title compound. LC/MS: [(M+1)]$^+$=357

Step B: 6-(3,9-diazaspiro[5.5]undecan-3-yl)nicotinonitrile
Step B was conducted in a similar fashion to Step B of INTERMEDIATE 60 to yield tile compound. LC/MS: [(M+1)]$^+$=257.

Intermediate 99

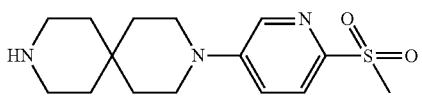

Step A: tert-butyl 9-(6-(methylsulfonyl)pyridin-3-yl)-3,9-diazaspiro[5.5]undecane-3-carboxylate:
A mixture of tert-butyl 3,9-diazaspiro[5.5]undecane-3-carboxylate (300 mg, 1.18 mmol), 5-bromo-2-(methylsulfonyl)pyridine (306 mg, 1.30 mmol), Pd$_2$(dba)$_3$ (54 mg, 0.06 mmol) and 2-dicyclohexylphosphino-2',6'-dimethoxybiphenyl (97 mg, 0.24 mmol) in THF (10 ml) was heated at reflux overnight, the reaction mixture was then diluted with water, extracted with EtOAc for three times, the combined extracts were washed with brine, dried over MgSO$_4$, filtered, concentrated and purified by flash chromatography (Biotage® SNAP 50 g, 30-100% EtOAc/hexane as eluent) to afford the title compound. LC/MS: (M+1)$^+$410.06.

Step B: 3-(6-(methylsulfonyl)pyridin-3-yl)-3,9-diazaspiro[5.5]undecane: tert-Butyl 9-(6-(methylsulfonyl)pyridin-3-yl)-3,9-diazaspiro[5.5]undecane-3-carboxylate (350 mg, 0.86 mmol) and 4N HCl/dioxane, 2.14 ml, 8.55 mmol) was stirred at rt for 2 hours, the reaction mixture was concentrated to dryness, the residue was dissolved in 0.1M NaOH solution, extracted with IPA/CHCl$_3$ (⅓) for three times, combined extracts were dried over MgSO$_4$, filtered and concentrated to afford 3-(6-(methylsulfonyl)pyridin-3-yl)-3,9-diazaspiro[5.5]undecane. LC/MS: (M+1)$^+$310.09.

Intermediate 100

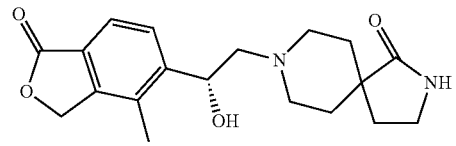 [SMILES: Cc1c([C@@H](O)CN2CCC3(CCNC3=O)CC2)ccc2c1COC2=O]

Step A: 2,8-diazaspiro[4.5]decan-1-one hydrochloride: To a solution of tert-butyl 1-oxo-2,8-diazaspiro[4.5]decane-8-carboxylate (Intermediate 14, 92 g, 0.36 mol) in CH$_2$Cl$_2$ (1 L) was slowly added a 4 M HCl solution (500 mL). The mixture was stirred for 8 h at RT. The mixture was concentrated under vacuum to afford the title compound. $^1$H NMR (400 MHz, DMSO-d$_6$) δ 9.35 (s, 1H), 9.02 (s, 1H), 7.72 (s, 1H), 3.30-3.20 (m, 2H), 3.16 (m, J=6.8 Hz, 2H), 2.98-2.85 (m, 2H), 1.96 (m, J=6.8 Hz, 2H), 1.90-1.80 (m, 2H), 1.55 (d, J=14 Hz, 2H).

Step B: (R)-8-(2-hydroxy-2-(4-methyl-1-oxo-1,3-dihydroisobenzofuran-5-yl)ethyl)-2,8-diazaspiro[4.5]decan-1-one: To a solution of 2, 8-diazaspiro[4.5]decan-1-one hydrochloride (68 g, 0.35 mol) in ethanol (1.5 L) was added Et$_3$N (55 mL). The mixture was stirred for 2 hours. Then (R)-4-methyl-5-(oxiran-2-yl)isobenzofuran-1(3H)-one (Intermediate 3B, 65 g, 0.34 mol) was added. The mixture was heated to reflux for 40 h. After filtration, the solid was collected to provide the title compound. The filtrate was concentrated and purified by SFC separation to provide additional title compound. $^1$H NMR (400 Hz, CDCl$_3$) δ 7.82-7.75 (m, 2H), 6.00 (s, 1H), 5.24 (s, 2H), 5.08 (dd, J=2.1 Hz and 10.4 Hz, 1H), 4.21 (s, 1H), 3.35 (t, J=6.8 Hz, 2H), 3.17-3.14 (m, 1H), 2.85-2.82 (m, 1H), 2.57 (dd, J=2.1 Hz and 10.4 Hz, 1H), 2.49 (t, J=8.8 Hz, 1H), 2.37 (t, J=10.8 Hz, 1H), 2.27 (s, 3H), 2.23 (J=6.8 Hz, 1H), 2.09-1.98 (m, 4H), 1.52 (t, J=12.8 Hz, 2H).

EXAMPLE 1

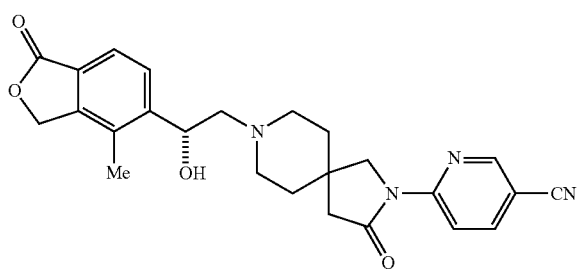 [SMILES: Cc1c([C@@H](O)CN2CCC3(CC2)CC(=O)N(c2ccc(C#N)cn2)C3)ccc2c1COC2=O]

To a microwave tube charged with 6-(3-oxo-2,8-diazaspiro[4.5]decan-2-yl)nicotinonitrile (30 mg, 0.12 mmol) and (R)-4-methyl-5-(oxiran-2-yl)isobenzofuran-1(3H)-one (33 mg, 0.18) and a stir bar was added EtOH (2 mL). The mixture was sealed and heated to 145° C. for 1.5 hours. The product was separated by reverse-phase HPLC with water and acetonitrile (with 0.1% TFA) to provide (R)-6-(8-(2-hydroxy-2-(4-methyl-1-oxo-1,3-dihydroisobenzofuran-5-yl)ethyl)-3-oxo-2,8-diazaspiro[4.5]decan-2-yl)nicotinonitrile. LCMS: m/z 447 (M+H)$^+$.

EXAMPLE 2

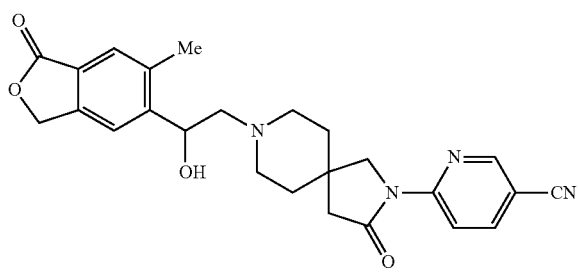 [SMILES: Cc1cc2c(cc1C(O)CN1CCC3(CC1)CC(=O)N(c1ccc(C#N)cn1)C3)COC2=O]

6-(8-(2-hydroxy-2-(6-methyl-1-oxo-1,3-dihydroisobenzofuran-5-yl)ethyl)-3-oxo-2,8-diazaspiro[4.5]decan-2-yl)nicotinonitrile was prepared via the same manner as Example 1 from 6-(3-oxo-2,8-diazaspiro[4.5]decan-2-yl)nicotinonitrile and 6-methyl-5-(oxiran-2-yl)isobenzofuran-1(3H)-one. LCMS: m/z 447 (M+H)$^+$.

EXAMPLE 3

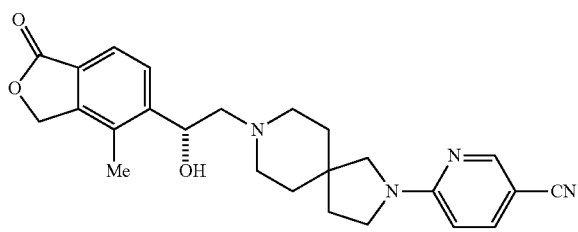 [SMILES: Cc1c([C@@H](O)CN2CCC3(CC2)CCN(c2ccc(C#N)cn2)C3)ccc2c1COC2=O]

(R)-6-(8-(2-hydroxy-2-(4-methyl-1-oxo-1,3-dihydroisobenzofuran-5-yl)ethyl)-2,8-diazaspiro[4.5]decan-2-yl)nicotinonitrile was prepared via the same manner as Example 1 from 6-(2,8-diazaspiro[4.5]decan-2-yl)nicotinonitrile and (R)-4-methyl-5-(oxiran-2-yl)isobenzofuran-1(3H)-one. LCMS: m/z 433 (M+H)$^+$.

EXAMPLE 4

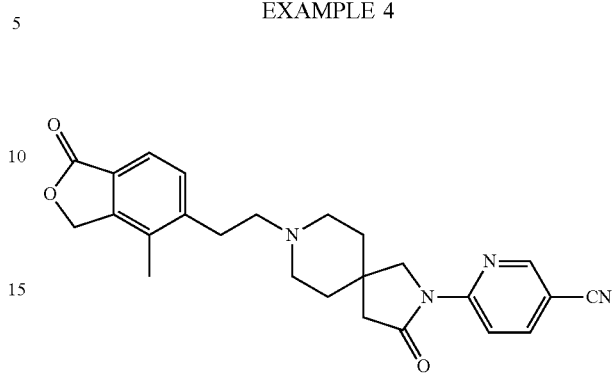

To a solution of 6-(3-oxo-2,8-diazaspiro[4.5]decan-2-yl)nicotinonitrile (30 mg, 0.12 mmol) and 2-(4-methyl-1-oxo-1,3-dihydroisobenzofuran-5-yl)acetaldehyde (40 mg, 0.21 mmol) in DCM was added sodium triacetoxyborohydride (50 mg, 0.23 mmol). The mixture was allowed to stir for 16 hours at RT. It was then quenched with MeOH and dried under vacuo. The residue was dissolved in DCM, filtered, concentrated and purified by silica gel chromatography to provide 6-(8-(2-(4-methyl-1-oxo-1,3-dihydroisobenzofuran-5-yl)ethyl)-3-oxo-2,8-diazaspiro[4.5]decan-2-yl)nicotinonitrile. LCMS: m/z 431 (M+H)$^+$.

EXAMPLE 5

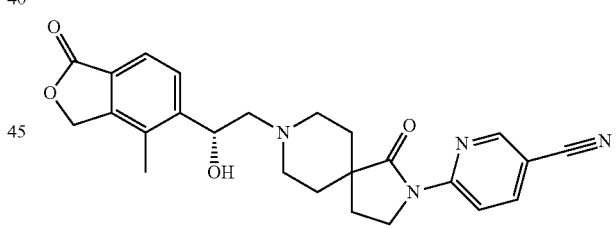

A solution of 6-(1-oxo-2,8-diazaspiro[4.5]dec-2-yl)pyridine-3-carbonitrile (0.03 g, 0.1 mmol) and 4-methyl-5-[(2R)-oxiran-2-yl]-2-benzofuran-1(3H)-one (0.03 mg, 0.1 mmol) in IPA were heated in a Biotage® microwave reactor at 130° C. for 3 h. The solution was diluted with water (w/0.5% TFA), filtered and purified via Reverse Phase HPLC. Collected fractions were concentrated and then re-dissolved in MeOH and stirred over sodium bicarbonate for 45 minutes to provide 6-{8-[(2R)-2-hydroxy-2-(4-methyl-1-oxo-1,3-dihydro-2-benzofuran-5-yl)ethyl]-1-oxo-2,8-diazaspiro[4.5]dec-2-yl}pyridine-3-carbonitrile. LCMS: m/z 447.30 (M+H)$^+$.

EXAMPLE 6

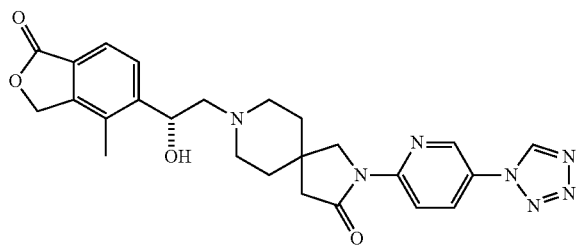 [SMILES: Cc1c([C@@H](O)CN2CCC3(CC2)CC(=O)N(c2ccc(-n4cnnn4)cn2)C3)ccc2c1COC2=O]

(R)-2-(5-(1H-tetrazol-1-yl)pyridin-2-yl)-8-(2-hydroxy-2-(4-methyl-1-oxo-1,3-dihydroisobenzofuran-5-yl)ethyl)-2,8-diazaspiro[4.5]decan-3-one was prepared via the same manner as Example 1 from 2-(5-(1H-tetrazol-1-yl)pyridin-2-yl)-2,8-diazaspiro[4.5]decan-3-one and (R)-4-methyl-5-(oxiran-2-yl)isobenzofuran-1(3H)-one. LCMS: m/z 490 (M+H)$^+$.

EXAMPLE 7

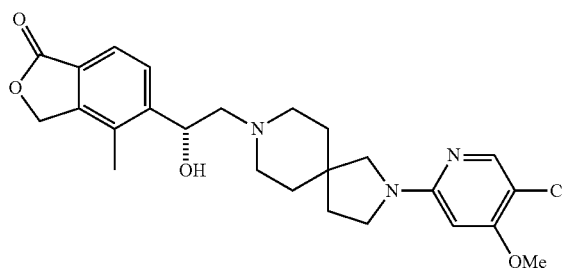

(R)-6-(8-(2-Hydroxy-2-(4-methyl-1-oxo-1,3-dihydroisobenzofuran-5-yl)ethyl)-2,8-diazaspiro[4.5]decan-2-yl)-4-methoxynicotinonitrile prepared via the same manner as Example 1 from 4-methoxy-6-(2,8-diazaspiro[4.5]decan-2-yl)nicotinonitrile and (R)-4-methyl-5-(oxiran-2-yl)isobenzofuran-1(3H)-one. LCMS: m/z 463 (M+H)$^+$.

EXAMPLE 8

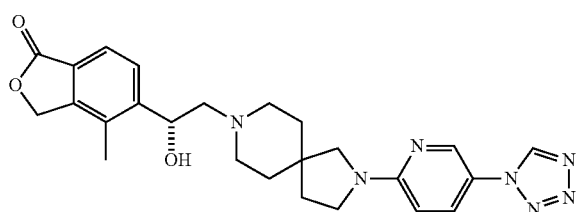

(R)-5-(2-(2-(5-(1H-tetrazol-1-yl)pyridin-2-yl)-2,8-diazaspiro[4.5]decan-8-yl)-1-hydroxyethyl)-4-methylisobenzofuran-1(3H)-one was prepared via the same manner as Example 1 from 2-(5-(1H-tetrazol-1-yl)pyridin-2-yl)-2,8-diazaspiro[4.5]decane and (R)-4-methyl-5-(oxiran-2-yl)isobenzofuran-1(3H)-one. LCMS: m/z 448 (M−N$_2$+H)$^+$.

EXAMPLE 9

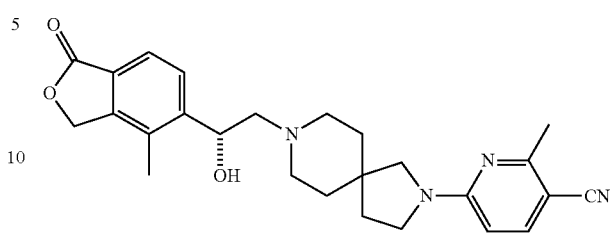

(R)-6-(8-(2-Hydroxy-2-(4-methyl-1-oxo-1,3-dihydroisobenzofuran-5-yl)ethyl)-2,8-diazaspiro[4.5]decan-2-yl)-2-methylnicotinonitrile was prepared via the same manner as Example 1 from 2-methyl-6-(2,8-diazaspiro[4.5]decan-2-yl)nicotinonitrile and (R)-4-methyl-5-(oxiran-2-yl)isobenzofuran-1(3H)-one. LCMS: m/z 448 (M+H)$^+$.

EXAMPLE 10

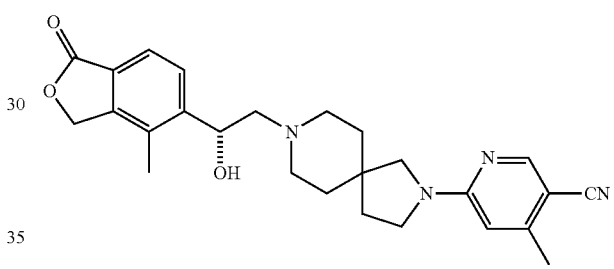

(R)-6-(8-(2-Hydroxy-2-(4-methyl-1-oxo-1,3-dihydroisobenzofuran-5-yl)ethyl)-2,8-diazaspiro[4.5]decan-2-yl)-4-methylnicotinonitrile was prepared via the same manner as Example 1 from 4-methyl-6-(2,8-diazaspiro[4.5]decan-2-yl)nicotinonitrile and (R)-4-methyl-5-(oxiran-2-yl)isobenzofuran-1(3H)-one. LCMS: m/z 448 (M+H)$^+$.

EXAMPLE 11

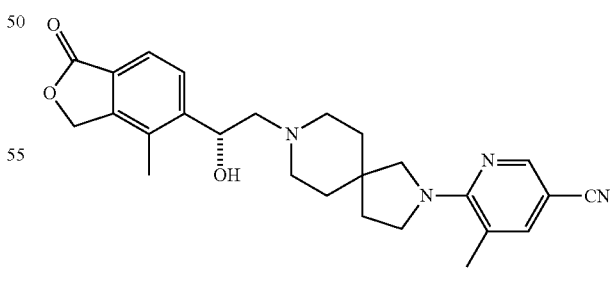

(R)-6-(8-(2-Hydroxy-2-(4-methyl-1-oxo-1,3-dihydroisobenzofuran-5-yl)ethyl)-2,8-diazaspiro[4.5]decan-2-yl)-5-methylnicotinonitrile was prepared via the same manner as Example 1 from 5-methyl-6-(2,8-diazaspiro[4.5]decan-2-yl)nicotinonitrile and (R)-4-methyl-5-(oxiran-2-yl)isobenzofuran-1(3H)-one. LCMS: m/z 448 (M+H)$^+$.

EXAMPLE 12

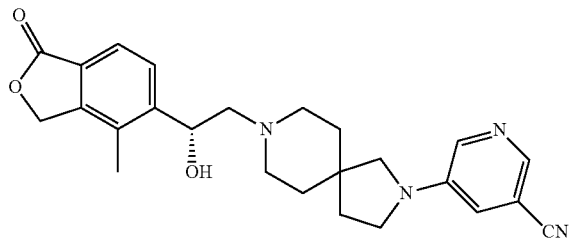 [SMILES: Cc1c([C@@H](O)CN2CCC3(CC2)CCN(c2cncc(C#N)c2)C3)ccc2c1COC2=O]

(R)-5-(8-(2-Hydroxy-2-(4-methyl-1-oxo-1,3-dihydroisobenzofuran-5-yl)ethyl)-2,8-diazaspiro[4.5]decan-2-yl)nicotinonitrile was prepared via the same manner as Example 1 from 5-(2,8-diazaspiro[4.5]decan-2-yl)nicotinonitrile and (R)-4-methyl-5-(oxiran-2-yl)isobenzofuran-1(3H)-one. LCMS: m/z 433 (M+H)+.

EXAMPLE 13

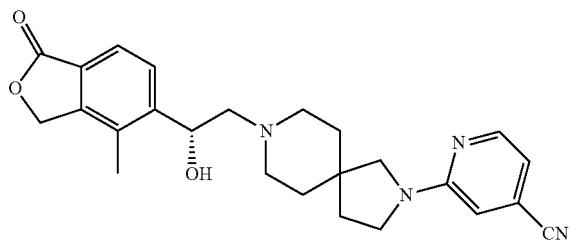 [SMILES: Cc1c([C@@H](O)CN2CCC3(CC2)CCN(c2cc(C#N)ccn2)C3)ccc2c1COC2=O]

(R)-2-(8-(2-Hydroxy-2-(4-methyl-1-oxo-1,3-dihydroisobenzofuran-5-yl)ethyl)-2,8-diazaspiro[4.5]decan-2-yl)isonicotinonitrile was prepared via the same manner as Example 1 from 2-(2,8-diazaspiro[4.5]decan-2-yl)isonicotinonitrile and (R)-4-methyl-5-(oxiran-2-yl)isobenzofuran-1(3H)-one. LCMS: m/z 433 (M+H)+.

EXAMPLE 14

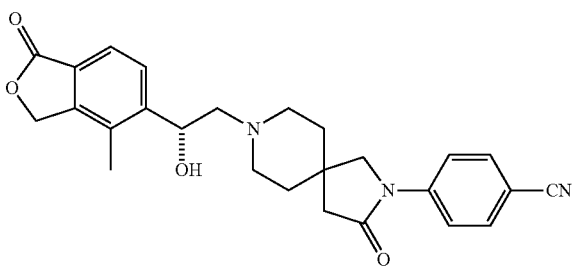 [SMILES: Cc1c([C@@H](O)CN2CCC3(CC2)CC(=O)N(c2ccc(C#N)cc2)C3)ccc2c1COC2=O]

(R)-4-(8-(2-Hydroxy-2-(4-methyl-1-oxo-1,3-dihydroisobenzofuran-5-yl)ethyl)-3-oxo-2,8-diazaspiro[4.5]decan-2-yl)benzonitrile was prepared via the same manner as Example 1 from 4-(3-oxo-2,8-diazaspiro[4.5]decan-2-yl)benzonitrile and (R)-4-methyl-5-(oxiran-2-yl)isobenzofuran-1(3H)-one. LCMS: m/z 446 (M+H)+.

EXAMPLE 15

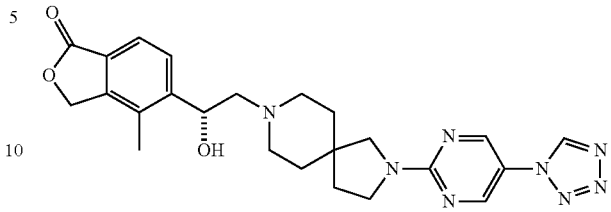

(R)-5-(2-(2-(5-(1H-tetrazol-1-yl)pyrimidin-2-yl)-2,8-diazaspiro[4.5]decan-8-yl)-1-hydroxyethyl)-4-methylisobenzofuran-1(3H)-one was prepared via the same manner as Example 1 from 2-(5-(1H-tetrazol-1-yl)pyrimidin-2-yl)-2,8-diazaspiro[4.5]decane and (R)-4-methyl-5-(oxiran-2-yl)isobenzofuran-1(3H)-one. LCMS: m/z 477 (M+H)+.

EXAMPLE 16

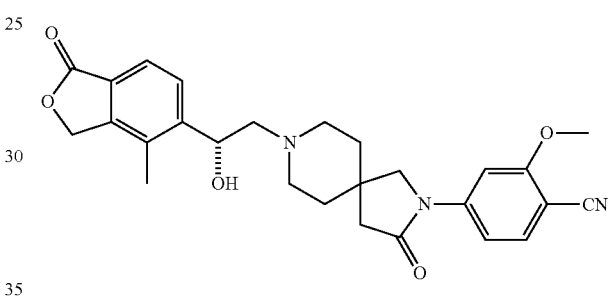

(R)-4-(8-(2-Hydroxy-2-(4-methyl-1-oxo-1,3-dihydroisobenzofuran-5-yl)ethyl)-3-oxo-2,8-diazaspiro[4.5]decan-2-yl)-2-methoxybenzonitrile was prepared via the same manner as Example 1 from 2-methoxy-4-(3-oxo-2,8-diazaspiro[4.5]decan-2-yl)benzonitrile and (R)-4-methyl-5-(oxiran-2-yl)isobenzofuran-1(3H)-one. LCMS: m/z 476 (M+H)+.

EXAMPLE 17

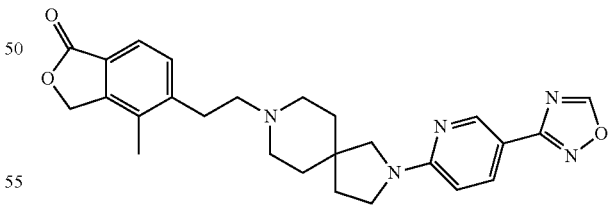

Step A: 6-(8-(2-(4-methyl-1-oxo-1,3-dihydroisobenzofuran-5-yl)ethyl)-2,8-diazaspiro[4.5]decan-2-yl)nicotinonitrile: A solution of 6-(2,8-diazaspiro[4.5]decan-2-yl)nicotinonitrile (255 mg, 1.0 mmol) in DCM was added directly into a flask containing (4-methyl-1-oxo-1,3-dihydro-2-benzofuran-5-yl)acetaldehyde (200 mg, 1.0 mmol). The mixture was allowed to stir for 20 minutes at rt before sodium triacetoxyborohydride (0.7 g, 3.0 mmol) was added in one portion. The reaction was quenched with MeOH, stirred vigorously for 30 minutes, and the excess solvent was removed. The crude material was redissolved in DCM, filtered, concentrated and purified via MPLC (EtOAc/ACN/IPA 8:1:1). LCMS: m/z 431 (M+H)⁺.

Step B: 5-(2-(2-(5-(1,2,4-oxadiazol-3-yl)pyridin-2-yl)-2,8-diazaspiro[4.5]decan-8-yl)ethyl)-4-methylisobenzofuran-1(3H)-one: To 6-(8-(2-(4-methyl-1-oxo-1,3-dihydroisobenzofuran-5-yl)ethyl)-2,8-diazaspiro[4.5]decan-2-yl)nicotinonitrile (80 mg, 0.20 mmol) in 2 mL EtOH was added 0.25 mL of 50% aqueous NH$_2$OH and catalytic amount of K$_2$CO$_3$. The reaction was heated at 120° C. for 1 h via microwave irradiation. The reaction mixture was concentrated to dryness and the residue was dissolved in 1 mL triethylorthoformate. A catalytic amount of TFA was added, and the reaction was heated at 130° C. for 3 h. The volatiles were removed and the residue was purified by reverse phase HPLC to afford 5-(2-(2-(5-(1,2,4-oxadiazol-3-yl)pyridin-2-yl)-2,8-diazaspiro[4.5]decan-8-yl)ethyl)-4-methylisobenzofuran-1(3H)-one. LCMS: m/z 460 (M+H)⁺.

EXAMPLE 18

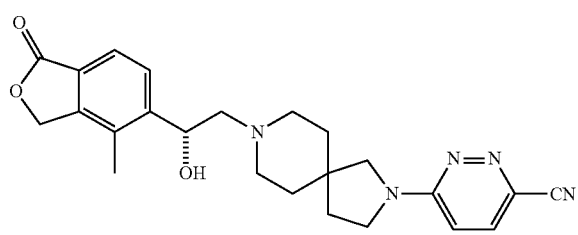 [SMILES: Cc1c([C@@H](O)CN2CCC3(CC2)CCN(c2ccc(C#N)nn2)C3)ccc2c1COC2=O]

(R)-6-(8-(2-Hydroxy-2-(4-methyl-1-oxo-1,3-dihydroisobenzofuran-5-yl)ethyl)-2,8-diazaspiro[4.5]decan-2-yl)pyridazine-3-carbonitrile was prepared via the same manner as Example 1 from 6-(2,8-diazaspiro[4.5]decan-2-yl)pyridazine-3-carbonitrile and (R)-4-methyl-5-(oxiran-2-yl)isobenzofuran-1(3H)-one. LCMS: m/z 434 (M+H)⁺.

EXAMPLE 19

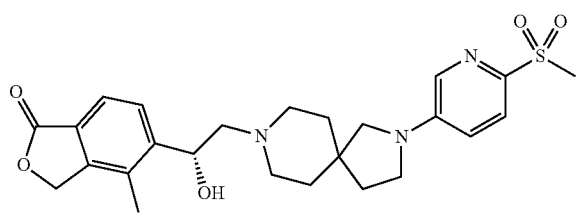 [SMILES: Cc1c([C@@H](O)CN2CCC3(CC2)CCN(c2ccc(S(C)(=O)=O)nc2)C3)ccc2c1COC2=O]

(R)-5-(1-Hydroxy-2-(2-(6-(methylsulfonyl)pyridin-3-yl)-2,8-diazaspiro[4.5]decan-8-yl)ethyl)-4-methylisobenzofuran-1(3H)-one was prepared via the same manner as Example 1 from 2-[6-(Methylsulfonyl)pyridin-3-yl]-2,8-diazaspiro[4.5]decane and (R)-4-methyl-5-(oxiran-2-yl)isobenzofuran-1(3H)-one. LCMS: m/z 434 (M+H)⁺.

EXAMPLE 20

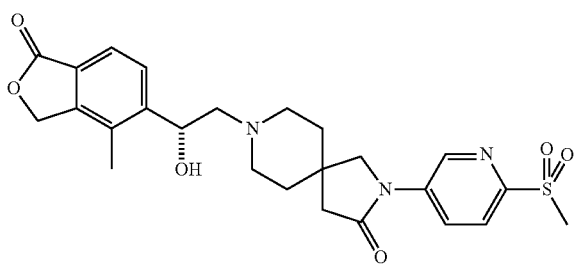 [SMILES: Cc1c([C@@H](O)CN2CCC3(CC2)CC(=O)N(c2ccc(S(C)(=O)=O)nc2)C3)ccc2c1COC2=O]

(R)-8-(2-Hydroxy-2-(4-methyl-1-oxo-1,3-dihydroisobenzofuran-5-yl)ethyl)-2-(6-(methylsulfonyl)pyridin-3-yl)-2,8-diazaspiro[4.5]decan-3-one was prepared via the same manner as Example 1 from 2-(6-(methylsulfonyl)pyridin-3-yl)-2,8-diazaspiro[4.5]decan-3-one and (R)-4-methyl-5-(oxiran-2-yl)isobenzofuran-1(3H)-one. LCMS: m/z 500 (M+H)⁺.

EXAMPLE 21

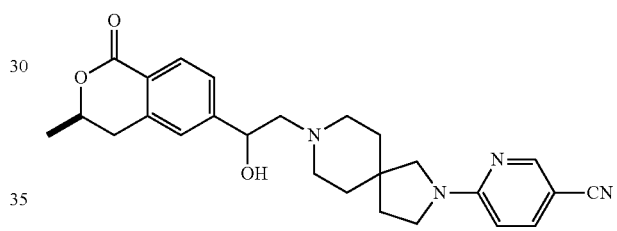

6-(8-(2-Hydroxy-2-((R)-3-methyl-1-oxoisochroman-6-yl)ethyl)-2,8-diazaspiro[4.5]decan-2-yl)nicotinonitrile was prepared via the same manner as Example 1 from 6-(2,8-diazaspiro[4.5]decan-2-yl)nicotinonitrile and (3R)-3-methyl-6-(oxiran-2-yl)isochroman-1-one. The diastereomers were separated by a Chiralcel® IA column under SFC conditions and the present compound was the second isomer to elute. LCMS: m/z 447 (M+H)⁺.

EXAMPLE 22

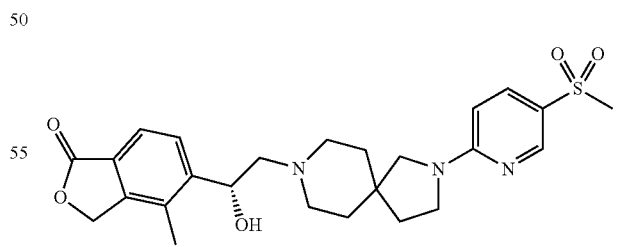

(R)-5-(1-Hydroxy-2-(2-(5-(methylsulfonyl)pyridin-2-yl)-2,8-diazaspiro[4.5]decan-8-yl)ethyl)-4-methylisobenzofuran-1(3H)-one: The title compound was prepared via the same manner as Example 1 from 2-(5-(methylsulfonyl)pyridin-2-yl)-2,8-diazaspiro[4.5]decane and (R)-4-methyl-5-(oxiran-2-yl)isobenzofuran-1(3H)-one. LCMS: m/z 486 (M+H)⁺.

EXAMPLE 23

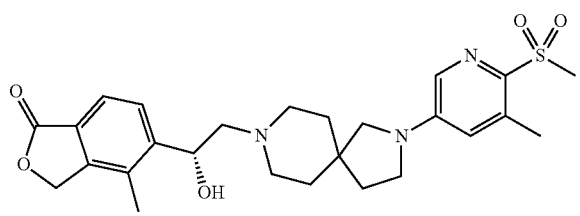 [SMILES: Cc1cc(N2CCC3(CCN(C[C@H](O)c4ccc5c(c4C)COC5=O)CC3)C2)cnc1S(C)(=O)=O]

(R)-5-(1-Hydroxy-2-(2-(5-methyl-6-(methylsulfonyl)pyridin-3-yl)-2,8-diazaspiro[4.5]decan-8-yl)ethyl)-4-methylisobenzofuran-1(3H)-one was prepared via the same manner as Example 1 from 2-(5-Methyl-6-(methylsulfonyl)pyridin-3-yl)-2,8-diazaspiro[4.5]decane and (R)-4-methyl-5-(oxiran-2-yl)isobenzofuran-1(3H)-one. LCMS: m/z 500 (M+H)+.

EXAMPLE 24A

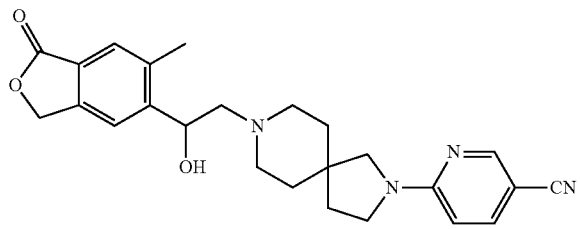 [SMILES: Cc1cc2c(cc1C(O)CN1CCC3(CC1)CCN(c1ccc(C#N)cn1)C3)COC2=O]

6-(8-(2-Hydroxy-2-(6-methyl-1-oxo-1,3-dihydroisobenzofuran-5-yl)ethyl)-2,8-diazaspiro[4.5]decan-2-yl)nicotinonitrile (A) was prepared via the same manner as Example 1 from 6-(2,8-diazaspiro[4.5]decan-2-yl)nicotinonitrile and 6-methyl-5-(oxiran-2-yl)isobenzofuran-1(3H)-one (Isomer A, first eluting). LCMS: m/z 433 (M+H)+.

EXAMPLE 24B

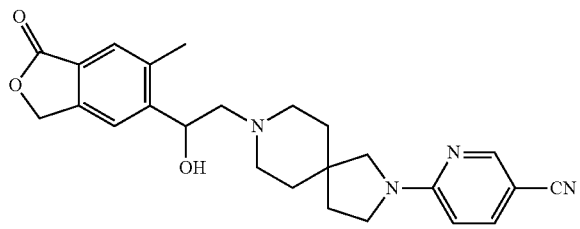 [SMILES: Cc1cc2c(cc1C(O)CN1CCC3(CC1)CCN(c1ccc(C#N)cn1)C3)COC2=O]

6-(8-(2-Hydroxy-2-(6-methyl-1-oxo-1,3-dihydroisobenzofuran-5-yl)ethyl)-2,8-diazaspiro[4.5]decan-2-yl)nicotinonitrile (B) was prepared via the same manner as Example 1 from 6-(2,8-diazaspiro[4.5]decan-2-yl)nicotinonitrile and 6-methyl-5-(oxiran-2-yl)isobenzofuran-1(3H)-one (Isomer B, second eluting). LCMS: m/z 433 (M+H)+.

EXAMPLE 25

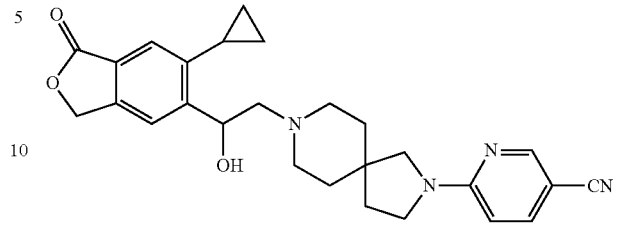

6-(8-(2-(6-Cyclopropyl-1-oxo-1,3-dihydroisobenzofuran-5-yl)-2-hydroxyethyl)-2,8-diazaspiro[4.5]decan-2-yl)nicotinonitrile was prepared via the same manner as Example 1 from 6-(2,8-diazaspiro[4.5]decan-2-yl)nicotinonitrile and 6-cyclopropyl-5-(oxiran-2-yl)isobenzofuran-1(3H)-one (Isomer A, faster eluting). LCMS: m/z 459 (M+H)+.

EXAMPLE 26

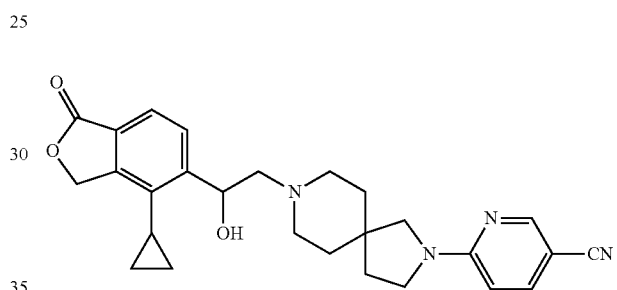

6-(8-(2-(4-Cyclopropyl-1-oxo-1,3-dihydroisobenzofuran-5-yl)-2-hydroxyethyl)-2,8-diazaspiro[4.5]decan-2-yl)nicotinonitrile (mixture of two diastereomers) was prepared via the same manner as Example 1 from 6-(2,8-diazaspiro[4.5]decan-2-yl)nicotinonitrile and 4-cyclopropyl-5-(oxiran-2-yl)isobenzofuran-1(3H)-one (racemic mixture). LCMS: m/z 459 (M+H)+.

EXAMPLE 27

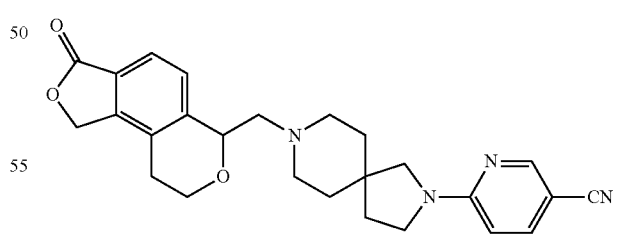

To a microwave tube charged with 6-(2,8-diazaspiro[4.5]decan-2-yl)nicotinonitrile (40 mg, 0.16 mmol) and a stir bar was added (3-oxo-3,6,8,9-tetrahydro-1H-furo[3,4-f]isochromen-6-yl)methyl 4-methylbenzenesulfonate (26 mg, 0.072 mmol) and acetonitrile (2 mL). The tube was sealed and heated to 120° C. for 1 hour. The solution was concentrated in vacuo, and purified by silica gel chromatography to afford 6-(8-((3-oxo-3,6,8,9-tetrahydro-1H-furo[3,4-f]isochromen-6-yl)methyl)-2,8-diazaspiro[4.5]decan-2-yl)nicotinonitrile as a mixture of two diastereomers. LCMS: m/z 445 (M+H)+.

EXAMPLE 28

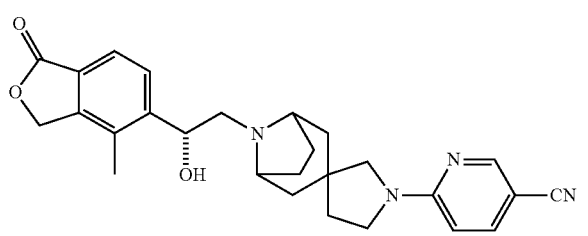 [SMILES: Cc1c([C@@H](O)CN2C3CCC2CC2(CCN(c4ccc(C#N)cn4)C2)C3)ccc2c1COC2=O]

6-(8-((R)-2-Hydroxy-2-(4-methyl-1-oxo-1,3-dihydroisobenzofuran-5-yl)ethyl)-8-azaspiro[bicyclo[3.2.1]octane-3,3'-pyrrolidin]-1'-yl)nicotinonitrile was prepared via the same manner as Example 1 from 6-(8-azaspiro[bicyclo[3.2.1]octane-3,3'-pyrrolidin]-1'-yl)nicotinonitrile and (R)-4-methyl-5-(oxiran-2-yl)isobenzofuran-1(3H)-one. LCMS: m/z 459 (M+H)+.

EXAMPLE 29

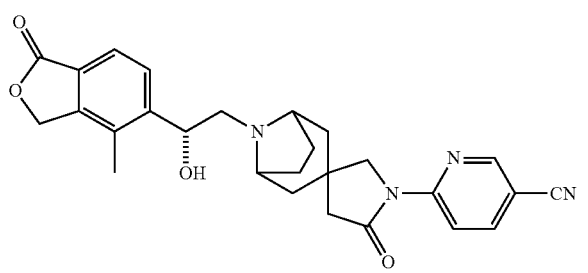 [SMILES: Cc1c([C@@H](O)CN2C3CCC2CC2(CC(=O)N(c4ccc(C#N)cn4)C2)C3)ccc2c1COC2=O]

6-(8-((R)-2-Hydroxy-2-(4-methyl-1-oxo-1,3-dihydroisobenzofuran-5-yl)ethyl)-5'-oxo-8-azaspiro[bicyclo[3.2.1]octane-3,3'-pyrrolidin]-1'-yl)nicotinonitrile was prepared via the same manner as Example 1 from 6-(5'-oxo-8-azaspiro[bicyclo[3.2.1]octane-3,3'-pyrrolidin]-1'-yl)nicotinonitrile and (R)-4-methyl-5-(oxiran-2-yl)isobenzofuran-1(3H)-one. LCMS: m/z 473 (M+H)+.

EXAMPLE 30

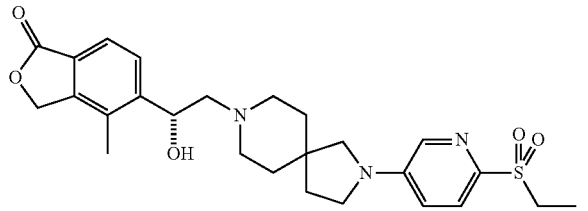 [SMILES: CCS(=O)(=O)c1ccc(N2CCC3(CCN(C[C@H](O)c4ccc5c(c4C)COC5=O)CC3)C2)cn1]

(R)-5-(2-(2-(6-(Ethylsulfonyl)pyridin-3-yl)-2,8-diazaspiro[4.5]decan-8-yl)-1-hydroxyethyl)-4-methylisobenzofuran-1(3H)-one was prepared via the same manner as Example 1 from 2-[6-(Ethylsulfonyl)pyridin-3-yl]-2,8-diazaspiro[4.5]decane and (R)-4-methyl-5-(oxiran-2-yl)isobenzofuran-1(3H)-one. LCMS: m/z 500 (M+H)+.

EXAMPLE 31

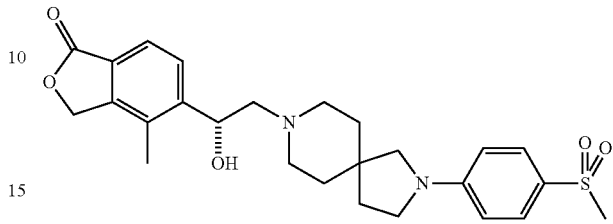

(R)-5-(1-Hydroxy-2-(2-(4-(methylsulfonyl)phenyl)-2,8-diazaspiro[4.5]decan-8-yl)ethyl)-4-methylisobenzofuran-1(3H)-one was prepared via the same manner as Example 1 from 2-(4-(methylsulfonyl)phenyl)-2,8-diazaspiro[4.5]decane and (R)-4-methyl-5-(oxiran-2-yl)isobenzofuran-1(3H)-one. LCMS: m/z 485 (M+H)+.

EXAMPLE 32

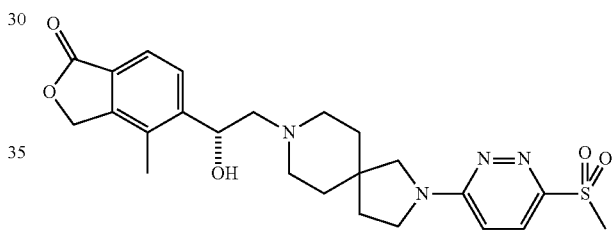

(R)-5-(1-Hydroxy-2-(2-(6-(methylsulfonyl)pyridazin-3-yl)-2,8-diazaspiro[4.5]decan-8-yl)ethyl)-4-methylisobenzofuran-1(3H)-one was prepared via the same manner as Example 1 from 2-[6-(methylsulfonyl)pyridazin-3-yl]-2,8-diazaspiro[4.5]decan-3-one and (R)-4-methyl-5-(oxiran-2-yl)isobenzofuran-1(3H)-one. LCMS: m/z 487 (M+H)+.

EXAMPLE 33

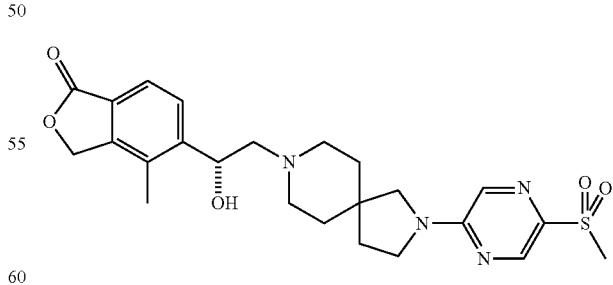

(R)-5-(1-Hydroxy-2-(2-(5-(methylsulfonyl)pyrazin-2-yl)-2,8-diazaspiro[4.5]decan-8-yl)ethyl)-4-methylisobenzofuran-1(3H)-one was prepared via the same manner as Example 1 from 2-[5-(methylsulfonyl)pyrazin-2-yl]-2,8-diazaspiro[4.5]decane and (R)-4-methyl-5-(oxiran-2-yl)isobenzofuran-1(3H)-one. LCMS: m/z 487 (M+H)+.

EXAMPLE 34

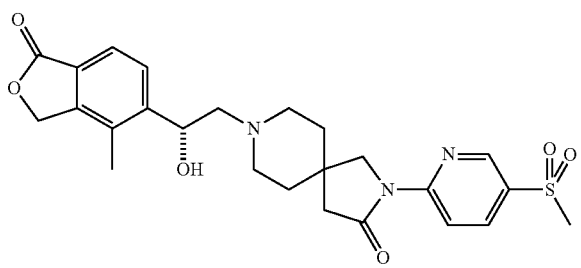 [SMILES: Cc1c([C@@H](O)CN2CCC3(CC2)CC(=O)N(c2ccc(S(C)(=O)=O)cn2)C3)ccc2c1COC2=O]

(R)-8-(2-Hydroxy-2-(4-methyl-1-oxo-1,3-dihydroisobenzofuran-5-yl)ethyl)-2-(5-(methylsulfonyl)pyridin-2-yl)-2,8-diazaspiro[4.5]decan-3-one was prepared via the same manner as Example 1 from 2-[5-(methylsulfonyl)pyridin-2-yl]-2,8-diazaspiro[4.5]decan-3-one and (R)-4-methyl-5-(oxiran-2-yl)isobenzofuran-1(3H)-one. LCMS: m/z 500 (M+H)+.

EXAMPLE 35

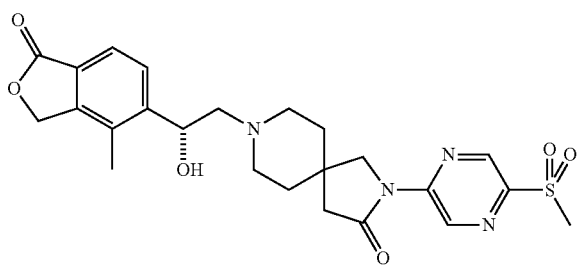 [SMILES: Cc1c([C@@H](O)CN2CCC3(CC2)CC(=O)N(c2cnc(S(C)(=O)=O)cn2)C3)ccc2c1COC2=O]

(R)-8-(2Hydroxy-2-(4-methyl-1-oxo-1,3-dihydroisobenzofuran-5-yl)ethyl)-2-(5-(methylsulfonyl)pyrazin-2-yl)-2,8-diazaspiro[4.5]decan-3-one was prepared via the same manner as Example 1 from 2-[5-(methylsulfonyl)pyrazin-2-yl]-2,8-diazaspiro[4.5]decan-3-one and (R)-4-methyl-5-(oxiran-2-yl)isobenzofuran-1(3H)-one. LCMS: m/z 501 (M+H)+.

EXAMPLE 36

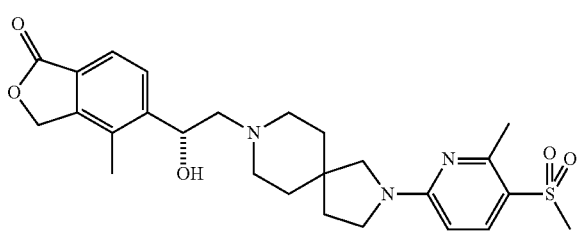 [SMILES: Cc1nc(N2CCC3(CCN(C[C@H](O)c4ccc5c(c4C)COC5=O)CC3)C2)ccc1S(C)(=O)=O]

(R)-5-(1-Hydroxy-2-(2-(6-methyl-5-(methylsulfonyl)pyridin-2-yl)-2,8-diazaspiro[4.5]decan-8-yl)ethyl)-4-methylisobenzofuran-1(3H)-one was prepared via the same manner as Example 1 from 2-[6-methyl-5-(methylsulfonyl)pyridin-2-yl]-2,8-diazaspiro[4.5]decane and (R)-4-methyl-5-(oxiran-2-yl)isobenzofuran-1(3H)-one. LCMS: m/z 500 (M+H)+.

EXAMPLE 37

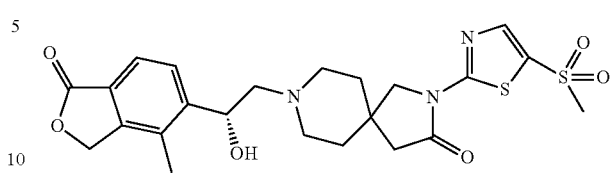

(R)-8-(2-Hydroxy-2-(4-methyl-1-oxo-1,3-dihydroisobenzofuran-5-yl)ethyl)-2-(5-(methylsulfonyl)thiazol-2-yl)-2,8-diazaspiro[4.5]decan-3-one was prepared via the same manner as Example 1 from 2-[5-(methylsulfonyl)-1,3-thiazol-2-yl]-2,8-diazaspiro[4.5]decan-3-on and (R)-4-methyl-5-(oxiran-2-yl)isobenzofuran-1(3H)-one. LCMS: m/z 506 (M+H)+.

EXAMPLE 38

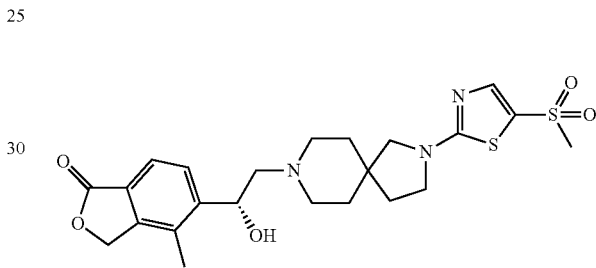

(R)-5-(1-Hydroxy-2-(2-(5-(methylsulfonyl)thiazol-2-yl)-2,8-diazaspiro[4.5]decan-8-yl)ethyl)-4-methylisobenzofuran-1(3H)-one was prepared via the same manner as Example 1 from 5-(methylsulfonyl)-2-(2,8-diazaspiro[4.5]decan-2-yl)thiazole and (R)-4-methyl-5-(oxiran-2-yl)isobenzofuran-1(3H)-one. LCMS: m/z 492 (M+H)+.

EXAMPLE 39

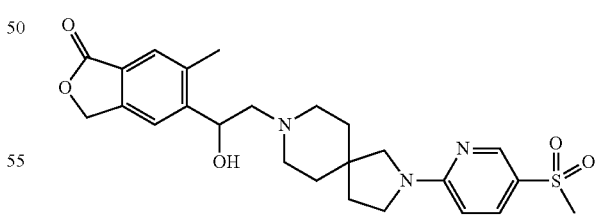

5-(1-Hydroxy-2-(2-(5-(methylsulfonyl)pyridin-2-yl)-2,8-diazaspiro[4.5]decan-8-yl)ethyl)-6-methylisobenzofuran-1(3H)-one (Isomer A) was prepared via the same manner as Example 1 from 2-(5-(methylsulfonyl)pyridin-2-yl)-2,8-diazaspiro[4.5]decane and 6-methyl-5-(oxiran-2-yl)isobenzofuran-1(3H)-one (Epoxide A, faster eluting). LCMS: m/z 486 (M+H)+.

EXAMPLE 40

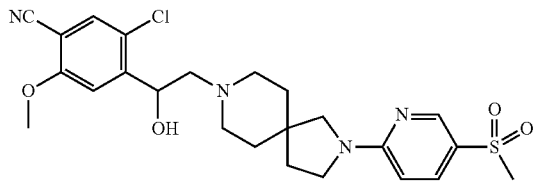 [SMILES: COc1cc(C(O)CN2CCC3(CC2)CCN(c2ccc(S(C)(=O)=O)cn2)C3)c(Cl)cc1C#N]

5-Chloro-4-(1-hydroxy-2-(2-(5-(methylsulfonyl)pyridin-2-yl)-2,8-diazaspiro[4.5]decan-8-yl)ethyl)-2-methoxybenzonitrile (mixture of two isomers) was prepared via the same manner as Example 1 from 2-(5-(methylsulfonyl)pyridin-2-yl)-2,8-diazaspiro[4.5]decane and 5-chloro-2-methoxy-4-(oxiran-2-yl)benzonitrile (racemic). LCMS: m/z 505 (M+H)$^+$.

EXAMPLE 41

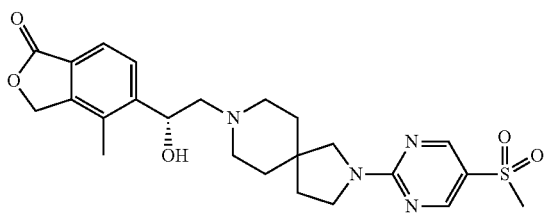 [SMILES: Cc1c([C@@H](O)CN2CCC3(CC2)CCN(c2ncc(S(C)(=O)=O)cn2)C3)ccc2c1COC2=O]

(R)-5-(1-Hydroxy-2-(2-(5-(methylsulfonyl)pyrimidin-2-yl)-2,8-diazaspiro[4.5]decan-8-yl)ethyl)-4-methylisobenzofuran-1(3H)-one was prepared via the same manner as Example 1 from 2-(5-(methylsulfonyl)pyrimidin-2-yl)-2,8-diazaspiro[4.5]decane and (R)-4-methyl-5-(oxiran-2-yl)isobenzofuran-1(3H)-one. LCMS: m/z 487 (M+H)$^+$.

EXAMPLE 42

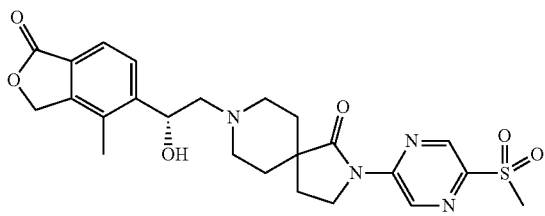 [SMILES: Cc1c([C@@H](O)CN2CCC3(CC2)CCN(c2cnc(S(C)(=O)=O)cn2)C3=O)ccc2c1COC2=O]

(R)-8-(2-Hydroxy-2-(4-methyl-1-oxo-1,3-dihydroisobenzofuran-5-yl)ethyl)-2-(5-(methylsulfonyl)pyrazin-2-yl)-2,8-diazaspiro[4.5]decan-1-one was prepared via the same manner as Example 1 from 2-(5-(Methylsulfonyl)pyrazin-2-yl)-2,8-diazaspiro[4.5]decan-1-one and (R)-4-methyl-5-(oxiran-2-yl)isobenzofuran-1(3H)-one. LCMS: m/z 501 (M+H)$^+$.

EXAMPLE 43

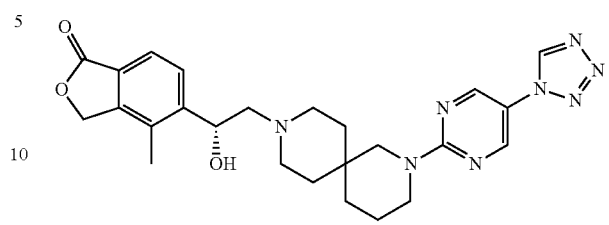

(R)-5-(2-(2-(5-(1H-tetrazol-1-yl)pyrimidin-2-yl)-2,9-diazaspiro[5.5]undecan-9-yl)-1-hydroxyethyl)-4-methylisobenzofuran-1(3H)-one was prepared via the same manner as Example 1 from 2-[5-(1H-tetrazol-1-yl)pyrimidin-2-yl]-2,9-diazaspiro[5.5]undecane and (R)-4-methyl-5-(oxiran-2-yl)isobenzofuran-1(3H)-one. LCMS: m/z 491 (M+H)$^+$.

EXAMPLE 44

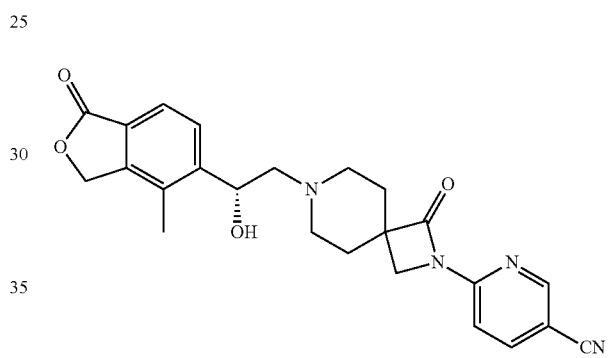

(R)-6-(7-(2-Hydroxy-2-(4-methyl-1-oxo-1,3-dihydroisobenzofuran-5-yl)ethyl)-1-oxo-2,7-diazaspiro[3.5]nonan-2-yl)nicotinonitrile was prepared via the same manner as Example 1 from 6-(1-Oxo-2,7-diazaspiro[3.5]nonan-2-yl)nicotinonitrile and (R)-4-methyl-5-(oxiran-2-yl)isobenzofuran-1(3H)-one. LCMS: m/z 433 (M+H)$^+$.

EXAMPLE 45

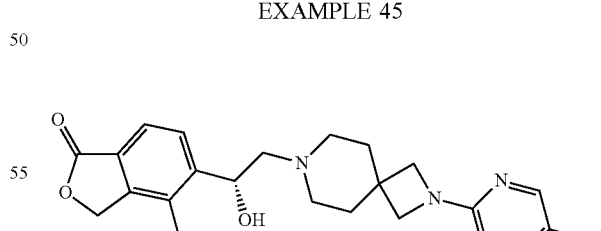

(R)-6-(7-(2-Hydroxy-2-(4-methyl-1-oxo-1,3-dihydroisobenzofuran-5-yl)ethyl)-2,7-diazaspiro[3.5]nonan-2-yl)nicotinonitrile was prepared via the same manner as Example 1 from 6-(2,7-diazaspiro[3.5]non-2-yl)pyridine-3-carbonitrile and (R)-4-methyl-5-(oxiran-2-yl)isobenzofuran-1(3H)-one. LCMS: m/z 419 (M+H)$^+$.

EXAMPLE 46

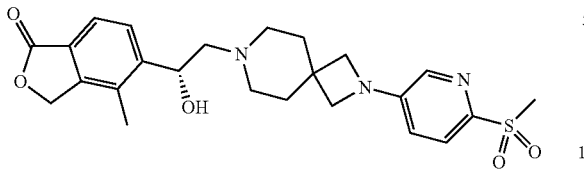

(R)-5-(1-Hydroxy-2-(2-(6-(methylsulfonyl)pyridin-3-yl)-2,7-diazaspiro[3.5]nonan-7-yl)ethyl)-4-methylisobenzofuran-1(3H)-one was prepared via the same manner as Example 1 from 2-(6-(methylsulfonyl)pyridin-3-yl)-2,7-diazaspiro[3.5]nonane and (R)-4-methyl-5-(oxiran-2-yl)isobenzofuran-1(3H)-one. LCMS: m/z 472 (M+H)+.

EXAMPLE 47

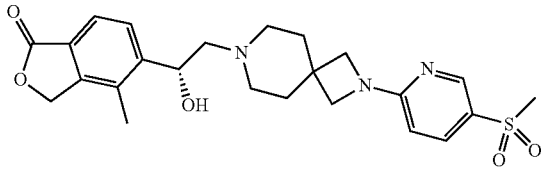 [SMILES: Cc1c([C@@H](O)CN2CCC3(CC2)CN(c2ccc(S(C)(=O)=O)cn2)C3)ccc2c1COC2=O]

(R)-5-(1-Hydroxy-2-(2-(5-(methylsulfonyl)pyridin-2-yl)-2,7-diazaspiro[3.5]nonan-7-yl)ethyl)-4-methylisobenzofuran-1(3H)-one was prepared via the same manner as Example 1 from 2-(5-(methylsulfonyl)pyridin-2-yl)-2,7-diazaspiro[3.5]nonane and (R)-4-methyl-5-(oxiran-2-yl)isobenzofuran-1(3H)-one. LCMS: m/z 472 (M+H)+.

EXAMPLE 48

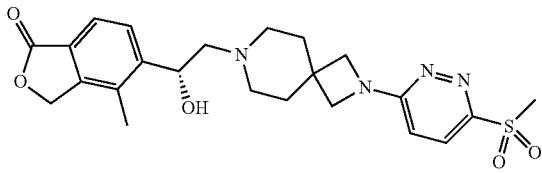 [SMILES: Cc1c([C@@H](O)CN2CCC3(CC2)CN(c2ccc(S(C)(=O)=O)nn2)C3)ccc2c1COC2=O]

(R)-5-(1-Hydroxy-2-(2-(6-(methylsulfonyl)pyridazin-3-yl)-2,7-diazaspiro[3.5]nonan-7-yl)ethyl)-4-methylisobenzofuran-1(3H)-one was prepared via the same manner as Example 1 from 2-[6-(methylsulfonyl)pyridazin-3-yl]-2,7-diazaspiro[3.5]nonane and (R)-4-methyl-5-(oxiran-2-yl)isobenzofuran-1(3H)-one. LCMS: m/z 473 (M+H)+.

EXAMPLE 49

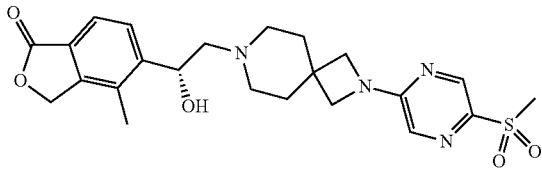

(R)-5-(1-Hydroxy-2-(2-(5-(methylsulfonyl)pyrazin-2-yl)-2,7-diazaspiro[3.5]nonan-7-yl)ethyl)-4-methylisobenzofuran-1(3H)-one via the same manner as Example 1 from 2-(5-(methylsulfonyl)pyrazin-2-yl)-2,7-diazaspiro[3.5]nonane and (R)-4-methyl-5-(oxiran-2-yl)isobenzofuran-1(3H)-one. LCMS: m/z 473 (M+H)+.

EXAMPLE 50

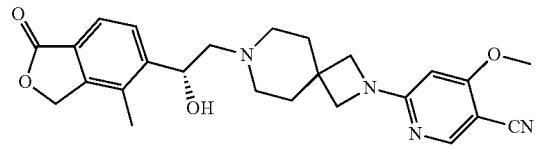 [SMILES: COc1cc(N2CC3(CCN(C[C@H](O)c4ccc5c(c4C)COC5=O)CC3)C2)ncc1C#N]

A mixture of 4-methoxy-6-(2,7-diazaspiro[3.5]nonan-2-yl)nicotinonitrile (50 mg, 0.19 mmol), (R)-4-methyl-5-(oxiran-2-yl)isobenzofuran-1(3H)-one (37 mg, 0.19 mmol), and Hunig's base (34 µL, 0.19 mmol) in EtOH (1 mL) was heated to 80° C. for 20 hours. The volatiles were removed, and the residue was purified by silica gel flash chromatography to give (R)-6-(7-(2-hydroxy-2-(4-methyl-1-oxo-1,3-dihydroisobenzofuran-5-yl)ethyl)-2,7-diazaspiro[3.5]nonan-2-yl)-4-methoxynicotinonitrile. LCMS: m/z 449 (M+H)+.

EXAMPLE 51A

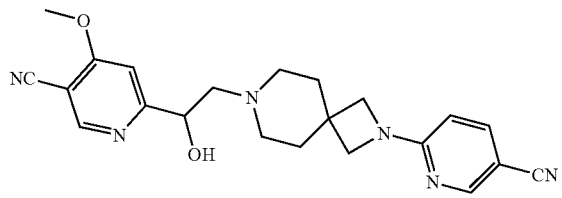 [SMILES: COc1cc(C(O)CN2CCC3(CC2)CN(c2ccc(C#N)cn2)C3)ncc1C#N]

6-(2-(2-(5-Cyanopyridin-2-yl)-2,7-diazaspiro[3.5]nonan-7-yl)-1-hydroxyethyl)-4-methoxynicotinonitrile (Isomer A) was prepared via the same manner as Example 1 from 6-(2,7-diazaspiro[3.5]nonan-2-yl)nicotinonitrile and 4-methoxy-6-(oxiran-2-yl)nicotinonitrile (Isomer A, faster eluting). LCMS: m/z 473 (M+H)+.

EXAMPLE 51B

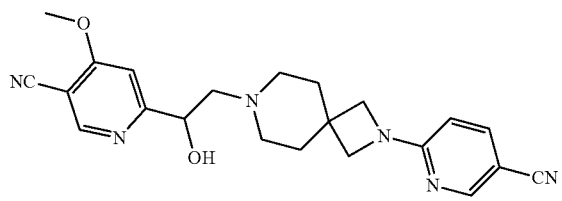 [SMILES: COc1cc(C(O)CN2CCC3(CC2)CN(c2ccc(C#N)cn2)C3)ncc1C#N]

6-(2-(2-(5-Cyanopyridin-2-yl)-2,7-diazaspiro[3.5]nonan-7-yl)-1-hydroxyethyl)-4-methoxynicotinonitrile (Isomer B) was prepared via the same manner as Example 1 from 6-(2,7-diazaspiro[3.5]nonan-2-yl)nicotinonitrile and 4-methoxy-6-(oxiran-2-yl)nicotinonitrile (Isomer B, slower eluting). LCMS: m/z 473 (M+H)+.

EXAMPLE 52A

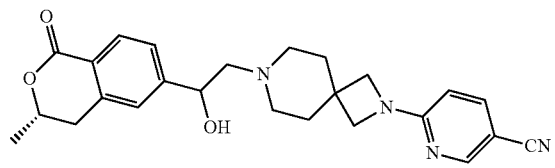 [SMILES: C[C@H]1Cc2cc(C(O)CN3CCC4(CC3)CN(c3ccc(C#N)cn3)C4)ccc2C(=O)O1]

6-(7-(2-Hydroxy-2-((S)-3-methyl-1-oxoisochroman-6-yl)ethyl)-2,7-diazaspiro[3.5]nonan-2-yl)nicotinonitrile was prepared via the same manner as Example 1 from 6-(2,7-diazaspiro[3.5]nonan-2-yl)nicotinonitrile and (3S)-3-methyl-6-(oxiran-2-yl)isochroman-1-one. LCMS: m/z 433 (M+H)⁺.

EXAMPLE 52B

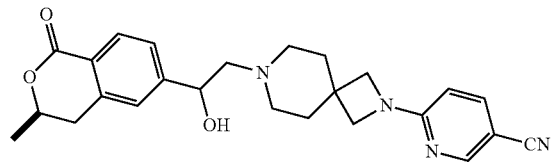 [SMILES: C[C@@H]1Cc2cc(C(O)CN3CCC4(CC3)CN(c3ccc(C#N)cn3)C4)ccc2C(=O)O1]

6-(7-(2-Hydroxy-2-((R)-3-methyl-1-oxoisochroman-6-yl)ethyl)-2,7-diazaspiro[3.5]nonan-2-yl)nicotinonitrile was prepared via the same manner as Example 1 from 6-(2,7-diazaspiro[3.5]nonan-2-yl)nicotinonitrile and (3R)-3-methyl-6-(oxiran-2-yl)isochroman-1-one. LCMS: m/z 433 (M+H)⁺.

EXAMPLE 53

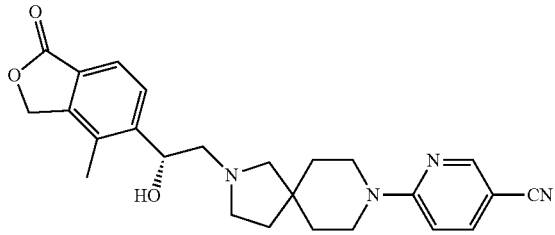 [SMILES: Cc1c([C@@H](O)CN2CCC3(CCN(c4ccc(C#N)cn4)CC3)C2)ccc2c1COC2=O]

Step A: (R)-tert-butyl 2-(2-hydroxy-2-(4-methyl-1-oxo-1,3-dihydroisobenzofuran-5-yl)ethyl)-2,8-diazaspiro[4.5]decane-8-carboxylate: A mixture of tert-butyl 2,8-diazaspiro[4.5]decane-8-carboxylate (150 mg, 0.62 mmol) and (R)-4-methyl-5-(oxiran-2-yl)isobenzofuran-1(3H)-one (120 mg, 0.62 mmol) in EtOH (2 mL) was heated to 135° C. in a microwave reactor for 1 hour. The solvent was removed, and the residue was purified by silica gel flash chromatography. LCMS: m/z 431 (M+H)⁺.

Step B: (R)-5-(1-Hydroxy-2-(2,8-diazaspiro[4.5]decan-2-yl)ethyl)-4-methylisobenzofuran-1(3H)-one: The material obtained above was treated with 4N HCl in dioxane at RT. When LC indicated complete reaction, the volatiles were removed under reduced pressure. The residue was dissolved in saturated NaHCO₃, and extracted twice with IPA-CHCl₃ (1:3). The extractions were combined, dried over Na₂SO₄, filtered and concentrated. The resulting solid was used directly in the next step.

Step C: (R)-6-(2-(2-Hydroxy-2-(4-methyl-1-oxo-1,3-dihydroisobenzofuran-5-yl)ethyl)-2,8-diazaspiro[4.5]decan-8-yl)nicotinonitrile: To a flask charged with (R)-5-(1-hydroxy-2-(2,8-diazaspiro[4.5]decan-2-yl)ethyl)-4-methylisobenzofuran-1(3H)-one and a stir bar was added 6-bromonicotinonitrile, Hunig's base and NMP. The mixture was heated to 110° C. for 16 hours. The reaction was cooled, diluted with water, and extracted with Chloform-IPA (3:1). The extractions were combined, dried over MgSO4, filtered and concentrated. The residue was purified by silica gel flash chromatography. LCMS: m/z 433 (M+H)⁺.

EXAMPLE 54

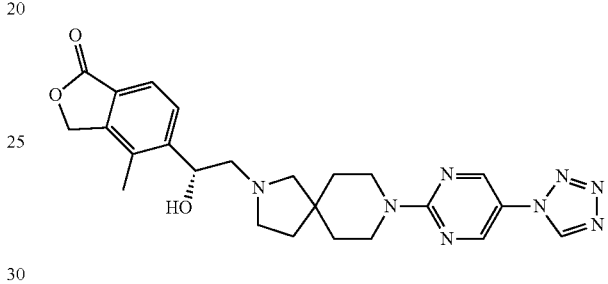

Step A: 8-(5-(1H-tetrazol-1-yl)pyrimidin-2-yl)-2,8-diazaspiro[4.5]decane: The title compound was prepared following the same procedure as for Intermediate 2-[5-(1H-tetrazol-1-yl)pyrimidin-2-yl]-2,9-diazaspiro[5.5]undecane (above) from tert-butyl 2,8-diazaspiro[4.5]decane-8-carboxylate and 2-chloro-5-nitropyrimidine. LCMS: m/z 287 (M+H)⁺.

Step B: (R)-5-(2-(8-(5-(1H-tetrazol-1-yl)pyrimidin-2-yl)-2,8-diazaspiro[4.5]decan-2-yl)-1-hydroxyethyl)-4-methylisobenzofuran-1(3H)-one: The title compound was prepared via the same manner as Example 1 from 8-(5-(1H-tetrazol-1-yl)pyrimidin-2-yl)-2,8-diazaspiro[4.5]decane and (R)-4-methyl-5-(oxiran-2-yl)isobenzofuran-1(3H)-one. LCMS: m/z 477 (M+H)⁺.

EXAMPLE 55

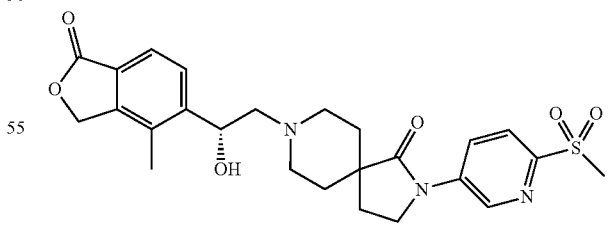

(R)-8-(2-Hydroxy-2-(4-methyl-1-oxo-1,3-dihydroisobenzofuran-5-yl)ethyl)-2-(6-(methylsulfonyl)pyridin-3-yl)-2,8-diazaspiro[4.5]decan-1-one was prepared via the same manner as Example 1 from 2-(6-(methylsulfonyl)pyridin-3-yl)-2,8-diazaspiro[4.5]decan-1-one and (R)-4-methyl-5-(oxiran-2-yl)isobenzofuran-1(3H)-one. LCMS: m/z 500 (M+H)⁺.

EXAMPLE 56

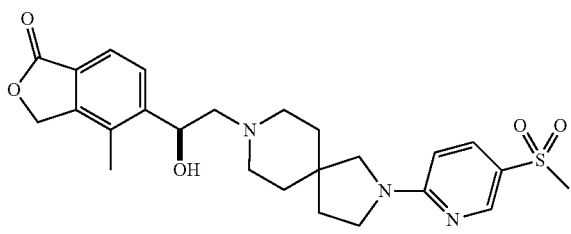 [SMILES: Cc1c([C@H](O)CN2CCC3(CC2)CCN(c2ccc(S(C)(=O)=O)cn2)C3)ccc2c1COC2=O]

(S)-5-(1-Hydroxy-2-(2-(5-(methylsulfonyl)pyridin-2-yl)-2,8-diazaspiro[4.5]decan-8-yl)ethyl)-4-methylisobenzofuran-1(3H)-one was prepared via the same manner as Example 1 from 2-(5-(methylsulfonyl)pyridin-2-yl)-2,8-diazaspiro[4.5]decane and (S)-4-methyl-5-(oxiran-2-yl)isobenzofuran-1(3H)-one. LCMS: m/z 486 (M+H)+.

EXAMPLE 57

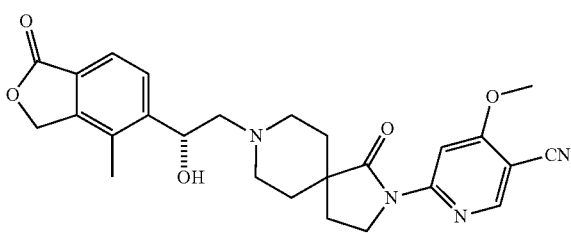 [SMILES: COc1cc(N2CCC3(CCN(C[C@H](O)c4ccc5c(c4C)COC5=O)CC3)C2=O)ncc1C#N]

(R)-8-(2-Hydroxy-2-(4-methyl-1-oxo-1,3-dihydroisobenzofuran-5-yl)ethyl)-2-(6-(methylsulfonyl)pyridazin-3-yl)-2,8-diazaspiro[4.5]decan-1-one was prepared via the same manner as Example 1 from 2-(6-(methylsulfonyl)pyridazin-3-yl)-2,8-diazaspiro[4.5]decan-1-one and (R)-4-methyl-5-(oxiran-2-yl)isobenzofuran-1(3H)-one. LCMS: m/z 501 (M+H)+.

EXAMPLE 58

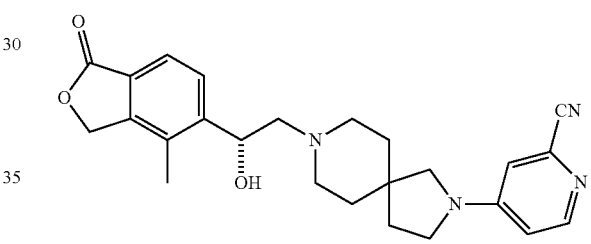

(R)-6-(8-(2-Hydroxy-2-(4-methyl-1-oxo-1,3-dihydroisobenzofuran-5-yl)ethyl)-1-oxo-2,8-diazaspiro[4.5]decan-2-yl)-4-methoxynicotinonitrile was prepared via the same manner as Example 1 from 4-methoxy-6-(1-oxo-2,8-diazaspiro[4.5]decan-2-yl)nicotinonitrile and (R)-4-methyl-5-(oxiran-2-yl)isobenzofuran-1(3H)-one. LCMS: m/z 477 (M+H)+.

EXAMPLE 59

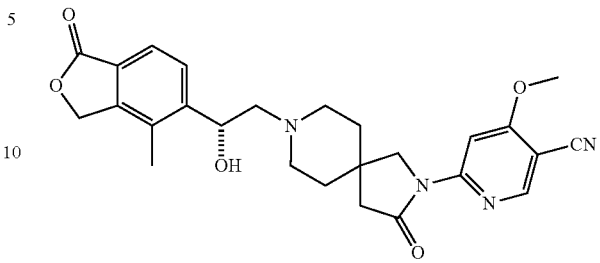

(R)-6-(8-(2-Hydroxy-2-(4-methyl-1-oxo-1,3-dihydroisobenzofuran-5-yl)ethyl)-3-oxo-2,8-diazaspiro[4.5]decan-2-yl)-4-methoxynicotinonitrile was prepared via the same manner as Example 1 from 4-methoxy-6-(3-oxo-2,8-diazaspiro[4.5]decan-2-yl)nicotinonitrile and (R)-4-methyl-5-(oxiran-2-yl)isobenzofuran-1(3H)-one. LCMS: m/z 477 (M+H)+.

EXAMPLE 60

(R)-4-(8-(2-Hydroxy-2-(4-methyl-1-oxo-1,3-dihydroisobenzofuran-5-yl)ethyl)-2,8-diazaspiro[4.5]decan-2-yl)picolinonitrile was prepared via the same manner as Example 1 from 4-(2,8-diazaspiro[4.5]decan-2-yl)picolinonitrile and (R)-4-methyl-5-(oxiran-2-yl)isobenzofuran-1(3H)-one. LCMS: m/z 433 (M+H)+.

EXAMPLE 61

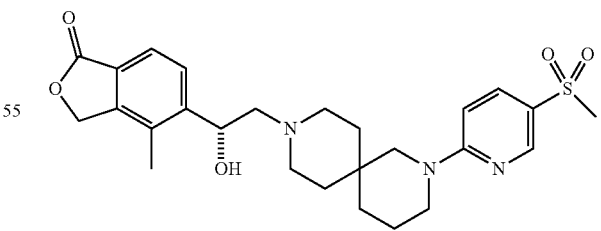

(R)-5-(1-hydroxy-2-(2-(5-(methylsulfonyl)pyridin-2-yl)-2,9-diazaspiro[5.5]undecan-9-yl)ethyl)-4-methylisobenzofuran-1(3H)-one was prepared via the same manner as Example 1 from 2-(5-(methylsulfonyl)pyridin-2-yl)-2,9-diazaspiro[5.5]undecane and (R)-4-methyl-5-(oxiran-2-yl)isobenzofuran-1(3H)-one. LCMS: m/z 500 (M+H)+.

EXAMPLE 62

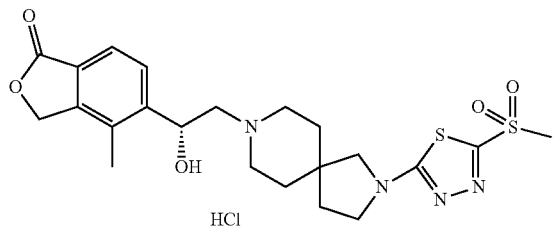 [SMILES: Cc1c([C@@H](O)CN2CCC3(CC2)CCN(c2nnc(S(C)(=O)=O)s2)C3)ccc2c1COC2=O ; Cl]

2-[5-(Methylsulfonyl)-1,3,4-thiadiazol-2-yl]-2,8-diazaspiro[4.5]decane hydrochloride (55 mg, 0.16 mmol) was diluted in EtOH (5 mL) and treated with triethylamine (112 µL, 0.81 mmol) for 15 minutes. After 15 minutes, 4-methyl-5-[(2R)-oxiran-2-yl]-2-benzofuran-1(3H)-one (30 mg, 0.16 mmol) was added and the reaction mixture was heated to reflux for 15 hours. Once cooled, the reaction was concentrated in vacuo, purified via prep TLC (ethyl acetate/acetonitrile/methanol/IPA—80/10/8/2) and treated with excess 1N HCl in ether solution to afford 5-[(1R)-1-hydroxy-2-{2-[5-(methylsulfonyl)-1,3,4-thiadiazol-2-yl]-2,8-diazaspiro[4.5]dec-8-yl}ethyl]-4-methyl-2-benzofuran-1(3H)-one hydrochloride. LCMS: m/z 493 (M+H)⁺.

EXAMPLE 63

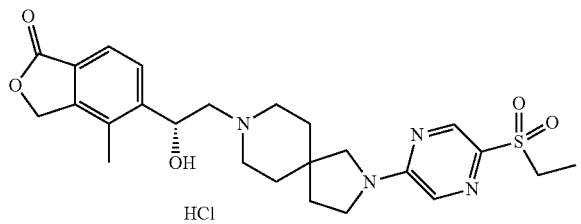 [SMILES: CCS(=O)(=O)c1cnc(N2CCC3(CCN(C[C@H](O)c4ccc5c(c4C)COC5=O)CC3)C2)cn1 ; Cl]

5-[(1R)-2-{2-[5-(Ethylsulfonyl)pyrazin-2-yl]-2,8-diazaspiro[4.5]dec-8-yl}-1-hydroxyethyl]-4-methyl-2-benzofuran-1(3H)-one hydrochloride was prepared via the same manner as Example 62 (5-[(1R)-1-hydroxy-2-{2-[5-(methylsulfonyl)-1,3,4-thiadiazol-2-yl]-2,8-diazaspiro[4.5]dec-8-yl}ethyl]-4-methyl-2-benzofuran-1(3H)-one hydrochloride) from 2-[5-(ethylsulfonyl)pyrazin-2-yl]-2,8-diazaspiro[4.5]decane hydrochloride and (R)-4-methyl-5-(oxiran-2-yl)isobenzofuran-1(3H)-one. LCMS: m/z 501 (M+H)⁺.

EXAMPLE 64

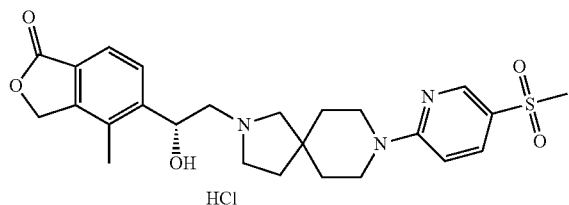 [SMILES: Cc1c([C@@H](O)CN2CCC3(CCN(c4ccc(S(C)(=O)=O)cn4)CC3)C2)ccc2c1COC2=O ; Cl]

5-[(1R)-1-Hydroxy-2-{8-[5-(methylsulfonyl)pyridin-2-yl]-2,8-diazaspiro[4.5]dec-2-yl}ethyl]-4-methyl-2-benzofuran-1(3H)-one hydrochloride was prepared via the same manner as Example 62 (5-[(1R)-1-hydroxy-2-{2-[5-(methylsulfonyl)-1,3,4-thiadiazol-2-yl]-2,8-diazaspiro[4.5]dec-8-yl}ethyl]-4-methyl-2-benzofuran-1(3H)-one hydrochloride) from 8-[5-(methylsulfonyl)pyridin-2-yl]-2,8-diazaspiro[4.5]decane hydrochloride and (R)-4-methyl-5-(oxiran-2-yl)isobenzofuran-1(3H)-one. LCMS: m/z 486 (M+H)⁺.

EXAMPLE 65

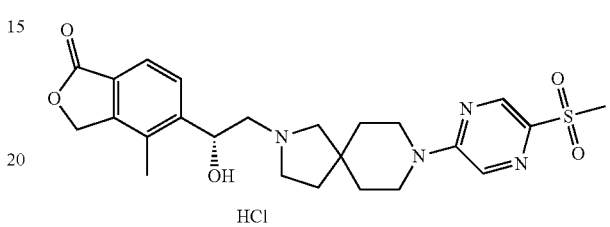

5-[(1R)-1-Hydroxy-2-{8-[5-(methylsulfonyl)pyrazin-2-yl]-2,8-diazaspiro[4.5]dec-2-yl}ethyl]-4-methyl-2-benzofuran-1(3H)-one hydrochloride was prepared via the same manner as Example 62 (5-[(1R)-1-hydroxy-2-{2-[5-(methylsulfonyl)-1,3,4-thiadiazol-2-yl]-2,8-diazaspiro[4.5]dec-8-yl}ethyl]-4-methyl-2-benzofuran-1(3H)-one hydrochloride) from 8-[5-(methylsulfonyl)pyrazin-2-yl]-2,8-diazaspiro[4.5]decane hydrochloride and (R)-4-methyl-5-(oxiran-2-yl)isobenzofuran-1(3H)-one. LCMS: m/z 487 (M+H)⁺.

EXAMPLE 66

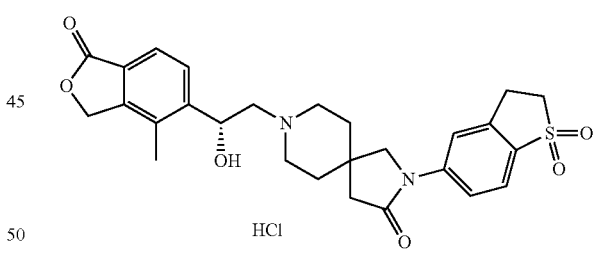

2-(1,1-Dioxido-2,3-dihydro-1-benzothiophen-5-yl)-8-[(2R)-2-hydroxy-2-(4-methyl-1-oxo-1,3-dihydro-2-benzofuran-5-yl)ethyl]-2,8-diazaspiro[4.5]decan-3-one hydrochloride was prepared via the same manner as Example 62 (5-[(1R)-1-hydroxy-2-{2-[5-(methylsulfonyl)-1,3,4-thiadiazol-2-yl]-2,8-diazaspiro[4.5]dec-8-yl}ethyl]-4-methyl-2-benzofuran-1(3H)-one hydrochloride) from 2-(1,1-dioxido-2,3-dihydro-1-benzothiophen-5-yl)-2,8-diazaspiro[4.5]decan-3-one hydrochloride and (R)-4-methyl-5-(oxiran-2-yl)isobenzofuran-1(3H)-one. LCMS: m/z 511 (M+H)⁺.

EXAMPLE 67

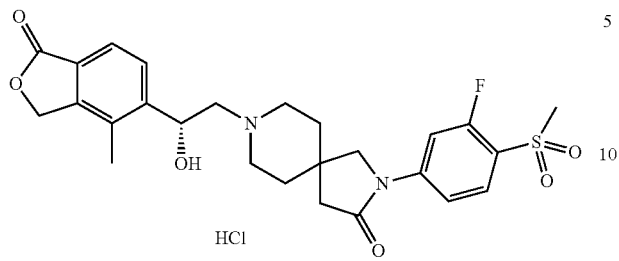

2-[3-Fluoro-4-(methylsulfonyl)phenyl]-8-[(2R)-2-hydroxy-2-(4-methyl-1-oxo-1,3-dihydro-2-benzofuran-5-yl)ethyl]-2,8-diazaspiro[4.5]decan-3-one hydrochloride was prepared via the same manner as Example 62 (5-[(1R)-1-hydroxy-2-{2-[5-(methylsulfonyl)-1,3,4-thiadiazol-2-yl]-2,8-diazaspiro[4.5]dec-8-yl}ethyl]-4-methyl-2-benzofuran-(3H)-one hydrochloride) from 2-[3-fluoro-4-(methylsulfonyl)phenyl]-2,8-diazaspiro[4.5]decan-3-one hydrochloride and (R)-4-methyl-5-(oxiran-2-yl)isobenzofuran-1(3H)-one. LCMS: m/z 517 (M+H)$^+$.

EXAMPLE 68

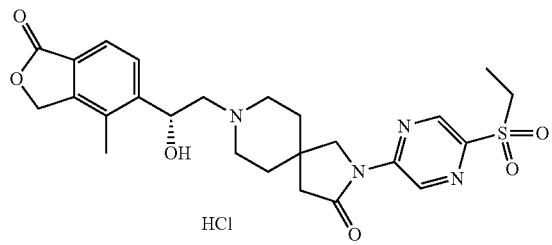 [SMILES: CCS(=O)(=O)c1cnc(N2CC3(CCN(C[C@H](O)c4ccc5c(c4C)COC5=O)CC3)CC2=O)cn1 ; Cl]

2-[5-(Ethylsulfonyl)pyrazin-2-yl]-8-[(2R)-2-hydroxy-2-(4-methyl-1-oxo-1,3-dihydro-2-benzofuran-5-yl)ethyl]-2,8-diazaspiro[4.5]decan-3-one hydrochloride was prepared via the same manner as Example 62 (5-[(1R)-1-hydroxy-2-{2-[5-(methylsulfonyl)-1,3,4-thiadiazol-2-yl]-2,8-diazaspiro[4.5]dec-8-yl}ethyl]-4-methyl-2-benzofuran-1(3H)-one hydrochloride) from 2-[5-(ethylsulfonyl)pyrazin-2-yl]-2,8-diazaspiro[4.5]decan-3-one hydrochloride and (R)-4-methyl-5-(oxiran-2-yl)isobenzofuran-1(3H)-one LCMS: m/z 515 (M+H)$^+$.

EXAMPLE 69

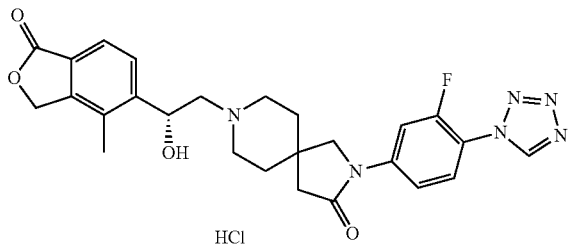 [SMILES: Cc1c([C@@H](O)CN2CCC3(CC2)CC(=O)N(c2ccc(-n4cnnn4)c(F)c2)C3)ccc2c1COC2=O ; Cl]

2-[3-Fluoro-4-(1H-tetrazol-1-yl)phenyl]-8-[(2R)-2-hydroxy-2-(4-methyl-1-oxo-1,3-dihydro-2-benzofuran-5-yl)ethyl]-2,8-diazaspiro[4.5]decan-3-one hydrochloride was prepared via the same manner as Example 62 (5-[(1R)-1-hydroxy-2-{2-[5-(methylsulfonyl)-1,3,4-thiadiazol-2-yl]-2,8-diazaspiro[4.5]dec-8-yl}ethyl]-4-methyl-2-benzofuran-(3H)-one hydrochloride) from 2-[3-fluoro-4-(1H-tetrazol-1-yl)phenyl]-2,8-diazaspiro[4.5]decan-3-one hydrochloride and (R)-4-methyl-5-(oxiran-2-yl)isobenzofuran-1(3H)-one. LCMS: m/z 507 (M+H)$^+$.

EXAMPLE 70

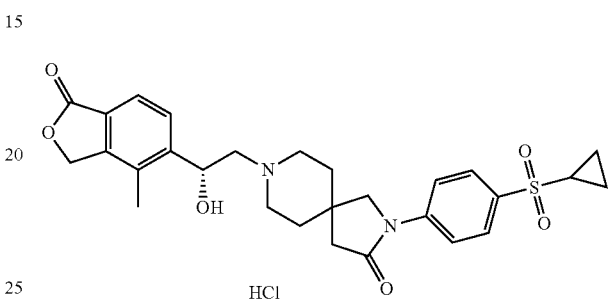

2-[4-(Cyclopropylsulfonyl)phenyl]-8-[(2R)-2-hydroxy-2-(4-methyl-1-oxo-1,3-dihydro-2-benzofuran-5-yl)ethyl]-2,8-diazaspiro[4.5]decan-3-one hydrochloride was prepared via the same manner as Example 62 (5-[(1R)-1-hydroxy-2-{2-[5-(methylsulfonyl)-1,3,4-thiadiazol-2-yl]-2,8-diazaspiro[4.5]dec-8-yl}ethyl]-4-methyl-2-benzofuran-1(3H)-one hydrochloride) from 2-[4-(cyclopropylsulfonyl)phenyl]-2,8-diazaspiro[4.5]decan-3-one hydrochloride and (R)-4-methyl-5-(oxiran-2-yl)isobenzofuran-1(3H)-one. LCMS: m/z 525 (M+H)$^+$.

EXAMPLE 71

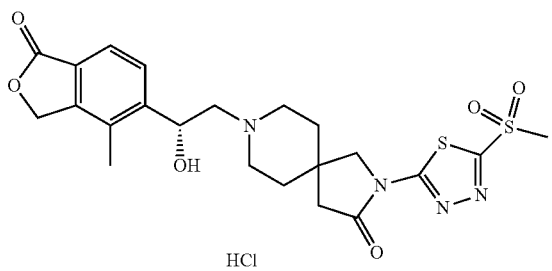 [SMILES: Cc1c([C@@H](O)CN2CCC3(CC2)CC(=O)N(c2nnc(S(C)(=O)=O)s2)C3)ccc2c1COC2=O ; Cl]

8-[(2R)-2-Hydroxy-2-(4-methyl-1-oxo-1,3-dihydro-2-benzofuran-5-yl)ethyl]-2-[5-(methylsulfonyl)-1,3,4-thiadiazol-2-yl]-2,8-diazaspiro[4.5]decan-3-one hydrochloride was prepared via the same manner as Example 62 (5-[(1R)-1-hydroxy-2-{2-[5-(methylsulfonyl)-1,3,4-thiadiazol-2-yl]-2,8-diazaspiro[4.5]dec-8-yl}ethyl]-4-methyl-2-benzofuran-1(3H)-one hydrochloride) from 2-[5-(methylsulfonyl)-1,3,4-thiadiazol-2-yl]-2,8-diazaspiro[4.5]decan-3-one hydrochloride and (R)-4-methyl-5-(oxiran-2-yl)isobenzofuran-1(3H)-one. LCMS: m/z 507 (M+H)$^+$.

EXAMPLE 72

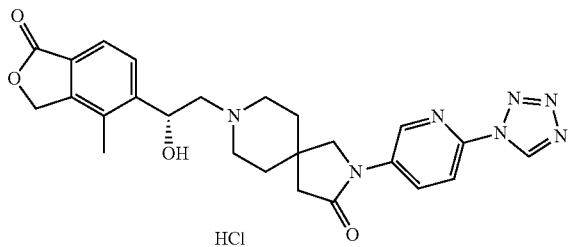 [SMILES: Cc1c([C@@H](O)CN2CCC3(CC2)CC(=O)N(c2ccc(-n4cnnn4)nc2)C3)ccc2c1COC2=O ; Cl]

8-[(2R)-2-Hydroxy-2-(4-methyl-1-oxo-1,3-dihydro-2-benzofuran-5-yl)ethyl]-2-[6-(1H-tetrazol-1-yl)pyridin-3-yl]-2,8-diazaspiro[4.5]decan-3-one hydrochloride was prepared via the same manner as Example 62 (5-[(1R)-1-hydroxy-2-{2-[5-(methylsulfonyl)-1,3,4-thiadiazol-2-yl]-2,8-diazaspiro[4.5]dec-8-yl}ethyl]-4-methyl-2-benzofuran-1(3H)-one hydrochloride) from 2-[6-(1H-tetrazol-1-yl)pyridin-3-yl]-2,8-diazaspiro[4.5]decan-3-one hydrochloride and (R)-4-methyl-5-(oxiran-2-yl)isobenzofuran-1(3H)-one. LCMS: m/z 490 (M+H)+.

EXAMPLE 73

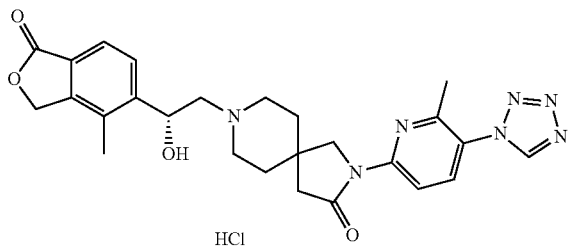 [SMILES: Cc1nc(N2CC3(CCN(C[C@H](O)c4ccc5c(c4C)COC5=O)CC3)CC2=O)ccc1-n1cnnn1 ; Cl]

8-[(2R)-2-Hydroxy-2-(4-methyl-1-oxo-1,3-dihydro-2-benzofuran-5-yl)ethyl]-2-[6-methyl-5-(1H-tetrazol-1-yl)pyridin-2-yl]-2,8-diazaspiro[4.5]decan-3-one hydrochloride was prepared via the same manner as Example 62 (5-[(1R)-1-hydroxy-2-{2-[5-(methylsulfonyl)-1,3,4-thiadiazol-2-yl]-2,8-diazaspiro[4.5]dec-8-yl}ethyl]-4-methyl-2-benzofuran-1(3H)-one hydrochloride) from 2-[6-methyl-5-(1H-tetrazol-1-yl)pyridin-2-yl]-2,8-diazaspiro[4.5]decan-3-one hydrochloride and (R)-4-methyl-5-(oxiran-2-yl)isobenzofuran-1(3H)-one. LCMS: m/z 504 (M+H)+.

EXAMPLE 74

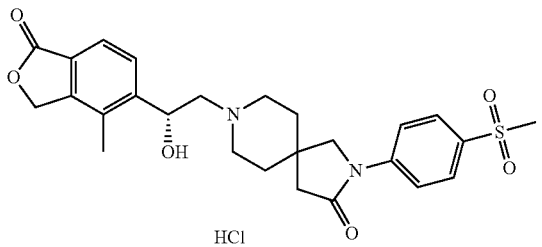 [SMILES: Cc1c([C@@H](O)CN2CCC3(CC2)CC(=O)N(c2ccc(S(C)(=O)=O)cc2)C3)ccc2c1COC2=O ; Cl]

8-[(2R)-2-Hydroxy-2-(4-methyl-1-oxo-1,3-dihydro-2-benzofuran-5-yl)ethyl]-2-[4-(methylsulfonyl)phenyl]-2,8-diazaspiro[4.5]decan-3-one hydrochloride was prepared via the same manner as Example 62 (5-[(1R)-1-hydroxy-2-{2-[5-(methylsulfonyl)-1,3,4-thiadiazol-2-yl]-2,8-diazaspiro[4.5]dec-8-yl}ethyl]-4-methyl-2-benzofuran-1(3H)-one hydrochloride) from 2-[4-(methylsulfonyl)phenyl]-2,8-diazaspiro[4.5]decan-3-one hydrochloride and (R)-4-methyl-5-(oxiran-2-yl)isobenzofuran-1(3H)-one. LCMS: m/z 499 (M+H)+.

EXAMPLE 75

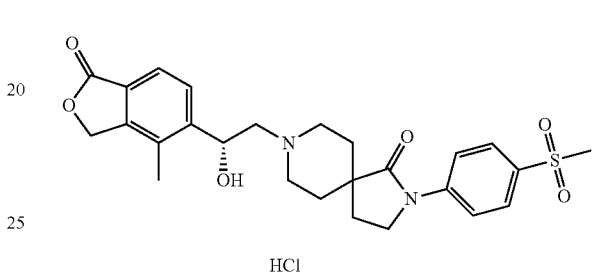

8-[(2R)-2Hydroxy-2-(4-methyl-1-oxo-1,3-dihydro-2-benzofuran-5-yl)ethyl]-2-[4-(methylsulfonyl)phenyl]-2,8-diazaspiro[4.5]decan-1-one hydrochloride was prepared via the same manner as Example 62 (5-[(1R)-1-hydroxy-2-{2-[5-(methylsulfonyl)-1,3,4-thiadiazol-2-yl]-2,8-diazaspiro[4.5]dec-8-yl}ethyl]-4-methyl-2-benzofuran-1(3H)-one hydrochloride) from 2-[4-(methylsulfonyl)phenyl]-2,8-diazaspiro[4.5]decan-1-one hydrochloride and (R)-4-methyl-5-(oxiran-2-yl)isobenzofuran-1(3H)-one. LCMS: m/z 499 (M+H)+.

EXAMPLE 76

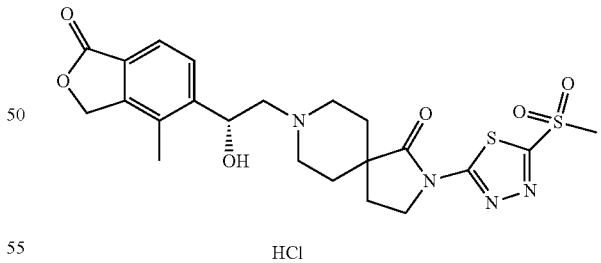

8-[(2R)-2-Hydroxy-2-(4-methyl-1-oxo-1,3-dihydro-2-benzofuran-5-yl)ethyl]-2-[5-(methylsulfonyl)-1,3,4-thiadiazol-2-yl]-2,8-diazaspiro[4.5]decan-1-one hydrochloride was prepared via the same manner as Example 62 (5-[(1R)-1-hydroxy-2-{2-[5-(methylsulfonyl)-1,3,4-thiadiazol-2-yl]-2,8-diazaspiro[4.5]dec-8-yl}ethyl]-4-methyl-2-benzofuran-1(3H)-one hydrochloride) from 2-[5-(methylsulfonyl)-1,3,4-thiadiazol-2-yl]-2,8-diazaspiro[4.5]decan-1-one hydrochloride and (R)-4-methyl-5-(oxiran-2-yl)isobenzofuran-1(3H)-one. LCMS: m/z 507 (M+H)+.

EXAMPLE 77

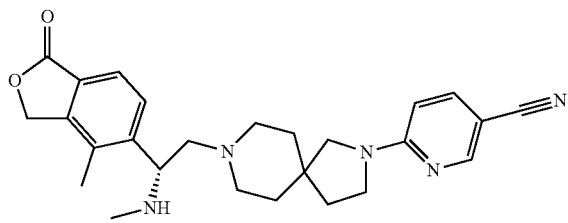 [SMILES: CN[C@@H](CN1CCC2(CC1)CCN(c1ccc(C#N)cn1)C2)c1ccc2c(c1C)COC2=O]

Step A: (S)-6-(8-(2-chloro-2-(4-methyl-1-oxo-1,3-dihydroisobenzofuran-5-yl)ethyl)-2,8-diazaspiro[4.5]decan-2-yl)nicotinonitrile: To a solution of (R)-6-(8-(2-hydroxy-2-(4-methyl-1-oxo-1,3-dihydroisobenzofuran-5-yl)ethyl)-2,8-diazaspiro[4.5]decan-2-yl)nicotinonitrile (0.11 g, 0.25 mmol) and methanesulfulonyl chloride (0.030 ml, 0.38 mmol) in DCM (10 mL) was added TEA (0.071 ml, 0.51 mmol) and DMAP (3.1 mg, 0.025 mmol) at −10-15° C. (ice-NaCl). The mixture was stirred at the same temperature for 20 min, quenched with NH4Cl aqueous. The organic layer was separated and the aqueous was extracted with DCM (20 ml). The combined organic layers were dried (MgSO$_4$) and concentrated. The residue was directly used in the next step. LCMS: 451 (M+H)$^+$.

Step B: (R)-6-(8-(2-(4-methyl-1-oxo-1,3-dihydroisobenzofuran-5-yl)-2-(methylamino)ethyl)-2,8-diazaspiro[4.5]decan-2-yl)nicotinonitrile: A mixture of (S)-6-(8-(2-chloro-2-(4-methyl-1-oxo-1,3-dihydroisobenzofuran-5-yl)ethyl)-2,8-diazaspiro[4.5]decan-2-yl)nicotinonitrile (0.1 g, 0.22 mmol), methylamine hydrochloride (0.075 g, 1.1 mmol) and N,N-diisopropylethylamine (0.19 ml, 1.1 mmol) in DCM (5 mL) was stirred at RT overnight. After concentration, the residue was purified on reverse phase HPLC-Gilson® (5-65 water-CH$_3$CN with 0.1% TFA) to give (R)-6-(8-(2-(4-methyl-1-oxo-1,3-dihydroisobenzofuran-5-yl)-2-(methylamino)ethyl)-2,8-diazaspiro[4.5]decan-2-yl)nicotinonitrile. LCMS: 446 (M+H)$^+$.

EXAMPLE 78

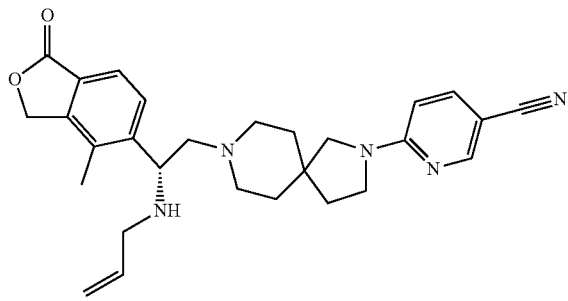 [SMILES: C=CCN[C@@H](CN1CCC2(CC1)CCN(c1ccc(C#N)cn1)C2)c1ccc2c(c1C)COC2=O]

A mixture of (S)-6-(8-(2-chloro-2-(4-methyl-1-oxo-1,3-dihydroisobenzofuran-5-yl)ethyl)-2,8-diazaspiro[4.5]decan-2-yl)nicotinonitrile (0.11 g, 0.24 mmol), ally amine (0.073 ml, 0.98 mmol) and N,N-diisopropylethylamine (0.083 ml, 0.49 mmol) in DCM (5 mL) was stirred at room temperature overnight. After concentration, the residue was purified on reverse phase HPLC-Gilson® (5-65 water-CH$_3$CN with 0.1% TFA). The TFA salt was converted to a free base by Bond Elute SCX column. A solution of the TFA salt in methanol was loaded on Bond Elute SCX column (small size) after the column was washed with 5 ml methanol. The column with the desired compound was eluted with methanol to remove TFA (~5 ml); the free base of (R)-6-(8-(2-(allylamino)-2-(4-methyl-1-oxo-1,3-dihydroisobenzofuran-5-yl)ethyl)-2,8-diazaspiro[4.5]decan-2-yl)nicotinonitrile was eluted out with 1N NH$_3$ in methanol (~10 ml). The solution was concentrated to give a free base. LCMS: 472 (M+H)$^+$.

EXAMPLE 79

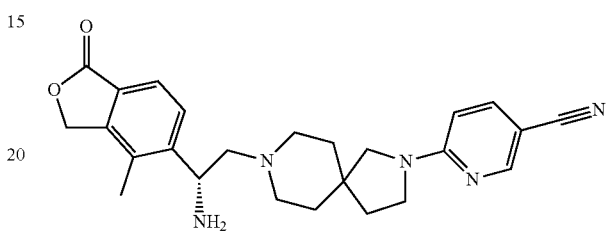

Under N$_2$, (R)-6-(8-(2-(allylamino)-2-(4-methyl-1-oxo-1,3-dihydroisobenzofuran-5-yl)ethyl)-2,8-diazaspiro[4.5]decan-2-yl)nicotinonitrile (50 mg, 0.11 mmol) in DCM (10 ml) was added 1,3-dimethylbarbituric acid (50 mg, 0.32 mmol) and tetrakis(triphenylphosphine) palladium (0) (12 mg, 10.6 µmol). The resulting mixture was heated at 40° C. under N$_2$ overnight. About 50% SM was not converted to the desired compound. The mixture was concentrated, and the desired compound was isolated by RP-Gilson® (5-45% water CH$_3$CN with 0.1% TFA). The TFA salt was converted to a free base by Bond Elute SCX column. A solution of the TFA salt in methanol was loaded on Bond Elute SCX column (small size) after the column was washed with 5 ml methanol. The column with (R)-6-(8-(2-amino-2-(4-methyl-1-oxo-1,3-dihydroisobenzofuran-5-yl)ethyl)-2,8-diazaspiro[4.5]decan-2-yl)nicotinonitrile was eluted with methanol to remove TFA (~5 mL); the free base of the desired compound was eluted out with 1N NH$_3$ in methanol (~10 mL). The solution was concentrated to give the free base. LCMS: 432 (M+H)$^+$.

SCHEME 8

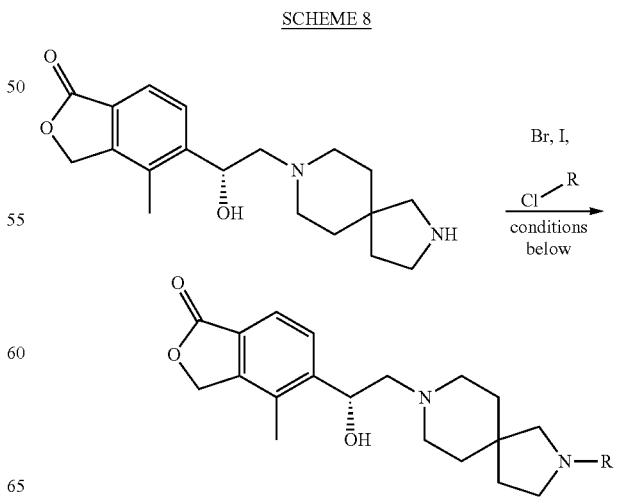

In Scheme 8 R—Cl, R—I, or R—Br represents a commercially available aryl or heterocyclic halide selected from a chloride, iodide, or bromide. Working in a parallel manner, the following protocol was applied to prepare arrays of compounds. To 4 mL, 1 dram vials were dispensed each building block (0.13 mmol each, 1.3 eq. commercially available R—Cl, I, Br halide reagent) and $Cs_2CO_3$ (0.097 g, 0.30 mmol). The scaffold (R)-5-(1-hydroxy-2-(2,8-diazaspiro[4.5]decan-8-yl)ethyl)-4-methylisobenzofuran-1(3H)-one free base (0.040 g, 0.099 mmol) was dissolved in 0.5 mL Dioxane which had been degassed under nitrogen for 1 hour and was added to each of the vials above with the halide building block. To 1 mL of degassed dioxane was added Xantphos (0.011 g, 0.020 mmol) and $Pd_2(dba)_3$ (4.5 mg, 5.0 µmol) where this cocktail was added to each of the above vials containing the building blocks. Finally, to each vial was added a stir bar, the vial blanketed with nitrogen gas and capped. The vials were placed in a heating block and stirred over night at 95° C. The following day, each solution was analyzed by LC/MS and those vials that contained the desired product were filtered and the solvents removed (GeneVac). Those samples were dissolved in 1.5 mL of DMSO and the filtered product was purified on a Gilson® semi-preparative HPLC system to afford the Examples 80-90 in Table 1. In each Example shown the aryl or heterocyclic group (representing R in the Scheme 8) was derived from the corresponding commercially available aryl or heterocyclic halide.

TABLE 1

| EX | Structure/Name | LC-MS (M + H) |
|---|---|---|
| 80 | (R)-5-(2-(2-(4-(1H-1,2,3-triazol-1-yl)phenyl)-2,8-diazaspiro[4.5]decan-8-yl)-1-hydroxyethyl)-4-methylisobenzofuran-1(3H)-one | 474 |
| 81 | (R)-5-(8-(2-hydroxy-2-(4-methyl-1-oxo-1,3-dihydroisobenzofuran-5-yl)ethyl)-2,8-diazaspiro[4.5]decan-2-yl)-3-methylpicolinonitrile | 447 |
| 82 | (R)-6-(8-(2-hydroxy-2-(4-methyl-1-oxo-1,3-dihydroisobenzofuran-5-yl)ethyl)-2,8-diazaspiro[4.5]decan-2-yl)-4-methoxynicotinonitrile | 463 |

TABLE 1-continued

| EX | Structure/Name | LC-MS (M + H) |
|---|---|---|
| 83 | 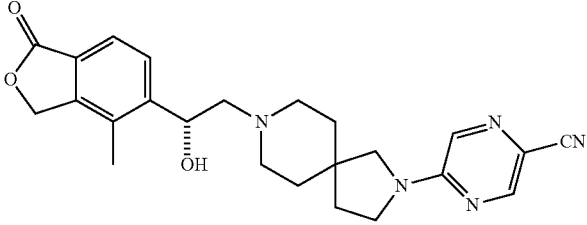<br>(R)-5-(8-(2-hydroxy-2-(4-methyl-1-oxo-1,3-dihydroisobenzofuran-5-yl)ethyl)-2,8-diazaspiro[4.5]decan-2-yl)pyrazine-2-carbonitrile | 434 |
| 84 | 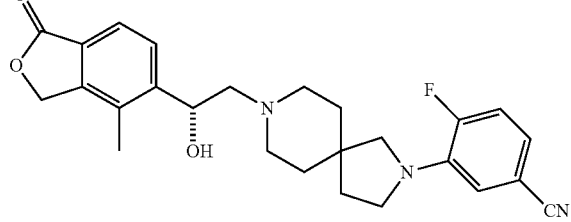<br>(R)-4-fluoro-3-(8-(2-hydroxy-2-(4-methyl-1-oxo-1,3-dihydroisobenzofuran-5-yl)ethyl)-2,8-diazaspiro[4.5]decan-2-yl)benzonitrile | 450 |
| 85 | 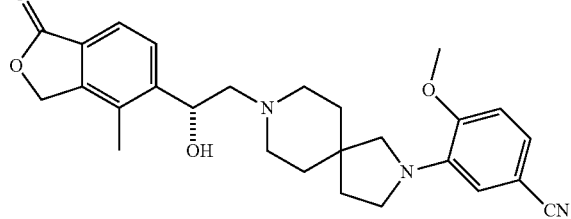<br>(R)-3-(8-(2-hydroxy-2-(4-methyl-1-oxo-1,3-dihydroisobenzofuran-5-yl)ethyl)-2,8-diazaspiro[4.5]decan-2-yl)-4-methoxybenzonitrile | 462 |
| 86 | 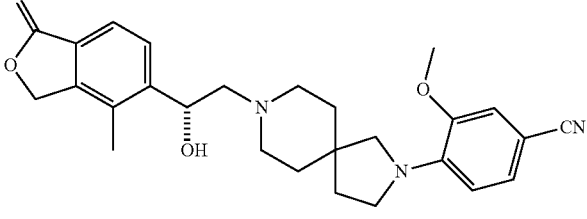<br>(R)-4-(8-(2-hydroxy-2-(4-methyl-1-oxo-1,3-dihydroisobenzofuran-5-yl)ethyl)-2,8-diazaspiro[4.5]decan-2-yl)-3-methoxybenzonitrile | 462 |

TABLE 1-continued

| EX | Structure/Name | LC-MS (M + H) |
|---|---|---|
| 87 | 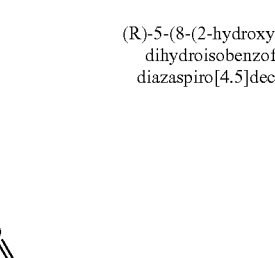<br>(R)-5-(8-(2-hydroxy-2-(4-methyl-1-oxo-1,3-dihydroisobenzofuran-5-yl)ethyl)-2,8-diazaspiro[4.5]decan-2-yl)picolinonitrile | 433 |
| 88 | 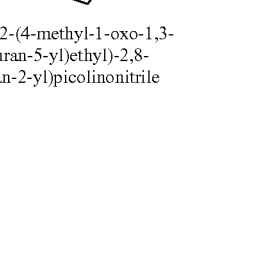<br>(R)-5-(1-hydroxy-2-(2-(3-methyl-1,1-dioxidobenzo[b]thiophen-5-yl)-2,8-diazaspiro[4.5]decan-8-yl)ethyl)-4-methylisobenzofuran-1(3H)-one | 509 |
| 89 | 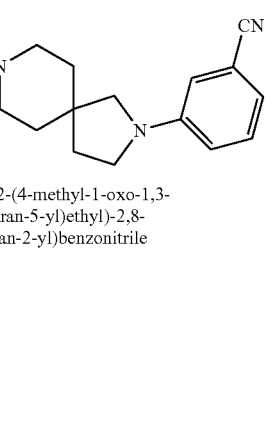<br>(R)-3-(8-(2-hydroxy-2-(4-methyl-1-oxo-1,3-dihydroisobenzofuran-5-yl)ethyl)-2,8-diazaspiro[4.5]decan-2-yl)benzonitrile | 432 |
| 90 | 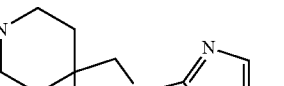<br>(R)-2-(8-(2-hydroxy-2-(4-methyl-1-oxo-1,3-dihydroisobenzofuran-5-yl)ethyl)-2,8-diazaspiro[4.5]decan-2-yl)thiazole-5-carbonitrile | 439 |

EXAMPLE 91

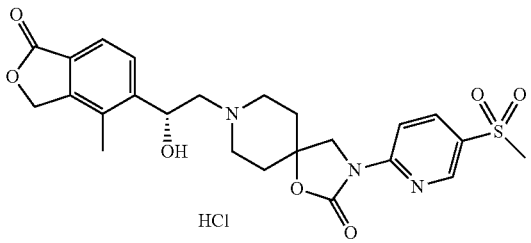 [SMILES: Cc1c([C@@H](O)CN2CCC3(CC2)CN(c2ccc(S(C)(=O)=O)cn2)C(=O)O3)ccc2c1COC2=O ; Cl]

HCl

To 3-(5-(methylsulfonyl)pyridin-2-yl)-1-oxa-3,8-diazaspiro[4.5]decan-2-one (30 mg, 0.096 mmol) in ethanol (1.0 mL) was added (R)-4-methyl-5-(oxiran-2-yl)isobenzofuran-1(3H)-one (21.99 mg, 0.116 mmol). The mixture was microwaved at 140° C. for 60 min. The reaction mixture was evaporated for purification by prep-TLC (2000 μM, 5% MeOH/DCM) to provide (R)-8-(2-hydroxy-2-(4-methyl-1-oxo-1,3-dihydroisobenzofuran-5-yl)ethyl)-3-(5-(methylsulfonyl)pyridin-2-yl)-1-oxa-3,8-diazaspiro[4.5]decan-2-one. LC/MS: [(M+1)]$^+$=502.

EXAMPLE 92

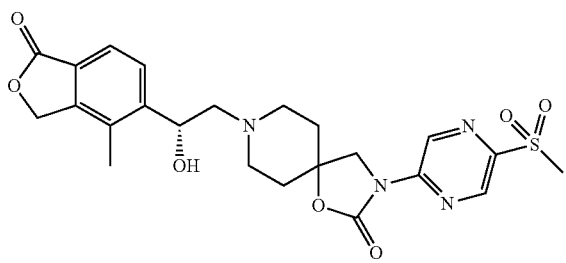 [SMILES: Cc1c([C@@H](O)CN2CCC3(CC2)CN(c2cnc(S(C)(=O)=O)cn2)C(=O)O3)ccc2c1COC2=O]

(R)-8-(2-Hydroxy-2-(4-methyl-1-oxo-1,3-dihydroisobenzofuran-5-yl)ethyl)-3-(5-(methylsulfonyl)pyrazin-2-yl)-1-oxa-3,8-diazaspiro[4.5]decan-2-one was prepared in an analogous fashion to that described for Example 91 ((R)-8-(2-hydroxy-2-(4-methyl-1-oxo-1,3-dihydroisobenzofuran-5-yl)ethyl)-3-(5-(methylsulfonyl)pyridin-2-yl)-1-oxa-3,8-diazaspiro[4.5]decan-2-one) from 3-(5-(methylsulfonyl)pyrazin-2-yl)-1-oxa-3,8-diazaspiro[4.5]decan-2-one and (R)-4-methyl-5-(oxiran-2-yl)isobenzofuran-1(3H)-one. LC/MS: [(M+1)]$^+$=503.

EXAMPLE 93

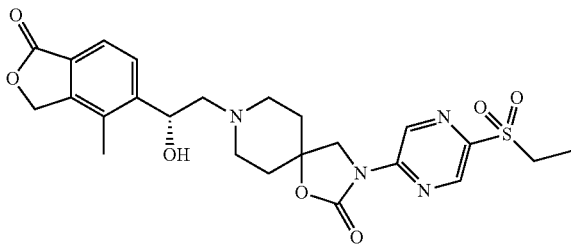 [SMILES: CCS(=O)(=O)c1cnc(N2CC3(CCN(C[C@H](O)c4ccc5c(c4C)COC5=O)CC3)OC2=O)cn1]

(R)-3-(5-(Ethylsulfonyl)pyrazin-2-yl)-8-(2-hydroxy-2-(4-methyl-1-oxo-1,3-dihydroisobenzofuran-5-yl)ethyl)-1-oxa-3,8-diazaspiro[4.5]decan-2-one was prepared in an analogous fashion to that described for Example 91 ((R)-8-(2-hydroxy-2-(4-methyl-1-oxo-1,3-dihydroisobenzofuran-5-yl)ethyl)-3-(5-(methylsulfonyl)pyridin-2-yl)-1-oxa-3,8-diazaspiro[4.5]decan-2-one) from 3-(5-(ethylsulfonyl)pyrazin-2-yl)-1-oxa-3,8-diazaspiro[4.5]decan-2-one and (R)-4-methyl-5-(oxiran-2-yl)isobenzofuran-1(3H)-one. LC/MS: [(M+1)]$^+$=517.

EXAMPLE 94

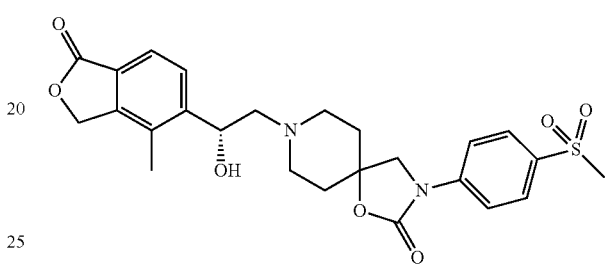

(R)-8-(2-Hydroxy-2-(4-methyl-1-oxo-1,3-dihydroisobenzofuran-5-yl)ethyl)-3-(4-(methylsulfonyl)phenyl)-1-oxa-3,8-diazaspiro[4.5]decan-2-one was prepared in an analogous fashion to that described for Example 91 ((R)-8-(2-hydroxy-2-(4-methyl-1-oxo-1,3-dihydroisobenzofuran-5-yl)ethyl)-3-(5-(methylsulfonyl)pyridin-2-yl)-1-oxa-3,8-diazaspiro[4.5]decan-2-one) from 3-(4-(methylsulfonyl)phenyl)-1-oxa-3,8-diazaspiro[4.5]decan-2-one and (R)-4-methyl-5-(oxiran-2-yl)isobenzofuran-1(3H)-one. LC/MS: [(M+1)]$^+$=501.

EXAMPLE 95

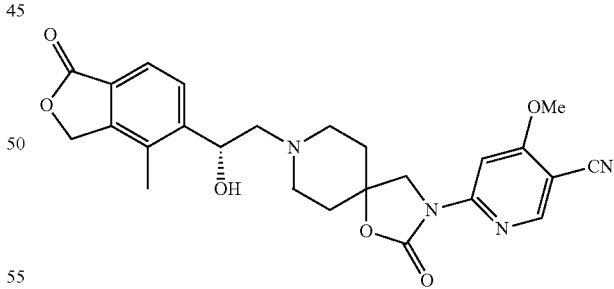

(R)-6-(8-(2-Hydroxy-2-(4-methyl-1-oxo-1,3-dihydroisobenzofuran-5-yl)ethyl)-2-oxo-1-oxa-3,8-diazaspiro[4.5]decan-3-yl)-4-methoxynicotinonitrile was prepared in an analogous fashion to that described for Example 91 ((R)-8-(2-hydroxy-2-(4-methyl-1-oxo-1,3-dihydroisobenzofuran-5-yl)ethyl)-3-(5-(methylsulfonyl)pyridin-2-yl)-1-oxa-3,8-diazaspiro[4.5]decan-2-one) from 3-(4-(methylsulfonyl)phenyl)-1-oxa-3,8-diazaspiro[4.5]decan-2-one and (R)-4-methyl-5-(oxiran-2-yl)isobenzofuran-1(3H)-one. LC/MS: [(M+1)]$^+$=479.

EXAMPLE 96

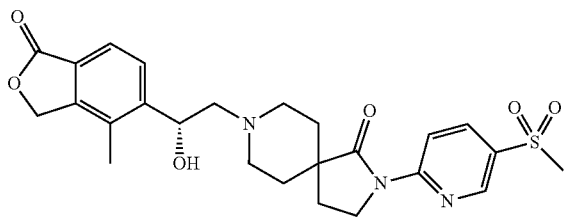 [SMILES: Cc1c([C@@H](O)CN2CCC3(CC2)CCN(c2ccc(S(C)(=O)=O)cn2)C3=O)ccc2c1COC2=O]

(R)-8-(2-Hydroxy-2-(4-methyl-1-oxo-1,3-dihydroisobenzofuran-5-yl)ethyl)-2-(5-(methylsulfonyl)pyridin-2-yl)-2,8-diazaspiro[4.5]decan-1-one was prepared via the same manner as Example 1 from 2-(5-(methylsulfonyl)pyridin-2-yl)-2,8-diazaspiro[4.5]decan-1-one and (R)-4-methyl-5-(oxiran-2-yl)isobenzofuran-1(3H)-one. LC/MS: [(M+1)]$^+$=500.

EXAMPLE 97

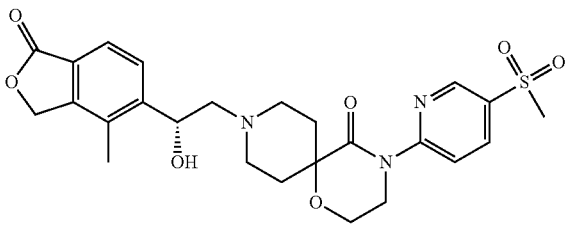 [SMILES: Cc1c([C@@H](O)CN2CCC3(CC2)OCCN(c2ccc(S(C)(=O)=O)cn2)C3=O)ccc2c1COC2=O]

(R)-9-(2-Hydroxy-2-(4-methyl-1-oxo-1,3-dihydroisobenzofuran-5-yl)ethyl)-4-(5-(methylsulfonyl)pyridin-2-yl)-1-oxa-4,9-diazaspiro[5.5]undecan-5-one: The title compound was prepared via the same manner as Example 1 from 4-(5-(methylsulfonyl)pyridin-2-yl)-1-oxa-4,9-diazaspiro[5.5]undecan-5-one and (R)-4-methyl-5-(oxiran-2-yl)isobenzofuran-1(3H)-one. LC/MS: [(M+1)]$^+$=516.

EXAMPLE 98

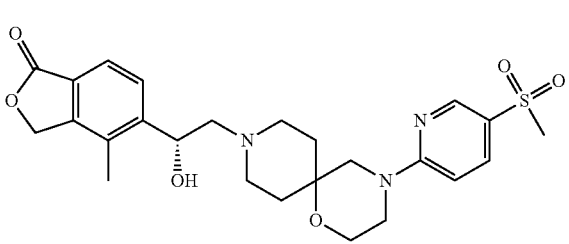 [SMILES: Cc1c([C@@H](O)CN2CCC3(CC2)CN(c2ccc(S(C)(=O)=O)cn2)CCO3)ccc2c1COC2=O]

(R)-5-(1-Hydroxy-2-(4-(5-(methylsulfonyl)pyridin-2-yl)-1-oxa-4,9-diazaspiro[5.5]undecan-9-yl)ethyl)-4-methyl-isobenzofuran-1(3H)-one was prepared via the same manner as Example 1 from 4-(5-(methylsulfonyl)pyridin-2-yl)-1-oxa-4,9-diazaspiro[5.5]undecane and (R)-4-methyl-5-(oxiran-2-yl)isobenzofuran-1(3H)-one. LC/MS: [(M+1)]$^+$=502.

EXAMPLE 99

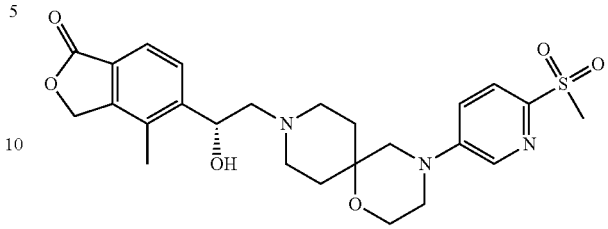

(R)-5-(1-Hydroxy-2-(4-(6-(methylsulfonyl)pyridin-3-yl)-1-oxa-4,9-diazaspiro[5.5]undecan-9-yl)ethyl)-4-methyl-isobenzofuran-1(3H)-one was prepared via the same manner as Example 1 from 4-(6-(methylsulfonyl)pyridin-3-yl)-1-oxa-4,9-diazaspiro[5.5]undecane and (R)-4-methyl-5-(oxiran-2-yl)isobenzofuran-1(3H)-one. LC/MS: [(M+1)]$^+$=502.

EXAMPLE 100

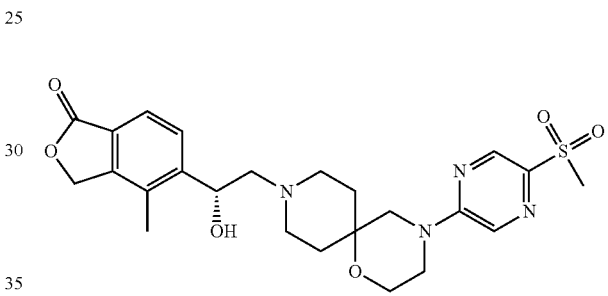

(R)-5-(1-Hydroxy-2-(4-(5-(methylsulfonyl)pyrazin-2-yl)-1-oxa-4,9-diazaspiro[5.5]undecan-9-yl)ethyl)-4-methyl-isobenzofuran-1(3H)-one was prepared via the same manner as Example 1 from 4-(5-(methylsulfonyl)pyrazin-2-yl)-1-oxa-4,9-diazaspiro[5.5]undecane and (R)-4-methyl-5-(oxiran-2-yl)isobenzofuran-1(3H)-one. LC/MS: [(M+1)]$^+$=503.

EXAMPLE 101

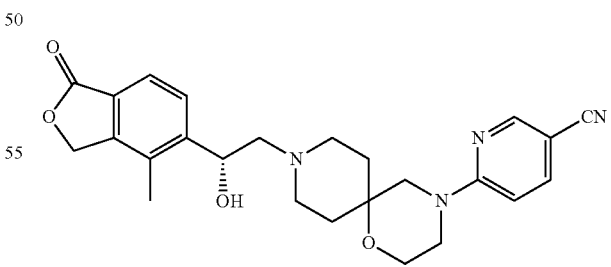

(R)-6-(9-(2-Hydroxy-2-(4-methyl-1-oxo-1,3-dihydroisobenzofuran-5-yl)ethyl)-1-oxa-4,9-diazaspiro[5.5]undecan-4-yl)nicotinonitrile was prepared via the same manner as Example 1 from 6-(1-oxa-4,9-diazaspiro[5.5]undecan-4-yl)nicotinonitrile and (R)-4-methyl-5-(oxiran-2-yl)isobenzofuran-1(3H)-one. LC/MS: [(M+1)]$^+$=449.

EXAMPLE 102

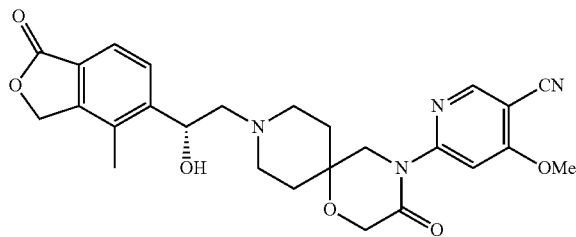 [SMILES: COc1cc(N2CC3(CCN(C[C@H](O)c4ccc5c(c4C)COC5=O)CC3)OCC2=O)ncc1C#N]

(R)-6-(9-(2-Hydroxy-2-(4-methyl-1-oxo-1,3-dihydroisobenzofuran-5-yl)ethyl)-3-oxo-1-oxa-4,9-diazaspiro[5.5]undecan-4-yl)-4-methoxynicotinonitrile was prepared via the same manner as Example 1 from 4-methoxy-6-(3-oxo-1-oxa-4,9-diazaspiro[5.5]undecan-4-yl) nicotinonitrile and (R)-4-methyl-5-(oxiran-2-yl)isobenzofuran-1(3H)-one. LC/MS: [(M+1)]$^+$=493.

EXAMPLE 103

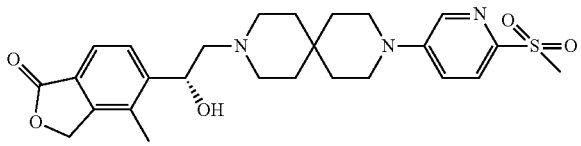 [SMILES: Cc1c([C@@H](O)CN2CCC3(CC2)CCN(c2ccc(S(C)(=O)=O)nc2)CC3)ccc2c1COC2=O]

A mixture of 3-(6-(methylsulfonyl)pyridin-3-yl)-3,9-diazaspiro[5.5]undecane (INTERMEDIATE 99, 100 mg, 0.32 mmol), (R)-4-methyl-5-(oxiran-2-yl)isobenzofuran-1(3H)-one (INTERMEDIATE 3B, 62 mg, 0.32 mmol) and diisopropylethyl amine (0.056 ml, 0.32 mmol) in ethanol (1 mL) was heated at 80° C. overnight. The reaction mixture was concentrated to dryness and purified by flash chromatography (Biotage® SNAP 50 g, 0-7% MeOH/DCM as eluent) to afford (R)-5-(1-hydroxy-2-(9-(6-(methylsulfonyl)148yridine-3-yl)-3,9-diazaspiro[5.5]undecan-3-yl)ethyl)-4-methylisobenzofuran-1(3H)-one. LC-MS m/z (M+H)$^+$500.09.

The compound in Table 2 was prepared in an analogous fashion to EXAMPLE 103 starting from the indicated piperidine and epoxide intermediates prepared as described above.

TABLE 2

| EX. | INT. | EXAMPLE STRUCTURE/NAME | LC/MS [M + 1]$^+$: |
|---|---|---|---|
| 104 | 3B, 98 | (R)-6-(9-(2-hydroxy-2-(4-methyl-1-oxo-1,3-dihydroisobenzofuran-5-yl)ethyl)-3,9-diazaspiro[5.5]undecan-3-yl)nicotinonitrile | 447 |

EXAMPLE 105

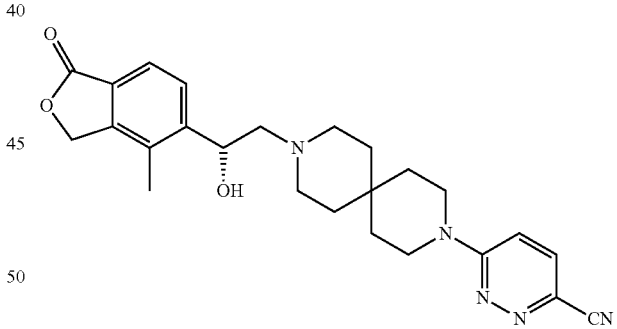

To a 2 dram vial were added (R)-5-(1-hydroxy-2-(3,9-diazaspiro[5.5]undecan-3-yl)ethyl)-4-methylisobenzofuran-1(3H)-one dihydrochloride (INTERMEDIATE 97, 25 mg, 0.060 mmol), cesium carbonate (58.5 mg, 0.180 mmol), 6-chloropyridazine-3-carbonitrile (16.7 mg, 0.120 mmol), 4,5-bis(diphenylphosphino)-9,9-dimethylxanthene (6.93 mg, 0.012 mmol) and tris(dibenzylideneacetone)dipalladium(0) (2.74 mg, 2.99 μmol) in THF (2 ml). The vial was degassed with N$_2$ and than stirred at 95° C. over night. The reaction mixture was filtered and purified with prep. LC/MS to give (R)-6-(9-(2-hydroxy-2-(4-methyl-1-oxo-1,3-dihydroisobenzofuran-5-yl)ethyl)-3,9-diazaspiro[5.5]undecan-3-yl)pyridazine-3-carbonitrile. LC-MS (IE, m/z): 448 [M+H]$^+$.

The compounds in Table 3 were prepared in an analogous fashion to Example 105 starting from (R)-5-(1-hydroxy-2-(3,9-diazaspiro[5.5]undecan-3-yl)ethyl)-4-methylisobenzofuran-1(3H)-one (INTERMEDIATE 97) and commercially available starting materials.

TABLE 3

| EX. | STRUCTURE/NAME | LC/MS [M + 1]+ |
|---|---|---|
| 106 | (R)-6-(9-(2-hydroxy-2-(4-methyl-1-oxo-1,3-dihydroisobenzofuran-5-yl)ethyl)-3,9-diazaspiro[5.5]undecan-3-yl)pyrimidine-4-carbonitrile | 448 |
| 107 | (R)-2-(9-(2-hydroxy-2-(4-methyl-1-oxo-1,3-dihydroisobenzofuran-5-yl)ethyl)-3,9-diazaspiro[5.5]undecan-3-yl)nicotinonitrile | 447 |
| 108 | (R)-6-(9-(2-hydroxy-2-(4-methyl-1-oxo-1,3-dihydroisobenzofuran-5-yl)ethyl)-3,9-diazaspiro[5.5]undecan-3-yl)-5-methylnicotinitrile | 461 |

TABLE 3-continued

| EX. | STRUCTURE/NAME | LC/MS [M + 1]⁺ |
|---|---|---|
| 109 | 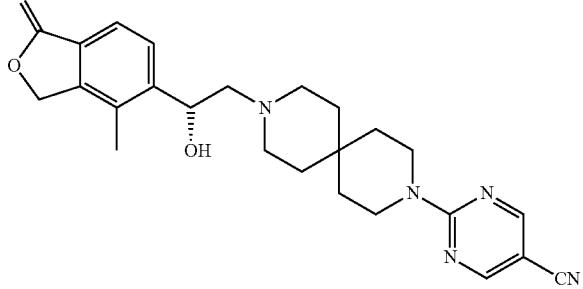<br>(R)-2-(9-(2-hydroxy-2-(4-methyl-1-oxo-1,3-dihydroisobenzofuran-5-yl)ethyl)-3,9-diazaspiro[5.5]undecan-3-yl)pyrimidine-5-carbonitrile | 448 |
| 110 | 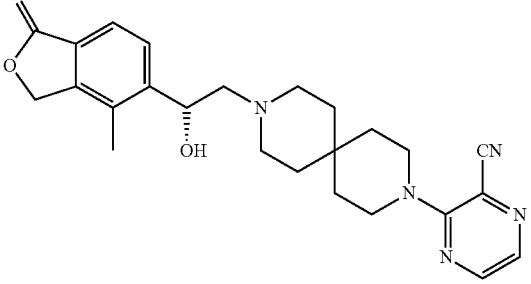<br>(R)-3-(9-(2-hydroxy-2-(4-methyl-1-oxo-1,3-dihydroisobenzofuran-5-yl)ethyl)-3,9-diazaspiro[5.5]undecan-3-yl)pyrazine-2-carbonitrile | 448 |
| 111 | 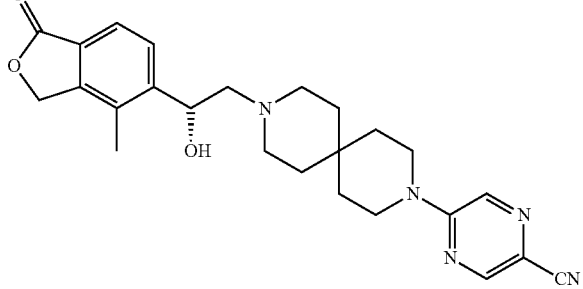<br>(R)-5-(9-(2-hydroxy-2-(4-methyl-1-oxo-1,3-dihydroisobenzofuran-5-yl)ethyl)-3,9-diazaspiro[5.5]undecan-3-yl)pyrazine-2-carbonitrile | 448 |
| 112 | 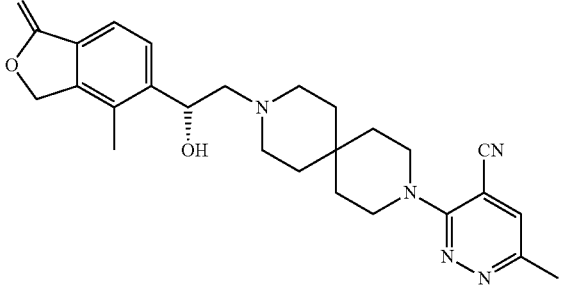<br>(R)-3-(9-(2-hydroxy-2-(4-methyl-1-oxo-1,3-dihydroisobenzofuran-5-yl)ethyl)-3,9-diazaspiro[5.5]undecan-3-yl)-6-methylpyridazine-4-carbonitrile | 462 |

TABLE 3-continued

| EX. | STRUCTURE/NAME | LC/MS [M + 1]+ |
|---|---|---|
| 113 | 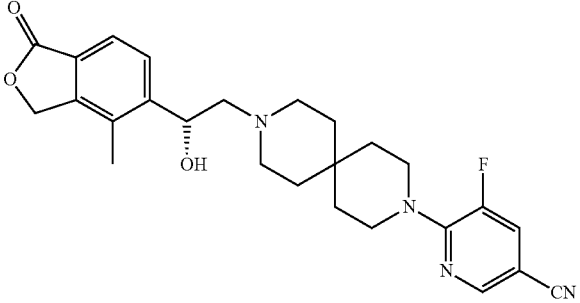
(R)-5-fluoro-6-(9-(2-hydroxy-2-(4-methyl-1-oxo-1,3-dihydroisobenzofuran-5-yl)ethyl)-3,9-diazaspiro[5.5]undecan-3-yl)nicotinonitrile | 465 |
| 114 | 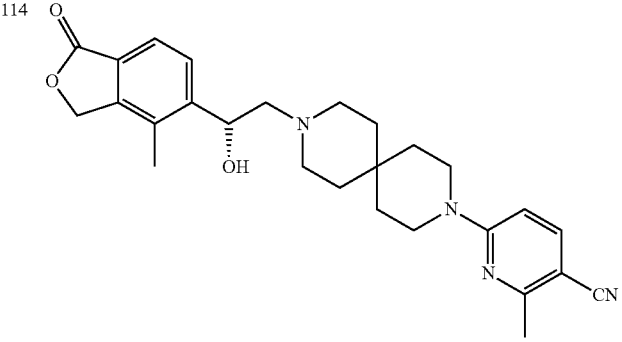
(R)-6-(9-(2-hydroxy-2-(4-methyl-1-oxo-1,3-dihydroisobenzofuran-5-yl)ethyl)-3,9-diazaspiro[5.5]undecan-3-yl)-2-methylnicotinonitrile | 461 |

EXAMPLE 115

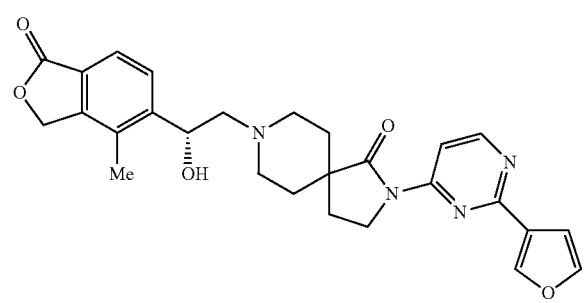 [SMILES: Cc1c([C@@H](O)CN2CCC3(CC2)CCN(c2ccnc(-c4ccoc4)n2)C3=O)ccc2c1COC2=O]

(R)-2-(2-(furan-3-yl)pyrimidin-4-yl)-8-(2-hydroxy-2-(4-methyl-1-oxo-1,3-dihydroisobenzofuran-5-yl)ethyl)-2,8-diazaspiro[4.5]decan-1-one was prepared via the same manner as Example 105 from (R)-8-(2-hydroxy-2-(4-methyl-1-oxo-1,3-dihydroisobenzofuran-5-yl)ethyl)-2,8-diazaspiro[4.5]decan-1-one (Intermediate 100) and commercially available 4-chloro-2-(3-furan)pyrimidine. LC/MS: [(M+1)]+=489.

The following Thallium Flux Assay was performed on each of the final product compounds in the Examples.

Thallium Flux Assay

Cell Culture Conditions—HEK293 cells stably expressing hROMK (hK$_{ir}$1.1) were grown at 37° C. in a 10% $CO_2$ humidified incubator in complete growth media: Dulbecco's Modified Eagle Medium supplemented with non-essential amino acids, Penicillin/Streptomycin/Glutamine, G418 and FBS. At >80% confluency, the media was aspirated from the flask and rinsed with 10 mL calcium/magnesium-free PBS. 5 mL of 1× trypsin (prepared in Ca/Mg Free PBS) was added to T-225 flask and flask was returned to 37° C./$CO_2$ incubator for 2-3 minutes. To dislodge the cell, the side of the flask was gently banged with one's hand. The cells completely titrated and then the cells were transferred to 25 mL complete media, centrifuged at 1,500 rpm for 6 min followed by resuspension in complete growth media and determine cell concentration. For typical re-seeding, 4E6 cells/T-225 flask will attain >80% confluency in 4 days. Under ideal growth conditions and appropriate tissue culture practices, this cell line is stable for 40-45 passages.

FluxOR Kit Components (Invitrogen F10017)
  FluxOR™ Reagent (Component A)
  FluxOR™ Assay Buffer (Component B)—10× Concentrate
  PowerLoad™ Concentrate (Component C)—100× Concentrate
  Probenecid (Component D)—Lyophilized sample is kept at −20° C. Water soluble, 100× after solubilization in 1 mL water. Store at 4° C.
  FluxOR™ Chloride-free Buffer (Component E)—5× Concentrate
  Potassium sulfate ($K_2SO_4$) Concentrate (Component F)—125 mM in water. Store at 4° C.

Thallium sulfate (Tl$_2$SO$_4$) Concentrate (Component G)—50 mM in water. Store at 4° C.

DMSO (dimethyl sulfoxide, Component H)—1 mL (100%)

Reagent Preparation: FluxOR Working Solutions
- 1000× FluxOR™ Reagent: Reconstitute a vial of component A in 100 μl DMSO; Mix well; Store 10 μl aliquots at −20° C.
- 1× FluxOR™ Assay Buffer: Dilute Component B 10-fold with water; Adjust pH to 7.4 with Hepes/NaOH; Filter and store at 4° C.
- Probenecid/Assay Buffer: 100 mL of 1× FluxOR™ Assay Buffer; 1 mL of reconstituted component D; Store at 4° C.
- Loading Buffer (per microplate): 10 μl 1000× FluxOR™ Reagent; 100 μl component C; 10 mL Probenecid/Assay Buffer
- Compound Buffer (per microplate): 20 mL Probenecid/Assay Buffer; 0.3 mM ouabain (10 mM ouabain in water can be stored in amber bottle/aluminum foil at room temperature); Test compound
- 1× FluxOR™Chloride-Free Buffer: Prepare 1× working solution in water. Can be stored at room temperature
- Stimulant Buffer (prepared at 5× final concentration in 1× FluxOR™Chloride-Free Buffer): 7.5 mM thallium sulfate and 0.75 mM potassium sulfate (to give a final assay concentration of 3 mM Thallium/0.3 mM potassium). Store at 4° C. when not in use. If kept sterile, this solution is good for months.

Assay Protocol—The ROMK channel functional thallium flux assay was performed in 384 wells, using the FLIPR-Tetra instrument. HEK-hKir1.1 cells were seeded in Poly-D-Lysine microplates and kept in a 37° C.-10% CO$_2$ incubator overnight. On the day of the experiment, the growth media was replaced with the FluxOR™ reagent loading buffer and incubated, protected from light, at ambient temperature (23-25° C.) for 90 min. The loading buffer was replaced with assay buffer±test compound followed by 30 min incubation at ambient temperature, where the thallium/potassium stimulant was added to the microplate.

Step Protocol
1. Seed HEK-hKir1.1 cells (50 μl at 20,000 cells/well) in 384-well PDL coated Microplates
2. Allow cells to adhere overnight in humidified 37° C./10% CO$_2$ incubator
3. Completely remove cell growth media from microplate and replace with 25 μl loading buffer
4. Incubate Microplate at room temperature, protected form light, for 90 min
5. Remove loading buffer and replace with 25 μl 1× Assay Buffer±test compound.
6. Incubate microplate at room temperature, protected from light, for 30 min
7. At FLIPR-Tetra 384: Add stimulant (thallium/potassium) solution to microplate and monitor fluorescence. Excitation=400 nm, Emission=460 & 580 nm. Collect data for ~10 min.

Data Calculation—The fluorescence intensity of wells containing 3 μM of a standard control ROMK inhibitor of the present invention was used to define the ROMK-sensitive component of thallium flux. Fluorescence in the presence of test compounds was normalized to control values to provide % fluorescence change. IC$_{50}$ values represent the concentration of compound that inhibited 50% of the ROMK thallium flux signal.

Assay Standard—Normally, a control compound is included to support that the assay is giving consistent results compared to previous measurements, although the control is not required to obtain the results for the test compounds. The control can be any compound of Formula I of the present invention, preferably with an IC$_{50}$ potency of less than 1 μM in this assay. Alternatively, the control could be another compound (outside the scope of Formula I) that has an IC$_{50}$ potency in this assay of less than 1 μM.

Data collected for compounds in the Examples of the present invention using the Thallium Flux Assay are shown in Table 4 below. All of the tested final product compounds in the Examples (diastereomeric mixtures and individual diastereomers) had IC$_{50}$ potencies less than 1 μM the Thallium Flux Assay.

TABLE 4

| Example No. | ROMK TI IC50 |
| --- | --- |
| 1 | 0.0105 |
| 2 | 0.023 |
| 3 | 0.01 |
| 4 | 0.012 |
| 5 | 0.037 |
| 6 | 0.0925 |
| 7 | 0.0215 |
| 8 | 0.037 |
| 9 | 0.014 |
| 10 | 0.017 |
| 11 | 0.02 |
| 12 | 0.033 |
| 13 | 0.026 |
| 14 | 0.015 |
| 15 | 0.057 |
| 16 | 0.051 |
| 17 | 0.19 |
| 18 | 0.156 |
| 19 | 0.226 |
| 20 | 0.308 |
| 21 | 0.05015 |
| 22 | 0.04111 |
| 23 | 0.1353 |
| 24A | 0.01756 |
| 24B | 0.03145 |
| 25 | 0.0744 |
| 26 | 0.4578 |
| 27 | 0.1031 |
| 28 | 0.0505 |
| 29 | 0.1984 |
| 30 | 0.271 |
| 31 | 0.04135 |
| 32 | 0.1767 |
| 33 | 0.04414 |
| 34 | 0.05345 |
| 35 | 0.07423 |
| 36 | 0.07572 |
| 37 | 0.08753 |
| 38 | 0.05997 |
| 39 | 0.1948 |
| 40 | 0.1682 |
| 41 | 0.1006 |
| 42 | 0.2159 |
| 43 | 0.037 |
| 44 | 0.369 |
| 45 | 0.1041 |
| 46 | 0.2563 |
| 47 | 0.2201 |
| 48 | 0.07097 |
| 49 | 0.1181 |
| 50 | 0.04235 |
| 51A | 0.4154 |
| 51B | 0.3546 |
| 52A | 0.0487 |
| 52B | 0.06988 |
| 53 | 0.019 |
| 54 | 0.262 |
| 55 | 0.0851 |
| 56 | 0.341 |
| 57 | 0.05922 |

TABLE 4-continued

| Example No. | ROMK TI IC50 |
|---|---|
| 58 | 0.04935 |
| 59 | 0.03288 |
| 60 | 0.05445 |
| 61 | 0.05604 |
| 62 | 0.2102 |
| 63 | 0.08325 |
| 64 | 0.2717 |
| 65 | 0.09984 |
| 66 | 0.1014 |
| 67 | 0.068 |
| 68 | 0.1266 |
| 69 | 0.1729 |
| 70 | 0.2484 |
| 71 | 0.1422 |
| 72 | 0.1004 |
| 73 | 0.3591 |
| 74 | 0.08217 |
| 75 | 0.08515 |
| 76 | 0.1004 |
| 77 | 0.0613 |
| 78 | 0.07062 |
| 79 | 0.01408 |
| 80 | 0.06351 |
| 81 | 0.01011 |
| 82 | 0.03284 |
| 83 | 0.0047 |
| 84 | 0.2547 |
| 85 | 0.2344 |
| 86 | 0.05041 |
| 87 | 0.08867 |
| 88 | 0.3534 |
| 89 | 0.1176 |
| 90 | 0.0067 |
| 91 | 0.208 |
| 92 | 0.125 |
| 93 | 0.148 |
| 94 | 0.1587 |
| 95 | 0.084 |
| 96 | 0.08595 |
| 97 | 0.1872 |
| 98 | 0.3762 |
| 99 | 0.1677 |
| 100 | 0.3079 |
| 101 | 0.03957 |
| 102 | 0.01667 |
| 103 | 0.5632 |
| 104 | 0.026 |
| 105 | 0.01347 |
| 106 | 0.02628 |
| 107 | 0.1798 |
| 108 | 0.2551 |
| 109 | 0.01452 |
| 110 | 0.135 |
| 111 | 0.009617 |
| 112 | 0.1611 |
| 113 | 0.4726 |
| 114 | 0.1357 |
| 115 | 0.2857 |

While the invention has been described with reference to certain particular embodiments thereof, numerous alternative embodiments will be apparent to those skilled in the art from the teachings described herein. The scope of the claims should not be limited by the preferred embodiments set forth in the examples, but should be given the broadest interpretation consistent with the description as a whole. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

The invention claimed is:
1. A compound of the formula

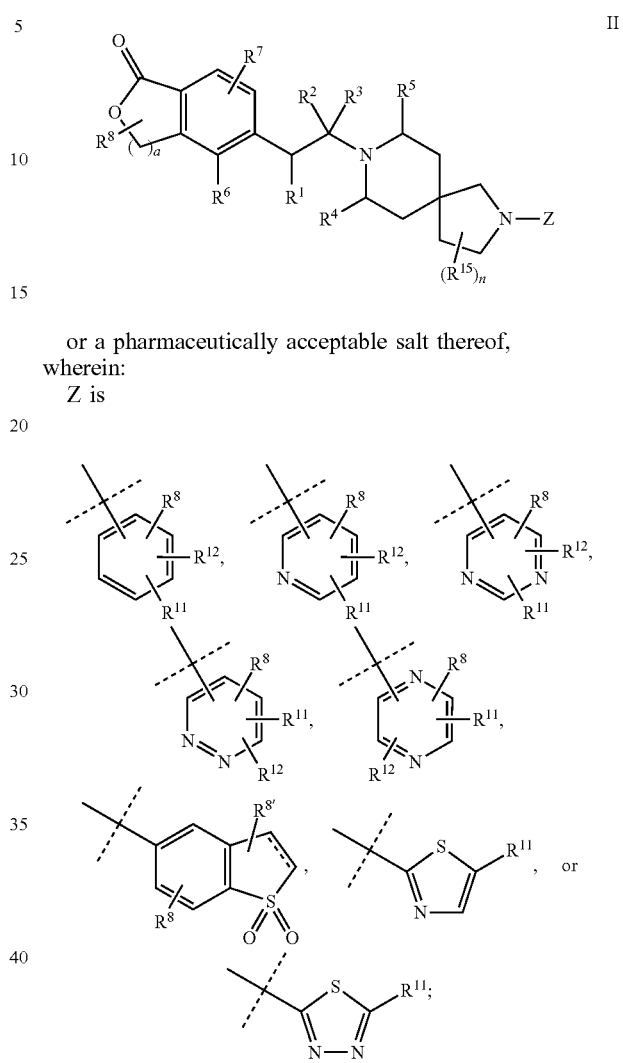

or a pharmaceutically acceptable salt thereof,
wherein:
Z is where ---- is a single or double bond;
R is independently H, alkyl or haloalkyl;
$R^1$ is H, alkyl, —F, —OR, or —N($R^{13}$)($R^{14}$);
$R^2$ is H or alkyl optionally substituted by 1-5 halogen atoms or —OR;
$R^3$ is H or alkyl;
$R^4$ is H or alkyl optionally substituted by 1-5 halogen atoms or —OR;
$R^5$ is H or alkyl optionally substituted by 1-5 halogen atoms or —OR;
or $R^4$ and $R^5$ are joined together to represent —CH$_2$CH$_2$-, —CH$_2$NCH$_2$-, —CH$_2$N(CH$_3$)CH$_2$- or —CH$_2$OCH$_2$-;
$R^6$ is H, halo, alkyl optionally substituted by 1-5 halogen atoms or —OR, cycloalkyl or —OR;
or $R^6$ and $R^1$ are joined together to represent —CH$_2$CH$_2$O—;
$R^7$ is H, halo, alkyl optionally substituted by 1-5 halogen atoms or —OR, cycloalkyl or —OR;
$R^8$ is independently H or alkyl;
$R^{8'}$ is H or alkyl;
$R^9$ is —CN, tetrazolyl, or —S(O)$_2$R$^{13}$;

R¹⁰ is halo, —OR, alkyl optionally substituted by 1-5 halogen atoms or —OR, —S-alkyl, —N-alkyl or —O-cyclopropyl;

R¹¹ is —CN, —S(O)₂R¹³, or optionally substituted heteroaryl wherein the optional substituent is halogen or alkyl;

R¹² is H, halo, alkyl, cycloalkyl, or —OR;

R¹³ is H, alkyl, allyl or cycloalkyl;

R¹⁴ is H, alkyl or cycloalkyl;

R¹⁵ independently oxo, —F, —CN, alkyl optionally substituted by 1-5 fluroine atoms or —OR, cycloalkyl, heteroaryl optionally substituted by halogen, —CN, alkyl or haloalkyl;

a is 1 or 2; and n is 0, 1 or 2.

2. The compound as defined in claim 1, or a pharmaceutically acceptable salt thereof, wherein:

Z is where ---- is a single or double bond;

R is independently H, alkyl or haloalkyl;

R¹ is H, alkyl, —F, —OR, or —N(R¹³)(R¹⁴);

R² is H or alkyl optionally substituted by 1-5 halogen atoms or —OR;

R³ is H or alkyl;

R⁴ is H or alkyl optionally substituted by 1-5 halogen atoms or —OR;

R⁵ is H or alkyl optionally substituted by 1-5 halogen atoms or —OR;

or R⁴ and R⁵ are joined together to represent —CH₂CH₂-, —CH₂NCH₂-, —CH₂N(CH₃)CH₂- or —CH₂OCH₂-;

R⁶ is H, halo, alkyl optionally substituted by 1-5 halogen atoms or —OR, cycloalkyl or —OR;

or R⁶ and R¹ are joined together to represent —CH₂CH₂O—;

R⁷ is H, halo, alkyl optionally substituted by 1-5 halogen atoms or —OR, cycloalkyl or —OR;

R⁸ is independently H or alkyl;

R⁸' is H or alkyl;

R⁹ is —CN, tetrazolyl, or —S(O)₂R¹³;

R¹⁰ is halo, —OR, alkyl optionally substituted by 1-5 halogen atoms or —OR, —S-alkyl, —N-alkyl or —O-cyclopropyl;

R¹¹ is —CN, —S(O)₂R¹³, or optionally substituted heteroaryl, wherein the optional subsitutent is halogen or alkyl;

R¹² is H, halo, alkyl, cycloalkyl, or —OR;

R¹³ is H, alkyl, allyl or cycloalkyl;

R¹⁴ is H, alkyl or cycloalkyl;

R¹⁵ independently oxo, —F, —CN, alkyl optionally substituted by 1-5 fluorine atoms or —OR, cycloalkyl, heteroaryl optionally substituted by halogen, —CN, alkyl or haloalkyl;

a is 1; and n is 0, 1 or 2.

3. The compound as defined in claim 1, which has the formula

VI or a pharmaceutically acceptable salt thereof wherein:

Z is

4. The compound as defined in claim 1, which has the formula:

IIa or a pharmaceutically acceptable salt thereof wherein:

R$^a$ is H, —F, —CN, alkyl optionally substituted by 1-5 fluorine atoms or —OR, or cycloalkyl; and Z is

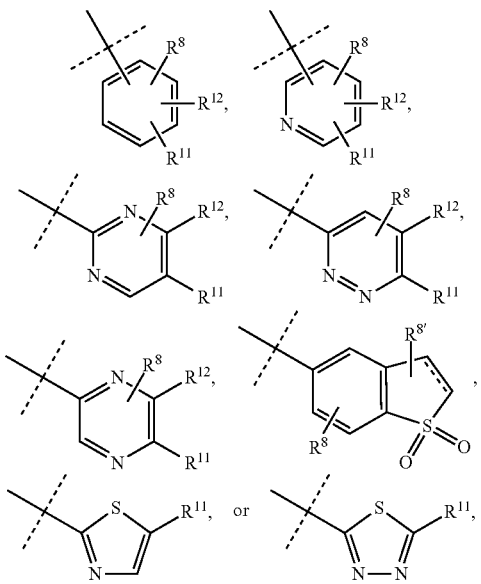

where ---- is a single or double bond.

5. The compound as defined in claim 1, which has the formula

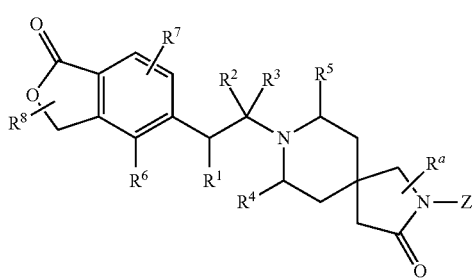

IIb or a pharmaceutically acceptable salt thereof wherein

R$^a$ is H, —F, —CN, alkyl optionally substituted by 1-5 fluorine atoms or —OR, or cycloalkyl; and Z is

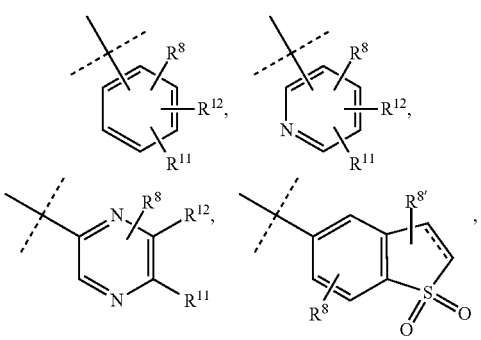

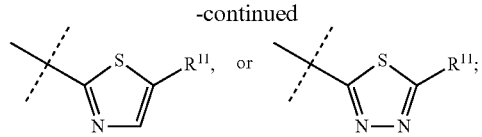

where ---- is a single or double bond.

6. The compound as defined in claim 1, which has the formula:

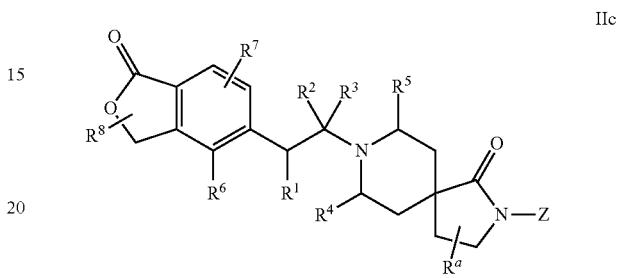

IIc or a pharmaceutically acceptable salt thereof wherein:

R$^a$ is H, —F, —CN, alkyl optionally substituted by 1-5 fluorine atoms or —OR, or cycloalkyl; and Z is

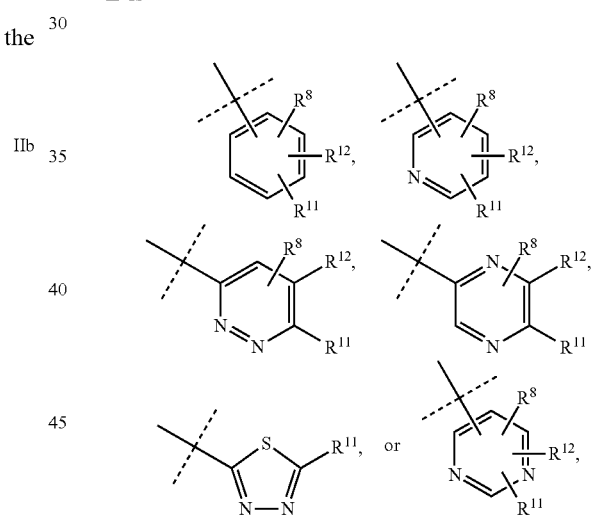

where ---- is a single or double bond.

7. A compound which is:
(R)-5-(1-Hydroxy-2-(2-(5-(methylsulfonyl)pyridin-2-yl)-2,8-diazaspiro[4.5]decan-8-yl)ethyl)-4-methylisobenzofuran-1(3H)-one;
(R)-5-(1-Hydroxy-2-(2-(5-(methylsulfonyl)pyrazin-2-yl)-2,8-diazaspiro[4.5]decan-8-yl)ethyl)-4-methylisobenzofuran-1(3H)-one;
(R)-8-(2-Hydroxy-2-(4-methyl-1-oxo-1,3-dihydroisobenzofuran-5-yl)ethyl)-2-(5-(methylsulfonyl)pyridin-2-yl)-2,8-diazaspiro[4.5]decan-3-one;
(R)-8-(2Hydroxy-2-(4-methyl-1-oxo-1,3-dihydroisobenzofuran-5-yl)ethyl)-2-(5-(methylsulfonyl)pyrazin-2-yl)-2,8-diazaspiro[4.5]decan-3-one;
(R)-6-(9-(2-Hydroxy-2-(4-methyl-1-oxo-1,3-dihydroisobenzofuran-5-yl)ethyl)-3-oxo-1-oxa-4,9-diazaspiro[5.5]undecan-4-yl)-4-methoxynicotinonitrile;

(R)-8-(2-Hydroxy-2-(4-methyl-1-oxo-1,3-dihydroisobenzofuran-5-yl)ethyl)-3-(5-(methylsulfonyl)pyrazin-2-yl)-1-oxa-3,8-diazaspiro[4.5]decan-2-one;

(R)-6-(8-(2-amino-2-(4-methyl-1-oxo-1,3-dihydroisobenzofuran-5-yl)ethyl)-2,8-diazaspiro[4.5]decan-2-yl)nicotinonitrile;

(R)-5-(8-(2-hydroxy-2-(4-methyl-1-oxo-1,3-dihydroisobenzofuran-5-yl)ethyl)-2,8-diazaspiro[4.5]decan-2-yl)pyrazine-2-carbonitrile;

(R)-6-(9-(2-hydroxy-2-(4-methyl-1-oxo-1,3-dihydroisobenzofuran-5-yl)ethyl)-3,9-diazaspiro[5.5]undecan-3-yl)pyrimidine-4-carbonitrile;

or a pharmaceutically acceptable salt thereof.

8. A pharmaceutical composition comprising a therapeutically effective amount of a compound as defined in claim 1 or a pharmaceutically acceptable salt thereof and a pharmaceutically acceptable carrier.

9. The pharmaceutical composition as defined in claim 8, which further comprises a therapeutically effective amount of at least one additional therapeutic agent selected from the group consisting of losartan, valsartan, candesartan, olmesartan, telmesartan, eprosartan, irbesartan, amlodipine, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril, amiloride, spironolactone, epleranone or triamterene, or a pharmaceutically acceptable salt of any of the foregoing.

10. A method for inhibiting ROMK comprising administering in a patient in need thereof an effective amount of a compound as defined in claim 1 or a pharmaceutically acceptable salt thereof.

* * * * *